US011834666B2

(12) United States Patent
Skraly et al.

(10) Patent No.: US 11,834,666 B2
(45) Date of Patent: *Dec. 5, 2023

(54) GENETICALLY ENGINEERED LAND PLANTS THAT EXPRESS A PLANT CCP1-LIKE MITOCHONDRIAL TRANSPORTER PROTEIN

(71) Applicant: YIELD10 BIOSCIENCE, INC., Woburn, MA (US)

(72) Inventors: Frank Anthony Skraly, Woburn, MA (US); Oliver P. Peoples, Woburn, MA (US); Kristi D. Snell, Woburn, MA (US); Meghna Malik, Woburn, MA (US)

(73) Assignee: YIELD10 BIOSCIENCE, INC., Woburn, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/622,000

(22) PCT Filed: Jun. 15, 2018

(86) PCT No.: PCT/US2018/037740
§ 371 (c)(1),
(2) Date: Dec. 12, 2019

(87) PCT Pub. No.: WO2018/232232
PCT Pub. Date: Dec. 20, 2018

(65) Prior Publication Data
US 2021/0147863 A1 May 20, 2021

Related U.S. Application Data

(60) Provisional application No. 62/520,785, filed on Jun. 16, 2017.

(51) Int. Cl.
*C12N 15/82* (2006.01)
*C07K 14/415* (2006.01)
*C07K 14/405* (2006.01)

(52) U.S. Cl.
CPC ........ *C12N 15/8261* (2013.01); *C07K 14/415* (2013.01); *C07K 14/405* (2013.01)

(58) Field of Classification Search
CPC .......................... Y02A 40/146; C12N 15/8261
See application file for complete search history.

(56) References Cited

U.S. PATENT DOCUMENTS

| 5,593,874 A | 1/1997 | Brown |
| 2005/0108791 A1 | 5/2005 | Edgerton |
| 2009/0130710 A1 | 5/2009 | Kermode |
| 2010/0229256 A1 | 9/2010 | Somleva |
| 2011/0321190 A1 | 12/2011 | Akula et al. |
| 2012/0060413 A1 | 3/2012 | Somleva |
| 2012/0216318 A1 | 8/2012 | La Rosa |
| 2013/0333061 A1 | 12/2013 | Wu |
| 2015/0307890 A1 | 10/2015 | Wu et al. |
| 2016/0186197 A1 | 6/2016 | Pankratov |
| 2016/0326541 A1* | 11/2016 | Schnell ................. C07K 14/405 |
| 2018/0291352 A1* | 10/2018 | Malik ............ C12Y 101/01082 |
| 2019/0338302 A1* | 11/2019 | Peoples ................ C07K 14/405 |
| 2020/0370063 A1* | 11/2020 | Skraly ................ C12N 15/8261 |

FOREIGN PATENT DOCUMENTS

| WO | 2014188428 A1 | 11/2014 |
| WO | 2015103074 A1 | 7/2015 |
| WO | 2016164810 A1 | 10/2016 |
| WO | 2017091309 A2 | 6/2017 |
| WO | 2017136668 A1 | 8/2017 |
| WO | 2018156686 A1 | 8/2018 |
| WO | 2019104278 A1 | 5/2019 |

OTHER PUBLICATIONS

Merchant et al (The Chlamydomonas Genome Reveals the Evolution of Key Animaland Plant Functions. Science vol. 318, 245-251, 2007) (Year: 2007).*
Atkinson et al (Introducing an algal carbon-concentrating mechanism into higher plants: location and incorporation of key components. Plant Biotechnology Journal 14, 1302-1315, 2016) (Year: 2016).*
Meyer et al (Origins and diversity of eukaryotic CO2-concentrating mechanisms: lessons for the future. Journal of Experimental Botany, vol. 64, No. 3, pp. 769-786, 2013) (Year: 2013).*
Kazusa DNA Research Institute (Sequence and analysis of chromosome 5 of the plant *Arabidopsis thaliana*. Nature 408: 823-826, 2000). (Year: 2000).*
Falk et al (Constitutive overexpression of barley 4-hydroxyphenylpyruvate dioxygenase in tobacco results in elevation of the vitamin E content in seeds but not in leaves. FEBS Letters 540: 35-40, 2003). (Year: 2003).*
Ferreira et al (Effect of planting density on nutritional quality of green-chopped corn for silage. J. Dairy Sci. 97:5918-5921, 2014). (Year: 2014).*

(Continued)

*Primary Examiner* — Charles Logsdon
*Assistant Examiner* — Wayne Zhong
(74) *Attorney, Agent, or Firm* — Pearne & Gordon LLP

(57) ABSTRACT

A genetically engineered land plant that expresses a plant CCP1-like mitochondrial transporter protein is provided. The genetically engineered land plant comprises a modified gene for the plant CCP1-like mitochondrial transporter protein. The plant CCP1-like mitochondrial transporter protein is an ortholog of CCP1 of *Chlamydomonas reinhardtii* of SEQ ID NO: 1 derived from a source land plant. The plant CCP1-like mitochondrial transporter protein is localized to mitochondria of the genetically engineered land plant based on a mitochondrial targeting signal intrinsic to the plant CCP1-like mitochondrial transporter protein. The modified gene comprises (i) a promoter and (ii) a nucleic acid sequence encoding the plant CCP1-like mitochondrial transporter protein. The promoter is non-cognate with respect to the nucleic acid sequence. The modified gene is configured such that transcription of the nucleic acid sequence is initiated from the promoter and results in expression of the plant CCP1-like mitochondrial transporter protein.

6 Claims, 28 Drawing Sheets

Specification includes a Sequence Listing.

(56) References Cited

OTHER PUBLICATIONS

Merchant et al (The Chlamydomonas Genome Reveals the Evolution of Key Animal and Plant Functions. Science 318: 245-252, 2007) (Year: 2007).*
Friedberg (Automated protein function prediction—the genomic challenge. Brief. Bioinformatics. 7:225-242, 2006) (Year: 2006).*
Wang et al. (From Protein Sequence to Protein Function via Multi-Label Linear Discriminant Analysis. IEEE/ACM Transactions on Computational Biology and Bioinformatics, vol. 14, No. 3, 503-513, 2017) (Year: 2017).*
Atkinson et al (Introducing an algal carbon-concentrating mechanism into higher plants: location and incorporation of key components. Plant Biotechnology Journal 14, pp. 1302-1315, 2016) (Year: 2016).*
International Search Report and Written Opinion for PCT/US2018/037740 dated Sep. 13, 2018.
McDougall, "The cost and time involved in the discovery, development and authorisation of a new plant biotechnology derived trait," Crop Life International, Sep. 2011, pp. 1-24, available at https://croplife.org/wp-content/uploads/pdf_files/Getting-a-Biotech-Crop-to-Market-Phillips-McDougall-Study.pdf, last accessed Apr. 29, 2020.
Belhaj et al., "Plant genome editing made easy: targeted mutagenesis in model and crop plants using the CRISPR/Cas system," Plant Methods (2013); 9:39, pp. 1-10.
Khandagale et al., "Genome editing for targeted improvement of plants," Plant Biotechnol. Rep. (Nov. 2016); vol. 10, pp. 327-343.
Du, et al., "Characterisation of Cyanobacterial Bicarbonate Transporters in *E. coli* Shows that SbtA Homologs are Functional in This Heterologous Expression System," PLoSONE 9(12): e115905. doi:10.1371/journal.pone. 0115905, pp. 1-25 (2014).
Iltis, et al., "*Zea nicaraguensis* (Poaceae), a New Teosinte from Pacific Coastal Nicaragua," Novon, vol. 10, No. 4 (Winter 2000), pp. 382-390, Missouri Botanical Garden Press (2000), Abstract Only.
Efloras, "Erigeron breviscapus," FOC vol. 20-21, p. 635, 638, 1 page, available at www.efloras.org/floratxon.aspx?flora_id-2&taxon_id=200023890, last accessed Nov. 30, 2021.

Herzig, et al., "Identification and functional expression of the mitochondrial pyruvate carrier," Science 337:pp. 93-96 (2012), Abstract Only.
Haferkamp, et al., "Functional integration of mitochondrial and hydrogenosomal ADP/ATP carriers in the *Escherichia coli* membrane reveals different biochemical characteristics for plants, mammals and anaerobic chytrids," Eur. J. Biochem, vol. 269, pp. 3172-3181 (2002).
Kunji, et al., "Lactococcus lactisas host for overproduction of functional membrane proteins," Biochimica et Biophysica Acta 1610, pp. 97-108 (2003).
Palmieri, et al., "Direct methods for measuring metabolite transport and distribution in mitochondria," Methods in Enzymology, vol. 56, pp. 279-301 (1979), Abstract Only.
Hoyos, et al., "Identification of a mitochondrial transporter for basic amino acids in *Arabidopsis thaliana* by functional reconstitution into liposomes and complementation in yeast," The Plant Journal, vol. 33, pp. 1027-1035 (2003).
Pollock, et al., "The Chlamydomonas reinhardtii proteins Ccp1 and Ccp2 are required for long-term growth, but are not necessary for efficient photosynthesis, in a low-Co2 environment", Plant Molecular Biology, vol. 56, pp. 125-132 (2004).
Sullivan, et al., "Isolation and characterization of a maize chlorophyll a]b binding protein gene that produces high levels of mRNA in the dark," Mol. Gen. Genet., vol. 215, pp. 431-440 (1989).
Becker, et al., "The cab-m7 gene: a light-inducible, mesophyll-specific gene of maize, " Plant Mol. Biol. vol. 20, pp. 19-60 (1992).
Que, et al., "Maize transformation technology development for commercial event generation," Front. Plant Sci., vol. 5, article 379, pp. 1-19 (2014).
Shepard, et al., "Construction and evaluation of a maize (*Zea mays*) chimaeric promoter with activity in kernel endosperm and embryo," Biotechnology and Applied Biochemistry, vol. 52, pp. 233-243, Abstract Only.
Simmonds, "10 Genetic Transformation of Soybean with Biolistics," in Genetic Transformation of Plants (eds. J.F. Jackson & H.F. Linskens), vol. 23, in Molecular Method of Plant Analysis (eds. .F. Jackson et al.), pp. I-XV and 159-174 (2003).
European Search Report for related European Appl. No. 18816558.3, dated Dec. 23, 2020, pp. 1-5.
Australian Examination Report for related Australian Appl. No. 2018283286, dated Feb. 26, 2021, pp. 1-5.

* cited by examiner

| | | |
|---|---|---|
| Zea | MPIATGQVMNDTLMEVEHTP--PVHKRILDILPGVSGGVARIMVGQPFDTIKTRLQVLGA | 58 |
| Cosmos | MPSATPQVINDTLMEVEHTP--AVHKRILDILPGVSGGVARIMVGQPFDTIKTRLQVLGK | 58 |
| Erigeron | -MPATPQLMNETLMEVEHTP--AVHKRILDILPGVSGGVARIMVGQPFDTIKTRLQVLGK | 57 |
| Ettlia | -MPATAQVMNDTLMEVEHTP--PVHKRILDILPGVSGGVARIMVGQPFDTIKTRLQVLGK | 57 |
| CCP1 | -MSSDAMTINESLMEVEHTP--PVHKRILDILPGISGGVARIMGQPFDTIKVRLQVLGQ | 57 |
| Volvox | -------MNDTLNQVEHTP--PVHKRILDILPGISGGVARIMGQPFDTIKVRLQVLGQ | 50 |
| GPECTOR_16g646 | ---MVSMTMNDTLNQVEHTPVNPPHKKVLELLPGISGGVARIMGQPFDTIKVRLQVLGA | 57 |
| GPECTOR_16g661 | ---MSSMTVNDTLNEVEHTPKDPPHKRVLELLPGISGGVARIMGQPFDTIKTRLQVLGA | 57 |
| | .*:::*.:****..::..:::::*.:*..:.*.***** | |
| Zea | GTIGAQGMPADMVYNNGMDCVRKMIKSEGPGSLYKGTVAPLLGNMVLLGIHFPTFTKTRA | 118 |
| Cosmos | GTIGAKGMPADMVYNNGMDCVRKMIKSEGAGSLYKGTVAPLLGNMVLLGIHFPTFTKTRA | 118 |
| Erigeron | GTIGAAGMPPEMVYTSGMDCVRKMIKSEGPLSLYKGTIAPLLGNMVLLGIHFPTFHKTRA | 117 |
| Ettlia | GTIGAAGMPPEMVYNSGMDCVRKMKSEGPMSLYKGTVAPLLGNMVLLGIHFPTFTKTRA | 117 |
| CCP1 | GTALAAKLPPSEVYKDSMDCIRKMIKSEGPLSFYKGTVAPLVGNMVLLGIHFPVFSAVRK | 117 |
| Volvox | GTALAAQLPPSEVYKDSLDCVRKMVRNEGPLSFYKGTVAPLVGNMVLLGIHFPTFSYVRK | 110 |
| GPECTOR_16g646 | GTALAAKLPPSEVYKDSMDCVRKMIRTEGPLSFYKGTVAPLIGNMILLGIHFPTFSSVRK | 117 |
| GPECTOR_16g661 | GTALAAKLPPSEVYKDSMDCVRKMVRSEGPLSFYKGTVAPLFGNMILLGIHFPVFSHVRK | 117 |
| | **.*..*.*:***..:.:****::.:*::****:*::*****.*. * | |
| Zea | YLEQGDAPGTFSPWKILAAGAAGAAGAAGSVVSTPTELIRTKMQMVRKNNLMAQMKGAA-AT | 177 |
| Cosmos | YLEQGDAPGTFSPAKILAAGAAGAAGAAGSVVSTPTELIRTKMQMVRKNNILAQMKGAA-AT | 177 |
| Erigeron | YLEREDAPGTHTPWKILAAGAAGATAGAAGSIVSTPTELIRTKMQMVRKNNILQQIKGAGAGG | 177 |
| Ettlia | YLEAGDAPGSFSPWKILAAGAAGAAGAAGSVVSSPTELIRTKMQMVRKNNILAQIKGSAAGG | 177 |
| CCP1 | QLEGDDHYSNFSHANVLLSGAAAGAAGSLISAPVELVRTKMQRRAALAGTVAAGAAAS | 177 |
| Volvox | QLEGDDHYTNFSYTNTLLSGAAAGAAGSLVSTPVELVRTKMQLQS---------AAS | 158 |
| GPECTOR_16g646 | QLEGDDHYSNFSYTNTLIAGAAAGAAGSIVSTPVELVRTKMQRRAALAGSVA-GSAAS | 176 |
| GPECTOR_16g661 | QLEGDDHYSNFSYTNALISGAAAGAAGSLVSTPVELVRTKMQRRAALAGSAG-SAAAS | 176 |
| | **. * .*. :*::::..:.*:*******.::.*.********:..* . . | |
| Zea | LNPEENYKGNWDCAKKILRNHGLRGIYSGYVSTLLRDMQGYAWFFFGYEATIHMCT--- | 234 |
| Cosmos | LNPEENYKGNWDCAKKILRNHGLRGIYSGYVSTLLRDMQGYAWFFFGYEATIHMCT--- | 234 |
| Erigeron | LNPEENYKGNWDCAKKIFRNHGVRGLYSGYLSTLLRDMQGYAWFFGYEATIHYLAG--- | 234 |
| Ettlia | LNPEENYKGNWDCAKKIFRNHGLRGMYSGYLSTLLRDMQGYAWFFGYEATIHYLAG--- | 234 |
| CCP1 | AGAEEFYKGSLDCFKQVMSKHGIKGLYRGFTSTILRDMQGYAWFLGYEATVNHFLQNAG | 237 |
| Volvox | SASDEFYKGSVDCFKQVLSKYGIKGLYRGFTATVLRDMQGYAWFLGYESTVNYFLQKAG | 218 |
| GPECTOR_16g646 | SGAEEFYKGSVDCFKQVLSKHGIKGLYRGFTSTVLRDMQGYAWFLGYEATVNYFLQNAG | 236 |
| GPECTOR_16g661 | SGAEVFYKGSVDCFKQVLSKHGVKGLYRGVTSTVLRDMQGYAWFLGYEATVNYFLQNAG | 236 |
| | . :::*** ** *::::::* :*:* .:*:::*******: ***:*:::::: : | |

FIG. 4A

```
Zea              EG-KTKADLNFLQVMGAGVIAGFGLWGSMFPIDTIKSKIQADSLSKPEFKGTMDCLKRSL    293
Cosmos           DG-KTKADLNFLQVMGAGVIAGFGLWGSMFPIDTIKSKIQADSLSKPEFKGTMDCLKRSL    293
Erigeron         PG-KTKADLDYTQVMLAGVIAGFGLWGSMFPIDTIKSKIQADSLSKPEFKGTLDCLKRSL    293
Ettlia           PG-KTKADLDYSQVMLAGVMAGFGLWGSMFPIDTIKSKIQADSLSKPEFKGTLDCVRRSV    293
CCP1             PGVHTKADLNYLQVMAAGVVAGFGLWGSMFPIDTIKSKLQADSFAKPQYSSTMDCLKKVL    297
Volvox           PGLHSKADLNYMQVMSAGVVAGFGLWGSMFPIDTVKSKLQADTLATPQYRSTYDCLSKVL    278
GPECTOR_16g646   PGVHSKADLNYLQVMAAGVVAGFGLWGSMFPIDTIKSKMQADSLAKPQYTTTMDCLRKVL    296
GPECTOR_16g661   PGVHSKADLNYLQVMAAGVVAGFGLWGSMFPIDTIKSKMQADSLVKPQYSTTYDCVRKVL    296
                  *  :***** :  *** :*** ***********:****:***: .*::. :. ::  :

Zea              AVEGHAGLWRGVTAALWRAIPVNAAIFVAVEGTRQLIADTEESVDAFVNNLTGSGSTAAA    353
Cosmos           AVEGHAGLWRGVTAALWRAIPVNAAIFVAVEGTRQLIADTEESVDAFVNNLTGSSSTTAA    353
Erigeron         AVEGQRGLWRGVTAALWRAIPVNAAIFLAVEGTRQLIADTEESVDKFVNNLTGKETAAV-    352
Ettlia           QIEGYGGLWRGVTAALWRAIPVNAAIFLAVEGTRQLIADTEESIDAFVDQVSGKTSEAAL    353
CCP1             ASEGQAGLWRGFSAAMYRAIPVNAGIFLAVEGTRQGIKWYEENVEHIYGGVIGPATPTAA    357
Volvox           KSEGQAGLWRGFSAAMYRAIPVNAGIFLAVEGTRQGIKWYEENVEHLYGGVVGPATPAAT    338
GPECTOR_16g646   KTEGQVGLWRGFSAAMYRAIPVNAGIFLAVEGSRQGIKWYEENVEHIYGGVVGAAPGAAS    356
GPECTOR_16g661   KTEGNNGLWRGFSAAMYRAIPVNAGIFLAVEATRQGIKLYEENVEHIYGGVVGTTTAA--    354
                  : *   ****..:::*******.:** ***.:**.:.  ****..  *  .   *

Zea              V    354    (SEQ ID NO: 7)
Cosmos           V    354    (SEQ ID NO: 9)
Erigeron         -    352    (SEQ ID NO: 6)
Ettlia           -    353    (SEQ ID NO: 5)
CCP1             Q    358    (SEQ ID NO: 1)
Volvox           S    339    (SEQ ID NO: 4)
GPECTOR_16g646   -    356    (SEQ ID NO: 2)
GPECTOR_16g661   -    354    (SEQ ID NO: 3)
```

FIG. 4B

```
C_reinhardtii_XM_001692145.1    MSSDA-------MTINESLMEVEHTPAVHKRILDLPGISGGVARVMIGQPFDTIKVRLQV      54
T_aestivum_CDM80555.1           -----------MEFWPEFLASSGGHEFVAGGVGGMAGVLAGHPLDTLIRLQQ            42
S_tuberosum_XP_006361187.1      MCDELSRCLIWCCLRSASISPISVFSQMDIMKDLTAGTVGGAAQLIVGHPFDTIKVKLQS    60
G_max_KRH74426.1                ---------------MGDVAKDLTAGTVGGAAQLIVGHPFDTIKVKLQS              34
O_sativa_XP_015614184.1         ---------------MGDVVKDLVAGTVGGAANLIVGHPFDTIKVKLQS              34
Zea_mays_NP_001141073.1         ---------------MGDVAKDLTAGTVGGAANLIVGHPFDTIKVKLQS              34
S_bicolor_XP_002464891.1        ---------------MGDVARDLTAGTVGGVANLVVGHPFDTIKVKLQS              34
                                                    : :*  *  ::  *:: :.***:::::**

C_reinhardtii_XM_001692145.1    LGQGTALAAKLPPSEVYKDSMDCIRKMIKSEGPLSFYKGTVAPLVGNMVLLGIHFPVFSA   114
T_aestivum_CDM80555.1           PPRPVSPGITAARVTRPPSAVALLRGILRAEGPSALYRGMGAPLASVAFQNAMFQVYAI   102
S_tuberosum_XP_006361187.1      QPTPLPGQP--------PKYAGAIDAVRKTVASEGPRGLYKGMGAPLATVAAFNALLFTVRGQ   115
G_max_KRH74426.1                QPTPLPGQL--------PKYSGAIDAVKQTVAAEGPRGLYKGMGAPLATVAAFNAVLFTVRGQ    89
O_sativa_XP_015614184.1         QPTPAPGQF--------PKYAGAVDAVKQTIATEGPRGLYKGMGAPLATVAAFNALLFTVRGQ    89
Zea_mays_NP_001141073.1         QPTPAPGQL--------PKYAGAIDAVKQTVAAEGPRGLYKGMGAPLATVAAFNAVLFSVRGQ    89
S_bicolor_XP_002464891.1        QPTPAPGQL--------PKYAGAIDAVKQTIAAEGPRGLYKGMGAPLATVAAFNALLFSVRGQ    89
                                              .:    *: *:: :.*::** .:*:*:.***:::.*::**:  : .

C_reinhardtii_XM_001692145.1    VRKQLEGDDH-YSNEFSHANVLLSGAAAGAAGSLISAPVELVRTKMQMQRRAALAGTVAAG   173
T_aestivum_CDM80555.1           LSRSLDRRMSTSEPPSYTSVALAGVGTGALQTLILSPVELVKIRLQLEAA-             152
S_tuberosum_XP_006361187.1      TEALLRS---EPGAPLTVKQIILCGAVAGTAASFLACPTELIKCRLQAHSALASVG       168
G_max_KRH74426.1                MEALLRS---HPGATLTINQQVVCGAGAGAVSFLACPTELIKCRLQAQSVLAGTG-       142
O_sativa_XP_015614184.1         MEALLRS---EPGQPLTVNQQVVAGAGAGAVSFLACPTELIKCRLQAQSALAEAA--      142
Zea_mays_NP_001141073.1         MEAFLRS---EPGVPLTVKQQVVAGAGAGAVSFLACPTELIKCRLQAQSSLAEAA--      142
S_bicolor_XP_002464891.1        MEALLRS---EPGVPLTVKQQVVAGAGAGAVSFLACPTELIKCRLQAQSSLAEAA--      142
                                 .  :          .    :  .*. :* .::*:***::  * :

C_reinhardtii_XM_001692145.1    AAAASAGAEEFYKGSLDCFKQVMSK-HGIKGLYRGFTSTILRDMQGYAWFFLGYEATVNHF   232
T_aestivum_CDM80555.1           ----GRKRQGPVDMARDIMRR-EGLRGIYRGLFKGMCPTLAREVPGNAVMFGVYEALKQYE   204
S_tuberosum_XP_006361187.1      ---SASVAIKYTGPMDVARHVLRSEGGVRGLFKGVRGLFKGMCPTLAREVPGNAVMFGVYEALKQYE   225
G_max_KRH74426.1                ----TAAVAVKYGGPMDVARQVLRSEGGVKGLFKGVPTMAREVPGNAAMFGVYEALKRLL   199
O_sativa_XP_015614184.1         -----AASGVALPKGPIDVAKHVVRE-AGMKGLFKGLVPTMGREVPGNALMFGVYEGTKQYL   198
Zea_mays_NP_001141073.1         -----TASGVALPKGPIDVAKHVVRD-AGAKGLFKGLVPTMGREVPGNALMFGVYEATKQYL   198
S_bicolor_XP_002464891.1        -----AASGVALPKGPIDVAKHVVRD-AGAKGLFKGLVPTMGREVPGNAMMFGVYEATKQYL   198
                                      : .:  * : :: :  :     .* :::  :   *  .   :    **: : :
```

FIG. 5A

```
C_reinhardtii_XM_001692145.1   LQNAGPGVHTKADLNYLQVMAAGVVAGEFGLMGSMFPIDTIKSKLQADSF---AKPQYSST    289
T_aestivum_CDM80555.1          ------HPGCRRTGQESLATMLVSGGLAGVASWVCCYPLDVVKSRLQAQTQTHPPSPRYRGV   260
S_tuberosum_XP_006361187.1     ------AGGMDTSG-LGRGSLIVAGGLAGGSVWFAVYPTDVIKSVIQVDDY----RSPKYSGS   277
G_max_KRH74426.1               ------AGGTDTSG-LGRGSLMLAGGVAGAAFWLMVYPTDVVKSVIQVDDY----KNPKFSGS   251
O_sativa_XP_015614184.1        ------AGGQDTSN-LGRGSLILSGGLAGAVFWLSVYPTDVVKSVIQVDDY----KKPRYSGS   250
Zea_mays_NP_001141073.1        ------AGGPDTSG-LGRGSQVLAGGLAGAAFWLSVYPTDVVKSVIQVDDY----KKPKYSGS   250
S_bicolor_XP_002464891.1       ------AGGPDTSN-LGRGSQILAGGLAGGLAGAAFWLSVYPTDVVKSVIQVDDY----KKPRYSGS   250
                                            *   * :.   :*  *   *:* **:**:****   *.::   .

C_reinhardtii_XM_001692145.1   MDCLKKVLASEGQAGLWRGFSAAMYRAIPVNAGIFLAVEGTRQGIKWYEENVEHIYGGVI    349
T_aestivum_CDM80555.1          VDCFRKSVREEGLPVLWRGLGTAVARAFVVNGAIFSAYELLALRFLVRNNGRQTLVMEEMK   320
S_tuberosum_XP_006361187.1     FDALKKILASEGVKGLYKGFGKGFEFGPAITRSIPANAACFLAYEMTRSSLG--------    323
G_max_KRH74426.1               IDAFRRISASEGIKGLYKGFGKGFEFGPAMARSVPANAACFLAYEMTRSALG--------    297
O_sativa_XP_015614184.1        VDAFKKILAADGVKGLYKGFGKGFEFGPAMARSVPANAATFLAYEITRSALG--------    296
Zea_mays_NP_001141073.1        LDALRKIVAADGVKGLYKGFGKGFEFGPAMARSVPANAATFVAYEITRSALG--------    296
S_bicolor_XP_002464891.1       LDALRKIVAADGVKGLYKGFGKGFEFGPAMARSVPANAATFVAYEITRSALG--------    296
                                *.: :  *  *   *  **   *   :  .. ** **   **   * *

C_reinhardtii_XM_001692145.1   GPATPTAAQ   353  (SEQ ID NO:  1)
T_aestivum_CDM80555.1          CHDH-----   324  (SEQ ID NO: 12)
S_tuberosum_XP_006361187.1     ---------   323  (SEQ ID NO: 13)
G_max_KRH74426.1               ---------   297  (SEQ ID NO: 14)
O_sativa_XP_015614184.1        ---------   296  (SEQ ID NO: 15)
Zea_mays_NP_001141073.1        ---------   296  (SEQ ID NO: 16)
S_bicolor_XP_002464891.1       ---------   296  (SEQ ID NO: 17)
```

FIG. 5B

GENETICALLY ENGINEERED LAND PLANTS THAT EXPRESS A PLANT CCP1-LIKE MITOCHONDRIAL TRANSPORTER PROTEIN

FIELD OF THE INVENTION

The present invention relates generally to genetically engineered land plants that express a plant CCP1-like mitochondrial transporter protein, and more particularly, to such genetically engineered land plants comprising a modified gene for the plant CCP1-like mitochondrial transporter protein.

BACKGROUND OF THE INVENTION

The world faces a major challenge in the next 35 years to meet the increased demands for food production to feed a growing global population, which is expected to reach 9 billion by the year 2050. Food output will need to be increased by up to 70% in view of the growing population. Increased demand for improved diet, concomitant land use changes for new living space and infrastructure, alternative uses for crops and changing weather patterns will add to the challenge.

Major agricultural crops include food crops, such as maize, wheat, oats, barley, soybean, millet, sorghum, pulses, bean, tomato, corn, rice, cassava, sugar beets, and potatoes, forage crop plants, such as hay, alfalfa, and silage corn, and oilseed crops, such as camelina, Brassica species (e.g. *B. napus* (canola), *B. rapa, B. juncea*, and *B. carinata*), crambe, soybean, sunflower, safflower, oil palm, flax, and cotton, among others. Productivity of these crops, and others, is limited by numerous factors, including for example relative inefficiency of photochemical conversion of light energy to fixed carbon during photosynthesis, as well as loss of fixed carbon by photorespiration and/or other essential metabolic pathways having enzymes catalyzing decarboxylation reactions. Crop productivity is also limited by the availability of water. Achieving step changes in crop yield requires new approaches.

One potential approach involves metabolic engineering of crop plants to express carbon-concentrating mechanisms of cyanobacteria or eukaryotic algae. Cyanobacteria and eukaryotic algae have evolved carbon-concentrating mechanisms to increase intracellular concentrations of dissolved inorganic carbon, particularly to increase concentrations of $CO_2$ at the active site of ribulose-1,5-bisphosphate carboxylase/oxygenase (also termed RuBisCO). It has recently been shown by Schnell et al., WO 2015/103074 that *Camelina* plants transformed to express CCP1 of the algal species *Chlamydomonas reinhardtii* have reduced transpiration rates, increased $CO_2$ assimilation rates and higher yield than control plants which do not express the CCP1 gene. More recently, Atkinson et al., (2015) Plant Biotechnol. J., doi: 10.1111/pbi.12497, discloses that CCP1 and its homolog CCP2, which were previously characterized as Ci transporters, previously reported to be in the chloroplast envelope, localized to mitochondria in both *Chlamydomonas reinhardtii*, as expressed naturally, and tobacco, when expressed heterologously, suggesting that the model for the carbon-concentrating mechanism of eukaryotic algae needs to be expanded to include a role for mitochondria. Atkinson et al. (2015) disclosed that expression of individual Ci (bicarbonate) transporters did not enhance growth of the plant *Arabidopsis*.

In co-pending Patent Application PCT/US2017/016421, to Yield10 Bioscience, a number of orthologs of CCP1 from algal species that share common protein sequence domains including mitochondrial membrane domains and transporter protein domains were shown to increase seed yield and reduce seed size when expressed constitutively in *Camelina* plants. Schnell et al., WO 2015/103074, also reported a decrease in seed size in higher yielding *Camelina* lines expressing CCP1.

In U.S. Provisional Patent Application 62/462,074, to Yield10 Bioscience, CCP1 and its orthologs from other eukaryotic algae are referred to as mitochondrial transporter proteins. The inventors tested the impact of expressing CCP1 or its algal orthologs using seed-specific promoters with the unexpected outcome that both seed yield and seed size increased. These inventors also recognized the benefits of combining constitutive expression and seed specific expression of CCP1 or any of its orthologs in the same plant.

Unfortunately, "transgenic plants," "GMO crops," and/or "biotech traits" are not widely accepted in some regions and countries and are subject to regulatory approval processes that are very time consuming and prohibitively expensive. The current regulatory framework for transgenic plants results in significant costs (~$136 million per trait; McDougall, P. 2011, *"The cost and time involved in the discovery, development, and authorization of a new plant biotechnology derived trait." Crop Life International*) and lengthy product development timelines that limit the number of technologies that are brought to market. This has severely impaired private investment and the adoption of innovation in this crucial sector. Recent advances in genome editing technologies provide an opportunity to precisely remove genes or edit control sequences to significantly improve plant productivity (Belhaj, K. 2013, Plant Methods, 9, 39; Khandagale & Nadal, 2016, Plant Biotechnol Rep, 10, 327) and open the way to produce plants that may benefit from an expedited regulatory path, or possibly unregulated status.

Given the costs and challenges associated with obtaining regulatory approval and societal acceptance of transgenic crops there is a need to identify, where possible, plant mitochondrial transporter proteins, ideally derived from crops or other land plants, that can be genetically engineered to enable enhanced carbon capture systems to improve crop yield and/or seed yield, particularly without relying on genes, control sequences, or proteins derived from non-land plants to the extent possible.

BRIEF SUMMARY OF THE INVENTION

In accordance with one aspect of the present invention, a genetically engineered land plant that expresses a plant CCP1-like mitochondrial transporter protein is disclosed. The genetically engineered land plant comprises a modified gene for the plant CCP1-like mitochondrial transporter protein. The plant CCP1-like mitochondrial transporter protein is an ortholog of CCP1 of *Chlamydomonas reinhardtii* of SEQ ID NO: 1 derived from a source land plant. The plant CCP1-like mitochondrial transporter protein is localized to mitochondria of the genetically engineered land plant based on a mitochondrial targeting signal intrinsic to the plant CCP1-like mitochondrial transporter protein. The modified gene comprises (i) a promoter and (ii) a nucleic acid sequence encoding the plant CCP1-like mitochondrial transporter protein. The promoter is non-cognate with respect to the nucleic acid sequence. The modified gene is configured such that transcription of the nucleic acid sequence is initiated from the promoter and results in expression of the plant CCP1-like mitochondrial transporter protein.

BRIEF DESCRIPTION OF THE DRAWINGS

FIG. 4A-B shows a multiple sequence alignment of *Chlamydomonas reinhardtii* CCP1 and seven algal or plant CCP1-like mitochondrial transporter proteins according to CLUSTAL O(1.2.4). Sequences are as follows: *Chlamydomonas reinhardtii* (SEQ ID NO: 1); *Gonium pectorale* (KXZ50472.1) (SEQ ID NO: 2); *Gonium pectorale* (KXZ50486.1) (SEQ ID NO: 3); *Volvox carteri* f. *nagariensis* (SEQ ID NO: 4); *Ettlia oleoabundans* (SEQ ID NO: 5); *Erigeron breviscapus* (SEQ ID NO: 6); *Zea nicaraguensis* (SEQ ID NO: 7); and *Cosmos bipinnatus* (SEQ ID NO: 9). The seven algal or plant CCP1-like mitochondrial transporter proteins are Tier 1 CCP1 orthologs as described in the text.

FIG. 5A-B shows a multiple sequence alignment of *Chlamydomonas reinhardtii* CCP1 and six closest orthologs to CCP1 from major crops according to CLUSTAL O(1.2.4). Sequences are as follows. *Chlamydomonas reinhardtii* (SEQ ID NO: 1); *Triticum aestivum* (SEQ ID NO: 12); *Solanum tuberosum* (SEQ ID NO: 13); *Glycine max* (SEQ ID NO: 14); *Oryza sativa* (SEQ ID NO: 15); *Zea mays* (SEQ ID NO: 16); and *Sorghum bicolor* (SEQ ID NO: 17).

DETAILED DESCRIPTION OF THE INVENTION

Figure 1A:
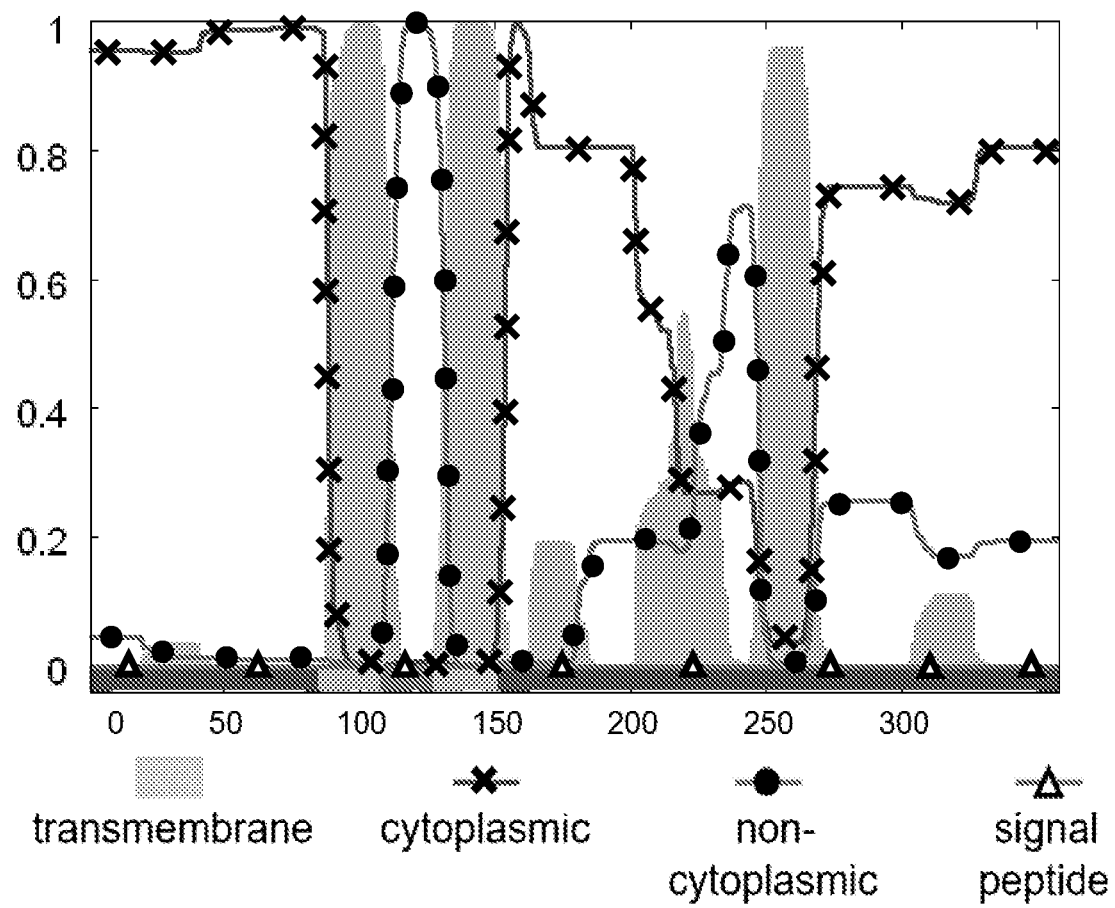
FIG. 1A-I shows Phobius-generated plots of predicted transmembrane domains of (A) *Chlamydomonas reinhardtii* CCP1 (SEQ ID NO: 1), Tier 1 algal CCP1-like mitochondrial transporter proteins of (B) *Gonium pectorale* (KXZ50472.1) (SEQ ID NO: 2), (C) *Gonium pectorale* (KXZ50486.1) (SEQ ID NO: 3), (D) *Volvox carteri* f. *nagariensis* (SEQ ID NO: 4), and (E) *Ettlia oleoabundans* (SEQ ID NO: 5), and Tier 1 plant CCP1-like mitochondrial transporter proteins of (F) *Erigeron breviscapus* (SEQ ID NO: 6), (G) *Zea nicaraguensis* (SEQ ID NO: 7), (H) *Poa pratensis* (SEQ ID NO: 8), and (I) *Cosmos bipinnatus* (SEQ ID NO: 9). The Phobius plots show predicted transmembrane domain (grey shading), cytoplasmic domain (line with X), non-cytoplasmic domain (line with filled circle), and signal peptide sequence (line with triangle). The Y-axis corresponds to posterior label probability, plotted from 0 to 1 in increments of 0.2. The X-axis corresponds to amino acid residue number of corresponding CCP1 or CCP1-like mitochondrial transporter protein, plotted from 0 to 300 in increments of 50 (A-G and I) or from 0 to 140 in increments of 20 (H).
Figure 1B:
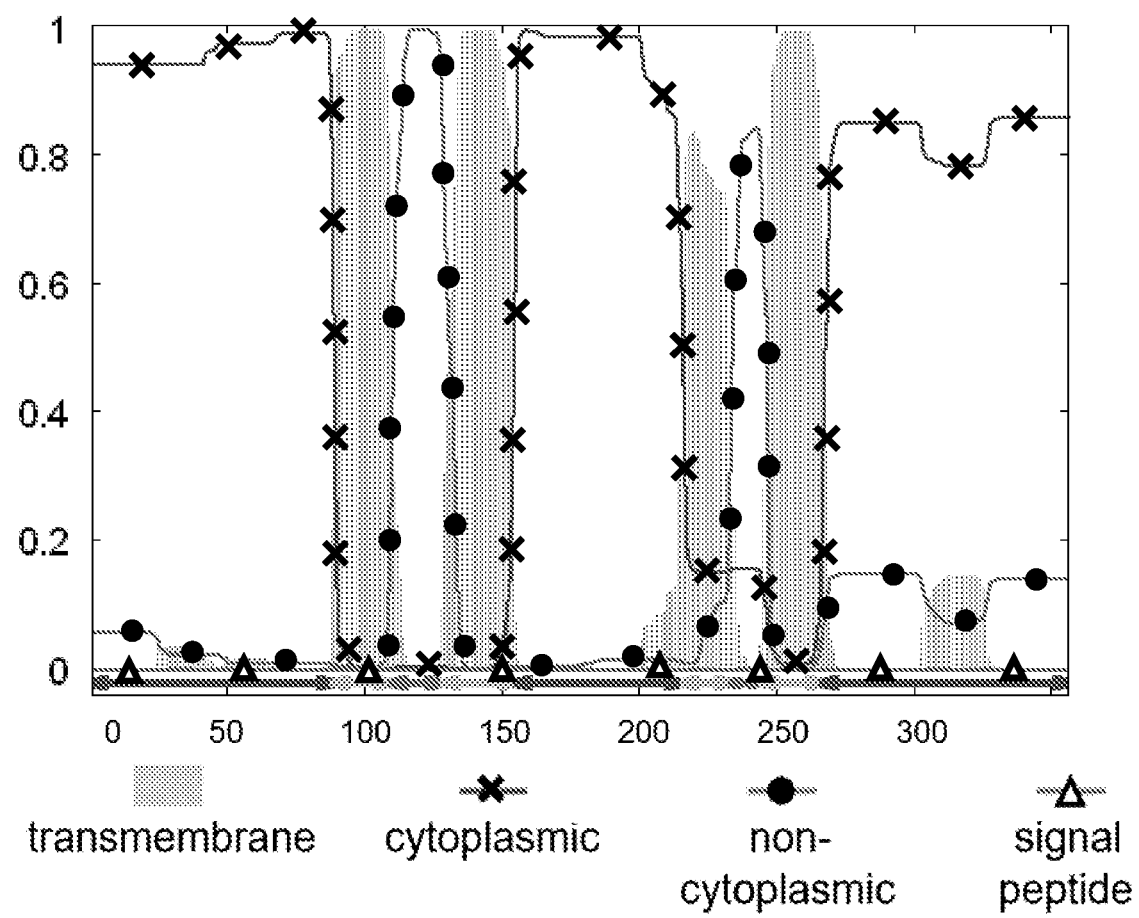
Figure 1C:
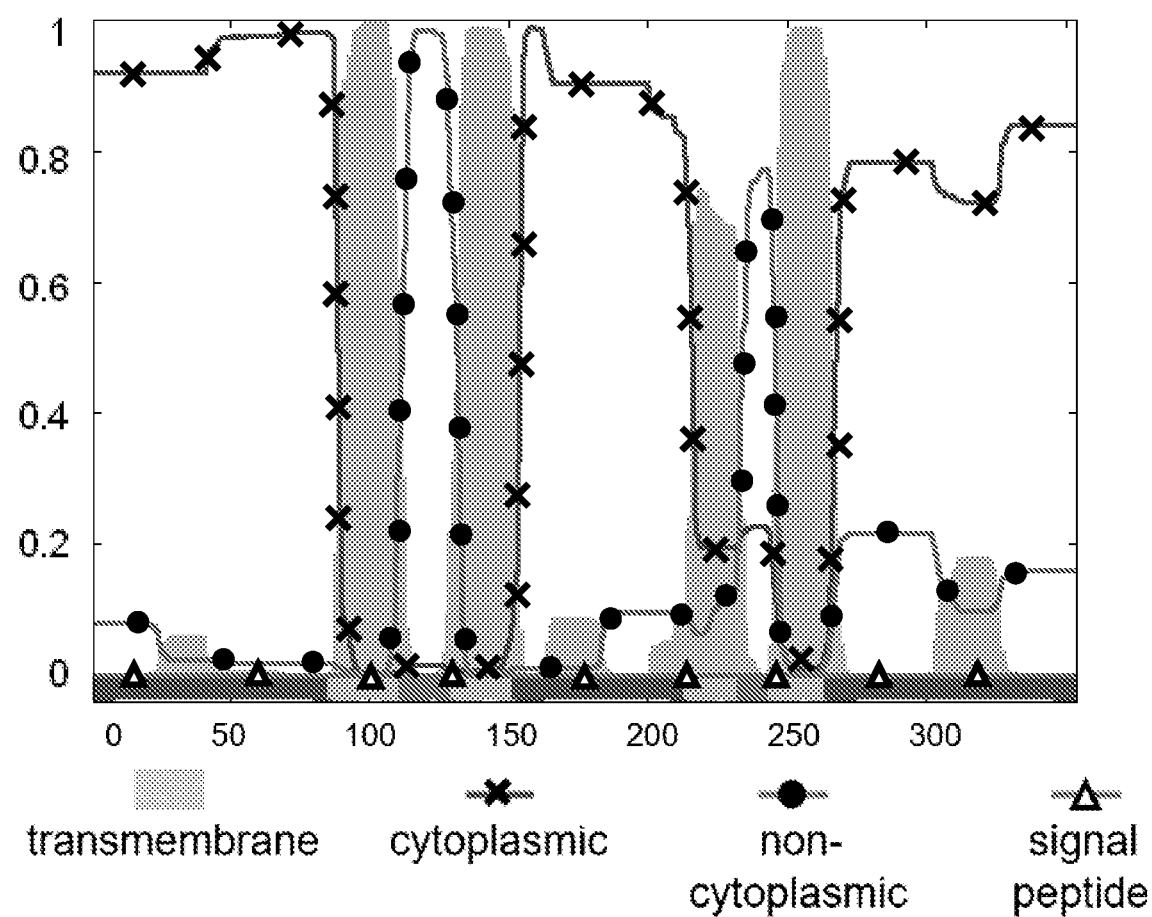
Figure 1D:
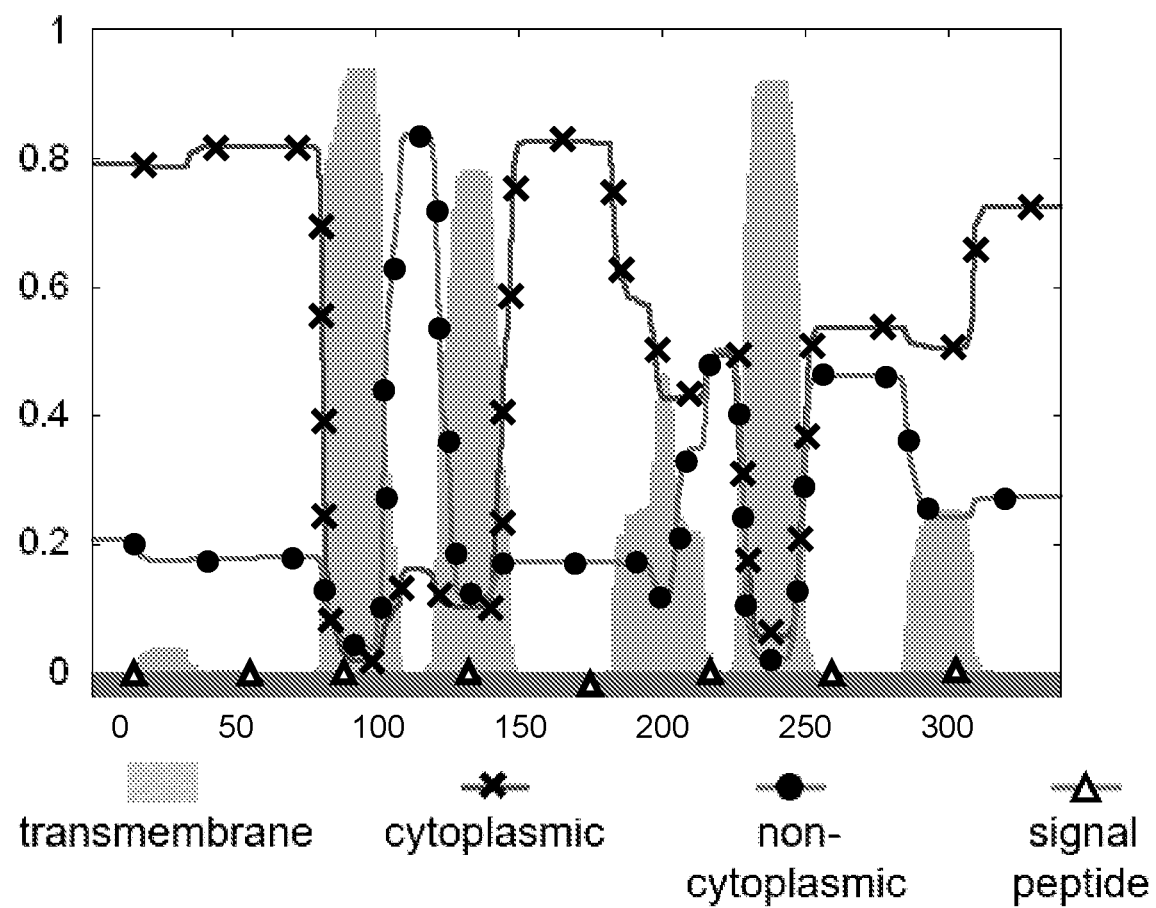
Figure 1E:
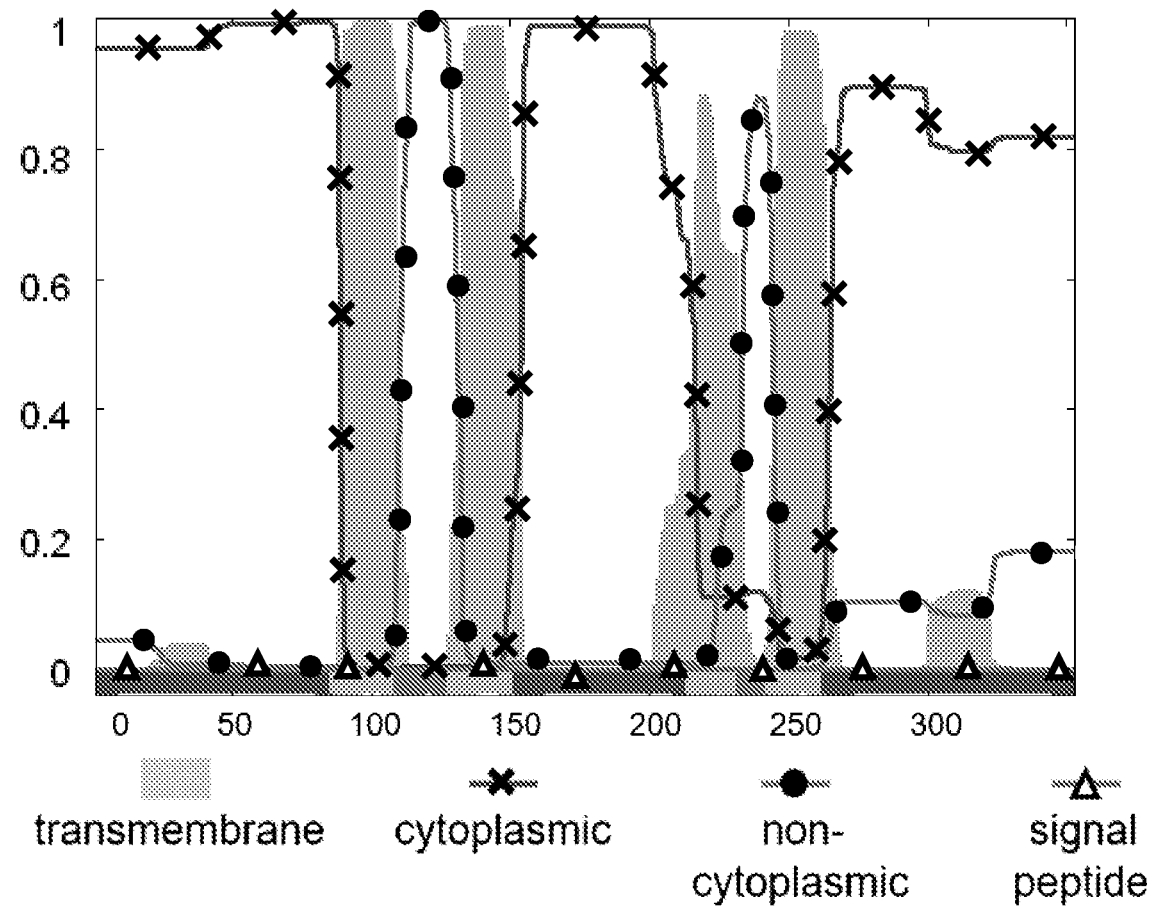
Figure 1F:
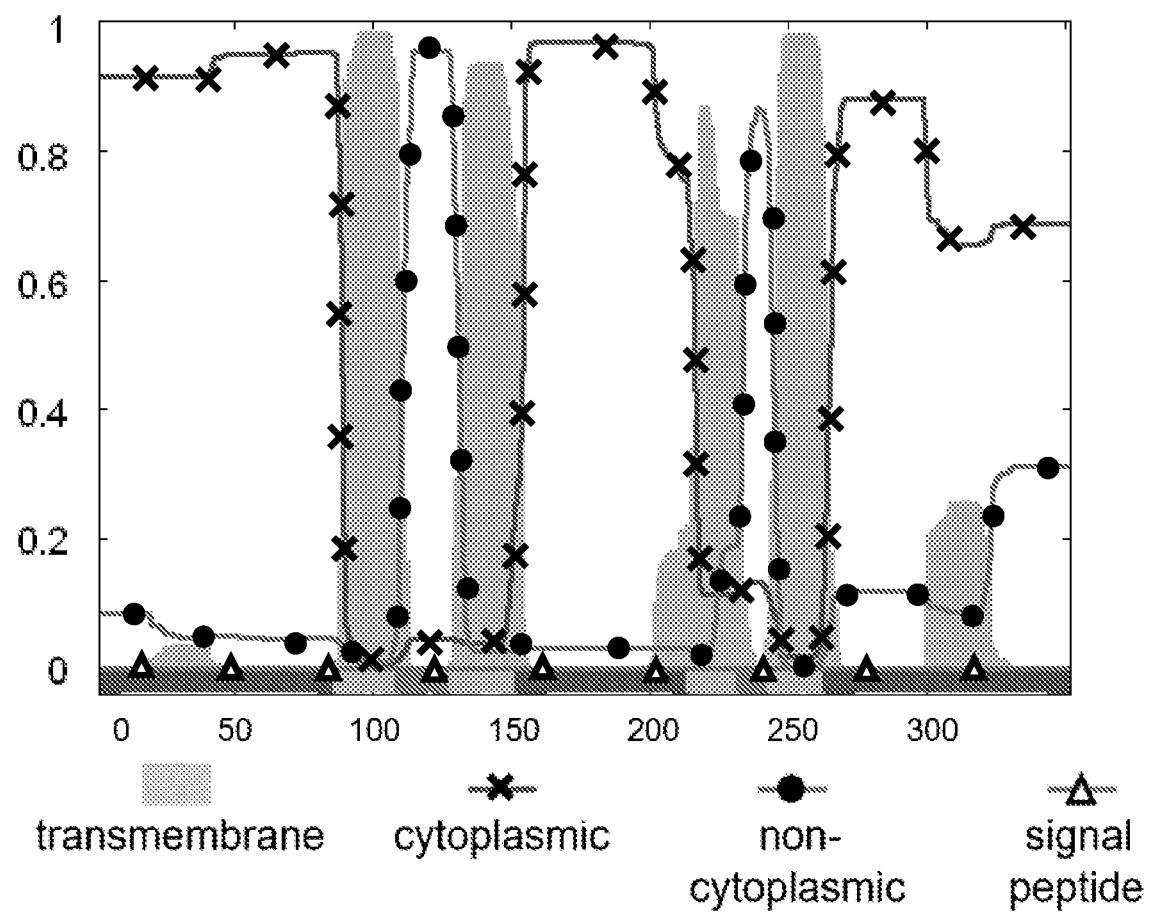

A genetically engineered land plant that expresses a plant CCP1-like mitochondrial transporter protein is disclosed. The genetically engineered land plant comprises a modified gene for the plant CCP1-like mitochondrial transporter protein. The plant CCP1-like mitochondrial transporter protein is an ortholog of CCP1 of *Chlamydomonas reinhardtii* of SEQ ID NO: 1 derived from a source land plant. The plant CCP1-like mitochondrial transporter protein is localized to mitochondria of the genetically engineered land plant based on a mitochondrial targeting signal intrinsic to the plant CCP1-like mitochondrial transporter protein. The modified gene comprises (i) a promoter and (ii) a nucleic acid sequence encoding the plant CCP1-like mitochondrial transporter protein. The promoter is non-cognate with respect to the nucleic acid sequence. The modified gene is configured such that transcription of the nucleic acid sequence is initiated from the promoter and results in expression of the plant CCP1-like mitochondrial transporter protein.

Surprisingly, it has been determined that certain land plants encode orthologs of algal CCP1 of *Chlamydomonas reinhardtii*, herein termed plant CCP1-like mitochondrial transporter proteins. This was surprising because, among other reasons, no plant CCP1-like mitochondrial transporter proteins of land plants were revealed in standard BLAST searches aimed at identifying CCP1 orthologs in land plants, and thus initial attempts to identify plant CCP1-like mitochondrial transporter proteins by conventional means suggested that land plants may not encode such proteins at all. Serendipitously, the plant CCP1-like mitochondrial transporter proteins were identified instead based on analyses of a Transcriptome Shotgun Assembly database, as discussed below.

Also surprisingly, the plant CCP1-like mitochondrial transporter proteins appear to cluster into two distinct groups, herein termed Tier 1 CCP1 orthologs and Tier 2

CCP1 orthologs, based on similarities of predicted amino acid sequence and structure with respect to CCP1. The plant Tier 1 CCP1 orthologs exhibit about 60% sequence identity with respect to CCP1 of *Chlamydomonas reinhardtii*, cluster narrowly based on the degree of their sequence similarity, and have been identified thus far only in four plant species, *Zea nicaraguensis* (also termed teosinte), *Erigeron breviscapus*, *Cosmos bipinnatus*, and *Poa pratensis*, none of which are particularly closely related phylogenetically. The plant Tier 2 CCP1 orthologs exhibit about 30% sequence identity with respect to CCP1 of *Chlamydomonas reinhardtii*, substantially lower than for Tier 1, also cluster narrowly based on the degree of their sequence similarity, and would appear to be more common, having been identified thus far in six major crop species, *Zea mays* (also termed maize), *Triticum aestivum, Solanum tuberosum, Glycine max, Oryza sativa*, and *Sorghum bicolor*. This was surprising because there had not been any apparent reason to expect any clustering of plant CCP1-like mitochondrial transporter proteins, let alone clustering into two distinct groups. This also was surprising because *Zea nicaraguensis*, again teosinte, is a wild progenitor of *Zea mays*, again maize, and thus the two are closely related phylogenetically, yet *Zea nicaraguensis* includes a Tier 1 CCP1, whereas *Zea mays* includes a Tier 2 CCP1.

Also surprisingly, it has been determined that further clustering occurs within the Tier 1 CCP1 orthologs when various algal CCP1 orthologs are included, specifically several algal Tier 1 CCP1 orthologs, namely those of *Gonium pectorale* (KXZ50472.1), *Gonium pectorale* (KXZ50486.1), and *Volvox carteri* f. *nagariensis*, herein termed Tier 1A, exhibit about 80% sequence identity in comparison to CCP1 of *Chlamydomonas reinhardtii*, whereas one algal Tier 1 CCP1 ortholog, namely *Ettlia oleoabundans*, herein termed Tier 1B, instead exhibits 60% sequence identity and clustering with the plant Tier 1 CCP1 orthologs, also herein termed Tier 1B. Strikingly, the algal and plant Tier 1B CCP1 orthologs seem to be more closely related to each other than to the other algal or plant CCP1 orthologs. This suggests that the intriguing possibility that the plant Tier 1B CCP1 orthologs may have resulted from horizontal gene transfer from *Ettlia oleoabundans* or related algae. This also suggests that *Zea nicaraguensis* and the other plant species encoding Tier 1B CCP1 orthologs may serve as sources of CCP1 orthologs that are proximally derived from land plants, rather than from algae, thus decreasing regulatory concerns and risk associated with genetic modification of crops, while still being able to provide increases in crop yield comparable to those observed for CCP1 and CCP1 orthologs derived from algae.

Without wishing to be bound by theory, it is believed that by genetically engineering a land plant to comprise a modified gene for a plant CCP1-like mitochondrial transporter protein, with the plant CCP1-like mitochondrial transporter protein being an ortholog of CCP1 of *Chlamydomonas reinhardtii* of SEQ ID NO: 1 derived from a source land plant, the plant CCP1-like mitochondrial transporter protein being localized to mitochondria of the genetically engineered land plant based on a mitochondrial targeting signal intrinsic to the plant CCP1-like mitochondrial transporter protein, the modified gene comprising a promoter and a nucleic acid sequence encoding the plant CCP1-like mitochondrial transporter protein, the promoter being non-cognate with respect to the nucleic acid sequence, and the modified gene being configured such that transcription of the nucleic acid sequence is initiated from the promoter and results in expression of the plant CCP1-like mitochondrial transporter protein, will result in enhanced yield, based for example on an increased $CO_2$ assimilation rate and/or a decreased transpiration rate of the genetically engineered land plant, in comparison to a reference land plant that does not comprise the modified gene. It is believed that the plant CCP1-like mitochondrial transporter protein will enhance transport of malate (also termed MAL) and/or oxaloacetate (also termed OAA) from or into the mitochondria and/or otherwise alter mitochondrial metabolism by transport of bicarbonate and/or other small molecules, thereby enhancing rates of carbon fixation by increasing $CO_2$ recovery from photorespiration and respiration. Alternatively, the increased transport of small molecules may prevent the accumulation of photorespiratory intermediates that may inhibit photosynthesis. Moreover, it is believed that by genetically engineering the land plant to express a plant CCP1-like mitochondrial transporter protein that is localized to mitochondria in particular, it will be possible to stack expression of the plant CCP1-like mitochondrial transporter protein with expression of other proteins in deliberate and complementary approaches to further enhance yield. In addition, it is believed that by modifying the land plant to express a plant CCP1-like mitochondrial transporter protein of a land plant in particular, it will be possible to generate genetically engineered crops that include only genes, control sequences, and proteins that are proximally derived from land plants, and thus are already generally recognized as safe for human consumption.

As noted, a genetically engineered land plant that expresses a plant CCP1-like mitochondrial transporter protein is disclosed. A land plant is a plant belonging to the plant subkingdom Embryophyta, including higher plants, also termed vascular plants, and mosses, liverworts, and hornworts.

The term "land plant" includes mature plants, seeds, shoots and seedlings, and parts, propagation material, plant organ tissue, protoplasts, callus and other cultures, for example cell cultures, derived from plants belonging to the plant subkingdom Embryophyta, and all other species of groups of plant cells giving functional or structural units, also belonging to the plant subkingdom Embryophyta. The term "mature plants" refers to plants at any developmental stage beyond the seedling. The term "seedlings" refers to young, immature plants at an early developmental stage.

Land plants encompass all annual and perennial monocotyledonous or dicotyledonous plants and includes by way of example, but not by limitation, those of the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solarium, Petunia, Digitalis, Majorana, Cichorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea, Populus, Camelina, Beta, Solanum*, and *Carthamus*. Preferred land plants are those from the following plant families: Amaranthaceae, Asteraceae, Brassicaceae, Carophyllaceae, Chenopodiaceae, Compositae, Cruciferae, Cucurbitaceae, Euphorbiaceae, Fabaceae, Labiatae, Leguminosae, Papilionoideae, Liliaceae, Linaceae, Malvaceae, Poaceae, Rosaceae, Rubiaceae, Saxifragaceae, Scrophulariaceae, Solanaceae, Sterculiaceae, Tetragoniaceae, Theaceae, Umbelliferae.

The land plant can be a monocotyledonous land plant or a dicotyledonous land plant. Preferred dicotyledonous plants are selected in particular from the dicotyledonous crop plants such as, for example, Asteraceae such as sunflower, tagetes or calendula and others; Compositae, especially the genus *Lactuca*, very particularly the species *sativa* (lettuce) and others; Cruciferae, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli) and other cabbages; and the genus *Arabidopsis*, very particularly the species *thaliana*, and cress or canola and others; Cucurbitaceae such as melon, pumpkin/squash or zucchini and others; Leguminosae, particularly the genus Glycine, very particularly the species max (soybean), soya, and alfalfa, pea, beans or peanut and others; Rubiaceae, preferably the subclass Lamiidae such as, for example *Coffea arabica* or *Coffea liberica* (coffee bush) and others; Solanaceae, particularly the genus *Lycopersicon*, very particularly the species *esculentum* (tomato), the genus *Solanum*, very particularly the species *tuberosum* (potato) and *melongena* (aubergine) and the genus *Capsicum*, very particularly the genus *annuum* (pepper) and tobacco or paprika and others; Sterculiaceae, preferably the subclass Dilleniidae such as, for example, *Theobroma cacao* (cacao bush) and others; Theaceae, preferably the subclass Dilleniidae such as, for example, *Camellia sinensis* or Thea *sinensis* (tea shrub) and others; Umbelliferae, particularly the genus *Daucus* (very particularly the species *carota* (carrot)) and *Apium* (very particularly the species *graveolens dulce* (celery)) and others; and linseed, cotton, hemp, flax, cucumber, spinach, carrot, sugar beet and the various tree, nut and grapevine species, in particular banana and kiwi fruit. Preferred monocotyledonous plants include maize, rice, wheat, sugarcane, sorghum, oats and barley.

Of particular interest are oilseed plants. In oilseed plants of interest the oil is accumulated in the seed and can account for greater than 10%, greater than 15%, greater than 18%, greater than 25%, greater than 35%, greater than 50% by weight of the weight of dry seed. Oil crops encompass by way of example: *Borago officinalis* (borage); *Camelina* (false flax); *Brassica* species such as *B. campestris, B. napus, B. rapa, B. carinata* (mustard, oilseed rape or turnip rape); *Cannabis sativa* (hemp); *Carthamus tinctorius* (safflower); *Cocos nucifera* (coconut); *Crambe abyssinica* (crambe); *Cuphea* species (*Cuphea* species yield fatty acids of medium chain length, in particular for industrial applications); *Elaeis guinensis* (African oil palm); *Elaeis oleifera* (American oil palm); *Glycine max* (soybean); *Gossypium hirsutum* (American cotton); *Gossypium barbadense* (Egyptian cotton); *Gossypium herbaceum* (Asian cotton); *Helianthus annuus* (sunflower); *Jatropha curcas* (jatropha); *Linum usitatissimum* (linseed or flax); *Oenothera biennis* (evening primrose); *Olea europaea* (olive); *Oryza sativa* (rice); *Ricinus communis* (castor); *Sesamum indicum* (sesame); *Thlaspi caerulescens* (pennycress); *Triticum* species (wheat); *Zea mays* (maize), and various nut species such as, for example, walnut or almond.

*Camelina* species, commonly known as false flax, are native to Mediterranean regions of Europe and Asia and seem to be particularly adapted to cold semiarid climate zones (steppes and prairies). The species *Camelina sativa* was historically cultivated as an oilseed crop to produce vegetable oil and animal feed. In addition to being useful as an industrial oilseed crop, *Camelina* is a very useful model system for developing new tools and genetically engineered approaches to enhancing the yield of crops in general and for enhancing the yield of seed and seed oil in particular. Demonstrated transgene improvements in *Camelina* can then be deployed in major oilseed crops including *Brassica* species including *B. napus* (canola), *B. rapa, B. juncea, B. carinata, crambe*, soybean, sunflower, safflower, oil palm, flax, and cotton.

As will be apparent, the land plant can be a C3 photosynthesis plant, i.e. a plant in which RuBisCO catalyzes carboxylation of ribulose-1,5-bisphosphate by use of $CO_2$ drawn directly from the atmosphere, such as for example, wheat, oat, and barley, among others. The land plant also can be a C4 plant, i.e. a plant in which RuBisCO catalyzes carboxylation of ribulose-1,5-bisphosphate by use of $CO_2$ shuttled via malate or aspartate from mesophyll cells to bundle sheath cells, such as for example maize, millet, and sorghum, among others.

Accordingly, in some examples the genetically engineered land plant is a C3 plant. Also, in some examples the genetically engineered land plant is a C4 plant. Also, in some examples the genetically engineered land plant is a major food crop plant selected from the group consisting of maize, wheat, oat, barley, soybean, millet, sorghum, potato, pulse, bean, tomato, and rice. In some of these examples, the genetically engineered land plant is maize. Also, in some examples the genetically engineered land plant is a forage crop plant selected from the group consisting of silage corn, hay, and alfalfa. In some of these examples, the genetically engineered land plant is silage corn. Also, in some examples the genetically engineered land plant is an oilseed crop plant selected from the group consisting of camelina, *Brassica* species (e.g. *B. napus* (canola), *B. rapa, B. juncea,* and *B. carinata*), crambe, soybean, sunflower, safflower, oil palm, flax, and cotton.

The land plant comprises a modified gene for the plant CCP1-like mitochondrial transporter protein.

The plant CCP1-like mitochondrial transporter protein is an ortholog of CCP1 of *Chlamydomonas reinhardtii* of SEQ ID NO: 1 derived from a source land plant.

The term "ortholog" means a polynucleotide sequence or polypeptide sequence possessing a high degree of homology, i.e. sequence relatedness, to a subject sequence and being a functional equivalent of the subject sequence, wherein the sequence that is orthologous is from a species that is different than that of the subject sequence. Homology may be quantified by determining the degree of identity and/or similarity between the sequences being compared.

As used herein, "percent homology" of two polynucleotide sequences or of two polypeptide sequences is determined using the algorithm of Karlin and Altschul (1990), Proc. Natl. Acad. Sci., U.S.A. 87: 2264-2268. Such an algorithm is incorporated into the NBLAST and XBLAST programs of Altschul et al. (1990), J. Mol. Biol. 215: 403-410. BLAST nucleotide searches are performed with the NBLAST program, score=100, word length 12, to obtain nucleotide sequences homologous to a reference polynucleotide sequence. BLAST protein searches are performed with the XBLAST program, score=50, word length=3, to obtain amino acid sequences homologous to a reference polypeptide sequence. To obtain gapped alignments for comparison purposes, Gapped BLAST is utilized as described in Altschul et al. (1997), Nucleic Acids Res. 25: 3389-3402. When utilizing BLAST and Gapped BLAST programs, the default parameters are typically used.

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Where a particular polypeptide is said to have a specific percent identity to a reference polypeptide of a defined length, the percent identity is relative to the reference peptide. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide that is 50% identical to the reference polypeptide over its entire length. Many other polypeptides will meet the same criteria.

For reference, as discussed above CCP1 is a mitochondrial transporter protein of *Chlamydomonas reinhardtii*. Moreover, CCP1 has an amino acid sequence in accordance with SEQ ID NO: 1. Accordingly, the plant CCP1-like mitochondrial transporter protein is a polypeptide sequence possessing a high degree of sequence relatedness to CCP1 of *Chlamydomonas reinhardtii* of SEQ ID NO: 1 and being a functional equivalent thereof.

As noted, the plant CCP1-like mitochondrial transporter protein is an ortholog of CCP1 of *Chlamydomonas reinhardtii* of SEQ ID NO: 1 derived from a source land plant.

For reference, *Chlamydomonas reinhardtii* is a eukaryotic alga. In contrast to a land plant, a eukaryotic alga is an aquatic plant, ranging from a microscopic unicellular form, e.g. a single-cell alga, to a macroscopic multicellular form, e.g. a seaweed, that includes chlorophyll a and, if multicellular, a thallus not differentiated into roots, stem, and leaves, and that is classified as chlorophyta (also termed green algae), rhodophyta (also termed red algae), or phaeophyta (also termed brown algae). Eukaryotic algae include, for example, single-cell algae, including the chlorophyta *Chlamydomonas reinhardtii*, *Chlorella sorokiniana*, and *Chlorella variabilis*. Eukaryotic algae also include, for example, seaweed, including the chlorophyta *Ulva lactuca* (also termed sea lettuce) and *Enteromorpha* (*Ulva*) *intenstinalis* (also termed sea grass), the rhodophyta *Chondrus crispus* (also termed Irish moss or carrigeen), *Porphyra umbilicalis* (also termed nori), and *Palmaria palmata* (also termed dulse or dillisk), and the phaeophyta *Ascophyllum nodosum* (also termed egg wrack), *Laminaria digitata* (also termed kombu/konbu), *Laminaria saccharina* (also termed royal or sweet kombu), *Himanthalia elongata* (also termed sea spaghetti), and *Undaria pinnatifida* (also termed wakame). Eukaryotic algae also include, for example, additional chlorophyta such as *Gonium pectorale*, *Volvox carteri* f. *nagariensis*, and *Ettlia oleoabundans*.

The source land plant from which the plant CCP1-like mitochondrial transporter protein is derived can be a land plant as described above, i.e. a plant belonging to the plant subkingdom Embryophyta.

In some examples the source land plant is a different type of land plant than the genetically engineered land plant. In accordance with these examples, the plant CCP1-like mitochondrial transporter protein can be heterologous with respect to the genetically engineered land plant. By this it is meant that the particular plant CCP1-like mitochondrial transporter protein derived from the source land plant is not normally encoded, expressed, or otherwise present in land plants of the type from which the genetically engineered land plant is derived. This can be because land plants of the type from which the genetically engineered land plant is derived do not normally encode, express, or otherwise include the particular plant CCP1-like mitochondrial transporter protein, and this can be so whether or not the land plants normally express a different, endogenous CCP1-like mitochondrial transporter protein. The genetically engineered land plant expresses the particular plant CCP1-like mitochondrial transporter protein based on comprising the modified gene for the plant CCP1-like mitochondrial transporter protein. Accordingly, the modified gene can be used to accomplish modified expression of the plant CCP1-like mitochondrial transporter protein, and particularly increased expression of CCP1 ortholog(s), including the plant CCP1-like mitochondrial transporter protein and any endogenous CCP1-like mitochondrial transporter proteins.

Also in some examples the source land plant is the same type of land plant as the genetically engineered land plant. In accordance with these examples, the plant CCP1-like mitochondrial transporter protein can be homologous with respect to the genetically engineered land plant. By this it is meant that the particular plant CCP1-like mitochondrial transporter protein is normally encoded, and may normally be expressed, in land plants of the type from which the genetically engineered land plant is derived. In accordance with these examples, the land plant can be genetically engineered to include additional copies of a gene for the plant CCP1-like mitochondrial transporter protein and/or to express an endogenous copy a gene for the plant CCP1-like mitochondrial transporter protein at higher levels and/or in a tissue-preferred manner based on modification and/or replacement of a promoter for the endogenous copy of the gene. Again, the genetically engineered land plant expresses the particular plant CCP1-like mitochondrial transporter protein based on comprising the modified gene for the plant CCP1-like mitochondrial transporter protein, resulting in modified expression of the plant CCP1-like mitochondrial transporter protein, and particularly increased expression of CCP1 ortholog(s).

As discussed above, it is believed that the plant CCP1-like mitochondrial transporter protein will enhance transport of malate and/or oxaloacetate from or into the mitochondria and/or otherwise alter mitochondrial metabolism by transport of bicarbonate and/or other small molecules. Accordingly, the plant CCP1-like mitochondrial transporter protein may be a protein that transports malate and/or oxaloacetate by any transport mechanism. Mitochondrial transporters useful for practicing the disclosed invention include transporters involved in the transport of dicarboxylic acids into and out of the mitochondria in plant cells. In particular these transporters can be involved in the transport of oxaloacetate (i.e. OAA) and/or malate (i.e. MAL). In the case of the transport of OAA and MAL, the transporter can be antiporters such that OAA and MAL are transported simultaneously in the opposite directions, for example such that OAA is transported in, while MAL is transported out. Basically the mitochondrial transporter acts as a malate/oxaloacetate shuttle. In other cases the shuttle may transport OAA and one or more other dicarboxylic acids or other metabolites. Transporters or shuttles which transport OAA are a preferred embodiment of this invention. The directionality of flow of either metabolite is determined by the growth conditions experienced by the plant at any particular time. The plant CCP1-like mitochondrial transporter protein also may be a protein that otherwise alters mitochondrial metabolism by transport of bicarbonate and/or other small molecules. Classes of bicarbonate transport proteins include anion exchangers and $Na^+/HCO_3^{-1}$ symporters. Increased transport of other small molecules may prevent their buildup which might otherwise inhibit photosynthesis.

The plant CCP1-like mitochondrial transporter protein is localized to mitochondria of the land plant based on a mitochondrial targeting signal intrinsic to the plant CCP1-like mitochondrial transporter protein. The plant CCP1-like mitochondrial transporter protein can be localized to mitochondria for example based on being encoded by DNA present in the nucleus of a plant cell, synthesized in the cytosol of the plant cell, targeted to the mitochondria of the plant cell, and inserted into outer membranes and/or inner membranes of the mitochondria. A mitochondrial targeting signal is a portion of a polypeptide sequence that targets the polypeptide sequence to mitochondria. A mitochondrial targeting signal intrinsic to the plant CCP1-like mitochondrial transporter protein is a mitochondrial targeting signal that is integral to the plant CCP1-like mitochondrial transporter protein, e.g. based on occurring naturally at the N-terminal end of the plant CCP1-like mitochondrial transporter protein or in discrete segments along the plant CCP1-like mitochondrial transporter protein. This is in contrast, for example, to fusion of a heterologous mitochondrial targeting signal to a mitochondrial transporter protein that would not otherwise be targeted to mitochondria. For reference, also as discussed above CCP1 is localized to mitochondria in both *Chlamydomonas reinhardtii*, as expressed naturally, and tobacco, when expressed heterologously. Accordingly, the plant CCP1-like mitochondrial transporter protein can be a mitochondrial transporter protein that is encoded by nuclear DNA, synthesized cytosolically, targeted to the mitochondria, and inserted into outer membranes and/or inner membranes thereof, based on targeting by a portion of the polypeptide sequence integral to plant CCP1-like mitochondrial transporter protein. The plant CCP1-like mitochondrial transporter protein does not have typical plastid targeting signals.

Suitable plant CCP1-like mitochondrial transporter proteins can be identified, for example, based on searching databases of polynucleotide sequences or polypeptide sequences for orthologs of CCP1 of *Chlamydomonas reinhardtii* of SEQ ID NO: 1, wherein the polynucleotide sequences or polypeptide sequences are derived from land plants, in view of the disclosure herein, as discussed below. Such searches can be carried out, for example, by use of BLAST, e.g. tblastn, and databases including translated polynucleotides, whole genome shotgun sequences, and/or transcriptome assembly sequences, among other sequences and databases. Potential orthologs of CCP1 may be identified, for example, based on percentage of identity and/or percentage of similarity, with respect to polypeptide sequence, of individual sequences in the databases in comparison to CCP1 of *Chlamydomonas reinhardtii*. For example, potential orthologs of CCP1 may be identified based on percentage of identity of an individual sequence in a database and CCP1 of *Chlamydomonas reinhardtii* of SEQ ID NO: 1 of at least 25%, e.g. at least 30%, at least 35%, at least 40%, at least 45%, at least 50%, at least 55%, at least 60%, at least 65%, at least 70%, at least 75%, at least 80%, at least 90%, or at least 95%, wherein the individual sequence is derived from a land plant. Also for example, potential orthologs of CCP1 may be identified based on percentage of similarity of an individual sequence in a database and CCP1 of *Chlamydomonas reinhardtii* of SEQ ID NO: 1 of at least 10%, e.g. at least 15%, at least 20%, at least 25%, at least 30%, at least 35%, at least 40%, at least 45%, at least 50%, at least 55%, at least 60%, at least 65%, at least 70%, at least 75%, at least 80%, at least 90%, or at least 95%, wherein the individual sequence is derived from a land plant. Also for example, potential orthologs of CCP1 may be identified based on both percentage of identity of at least 25%, e.g. at least 30%, at least 35%, at least 40%, at least 45%, at least 50%, at least 55%, at least 60%, at least 65%, at least 70%, at least 75%, at least 80%, at least 90%, or at least 95%, and percentage of similarity of at least 10%, e.g. at least 15%, at least 20%, at least 25%, at least 30%, at least 35%, at least 40%, at least 45%, at least 50%, at least 55%, at least 60%, at least 65%, at least 70%, at least 75%, at least 80%, at least 90%, or at least 95%, wherein the individual sequence is derived from a land plant.

Suitable plant CCP1-like mitochondrial transporter proteins also can be identified, for example, based on functional screens.

For example, some cyanobacterial bicarbonate transporters have previously been shown to functionally localize into the *Escherichia coli* cytoplasmic membrane, including some bicarbonate transporters, as reported by Du et al. (2014), PLoS One 9, e115905. Expression of six particular cyanobacterial bicarbonate transporters in *E. coli* using a mutant *E. coli* strain, termed EDCM636, that is deficient in carbonic anhydrase activity and that is unable to grow on LB or M9 plates without supplementation with high levels of $CO_2$, restored growth of the *E. coli* mutant at atmospheric levels of $CO_2$, whereas expression of various others did not, as reported by Du et al. (2014). Function of CCP1 and potential orthologs thereof with respect to transport of malate and/or oxaloacetate, bicarbonate, or other metabolites may be tested by an analogous approach, and corresponding functional screens developed, also based on restoring growth of mutant *E. coli* strains.

Function of CCP1 and potential orthologs thereof with respect to transport of malate and/or oxaloacetate, bicarbonate, or other metabolites also may be tested, and corresponding functional screens developed, based on use of yeast modified to express CCP1 and potential orthologs thereof. Transport of bicarbonate or other metabolites from mitochondria of yeast so modified would indicate that these sequences also enable transport of bicarbonate in yeast.

Following identification of a plant CCP1-like mitochondrial transporter protein, genetic engineering of a land plant to express the plant CCP1-like mitochondrial transporter protein can be carried out by methods that are known in the art, as discussed in detail below.

The genetically engineered land plant can be a genetically engineered land plant that includes no heterologous proteins, e.g. wherein the plant CCP1-like mitochondrial transporter protein is homologous with respect to the genetically engineered land plant, or only one heterologous protein, e.g. wherein the only heterologous plant protein that the genetically engineered land plant comprises is the plant CCP1-like mitochondrial transporter protein. As noted above, Atkinson et al. (2015) also discloses that expression of individual putative Ci transporters did not enhance *Arabidopsis* growth, and suggests that stacking of further components of carbon-concentrating mechanisms will probably be required to achieve a significant increase in photosynthetic efficiency in this species, albeit without having tested expression of CCP1 in particular. In contrast, without wishing to be bound by theory, it is believed that a genetically engineered land plant that expresses a plant CCP1-like mitochondrial transporter protein as described herein will achieve a significant increase in photosynthetic efficiency in the genetically engineered land plant without need for stacking of further components of carbon-concentrating mechanisms, and thus without heterologous and/or modified expression of any other protein by the genetically engineered land plant. The corresponding genetically engineered land plant will provide advantages relative to plants that are modified to express multiple genes, for example in terms of simpler methods of making the genetically engineered land plant, and lower risk of harmful effects of other proteins subject to heterologous and/or modified expression with respect to use of the genetically engineered land plant as a food crop, a forage crop, or an oilseed crop.

Considering the plant CCP1-like mitochondrial transporter protein in more detail, the plant CCP1-like mitochondrial transporter protein can correspond to a plant CCP1-like mitochondrial transporter protein selected from among specific polypeptide sequences of source land plants. As noted above, mitochondrial transporter proteins include CCP1 of *Chlamydomonas reinhardtii* of SEQ ID NO: 1. As also noted, plant CCP1-like mitochondrial transporter protein may be identified based on homology to CCP1. Exemplary CCP1-like mitochondrial transporter proteins identified this way include (a) a plant CCP1-like mitochondrial transporter protein of *Zea nicaraguensis* of SEQ ID NO: 7, (b) a plant CCP1-like mitochondrial transporter protein of *Erigeron breviscapus* of SEQ ID NO: 6, (c) a plant CCP1-like mitochondrial transporter protein of *Poa pratensis* of SEQ ID NO: 8, and (d) a plant CCP1-like mitochondrial transporter protein of *Cosmos bipinnatus* of SEQ ID NO: 9. These correspond to Tier 1 plant CCP1-like mitochondrial transporter proteins. Exemplary CCP1-like mitochondrial transporter protein identified this way also include (a) a plant CCP1-like mitochondrial transporter protein of *Zea mays* of SEQ ID NO: 16, (b) a plant CCP1-like mitochondrial transporter protein of *Triticum aestivum* of SEQ ID NO: 12, (c) a plant CCP1-like mitochondrial transporter protein of *Solanum tuberosum* of SEQ ID NO: 13, (d) a plant CCP1-like mitochondrial transporter protein of *Glycine max* of SEQ ID NO: 14, (e) a plant CCP1-like mitochondrial transporter protein of *Oryza sativa* of SEQ ID NO: 15, and (f) a plant CCP1-like mitochondrial transporter protein of *Sorghum bicolor* of SEQ ID NO: 17. These correspond to Tier 2 plant CCP1-like mitochondrial transporter proteins.

Accordingly, in some embodiments the plant CCP1-like mitochondrial transporter protein comprises at least one of (a) a plant CCP1-like mitochondrial transporter protein of *Zea nicaraguensis*, (b) a plant CCP1-like mitochondrial transporter protein of *Erigeron breviscapus*, (c) a plant CCP1-like mitochondrial transporter protein of *Poa pratensis*, or (d) a plant CCP1-like mitochondrial transporter protein of *Cosmos bipinnatus*. For example, in some embodiments the plant CCP1-like mitochondrial transporter protein comprises a plant CCP1-like mitochondrial transporter protein of *Zea nicaraguensis*.

Also in some embodiments, the plant CCP1-like mitochondrial transporter protein comprises at least one of (a) a plant CCP1-like mitochondrial transporter protein of *Zea nicaraguensis* of SEQ ID NO: 7, (b) a plant CCP1-like mitochondrial transporter protein of *Erigeron breviscapus* of SEQ ID NO: 6, (c) a plant CCP1-like mitochondrial transporter protein of *Poa pratensis* of SEQ ID NO: 8, or (d) a plant CCP1-like mitochondrial transporter protein of *Cosmos bipinnatus* of SEQ ID NO: 9. For example, in some embodiments the plant CCP1-like mitochondrial transporter protein comprises a plant CCP1-like mitochondrial transporter protein of *Zea nicaraguensis* of SEQ ID NO: 7.

Also in some embodiments, the plant CCP1-like mitochondrial transporter protein comprises one or more of (a) a plant CCP1-like mitochondrial transporter protein of *Zea mays*, (b) a plant CCP1-like mitochondrial transporter protein of *Triticum aestivum*, (c) a plant CCP1-like mitochondrial transporter protein of *Solanum tuberosum*, (d) a plant CCP1-like mitochondrial transporter protein of *Glycine max*, (e) a plant CCP1-like mitochondrial transporter protein of *Oryza sativa*, or (f) a plant CCP1-like mitochondrial transporter protein of *Sorghum bicolor*. For example, in some embodiments the plant CCP1-like mitochondrial transporter protein comprises a plant CCP1-like mitochondrial transporter protein of *Zea mays*.

Also in some embodiments, the plant CCP1-like mitochondrial transporter protein comprises one or more of (a) a plant CCP1-like mitochondrial transporter protein of *Zea mays* of SEQ ID NO: 16, (b) a plant CCP1-like mitochondrial transporter protein of *Triticum aestivum* of SEQ ID NO: 12, (c) a plant CCP1-like mitochondrial transporter protein of *Solanum tuberosum* of SEQ ID NO: 13, (d) a plant CCP1-like mitochondrial transporter protein of *Glycine max* of SEQ ID NO: 14, (e) a plant CCP1-like mitochondrial transporter protein of *Oryza sativa* of SEQ ID NO: 15, or (f) a plant CCP1-like mitochondrial transporter protein of *Sorghum bicolor* of SEQ ID NO: 17. For example, in some embodiments the plant CCP1-like mitochondrial transporter protein comprises a plant CCP1-like mitochondrial transporter protein of *Zea mays* of SEQ ID NO: 16.

The plant CCP1-like mitochondrial transporter protein also can correspond to a plant CCP1-like mitochondrial transporter protein including specific structural features and characteristics shared among various orthologs of CCP1 of *Chlamydomonas reinhardtii* of SEQ ID NO: 1. Such structural features and characteristics shared among the various orthologs of CCP1, namely the Tier 1 algal CCP1-like mitochondrial transporter proteins of *Gonium pectorale* (KXZ50472.1) (SEQ ID NO: 2), *Gonium pectorale* (KXZ50486.1) (SEQ ID NO: 3), *Volvox carteri* f. *nagariensis* (SEQ ID NO: 4), and *Ettlia oleoabundans* (SEQ ID NO: 5), and Tier 1 plant CCP1-like mitochondrial transporter proteins of *Erigeron breviscapus* (SEQ ID NO: 6), *Zea nicaraguensis* (SEQ ID NO: 7), and *Cosmos bipinnatus* (SEQ ID NO: 9), include (i) (a) a proline residue at position 268, (b) an aspartate residue or glutamine residue at position 270, (c) a lysine residue or arginine residue at position 273, and (d) a serine residue or threonine residue at position 274, with numbering of positions relative to CCP1 of *Chlamydomonas reinhardtii* of SEQ ID NO: 1, and (ii) an overall identity of at least 15%. These noted amino acid residues occur at or after the C-terminal portion of a potential transmembrane region of each of CCP1 and the various Tier 1 algal and plant orthologs, namely that of *Gonium pectorale* (KXZ50472.1) (SEQ ID NO: 2), *Gonium pectorale* (KXZ50486.1) (SEQ ID NO: 3), *Volvox carteri* f. *nagariensis* (SEQ ID NO: 4), and *Ettlia oleoabundans* (SEQ ID NO: 5), *Erigeron breviscapus* (SEQ ID NO: 6), *Zea nicaraguensis* (SEQ ID NO: 7), and *Cosmos bipinnatus* (SEQ ID NO: 9), as well as among various other orthologs of CCP1. Conservation of the noted amino acid residues, in combination with an overall identity of at least 15%, suggests a structure/function relationship shared among such mitochondrial transporter proteins. Thus, for example, the plant CCP1-like mitochondrial transporter protein can be an ortholog of CCP1 of *Chlamydomonas reinhardtii* of SEQ ID NO: 1 based on comprising: (i) (a) a proline residue at position 268, (b) an aspartate residue or glutamine residue at position 270, (c) a lysine residue or arginine residue at position 273, and (d) a serine residue or threonine residue at position 274, with numbering of positions relative to CCP1 of *Chlamydomonas reinhardtii* of SEQ ID NO: 1, and (ii) an overall identity of at least 15%.

The plant CCP1-like mitochondrial transporter protein also can correspond to a plant CCP1-like mitochondrial transporter protein including additional specific structural features and characteristics shared among orthologs of CCP1 of *Chlamydomonas reinhardtii* of SEQ ID NO: 1. For example, the plant CCP1-like mitochondrial transporter protein can be an ortholog of CCP1 of *Chlamydomonas reinhardtii* of SEQ ID NO: 1 based on comprising: (i) (a) a glycine residue at position 301, (b) a glycine residue at position 308, and (c) an arginine residue at position 315, with numbering of positions relative to CCP1 of *Chlamydomonas reinhardtii* of SEQ ID NO: 1, and (ii) an overall identity of at least 15%. These noted amino acid residues also are conserved among CCP1 and the various Tier 1 algal and plant orthologs, as well as other CCP1 orthologs.

The plant CCP1-like mitochondrial transporter protein also can correspond to a plant CCP1-like mitochondrial transporter protein including Tier 1 CCP1 signature sequences shared specifically among Tier 1 algal and plant orthologs of CCP1 of *Chlamydomonas reinhardtii* of SEQ ID NO: 1. For example, the plant CCP1-like mitochondrial transporter protein can be an ortholog of CCP1 of *Chlamydomonas reinhardtii* of SEQ ID NO: 1 based on comprising: (i) one or more Tier 1 CCP1 signature sequences of (a) LLGIHFP (SEQ ID NO: 18) at position 104-110, (b) LRDMQGYAWFF (SEQ ID NO: 19) at position 212-222, (c) AGFGLWGSMF (SEQ ID NO: 20) at position 258-267, or (d) AIPVNA (SEQ ID NO: 21) at position 316-321, with numbering of positions relative to CCP1 of *Chlamydomonas reinhardtii* of SEQ ID NO: 1, and (ii) an overall identity of at least 60%. These noted Tier 1 CCP1 signature sequences also are conserved specifically among CCP1 and the various Tier 1 algal and plant orthologs.

The plant CCP1-like mitochondrial transporter protein also can correspond to a plant CCP1-like mitochondrial transporter protein that does not only localize to mitochondria, but that also localizes to chloroplasts. As noted above, Atkinson et al. (2015) discloses that CCP1 and its homolog CCP2, which are characterized as putative Ci transporters previously reported to be in the chloroplast envelope, localized to mitochondria in both *Chlamydomonas reinhardtii*, as expressed naturally, and tobacco, when expressed heterologously. Without wishing to be bound by theory, it is believed that localization of plant CCP1-like mitochondrial transporter proteins to mitochondria to a greater extent than to chloroplasts promotes enhanced yield. Thus, for example, the plant CCP1-like mitochondrial transporter protein can be localized to mitochondria of the genetically engineered land plant to a greater extent than to chloroplasts of the genetically engineered land plant by a factor of at least 2, at least 5, or at least 10.

The plant CCP1-like mitochondrial transporter protein also can correspond to a plant CCP1-like mitochondrial transporter protein that does not differ in any biologically significant way from a wild-type plant CCP1-like mitochondrial transporter protein. As noted above, the plant CCP1-like mitochondrial transporter protein is localized to mitochondria of the genetically engineered land plant based on a mitochondrial targeting signal intrinsic to the plant CCP1-like mitochondrial transporter protein, and this is in contrast, for example, to fusion of a heterologous mitochondrial targeting signal to a plant protein that would not otherwise be targeted to mitochondria. In some examples, the plant CCP1-like mitochondrial transporter protein also does not include any other modifications that might result in the plant CCP1-like mitochondrial transporter protein differing in a biologically significant way from a wild-type plant CCP1-like mitochondrial transporter protein. Thus, for example the plant CCP1-like mitochondrial transporter protein can consist essentially of an amino acid sequence that is identical to that of a wild-type plant CCP1-like mitochondrial transporter protein. The corresponding genetically engineered land plant will provide advantages, e.g. again in terms of lower risk of harmful effects with respect to use of the genetically engineered land plant as a food crop, a forage crop, or an oilseed crop.

The modified gene comprises (i) a promoter and (ii) a nucleic acid sequence encoding the plant CCP1-like mitochondrial transporter protein.

The promoter is non-cognate with respect to the nucleic acid sequence. A promoter that is non-cognate with respect to a nucleic acid sequence means that the promoter is not naturally paired with the nucleic acid sequence in organisms from which the promoter and/or the nucleic acid sequence are derived. Instead, the promoter has been paired with the nucleic acid sequence based on use of recombinant DNA techniques to create a modified gene. Accordingly, in this case, the promoter is not naturally paired with the nucleic acid sequence in the source land plant, i.e. the land plant from which the nucleic acid sequence encoding the plant CCP1-like mitochondrial transporter protein had been derived, nor in the organism from which the promoter has been derived, whether that organism is the source land plant or another organism. Instead, the promoter has been paired with the nucleic acid sequence based on use of recombinant DNA techniques to create the modified gene.

The modified gene is configured such that transcription of the nucleic acid sequence is initiated from the promoter and results in expression of the plant CCP1-like mitochondrial transporter protein. Accordingly, in the context of the modified gene, the promoter functions as a promoter of transcription of the nucleic acid sequence, and thus of expression of the plant CCP1-like mitochondrial transporter protein.

In some examples, the promoter is a constitutive promoter. In some examples, the promoter is a seed-specific promoter. In some examples, the modified gene is integrated into genomic DNA of the genetically engineered land plant. In some examples, the modified gene is stably expressed in the genetically engineered land plant. In some examples the nucleic acid sequence encodes a wild-type plant CCP1-like mitochondrial transporter protein. In some examples, the nucleic acid sequence encodes a variant, modified, mutant, or otherwise non-wild-type plant CCP1-like mitochondrial transporter protein. These exemplary features, and others, of the promoter, the nucleic acid sequence, and the modified gene are discussed in detail below.

The genetically engineered land plant also can be a genetically engineered land plant that expresses nucleic acid sequences encoding plant CCP1-like mitochondrial transporter proteins in both a seed-specific and a constitutive manner, wherein the nucleic acid sequences encoding the plant CCP1-like mitochondrial transporter proteins may be the same or different nucleic acid sequences, from the same source land plant or from different source land plants. Without wishing to be bound by theory, it is believed that constitutive expression of plant CCP1-like mitochondrial transporter proteins results in much higher numbers of pods, and that seed-specific expression of plant CCP1-like mitochondrial transporter proteins can supply the carbon needed to fill seeds to a full size, and that thus the yield should be higher. Accordingly, in some examples the genetically engineered land plant (i) expresses the plant CCP1-like mitochondrial transporter protein in a seed-specific manner, and (ii) expresses another plant CCP1-like mitochondrial transporter protein constitutively, the other plant CCP1-like mitochondrial transporter protein also corresponding to an ortholog of CCP1 of *Chlamydomonas reinhardtii* of SEQ ID NO: 1 derived from a source land plant.

The genetically engineered land plant can have a $CO_2$ assimilation rate that is higher than for a corresponding reference land plant not comprising the modified gene. For example, the genetically engineered land plant can have a $CO_2$ assimilation rate that is at least 5% higher, at least 10% higher, at least 20% higher, or at least 40% higher, than for a corresponding reference land plant that does not comprise the modified gene.

The genetically engineered land plant also can have a transpiration rate that is lower than for a corresponding reference land plant not comprising the modified gene. For example, the genetically engineered land plant can have a transpiration rate that is at least 5% lower, at least 10% lower, at least 20% lower, or at least 40% lower, than for a corresponding reference land plant that does not comprise the modified gene.

The genetically engineered land plant also can have a seed yield that is higher than for a corresponding reference land plant not comprising the modified gene. For example, the genetically engineered land plant can have a seed yield that is at least 5% higher, at least 10% higher, at least 20% higher, at least 40% higher, at least 60% higher, or at least 80% higher, than for a corresponding reference land plant that does not comprise the modified gene.

As noted above, following identification of a plant CCP1-like mitochondrial transporter protein of a source land plant, genetic engineering of a land plant to express the plant CCP1-like mitochondrial transporter protein can be carried out by methods that are known in the art, for example as follows.

DNA constructs useful in the methods described herein include transformation vectors capable of introducing transgenes or other modified nucleic acid sequences into land plants. As used herein, "genetically engineered" refers to an organism in which a nucleic acid fragment containing a heterologous nucleotide sequence has been introduced, or in which the expression of a homologous gene has been modified, for example by genome editing. Transgenes in the genetically engineered organism are preferably stable and inheritable. Heterologous nucleic acid fragments may or may not be integrated into the host genome.

Several plant transformation vector options are available, including those described in *Gene Transfer to Plants,* 1995, Potrykus et al., eds., Springer-Verlag Berlin Heidelberg New York, *Genetically engineered Plants: A Production System for Industrial and Pharmaceutical Proteins,* 1996, Owen et al., eds., John Wiley & Sons Ltd. England, and *Methods in Plant Molecular Biology: A Laboratory Course Manual,* 1995, Maliga et al., eds., Cold Spring Laboratory Press, New York. Plant transformation vectors generally include one or more coding sequences of interest under the transcriptional control of 5' and 3' regulatory sequences, including a promoter, a transcription termination and/or polyadenylation signal, and a selectable or screenable marker gene.

Many vectors are available for transformation using *Agrobacterium tumefaciens*. These typically carry at least one T-DNA sequence and include vectors such as pBIN19. Typical vectors suitable for *Agrobacterium* transformation include the binary vectors pCIB200 and pCIB2001, as well as the binary vector pCIB 10 and hygromycin selection derivatives thereof. See, for example, U.S. Pat. No. 5,639, 949.

Transformation without the use of *Agrobacterium tumefaciens* circumvents the requirement for T-DNA sequences in the chosen transformation vector and consequently vectors lacking these sequences are utilized in addition to vectors such as the ones described above which contain T-DNA sequences. The choice of vector for transformation techniques that do not rely on *Agrobacterium* depends largely on the preferred selection for the species being transformed. Typical vectors suitable for non-*Agrobacterium* transformation include pCIB3064, pSOG 19, and pSOG35. See, for example, U.S. Pat. No. 5,639,949. Alternatively, DNA fragments containing the transgene and the necessary regulatory elements for expression of the transgene can be excised from a plasmid and delivered to the plant cell using microprojectile bombardment-mediated methods.

Zinc-finger nucleases (ZFNs) are also useful in that they allow double strand DNA cleavage at specific sites in plant chromosomes such that targeted gene insertion or deletion can be performed (Shukla et al., 2009, *Nature* 459: 437-441; Townsend et al., 2009, *Nature* 459: 442-445).

The CRISPR/Cas9 system (Sander, J. D. and Joung, J. K., Nature Biotechnology, published online Mar. 2, 2014; doi; 10.1038/nbt.2842) is particularly useful for editing plant genomes to modulate the expression of homologous genes encoding enzymes. All that is required to achieve a CRISPR/Cas edit is a Cas enzyme, or other CRISPR nuclease (Murugan et al. Mol Cell 2017, 68:15), and a single guide RNA (sgRNA) as reviewed extensively by others (Belhag et al. Curr Opin Biotech 2015, 32: 76; Khandagale and Nadaf, Plant Biotechnol Rep 2016, 10:327). Several examples of the use of this technology to edit the genomes of plants have now been reported (Belhaj et al. Plant Methods 2013, 9:39; Zhang et al. Journal of Genetics and Genomics 2016, 43: 251).

TALENs (transcriptional activator-like effector nucleases) or meganucleases can also be used for plant genome editing (Malzahn et al., Cell Biosci, 2017, 7:21)

Transformation protocols as well as protocols for introducing nucleotide sequences into plants may vary depending on the type of plant or plant cell targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606), *Agrobacterium*-mediated transformation (Townsend et al., U.S. Pat. No. 5,563, 055; Zhao et al. WO US98/01268), direct gene transfer (Paszkowski et al. (1984) EMBO J. 3:2717-2722), and ballistic particle acceleration (see, for example, Sanford et al., U.S. Pat. No. 4,945,050; Tomes et al. (1995) *Plant Cell, Tissue, and Organ Culture: Fundamental Methods*, ed. Gamborg and Phillips (Springer-Verlag, Berlin); and McCabe et al. *Biotechnology* 6:923-926 (1988)). Also see Weissinger et al. *Ann. Rev. Genet.* 22:421-477 (1988); Sanford et al. Particulate Science and Technology 5:27-37 (1987) (onion); Christou et al. *Plant Physiol.* 87:671-674 (1988) (soybean); McCabe et al. (1988) BioTechnology 6:923-926 (soybean); Finer and McMullen *In Vitro Cell Dev. Biol.* 27P:175-182 (1991) (soybean); Singh et al. *Theor. Appl. Genet.* 96:319-324 (1998)(soybean); Dafta et al. (1990) *Biotechnology* 8:736-740 (rice); Klein et al. *Proc. Natl. Acad. Sci. USA* 85:4305-4309 (1988) (maize); Klein et al. *Biotechnology* 6:559-563 (1988) (maize); Tomes, U.S. Pat. No. 5,240,855; Buising et al., U.S. Pat. Nos. 5,322,783 and 5,324,646; Tomes et al. (1995) in Plant Cell, Tissue, and Organ Culture: Fundamental Methods, ed. Gamborg (Springer-Verlag, Berlin) (maize); Klein et al. Plant Physiol. 91:440-444 (1988) (maize); Fromm et al. *Biotechnology* 8:833-839 (1990) (maize); Hooykaas-Van Slogteren et al.

*Nature* 311:763-764 (1984); Bowen et al., U.S. Pat. No. 5,736,369 (cereals); Bytebier et al. *Proc. Natl. Acad. Sci. USA* 84:5345-5349 (1987) (Liliaceae); De Wet et al. in The Experimental Manipulation of Ovule Tissues, ed. Chapman et al. (Longman, N.Y.), pp. 197-209 (1985) (pollen); Kaeppler et al. *Plant Cell Reports* 9:415-418 (1990) and Kaeppler et al. *Theor. Appl. Genet.* 84:560-566 (1992) (whisker-mediated transformation); D'Halluin et al. *Plant Cell* 4:1495-1505 (1992) (electroporation); Li et al. *Plant Cell Reports* 12:250-255 (1993) and Christou and Ford Annals of Botany 75:407-413 (1995) (rice); Osjoda et al. *Nature Biotechnology* 14:745-750 (1996) (maize via *Agrobacterium tumefaciens*). References for protoplast transformation and/or gene gun for Agrisoma technology are described in WO 2010/037209. Methods for transforming plant protoplasts are available including transformation using polyethylene glycol (PEG), electroporation, and calcium phosphate precipitation (see for example Potrykus et al., 1985, Mol. Gen. Genet., 199, 183-188; Potrykus et al., 1985, Plant Molecular Biology Reporter, 3, 117-128), Methods for plant regeneration from protoplasts have also been described [Evans et al., in Handbook of Plant Cell Culture, Vol 1, (Macmillan Publishing Co., New York, 1983); Vasil, I K in Cell Culture and Somatic Cell Genetics (Academic, Orlando, 1984)].

Recombinase technologies which are useful for producing the disclosed genetically engineered plants include the cre-lox, FLP/FRT and Gin systems. Methods by which these technologies can be used for the purpose described herein are described for example in (U.S. Pat. No. 5,527,695; Dale and Ow, 1991, *Proc. Natl. Acad. Sci. USA* 88: 10558-10562; Medberry et al., 1995, *Nucleic Acids Res.* 23: 485-490).

Transformation protocols as well as protocols for introducing nucleotide sequences into plants may vary depending on the type of plant or plant cell, i.e., monocot or dicot, targeted for transformation.

Suitable methods of introducing nucleotide sequences into plant cells and subsequent insertion into the plant genome are described in US 2010/0229256 A1 to Somleva & Ali and US 2012/0060413 to Somleva et al.

The transformed cells are grown into plants in accordance with conventional techniques. See, for example, McCormick et al., 1986, Plant Cell Rep. 5: 81-84. These plants may then be grown, and either pollinated with the same transformed variety or different varieties, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

Procedures for in planta transformation can be simple. Tissue culture manipulations and possible somaclonal variations are avoided and only a short time is required to obtain genetically engineered plants. However, the frequency of transformants in the progeny of such inoculated plants is relatively low and variable. At present, there are very few species that can be routinely transformed in the absence of a tissue culture-based regeneration system. Stable *Arabidopsis* transformants can be obtained by several in planta methods including vacuum infiltration (Clough & Bent, 1998, *The Plant J.* 16: 735-743), transformation of germinating seeds (Feldmann & Marks, 1987, *Mol. Gen. Genet.* 208: 1-9), floral dip (Clough and Bent, 1998, *Plant J.* 16: 735-743), and floral spray (Chung et al., 2000, *Genetically engineered Res.* 9: 471-476). Other plants that have successfully been transformed by in planta methods include rapeseed and radish (vacuum infiltration, Ian and Hong, 2001, *Genetically engineered Res.*, 10: 363-371; Desfeux et al., 2000, *Plant Physiol.* 123: 895-904), *Medicago truncatula* (vacuum infiltration, Trieu et al., 2000, *Plant J.* 22: 531-541), camelina (floral dip, WO/2009/117555 to Nguyen et al.), and wheat (floral dip, Zale et al., 2009, *Plant Cell Rep.* 28: 903-913). In planta methods have also been used for transformation of germ cells in maize (pollen, Wang et al. 2001, *Acta Botanica Sin.*, 43, 275-279; Zhang et al., 2005, *Euphytica*, 144, 11-22; pistils, Chumakov et al. 2006, *Russian J. Genetics*, 42, 893-897; Mamontova et al. 2010, *Russian J. Genetics*, 46, 501-504) and Sorghum (pollen, Wang et al. 2007, *Biotechnol. Appl. Biochem.*, 48, 79-83).

Following transformation by any one of the methods described above, the following procedures can be used to obtain a transformed plant expressing the transgenes: select the plant cells that have been transformed on a selective medium; regenerate the plant cells that have been transformed to produce differentiated plants; select transformed plants expressing the transgene producing the desired level of desired polypeptide(s) in the desired tissue and cellular location.

The cells that have been transformed may be grown into plants in accordance with conventional techniques. See, for example, McCormick et al. *Plant Cell Reports* 5:81-84 (1986). These plants may then be grown, and either pollinated with the same transformed variety or different varieties, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

Genetically engineered plants can be produced using conventional techniques to express any genes of interest in plants or plant cells (*Methods in Molecular Biology*, 2005, vol. 286, Genetically engineered Plants: Methods and Protocols, Pena L., ed., Humana Press, Inc. Totowa, NJ; Shyamkumar Barampuram and Zhanyuan J. Zhang, Recent Advances in Plant Transformation, in James A. Birchler (ed.), *Plant Chromosome Engineering: Methods and Protocols*, Methods in Molecular Biology, vol. 701, Springer Science+Business Media). Typically, gene transfer, or transformation, is carried out using explants capable of regeneration to produce complete, fertile plants. Generally, a DNA or an RNA molecule to be introduced into the organism is part of a transformation vector. A large number of such vector systems known in the art may be used, such as plasmids. The components of the expression system can be modified, e.g., to increase expression of the introduced nucleic acids. For example, truncated sequences, nucleotide substitutions or other modifications may be employed. Expression systems known in the art may be used to transform virtually any plant cell under suitable conditions. A transgene comprising a DNA molecule encoding a gene of interest is preferably stably transformed and integrated into the genome of the host cells. Transformed cells are preferably regenerated into whole fertile plants. Detailed description of transformation techniques are within the knowledge of those skilled in the art.

Plant promoters can be selected to control the expression of the transgene in different plant tissues or organelles for all of which methods are known to those skilled in the art (Gasser & Fraley, 1989, *Science* 244: 1293-1299). In one embodiment, promoters are selected from those of eukaryotic or synthetic origin that are known to yield high levels of expression in plants and algae. In a preferred embodiment, promoters are selected from those that are known to provide high levels of expression in monocots.

Constitutive promoters include, for example, the core promoter of the Rsyn7 promoter and other constitutive promoters disclosed in WO 99/43838 and U.S. Pat. No. 6,072,050, the core CaMV 35S promoter (Odell et al., 1985, *Nature* 313: 810-812), rice actin (McElroy et al., 1990, *Plant Cell* 2: 163-171), ubiquitin (Christensen et al., 1989, *Plant Mol. Biol.* 12: 619-632; Christensen et al., 1992, *Plant Mol. Biol.* 18: 675-689), pEMU (Last et al., 1991, *Theor. Appl. Genet.* 81: 581-588), MAS (Velten et al., 1984, *EMBO J.* 3: 2723-2730), and ALS promoter (U.S. Pat. No. 5,659,026). Other constitutive promoters are described in U.S. Pat. Nos. 5,608,149; 5,608,144; 5,604,121; 5,569,597; 5,466,785; 5,399,680; 5,268,463; and 5,608,142.

"Tissue-preferred" promoters can be used to target gene expression within a particular tissue. Tissue-preferred promoters include those described by Van Ex et al., 2009, *Plant Cell Rep.* 28: 1509-1520; Yamamoto et al., 1997, *Plant J.* 12: 255-265; Kawamata et al., 1997, *Plant Cell Physiol.* 38: 792-803; Hansen et al., 1997, *Mol. Gen. Genet.* 254: 337-343; Russell et al., 199), *Transgenic Res.* 6: 157-168; Rinehart et al., 1996, *Plant Physiol.* 112: 1331-1341; Van Camp et al., 1996, *Plant Physiol.* 112: 525-535; Canevascini et al., 1996, *Plant Physiol.* 112: 513-524; Yamamoto et al., 1994, *Plant Cell Physiol.* 35: 773-778; Lam, 1994, *Results Probl. Cell Differ.* 20: 181-196, Orozco et al., 1993, *Plant Mol. Biol.* 23: 1129-1138; Matsuoka et al., 1993, *Proc. Natl. Acad. Sci. USA* 90: 9586-9590, and Guevara-Garcia et al., 1993, *Plant J.* 4: 495-505. Such promoters can be modified, if necessary, for weak expression.

Seed-specific promoters can be used to target gene expression to seeds in particular. Seed-specific promoters include promoters that are expressed in various tissues within seeds and at various stages of development of seeds. Seed-specific promoters can be absolutely specific to seeds, such that the promoters are only expressed in seeds, or can be expressed preferentially in seeds, e.g. at rates that are higher by 2-fold, 5-fold, 10-fold, or more, in seeds relative to one or more other tissues of a plant, e.g. stems, leaves, and/or roots, among other tissues. Seed-specific promoters include, for example, seed-specific promoters of dicots and seed-specific promoters of monocots, among others. For dicots, seed-specific promoters include, but are not limited to, bean β-phaseolin, napin, β-conglycinin, soybean oleosin 1, *Arabidopsis thaliana* sucrose synthase, flax conlinin soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, and globulin 1.

Chemical-regulated promoters can be used to modulate the expression of a gene in a plant through the application of an exogenous chemical regulator.

Specific exemplary promoters useful for expression of genes in dicots and monocots are provided in TABLE 1 and TABLE 2, respectively.

TABLE 1

Promoters useful for expression of genes in dicots.

| Gene/Promoter | Expression | Native organism of promoter | Gene ID* |
|---|---|---|---|
| Hsp70 | Constitutive | *Glycine max* | Glyma.02G093200 (SEQ ID NO: 39) |
| Chlorophyll A/B Binding Protein (Cab5) | Constitutive | *Glycine max* | Glyma.08G082900 (SEQ ID NO: 40) |
| Pyruvate phosphate dikinase (PPDK) | Constitutive | *Glycine max* | Glyma.06G252400 (SEQ ID NO: 41) |
| Actin | Constitutive | *Glycine max* | Glyma.19G147900 (SEQ ID NO: 42) |
| ADP-glucose pyrophosphorylase (AGPase) | Seed specific | *Glycine max* | Glyma.04G011900 (SEQ ID NO: 43) |
| Glutelin C (GluC) | Seed specific | *Glycine max* | Glyma.03G163500 (SEQ ID NO: 44) |
| β-fructofuranosidase insoluble isoenzyme 1 (CIN1) | Seed specific | *Glycine max* | Glyma.17G227800 (SEQ ID NO: 45) |
| MADS-Box | Cob specific | *Glycine max* | Glyma.04G257100 (SEQ ID NO: 46) |
| Glycinin (subunit G1) | Seed specific | *Glycine max* | Glyma.03G163500 (SEQ ID NO: 47) |
| oleosin isoform A | Seed specific | *Glycine max* | Glyma.16G071800 (SEQ ID NO: 48) |
| Hsp70 | Constitutive | *Brassica napus* | BnaA09g05860D |
| Chlorophyll A/B Binding Protein (Cab5) | Constitutive | *Brassica napus* | BnaA04g20150D |
| Pyruvate phosphate dikinase (PPDK) | Constitutive | *Brassica napus* | BnaA01g18440D |
| Actin | Constitutive | *Brassica napus* | BnaA03g34950D |
| ADP-glucose pyrophosphorylase (AGPase) | Seed specific | *Brassica napus* | BnaA06g40730D |
| Glutelin C (GluC) | Seed specific | *Brassica napus* | BnaA09g50780D |
| β-fructofuranosidase insoluble isoenzyme 1 (CIN1) | Seed specific | *Brassica napus* | BnaA04g05320D |
| MADS-Box | Cob specific | *Brassica napus* | BnaA05g02990D |
| Glycinin (subunit G1) | Seed specific | *Brassica napus* | BnaA01g08350D |
| oleosin isoform A | Seed specific | *Brassica napus* | BnaC06g12930D |
| 1.7S napin (napA) | Seed specific | *Brassica napus* | BnaA01g17200D |

*Gene ID includes sequence information for coding regions as well as associated promoters. 5' UTRs, and 3' UTRs and are available at Phytozome (see JGI website phytozome.jgi.doe.gov/pz/portal.html).

TABLE 2

Promoters useful for expression of genes in monocots, including maize and rice.

| Gene/Promoter | Expression | Rice* | Maize* |
| --- | --- | --- | --- |
| Hsp70 | Constitutive | LOC_Os05g38530 (SEQ ID NO: 31) | GRMZM2G 310431 (SEQ ID NO: 22) |
| Chlorophyll A/B Binding Protein (Cab5) | Constitutive | LOC_Os01g41710 (SEQ ID NO: 32) | AC207722.2_FG009 (SEQ ID NO: 23) GRMZM2G 351977 (SEQ ID NO: 24) |
| Pyruvate phosphate dikinase (PPDK) | Constitutive | LOC_Os05g33570 (SEQ ID NO: 33) | GRMZM2G 306345 (SEQ ID NO: 25) |
| Actin | Constitutive | LOC_Os03g50885 (SEQ ID NO: 34) | GRMZM2B 047055 (SEQ ID NO: 26) |
| Hybrid cab5/hsp70 intron promoter | Constitutive | N/A | SEQ ID NO: 27 |
| ADP-glucose pyrophos-phorylase (AGPase) | Seed specific | LOC_Os01g44220 (SEQ ID NO: 35) | GRMZM2G 429899 (SEQ ID NO: 28) |
| Glutelin C (GluC) | Seed specific | LOC_Os02g25640 (SEQ ID NO: 36) | N/A |
| β-fructofuranosidase insoluble isoenzyme 1 (CIN1) | Seed specific | LOC_Os02g33110 (SEQ ID NO: 37) | GRMZM2G 139300 (SEQ ID NO: 29) |
| MADS-Box | Cob specific | LOC_Os12g01540 (SEQ ID NO: 38) | GRMZM2G 160687 (SEQ ID NO: 30) |

*Gene ID includes sequence information for coding regions as well as associated promoters, 5' UTRs, and 3' UTRs and are available at Phytozome (see JGI website phytozome.jgi.doe.gov/pz/portal.html).

Certain embodiments use genetically engineered plants or plant cells having multi-gene expression constructs harboring more than one transgene and promoter. The promoters can be the same or different.

Any of the described promoters can be used to control the expression of one or more of genes, their homologs and/or orthologs as well as any other genes of interest in a defined spatiotemporal manner.

Nucleic acid sequences intended for expression in genetically engineered plants are first assembled in expression cassettes behind a suitable promoter active in plants. The expression cassettes may also include any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be transferred to the plant transformation vectors described infra. The following is a description of various components of typical expression cassettes.

A variety of transcriptional terminators are available for use in expression cassettes. These are responsible for the termination of transcription beyond the transgene and the correct polyadenylation of the transcripts. Appropriate transcriptional terminators are those that are known to function in plants and include the CaMV 35S terminator, the tm1 terminator, the nopaline synthase terminator and the pea rbcS E9 terminator. These are used in both monocotyledonous and dicotyledonous plants.

The coding sequence of the selected gene may be genetically engineered by altering the coding sequence for optimal expression in the crop species of interest. Methods for modifying coding sequences to achieve optimal expression in a particular crop species are well known (Perlak et al., 1991, *Proc. Natl. Acad. Sci. USA* 88: 3324 and Koziel et al., 1993, *Biotechnology* 11: 194-200).

Individual plants within a population of genetically engineered plants that express a recombinant gene(s) may have different levels of gene expression. The variable gene expression is due to multiple factors including multiple copies of the recombinant gene, chromatin effects, and gene suppression. Accordingly, a phenotype of the genetically engineered plant may be measured as a percentage of individual plants within a population. The yield of a plant can be measured simply by weighing. The yield of seed from a plant can also be determined by weighing. The increase in seed weight from a plant can be due to a number of factors, including an increase in the number or size of the seed pods, an increase in the number of seed and/or an increase in the number of seed per plant. In the laboratory or greenhouse seed yield is usually reported as the weight of seed produced per plant and in a commercial crop production setting yield is usually expressed as weight per acre or weight per hectare.

A recombinant DNA construct including a plant-expressible gene or other DNA of interest is inserted into the genome of a plant by a suitable method. Suitable methods include, for example, *Agrobacterium tumefaciens*-mediated DNA transfer, direct DNA transfer, liposome-mediated DNA transfer, electroporation, co-cultivation, diffusion, particle bombardment, microinjection, gene gun, calcium phosphate coprecipitation, viral vectors, and other techniques. Suitable plant transformation vectors include those derived from a Ti plasmid of *Agrobacterium tumefaciens*. In addition to plant transformation vectors derived from the Ti or root-inducing (Ri) plasmids of *Agrobacterium*, alternative methods can be used to insert DNA constructs into plant cells. A genetically engineered plant can be produced by selection of transformed seeds or by selection of transformed plant cells and subsequent regeneration.

In some embodiments, the genetically engineered plants are grown (e.g., on soil) and harvested. In some embodiments, above ground tissue is harvested separately from below ground tissue. Suitable above ground tissues include shoots, stems, leaves, flowers, grain, and seed. Exemplary below ground tissues include roots and root hairs. In some embodiments, whole plants are harvested and the above ground tissue is subsequently separated from the below ground tissue.

Genetic constructs may encode a selectable marker to enable selection of transformation events. There are many methods that have been described for the selection of transformed plants (for review see (Miki et al., *Journal of Biotechnology*, 2004, 107, 193-232) and references incorporated within). Selectable marker genes that have been used extensively in plants include the neomycin phosphotransferase gene nptII (U.S. Pat. Nos. 5,034,322, U.S. Pat. No. 5,530,196), hygromycin resistance gene (U.S. Pat. No. 5,668,298, Waldron et al., (1985), *Plant Mol Biol*, 5:103-108; Zhijian et al., (1995), *Plant Sci*, 108:219-227), the bar gene encoding resistance to phosphinothricin (U.S. Pat. No. 5,276,268), the expression of aminoglycoside 3"-adenyltransferase (aadA) to confer spectinomycin resistance (U.S. Pat. No. 5,073,675), the use of inhibition resistant 5-enolpyruvyl-3-phosphoshikimate synthetase (U.S. Pat. No. 4,535,060) and methods for producing glyphosate tolerant plants (U.S. Pat. Nos. 5,463,175; 7,045,684). Other suitable selectable markers include, but are not limited to, genes encoding resistance to chloramphenicol (Herrera Estrella et al., (1983), *EMBO J*, 2:987-992), methotrexate (Herrera Estrella et al., (1983), *Nature*, 303:209-213; Meijer et al, (1991), *Plant Mol Biol*, 16:807-820); streptomycin (Jones et al., (1987), *Mol Gen Genet*, 210:86-91); bleomycin (Hille et al., (1990), *Plant Mol Biol*, 7:171-176); sulfonamide (Guerineau et al., (1990), *Plant Mol Biol*, 15:127-136); bromoxynil (Stalker et al., (1988), *Science*, 242:419-423); glyphosate (Shaw et al., (1986), *Science*, 233:478-481); phosphinothricin (DeBlock et al., (1987), *EMBO J*, 6:2513-2518).

Methods of plant selection that do not use antibiotics or herbicides as a selective agent have been previously described and include expression of glucosamine-6-phosphate deaminase to inactive glucosamine in plant selection medium (U.S. Pat. No. 6,444,878) and a positive/negative system that utilizes D-amino acids (Erikson et al., *Nat Biotechnol*, 2004, 22, 455-8). European Patent Publication No. EP 0 530 129 A1 describes a positive selection system which enables the transformed plants to outgrow the non-transformed lines by expressing a transgene encoding an enzyme that activates an inactive compound added to the growth media. U.S. Pat. No. 5,767,378 describes the use of mannose or xylose for the positive selection of genetically engineered plants.

Methods for positive selection using sorbitol dehydrogenase to convert sorbitol to fructose for plant growth have also been described (WO 2010/102293). Screenable marker genes include the beta-glucuronidase gene (Jefferson et al., 1987, *EMBO J*. 6: 3901-3907; U.S. Pat. No. 5,268,463) and native or modified green fluorescent protein gene (Cubitt et al., 1995, *Trends Biochem. Sci.* 20: 448-455; Pan et al., 1996, *Plant Physiol.* 112: 893-900).

Transformation events can also be selected through visualization of fluorescent proteins such as the fluorescent proteins from the nonbioluminescent Anthozoa species which include DsRed, a red fluorescent protein from the *Discosoma* genus of coral (Matz et al. (1999), Nat Biotechnol 17: 969-73). An improved version of the DsRed protein has been developed (Bevis and Glick (2002), Nat Biotech 20: 83-87) for reducing aggregation of the protein.

Visual selection can also be performed with the yellow fluorescent proteins (YFP) including the variant with accelerated maturation of the signal (Nagai, T. et al. (2002), Nat Biotech 20: 87-90), the blue fluorescent protein, the cyan fluorescent protein, and the green fluorescent protein (Sheen et al. (1995), Plant J 8: 777-84; Davis and Vierstra (1998), Plant Molecular Biology 36: 521-528). A summary of fluorescent proteins can be found in Tzfira et al. (Tzfira et al. (2005), Plant Molecular Biology 57: 503-516) and Verkhusha and Lukyanov (Verkhusha, V. V. and K. A. Lukyanov (2004), Nat Biotech 22: 289-296). Improved versions of many of the fluorescent proteins have been made for various applications. It will be apparent to those skilled in the art how to use the improved versions of these proteins, including combinations, for selection of transformants.

The plants modified for enhanced yield may have stacked input traits that include herbicide resistance and insect tolerance, for example a plant that is tolerant to the herbicide glyphosate and that produces the *Bacillus thuringiensis* (BT) toxin. Glyphosate is a herbicide that prevents the production of aromatic amino acids in plants by inhibiting the enzyme 5-enolpyruvylshikimate-3-phosphate synthase (EPSP synthase). The overexpression of EPSP synthase in a crop of interest allows the application of glyphosate as a weed killer without killing the modified plant (Suh, et al., J. M Plant Mol. Biol. 1993, 22, 195-205). BT toxin is a protein that is lethal to many insects providing the plant that produces it protection against pests (Barton, et al. Plant Physiol. 1987, 85, 1103-1109). Other useful herbicide tolerance traits include but are not limited to tolerance to Dicamba by expression of the dicamba monoxygenase gene (Behrens et al, 2007, Science, 316, 1185), tolerance to 2,4-D and 2,4-D choline by expression of a bacterial aad-1 gene that encodes for an aryloxyalkanoate dioxygenase enzyme (Wright et al., Proceedings of the National Academy of Sciences, 2010, 107, 20240), glufosinate tolerance by expression of the bialophos resistance gene (bar) or the pat gene encoding the enzyme phosphinotricin acetyl transferase (Droge et al., Planta, 1992, 187, 142), as well as genes encoding a modified 4-hydroxyphenylpyruvate dioxygenase (HPPD) that provides tolerance to the herbicides mesotrione, isoxaflutole, and tembotrione (Siehl et al., Plant Physiol, 2014, 166, 1162).

The genetically engineered land plant that expresses a plant-CCP1 like mitochondrial transporter protein, as disclosed, can be further modified for further enhanced yield too.

EXAMPLES

Example 1. Identification of CCP1-Like Orthologs in Land Plants

Initial Attempts to Identify CCP1-Like Orthologs in Land Plants

Initial attempts to determine whether land plants encode CCP1 orthologs suggested that land plants do not. Typical BLAST searches do not reveal CCP1 homologs in higher plants. For example, a conventional BLAST search using CCP1 of *Chlamydomonas reinhardtii* as the query sequence and the standard protein database (nr) did not yield any Tier 1 CCP1 ortholog matches from higher plants. The top hits in that type of search are shown in TABLE 3.

TABLE 3

Results of conventional BLAST search using CCP1 as query sequence and the standard protein database.

| Description | Total Score | E Value | Identity (%) | Accession |
|---|---|---|---|---|
| low-CO2-inducible chloroplast envelope protein [*Chlamydomonas reinhardtii*] | 738 | 0.0 | 100% | XP_001692197.1 |
| envelope protein [*Chlamydomonas reinhardtii*] | 738 | 0.0 | 99% | AAB71743.1 |
| low-CO2-inducible chloroplast envelope protein [*Chlamydomonas reinhardtii*] | 652 | 0.0 | 96% | XP_001692288.1 |
| hypothetical protein GPECTOR_16g646 [*Gonium pectorale*] | 629 | 0.0 | 86% | KXZ50472.1 |
| hypothetical protein VOLCADRAFT_61165 [*Volvox carteri f. nagariensis*] | 593 | 0.0 | 82% | XP_002951243.1 |
| hypothetical protein GPECTOR_16g661 [*Gonium pectorale*] | 586 | 0.0 | 83% | KXZ50486.1 |
| hypothetical protein SOVF_089040 [*Spinacia oleracea*] | 187 | 9e−55 | 37% | KNA16433.1 |

Strikingly, the results reveal only three non-CCP1 hits, corresponding to hypothetical proteins of the algae *Gonium pectorale* (KXZ50472.1), *Volvox carteri* f. *nagariensis* (XP_002951243.1), and *Gonium pectorale* (KXZ50486.1), respectively, all with 80+% identity to CCP1, then an immediate drop-off to a spinach protein with only 37% identity. Following the spinach protein are hundreds of proteins with 30+% identity that probably derive most of their identity from the mere fact that they are mitochondrial carrier proteins.

Successful Identification of CCP1-Like Orthologs in Land Plants

Serendipitously, higher-plant homologs to CCP1 were found in the Transcriptome Shotgun Assembly (tsa_nr) database based on further sequence comparisons. This revealed that land plants do encode CCP1 orthologs. This also implied that the only higher plants that contain CCP1 homologs have yet to be genome-sequenced.

Results are shown in TABLE 4 and TABLE 5.

TABLE 4

CCP1 of *Chlamydomonas reinhardtii* and orthologs from land plants (Tier 1) and algae (Tier 1), along with fungi (Tier 2) for comparison.

| | | | Homology to CCP1 | | | Program | |
| | | | | | | Motif Finder[b] | ProSite[c] |
| Organism | Type | GenBank Accession | Number of Amino Acids | Consensus Positions (%) | Identity Positions (%) | Mito_carr domains predicted (residues) | SOLCAR domains predicted (residues) |
|---|---|---|---|---|---|---|---|
| *Chlamydomonas reinhardtii* | Algae | XM_001692145.1 (SEQ ID NO: 1) | 358 | 100 | 100 | 28-119, 129-235, 245-334 | 22-118, 131-231, 246-333 |
| *Gonium pectorale* | Algae | KXZ50472.1 (SEQ ID NO: 2) | 356 | 94 | 85 | 27-119, 129-234, 244-333 | 22-118, 128-230, 245-332 |
| *Gonium pectorale* | Algae | KXZ50486.1 (SEQ ID NO: 3) | 354 | 91 | 83 | 27-119, 129-234, 244-333 | 22-118, 128-230, 245-332 |
| *Volvox carteri* f. *nagariensis* | Algae | XP_002951243.1 (SEQ ID NO: 4) | 339 | 91 | 83 | 21-112, 122-215, 227-315 | 15-111, 121-212, 227-314 |
| *Ettlia oleoabundans* | Algae | GEEU01047164.1 (SEQ ID NO: 5) | 353[a] | 76 | 62 | 28-119, 128-233, 243-331 | 22-118, 131-231, 242-329 |
| *Erigeron breviscapus* | Land plants | GDQF01162509.1 (SEQ ID NO: 6) | 352[a] | 75 | 63 | 28-120, 128-233, 242-331 | 22-118, 128-231, 242-329 |
| *Zea nicaraguensis* | Land plants | GBZQ01039302.1 (SEQ ID NO: 7) | 354[a] | 74 | 62 | 29-121, 129-233, 241-331 | 23-119, 132-231, 242-329 |
| *Poa pratensis* | Land plants | GEBH01135677.1 (SEQ ID NO: 8) | 141[d] | 82 | 67 | 5-51, 59-139 | 1-48, 60-141 |

TABLE 4-continued

CCP1 of *Chlamydomonas reinhardtii* and orthologs from land plants (Tier 1) and algae (Tier 1), along with fungi (Tier 2) for comparison.

| | | | | Homology to CCP1 | | Program | |
| | | | | | | Motif Finder[b] | ProSite[c] |
| Organism | Type | GenBank Accession | Number of Amino Acids | Consensus Positions (%) | Identity Positions (%) | Mito_carr domains predicted (residues) | SOLCAR domains predicted (residues) |
|---|---|---|---|---|---|---|---|
| *Cosmos bipinnatus* | Land plants | GEZQ01046902.1 (SEQ ID NO: 9) | 354 | 76 | 63 | 29-121, 130-233, 241-331 | 23-119, 132-231, 242-329 |
| *Talaromyces stipitatus*[e] | Fungi | XM_002341226.1 (SEQ ID NO: 10) | 307 | 53 | 36 | 17-104, 116-203, 217-305 | 18-101, 116-205, 217-305 |
| *Saitoella complicata*[e] | Fungi | XM_019169629.1 (SEQ ID NO: 11) | 303 | 51 | 35 | 17-107, 119-198, 211-302 | 16-103, 116-200, 212-301 |

[a]Sequence from first methionine of deposited transcribed mRNA sequence to first stop codon.
[b]Website: genome.jp/tools/motif
[c]Website: prosite.expasy.org
[d]Partial protein sequence
[e]Top two Tier 2 CCP1 orthologs in tblastn search shown for comparison.

TABLE 5

CCP1 of *Chlamydomonas reinhardtii* and CCP1 orthologs from land plants (Tier 2) corresponding to major crops.

| | | Number of | Homology to CCP1 | |
| Organism | GenBank Accession | Amino Acids | Consensus Positions (%) | Identity Positions (%) |
|---|---|---|---|---|
| *Chlamydomonas reinhardtii* | XM_001692145.1 (SEQ ID NO: 1) | 358 | 100 | 100 |
| *Glycine max* | KRH74426.1 (SEQ ID NO: 14) | 297 | 46.0 | 29.5 |
| *Zea mays* | NP_001141073.1 (SEQ ID NO: 16) | 296 | 47.2 | 28.8 |
| *Oryza sativa* Japonica Group | XP_015614184.1 (SEQ ID NO: 15) | 296 | 47.5 | 29.1 |
| *Triticum aestivum* | CDM80555.1 (SEQ ID NO: 12) | 324 | 42.8 | 24.9 |
| *Sorghum bicolor* | XP_002464891.1 (SEQ ID NO: 17) | 296 | 47.2 | 29.3 |
| *Solanum tuberosum* | XP_006361187.1 (SEQ ID NO: 13) | 323 | 46.0 | 29.9 |

The results indicate that certain land plants encode orthologs of algal CCP1 of *Chlamydomonas reinhardtii*. Moreover, the plant CCP1-like mitochondrial transporter proteins encoded by these land plants appear to cluster into two groups, termed Tier 1 CCP1 orthologs and Tier 2 CCP1 orthologs, based on sequence and structural similarity to CCP1. As shown in TABLE 4, the plant Tier 1 CCP1 orthologs exhibit about 60% sequence identity in comparison to CCP1 of *Chlamydomonas reinhardtii*, cluster narrowly based on their similar degrees of identity, and have been identified thus far only in four plant species, *Zea nicaraguensis* (also termed teosinte), *Erigeron breviscapus*, *Cosmos bipinnatus*, and *Poa pratensis*, none of which are particularly closely related phylogenetically. As shown in TABLE 5, the plant Tier 2 CCP1 orthologs exhibit about 30% sequence identity in comparison to CCP1 of *Chlamydomonas reinhardtii*, substantially lower than for Tier 1, also cluster narrowly based on their similar degrees of identity, and would appear to be more common, having been identified thus far in six major crop species, *Zea mays* (also termed maize), *Triticum aestivum, Solanum tuberosum, Glycine max, Oryza sativa*, and *Sorghum bicolor*. This was surprising because there had not been any apparent reason to expect any clustering of plant CCP1-like mitochondrial transporter proteins, let alone clustering into two distinct groups. This was also surprising because *Zea nicaraguensis*, again teosinte, is a wild progenitor of *Zea mays*, again maize, and *Zea nicaraguensis* includes a Tier 1 CCP1 ortholog, whereas *Zea mays* includes a Tier 2 CCP1 ortholog.

It also has been determined that further clustering occurs within the Tier 1 CCP1 orthologs, with several algal Tier 1 CCP1 orthologs, namely those of *Gonium pectorale* (KXZ50472.1), *Gonium pectorale* (KXZ50486.1), and *Volvox carteri* f. *nagariensis*, termed Tier 1A, exhibiting about 80% sequence identity in comparison to CCP1 of *Chlamydomonas reinhardtii*, and with one algal Tier 1 CCP1 ortholog, namely that of *Ettlia oleoabundans*, termed Tier 1B, instead exhibiting 60% sequence identity and clustering with the plant Tier 1 CCP1 orthologs, also termed Tier 1B. Strikingly, the algal and plant Tier 1B CCP1 orthologs seem to be more closely related to each other than to the other algal or plant CCP1 orthologs, suggesting the intriguing possibility that the plant Tier 1B CCP1 orthologs may have resulted from horizontal gene transfer from *Ettlia oleoabundans* or related algae. This also suggests that *Zea nicaraguensis* and the other plant species encoding Tier 1B CCP1 orthologs may serve as sources of CCP1 orthologs that are proximally derived from land plants, rather than from algae, thus decreasing regulatory concerns and risk associated with genetic modification of crops, while providing increases in crop yield comparable to those observed for CCP1 of *Chlamydomonas reinhardtii* and CCP1 orthologs derived from other algae.

Considering the results in more detail, Tier 1A CCP1 orthologs are very similar to CCP1 and include only the other algae *Volvox* and *Gonium*. These algal CCP1 orthologs are 80+% identical to CCP1. Tier 1B identity drops to 60+%, but Phobius plots of transmembrane domains of these proteins continue to look very similar to that of CCP1, whereas Phobius plots of Tier 2 proteins do not.

Tier 1B includes just one alga, *Ettlia oleoabundans*, and several higher plants, suggesting that *Ettlia oleoabundans* may be the source of the CCP1 homolog in higher plants, or at least that *Ettlia oleoabundans* and the higher plants ultimately acquired the CCP1 homolog from a common source.

Plants that Encode Tier 1B CCP1 Orthologs

Considering the plants that encode Tier 1B CCP1 orthologs in more detail, these plants exhibit some distinctive characteristics.

*Zea nicaraguensis* is a wild progenitor of maize that thrives along often-flooded banks of rivers and streams, so it is tempting to speculate that it acquired its CCP1 ortholog from a species of algae that populates the waters nearby. The original paper that describes *Zea nicaraguensis* says of it: "Now evidently extremely local and rare, the teosinte at this location is remarkable for its ability to grow in as much as 0.4 m of standing or slowly moving water," and that "we anticipate that this species will provide maize breeders with a potentially valuable source of germ plasm that may lead to the development of maize capable of growing in waterlogged soils" (Iltis et al., *Novon* 10:382-390 (2000)).

*Erigeron breviscapus* is a flower used for medicinal purposes found at higher elevations in China. Distribution of *Erigeron breviscapus* has been described as follows: "Mid-elevation mountains, alpine to montane meadows, forest margins, *Pinus* forests, streamsides, grasslands, disturbed slopes, roadsides; 1200-3600 m. Guangxi, Guizhou, Hunan, Sichuan, E and S Xizang, Yunnan" (website: efloras.org). So *Erigeron breviscapus*, like *Zea nicaraguensis*, is found on stream banks as well.

*Cosmos bipinnatus* is a large aster that grows in temperate climates. *Cosmos bipinnatus* is used as an ornamental flower, but can spread as a weed.

*Poa pratensis* is native to North America, according to the USDA (National Resources Conservation Service, USDA, Plant Guide: Kentucky Blue Grass, *Poa pratensis* L., website: plants.usda.gov/plantguide/pdf/pg_popr.pdf). *Poa pratensis* grows preferentially in cool and humid climates and is a common dominant of Midwestern prairies.

Homology Searches

Considering approaches for identifying CCP1 orthologs in land plants in more detail, various BLAST searches (e.g. tblastn; website blast.ncbi.nlm.nih.gov/Blast.cgi) were conducted using a translated nucleotide database, a whole-genome shotgun (also termed WGS) database, and a transcriptome assembly (also termed TSA) database to find sequences highly similar to the CCP1 protein from *Chlamydomonas reinhardtii* in land plants and inedible algae species (TABLE 4 and TABLE 5). Several sequences with 60% or greater identity to CCP1 were found, followed by a much larger number of sequences with identities of about 30% and below, with no representatives in between. As noted above, these groups were named Tier 1 and Tier 2, respectively. Publicly available internet algorithms were used to predict putative transmembrane regions to further characterize the sequences, including Motif Finder (website: genome.jp/tools/motif/), ProSite (website: prosite.expasy.org/), and Phobius (website: phobius.sbc.su.se/). The Motif Finder program identified Mito_carr (PF00153) domains in each of the Tier 1 proteins (TABLE 4), indicating that they are likely mitochondrial carrier proteins that transport solutes into and out of mitochondria (website: pfam.xfam.org/family/PF00153). The ProSite program predicted that CCP1 and the Tier 1 proteins contain SOLCAR (PS50920) domains (TABLE 4), indicating that they are likely solute carrier proteins involved in energy transfer in the inner mitochondrial membrane (website: prosite.expasy.org/cgi-bin/prosite/nicedoc.pl?PS50920). The Phobius tool (website: phobius.sbc.su.se) was used to compare predicted transmembrane domains of the proteins to those of CCP1 (FIG. 1A-I, FIG. 2A-C, and FIG. 3A-G). Mapping of predicted transmembrane regions of CCP1 and comparison of the results to the orthologs with the highest homology were used to further characterize the proteins. Each of the Tier 1 proteins shared a very similar predicted transmembrane domain structure with CCP1, while the Tier 2 proteins were markedly different from CCP1 in this regard.

Multiple Sequence Alignment

Multiple sequence alignments of CCP1 of *Chlamydomonas reinhardtii* and the orthologs described above were prepared using a Multiple Sequence Alignment tool (EMBL-EBI; ebi.ac.uk/Tools/msa/clustalo/). FIG. 4A-B and FIG. 5A-B show results of CLUSTAL alignments using default parameters (dealign input sequences [no]; MBED-like clustering guide-tree [yes]; MBED-like clustering iteration [yes]; number of combined iterations [default(0)]; max guide tree iterations [default (−1)]; max HMM iterations [default(−1)]; and order [aligned]).

Common Features

There are several features shared by the orthologs that now can be used to identify further representatives as sequence data of additional plants become available. Aside from their high degree of identity to CCP1 (60% or greater), the Tier 1 CCP1 orthologs also share very similar transmembrane architecture (FIG. 1A-I). Each Tier 1 CCP1 ortholog has four putative transmembrane domains with posterior label probability peaking at 0.4 or higher. These have very similar placement in all of the Tier 1 CCP1 orthologs according to the Phobius plots, though Phobius did not always explicitly predict a transmembrane domain in each case of high probability. The Phobius transmembrane-domain predictions are shown in TABLE 6. Despite the absence of some values, the Phobius transmembrane-domain predictions do, along with the plots of FIG. 1A-I, allow defining common regions with significant likelihood of transmembrane location. Inclusively, these ranges span residues 89-113, 129-154, 216-235, and 245-266. Some CCP1 orthologs, such as the example from *Volvox carteri* f. *nagariensis* cited here, may have gaps that change the absolute values of one or more of these ranges, but the transmembrane domains would be at very similar relative positions in a multiple protein alignment. Thus, for example, the Phobius plot for *Volvox carteri* f. *nagariensis*, as shown in FIG. 1D, shows the fourth transmembrane domain shifted forward relative to the others. As shown in the multiple sequence alignment of FIG. 4A, a 12-residue gap occurs between the predicted locations of the third and fourth transmembrane domains for the CCP1 ortholog of *Volvox carteri* f. *nagariensis* in comparison to the corresponding sequence of CCP1 of *Chlamydomonas reinhardtii*, thus explaining the forward shift.

TABLE 6

Putative transmembrane domains of CCP1 of *Chlamydomonas reinhardtii* and Tier 1 CCP1 orthologs.

| Organism | Transmembrane Domain 1 | Transmembrane Domain 2 | Transmembrane Domain 3 | Transmembrane Domain 4 |
|---|---|---|---|---|
| *Chlamydomonas reinhardtii* | 89-111 | 131-154 | | |
| *Erigeron breviscapus* | 89-111 | 131-154 | 217-234 | 246-265 |
| *Zea nicaraguensis* | Not applicable* | Not applicable* | Not applicable* | Not applicable* |
| *Gonium pectorale* 16g646 | 89-109 | 129-154 | 216-233 | 245-266 |
| *Gonium pectorale* 16g661 | 89-113 | 133-154 | 217-235 | 247-266 |
| *Volvox carteri* f. *nagariensis* | Not applicable* | Not applicable* | Not applicable* | Not applicable* |
| *Ettlia oleoabundans* | 89-111 | 131-154 | 217-234 | 246-265 |
| *Cosmos bipinnatus* | Not applicable* | Not applicable* | Not applicable* | Not applicable* |

Figure 1G:
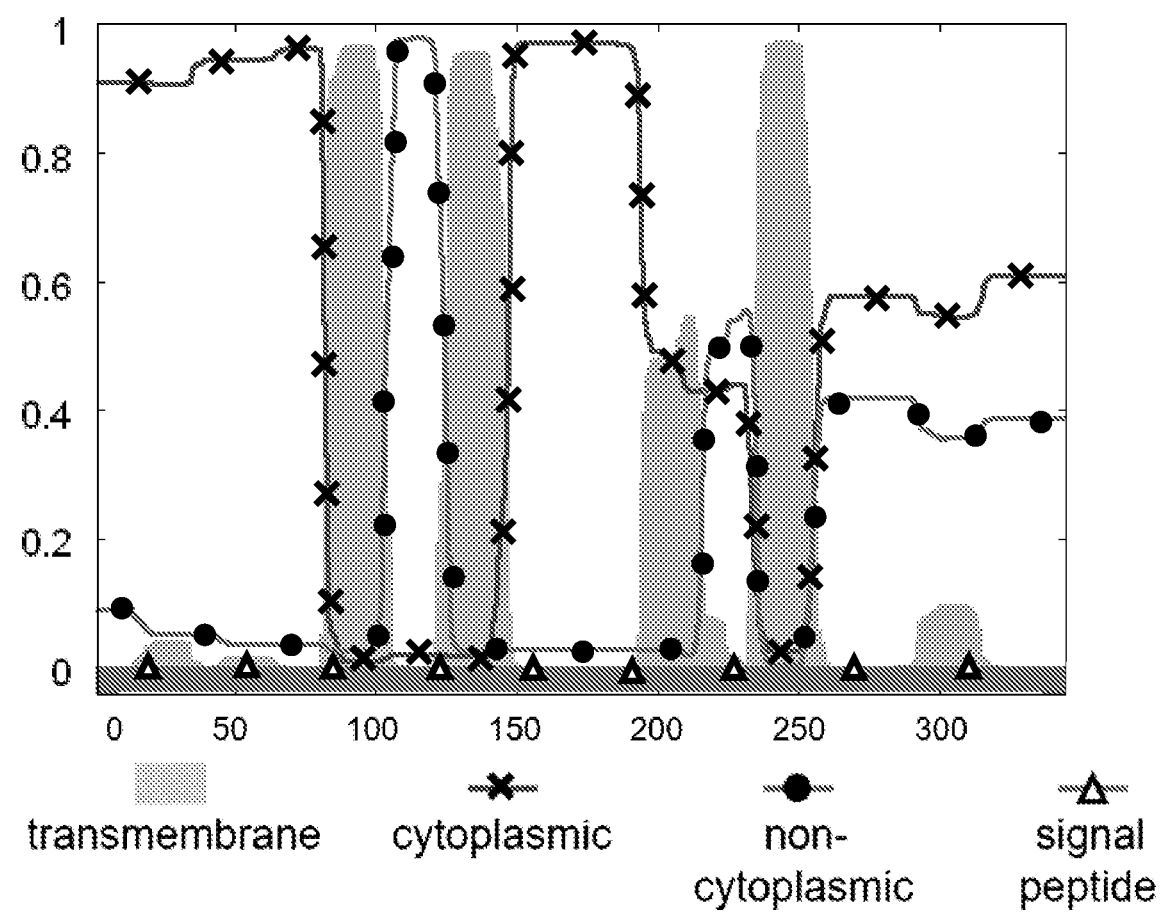
Figure 1H:
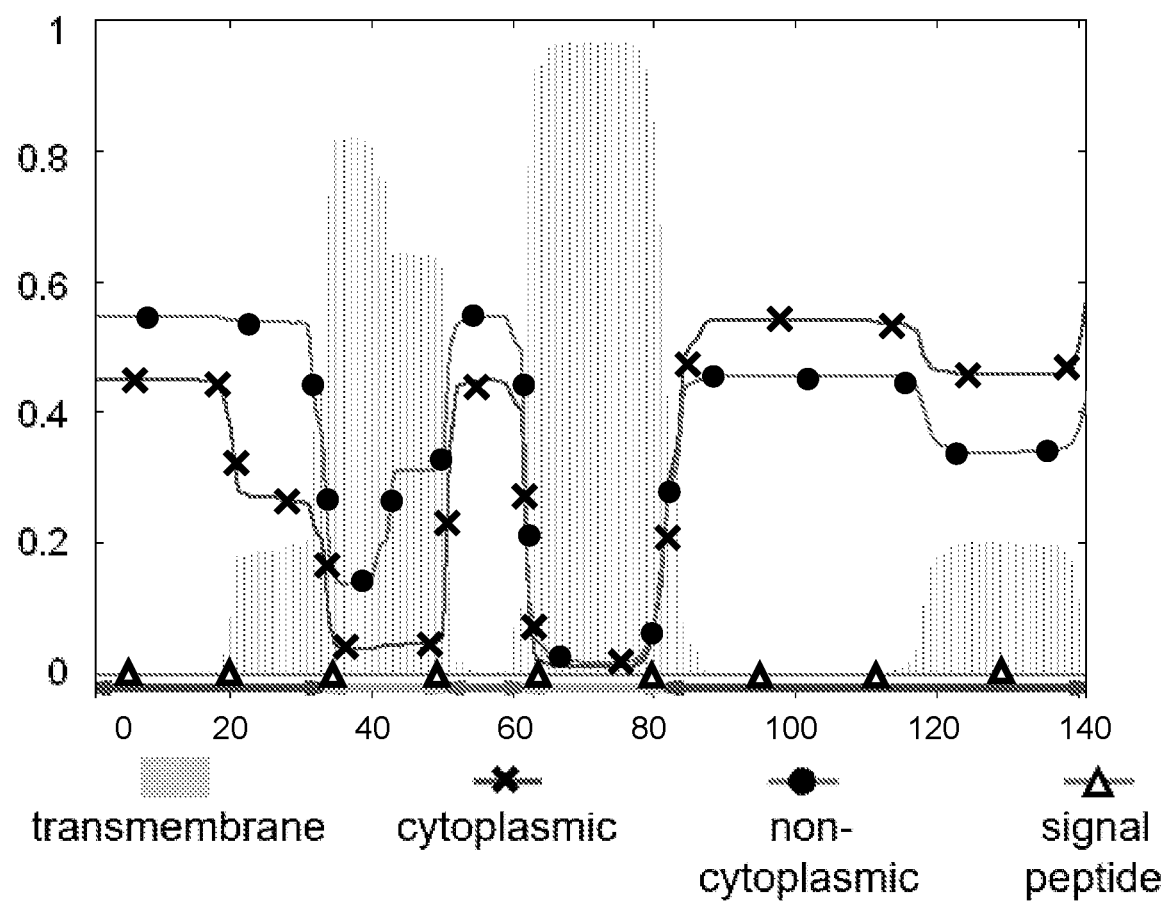
Figure 1I:
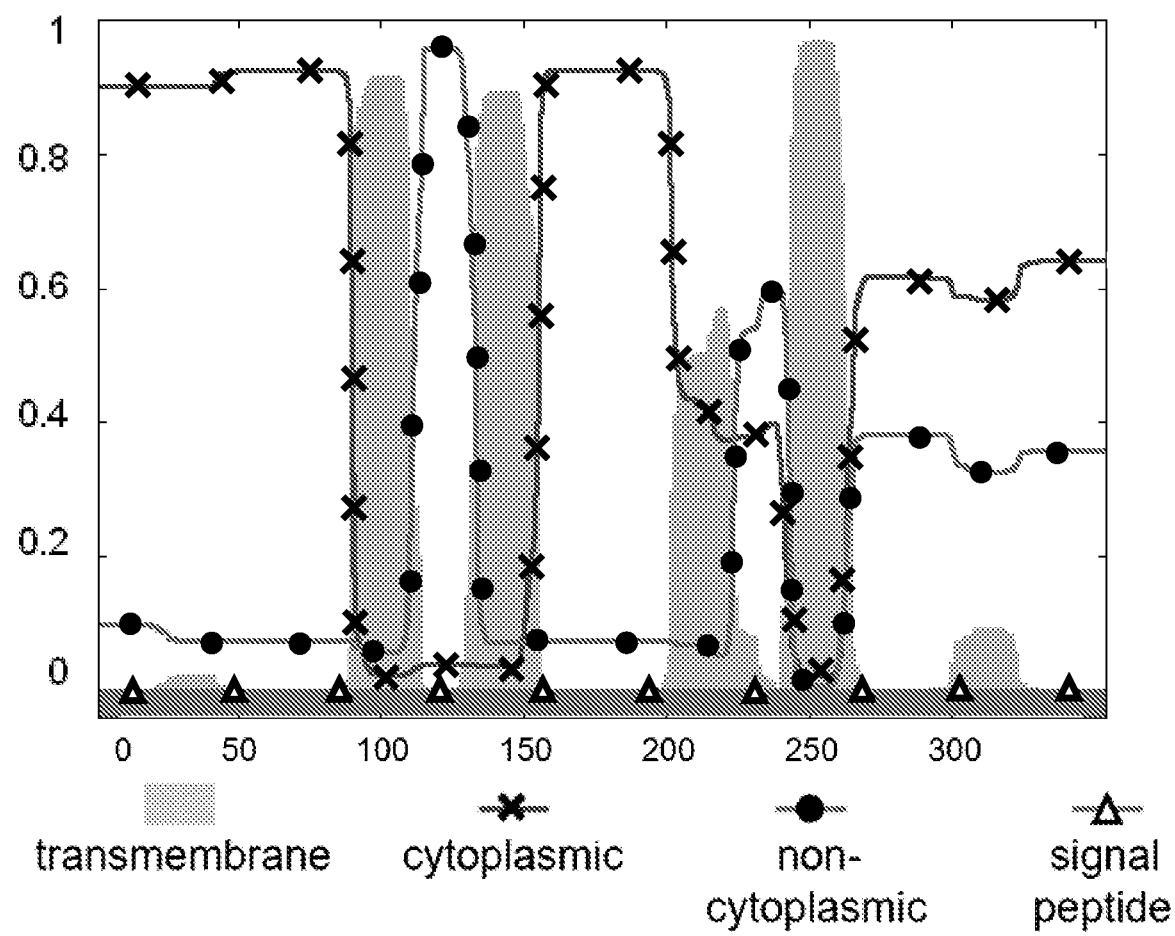
Figure 2A:
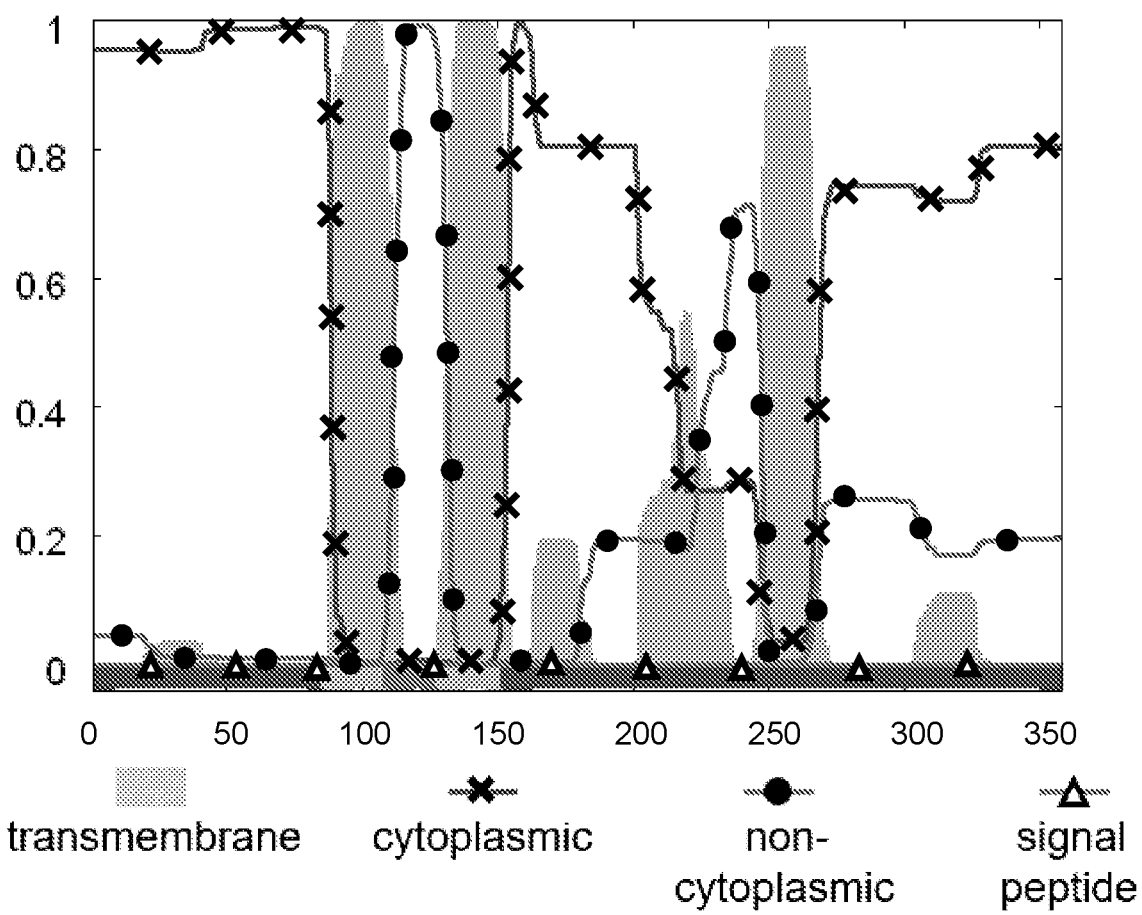
FIG. 2A-C shows Phobius-generated plots of predicted transmembrane domains of (A) *Chlamydomonas reinhardtii* CCP1 (SEQ ID NO: 1) and Tier 2 fungal CCP1-like mitochondrial transporter proteins of (B) *Talaromyces stipitatus* (SEQ ID NO: 10) and (C) *Saitoella complicata* (SEQ ID NO: 11). The Phobius plots show predicted transmembrane domain (grey shading), cytoplasmic domain (line with X), non-cytoplasmic domain (line with filled circle), and signal peptide sequence (line with triangle). The Y-axis corresponds to posterior label probability, plotted from 0 to 1 in increments of 0.2. The X-axis corresponds to amino acid residue number of corresponding CCP1 or CCP1-like mitochondrial transporter protein, plotted from 0 to 350 in increments of 50 (A) or from 0 to 300 in increments of 50 (B and C).
Figure 2B:
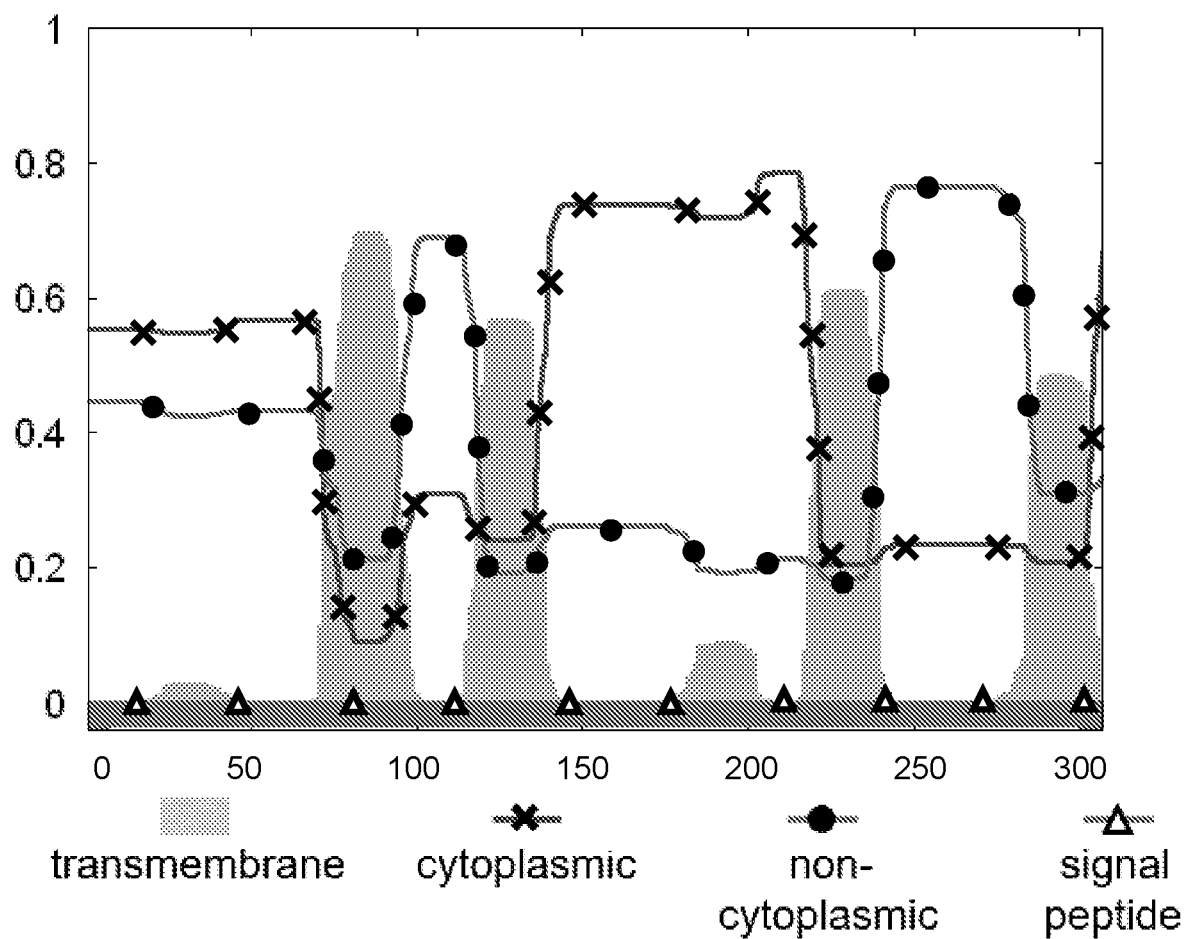
Figure 2C:
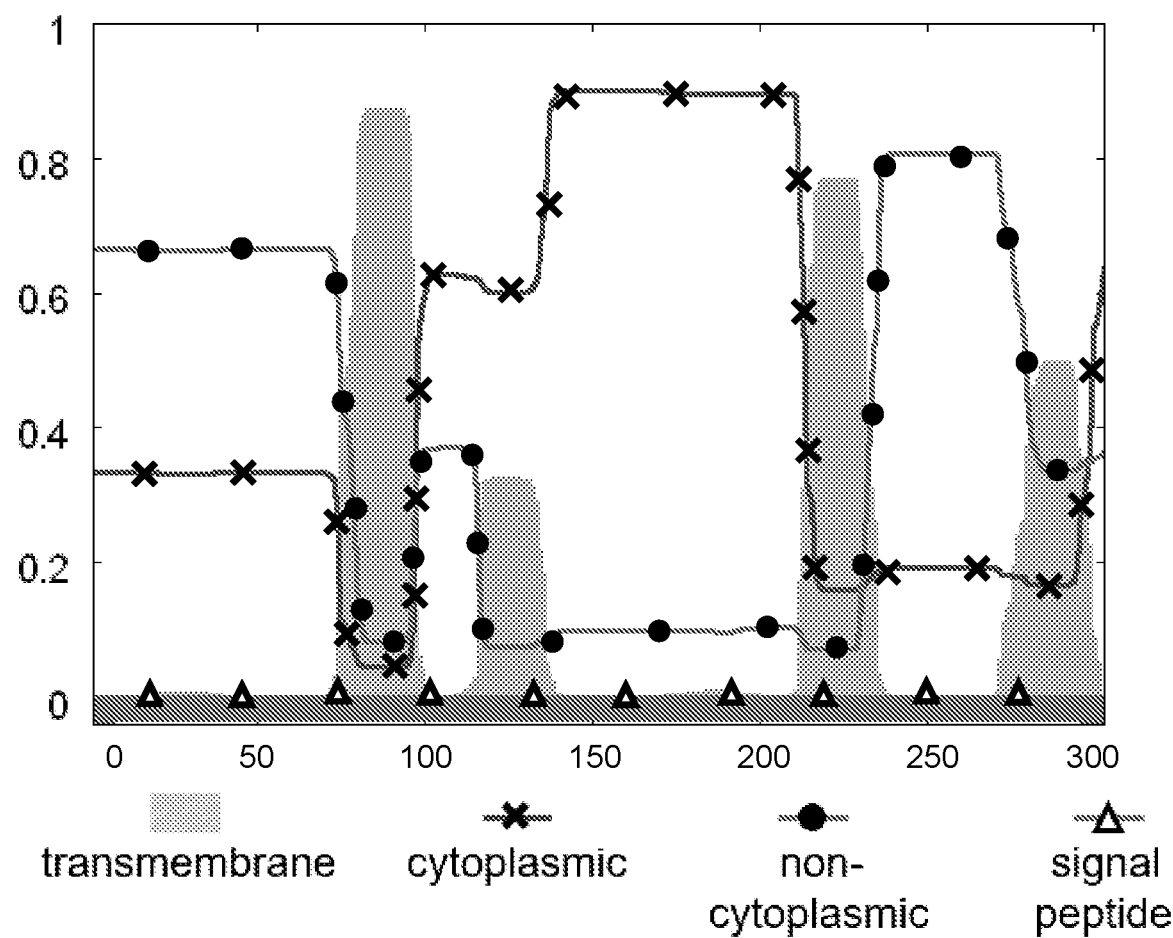
Figure 3A:
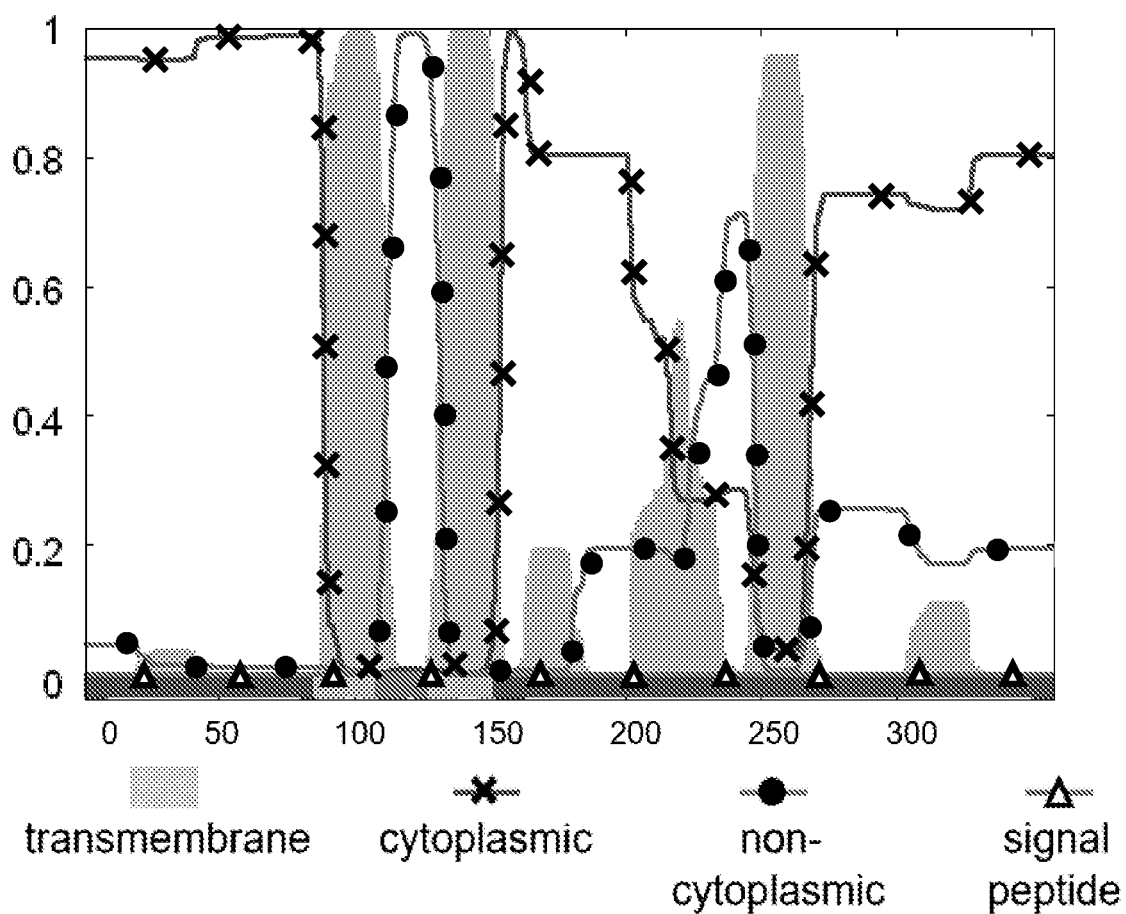
FIG. 3A-G shows Phobius-generated plots of predicted transmembrane domains of (A) *Chlamydomonas reinhardtii* CCP1 (SEQ ID NO: 1) and the best BLAST matches to CCP1 from (B) *Glycine max* (KRH74426.1) (SEQ ID NO: 14), (C) *Zea mays* (NP 001141073.1) (SEQ ID NO: 16), (D) *Oryza sativa, Japonica* group (XP_015614184.1) (SEQ ID NO: 15), (E) *Triticum aestivum* (CDM80555.1) (SEQ ID NO: 12), (F) *Sorghum bicolor* (XP 002464891.1) (SEQ ID NO: 17), and (G) *Solanum tuberosum* (XP_006361187.1) (SEQ ID NO: 13). The Phobius plots show predicted transmembrane domain (grey shading), cytoplasmic domain (line with X), non-cytoplasmic domain (line with filled circle), and signal peptide sequence (line with triangle). The Y-axis corresponds to posterior label probability, plotted from 0 to 1 in increments of 0.2. The X-axis corresponds to amino acid residue number of corresponding CCP1 or CCP1-like mitochondrial transporter protein, plotted from 0 to 300 in increments of 50 (A, E, and G) or from 0 to 250 in increments of 50 (B-D and F).
Figure 3B:
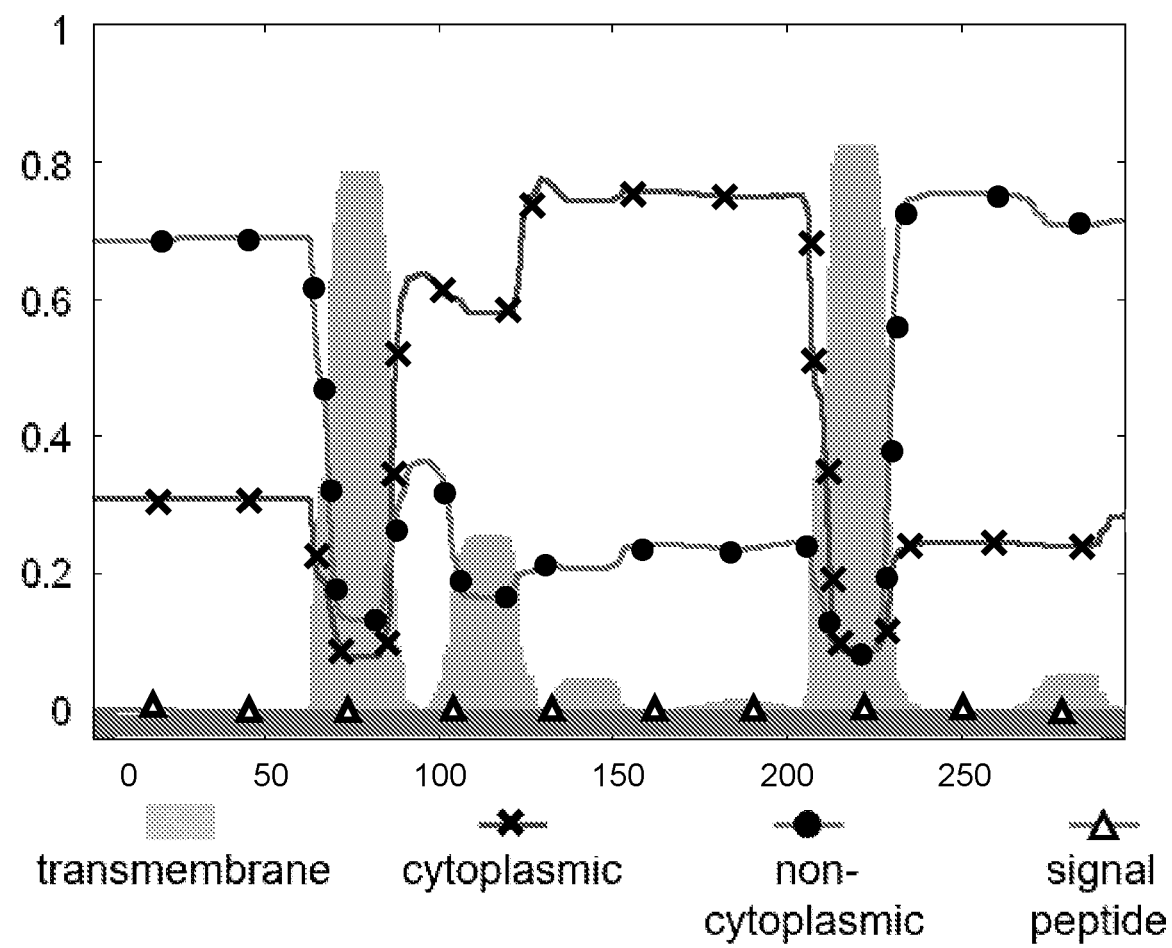
Figure 3C:
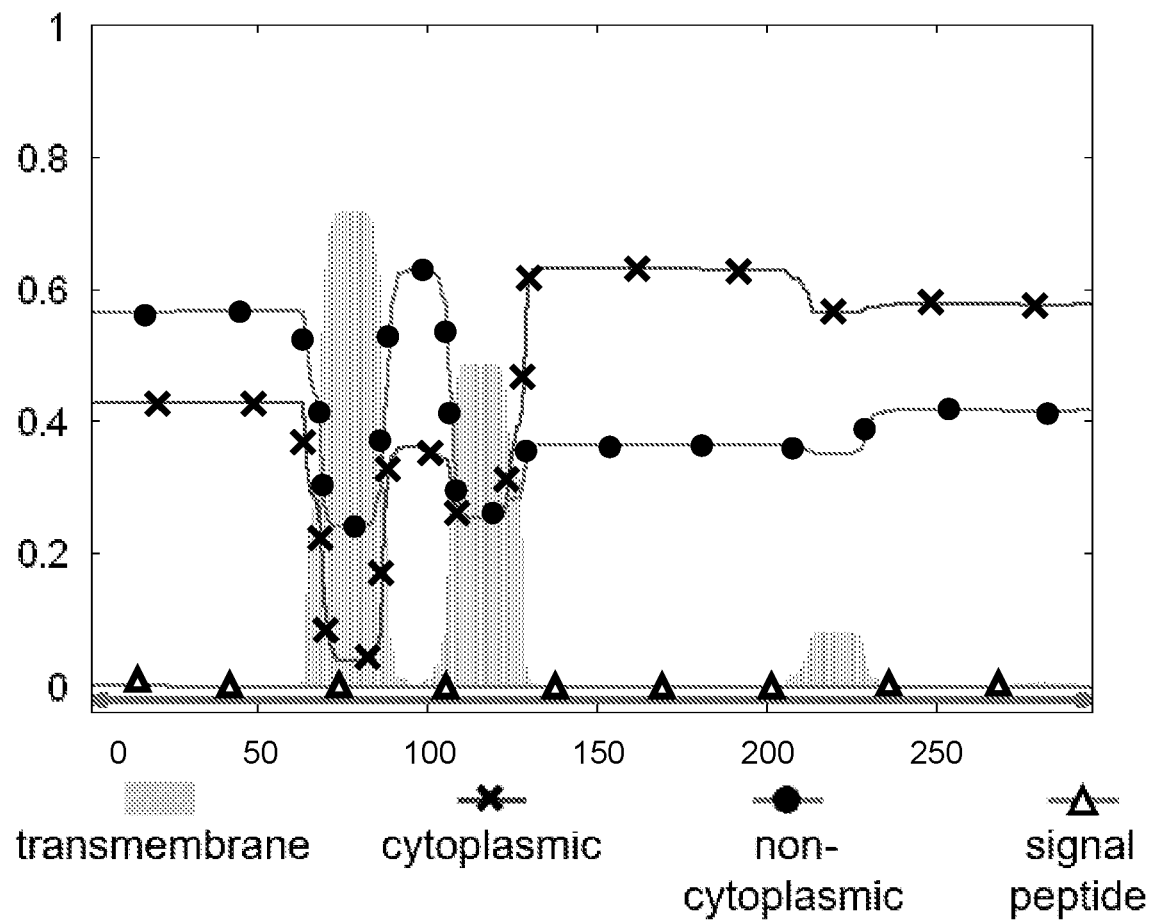
Figure 3D:
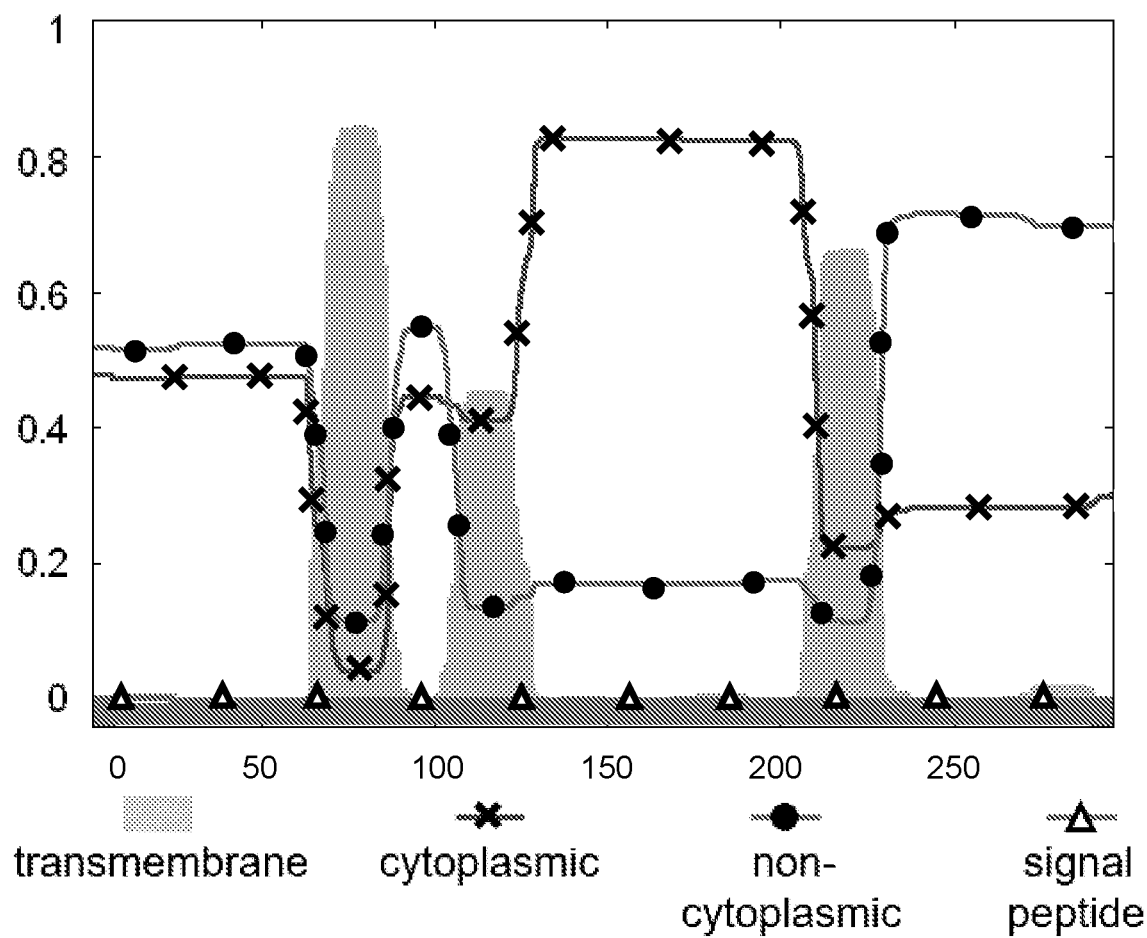
Figure 3E:
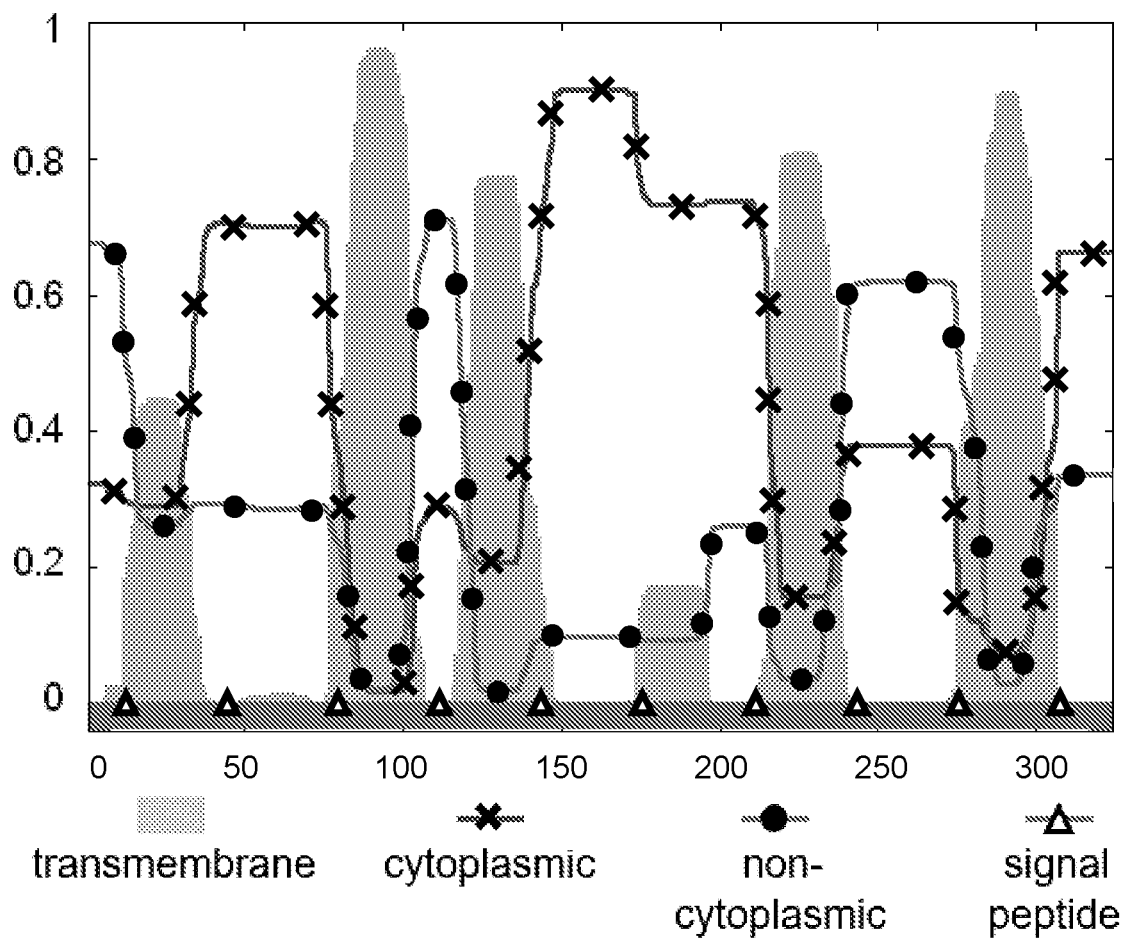
Figure 3F:
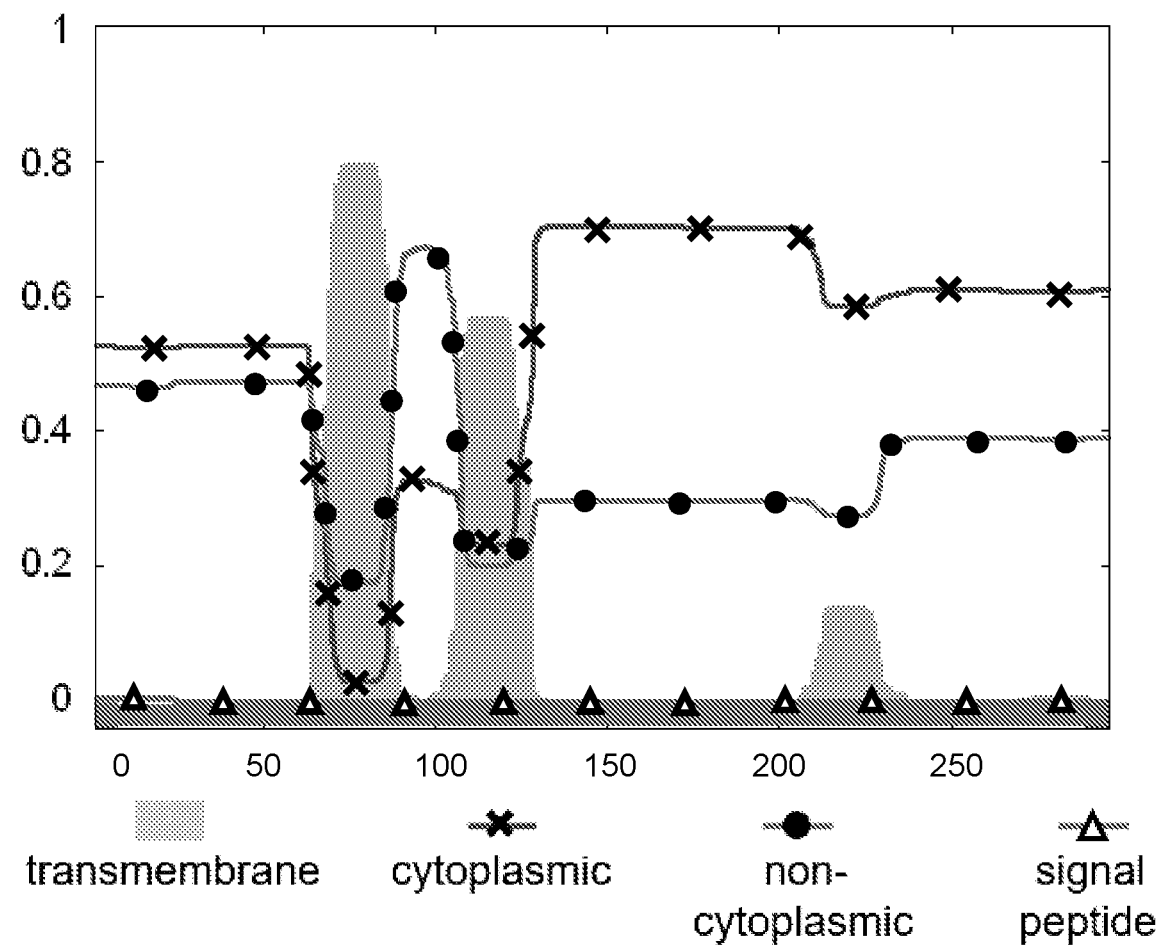
Figure 3G:
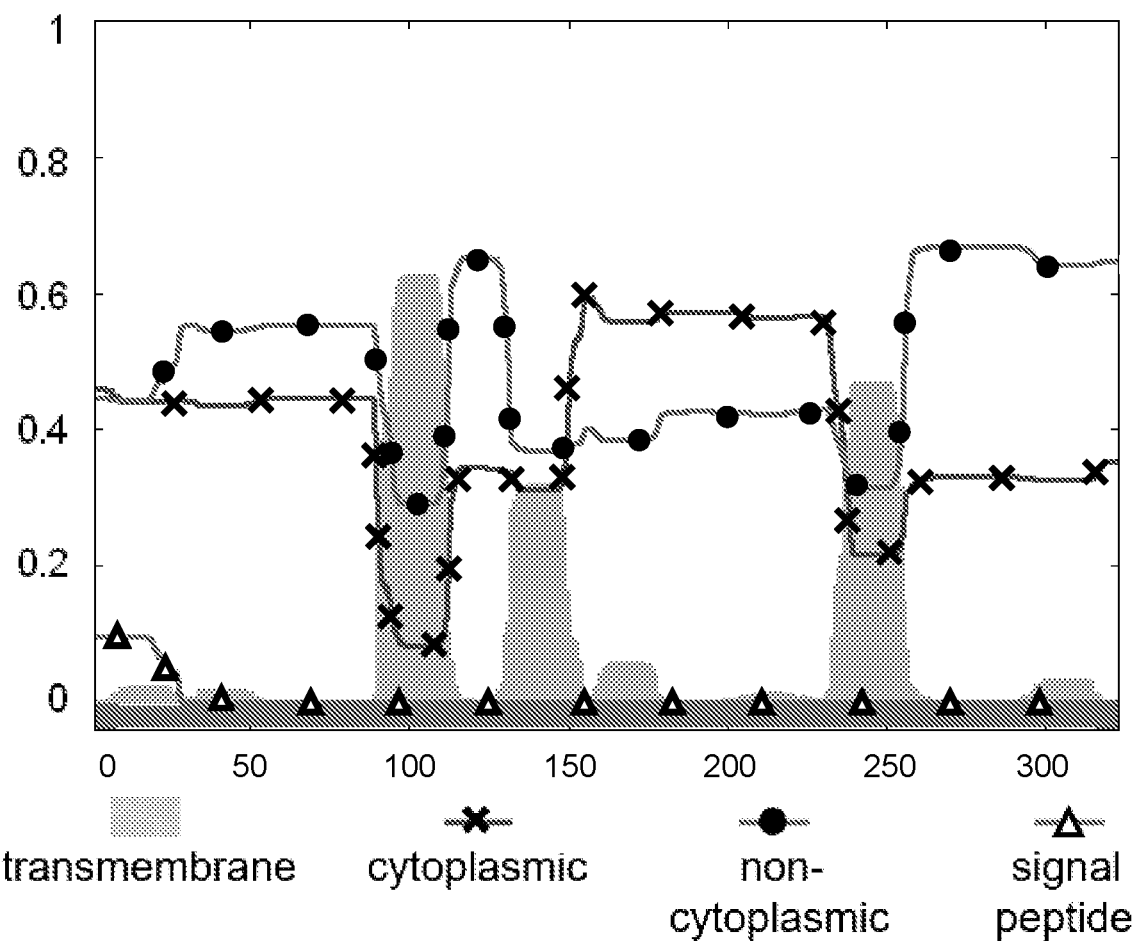

*Phobius does not assign a transmembrane region despite graph in FIG. 1G, I.

Example 2. Functional Tests for Screening for Crop Gene Encoded CCP1-Like Activity When defining a class of plant genes or proteins such as those with functions complementary to, or similar to, CCP1 of *Chlamydomonas reinhardtii*, it is beneficial to utilize a screen, selection, or other test that identifies candidates as members or non-members of the useful family. The most thorough screen of such activity is in whole plants over a sustained period to insure that yield and efficiency of carbon capture are indeed improved. However, a more-facile screen in a simpler system that requires less time and still serves as a good predictor of yield improvement by virtue of demonstration of similar function to CCP1 would be valuable. There are many systems in which such a screen could reasonably be conducted, of which some examples are as follows.

Yeast

A useful eukaryotic model system is *Saccharomyces cerevisiae*, whose genome has been sequenced and for which databases with functional information such as that hosted by Stanford University (website: yeastgenome.org) are available. Knockout mutants and libraries are available for this organism, such as the Yeast Knockout Collection at GE Life Sciences (website: dharmacon.gelifesciences.com). CCP1-like candidates can therefore be expressed in yeast using standard molecular biology techniques to complement various known yeast mitochondrial transporter mutants in order to classify the candidates according to function and identify whether or not they are similar in function to CCP1. An example of this approach is found in Herzig et al., *Science* 337:93-96 (2012), in which mitochondrial transporters from mouse complemented yeast mutants deficient in the ability to transport pyruvate into the mitochondrion.

*Escherichia coli*

The Gram-negative bacterium *E. coli* can serve as a model for mitochondria, because both systems have a double-membrane structure. Using standard techniques of molecular biology and bacterial transformation, CCP1 orthologs can be expressed functionally in *E. coli* and the resulting phenotype examined. Mutants of *E. coli* lacking one or more transporter proteins can be especially useful in this regard. *E. coli* mutants are widely available, such as in the Keio collection, which contains all single-gene mutants producing viable cells (website: cgsc2.biology.yale.edu/KeioList.php). For example, ADP/ATP carrier proteins from various plants were functionally expressed and characterized in *E. coli* (Haferkamp et al., *Eur. J. Biochem.* 269:3172 (2002)), in which the transport of radiolabelled ADP and ATP was measured.

*Lactococcus lactis*

The Gram-positive bacterium *Lactococcus lactis* has only a single cell membrane and is amenable to genetic manipulation. Therefore, standard molecular biology techniques can be utilized to introduce CCP1 homologs into this organism as a screening platform. An example of this approach can be found in Kunji et al., *Biochimica et Biophysica Acta* 1610:97 (2003), in which eukaryotic mitochondrial carrier proteins were functionally expressed and characterized using transport of radiolabelled ATP in both intact cells and in membrane vesicles prepared from whole cells.

Isolated Mitochondria

Direct methods for the measurement of mitochondrial solute transport exist, such as those outlined in Palmieri and Klingenberg, *Methods Enzymol.* 56:279 (1979). Such methods can be used, for example, on yeast mitochondria expressing CCP1 vs. wild-type yeast mitochondria or mitochondria isolated from various yeast mutants. Such tests can also be carried out on mitochondria isolated from *Chlamydomonas reinhardtii* (wild-type vs. CCP1 mutants).

Liposomes

Mitochondrial carrier proteins can be expressed to high levels in a facile system such as *E. coli* and reconstituted into liposomes. For example, the *Arabidopsis thaliana* mitochondrial basic amino acid carrier AtmBAC1 was expressed in *E. coli*, purified, and reconstituted into phospholipid vesicles and was shown to transport arginine, lysine, ornithine, and histidine (Hoyos et al., *Plant J.* 33:1027 (2003)).

*Chlamydomonas reinhardtii*

It has been shown, for example by Pollock et al., Plant Mol. Biol. 56:125 (2004), that *Chlamydomonas reinhardtii* double mutants in CCP1 and CCP2 suffer growth defects in long-term (>48-hour) cultures. Therefore, a complementation test can be used with such mutants that defines CCP1 complementation as the ability of a gene to complement the loss of CCP1 and CCP2 in *Chlamydomonas reinhardtii* by restoring long-term growth rates to normal.

Figure 6:
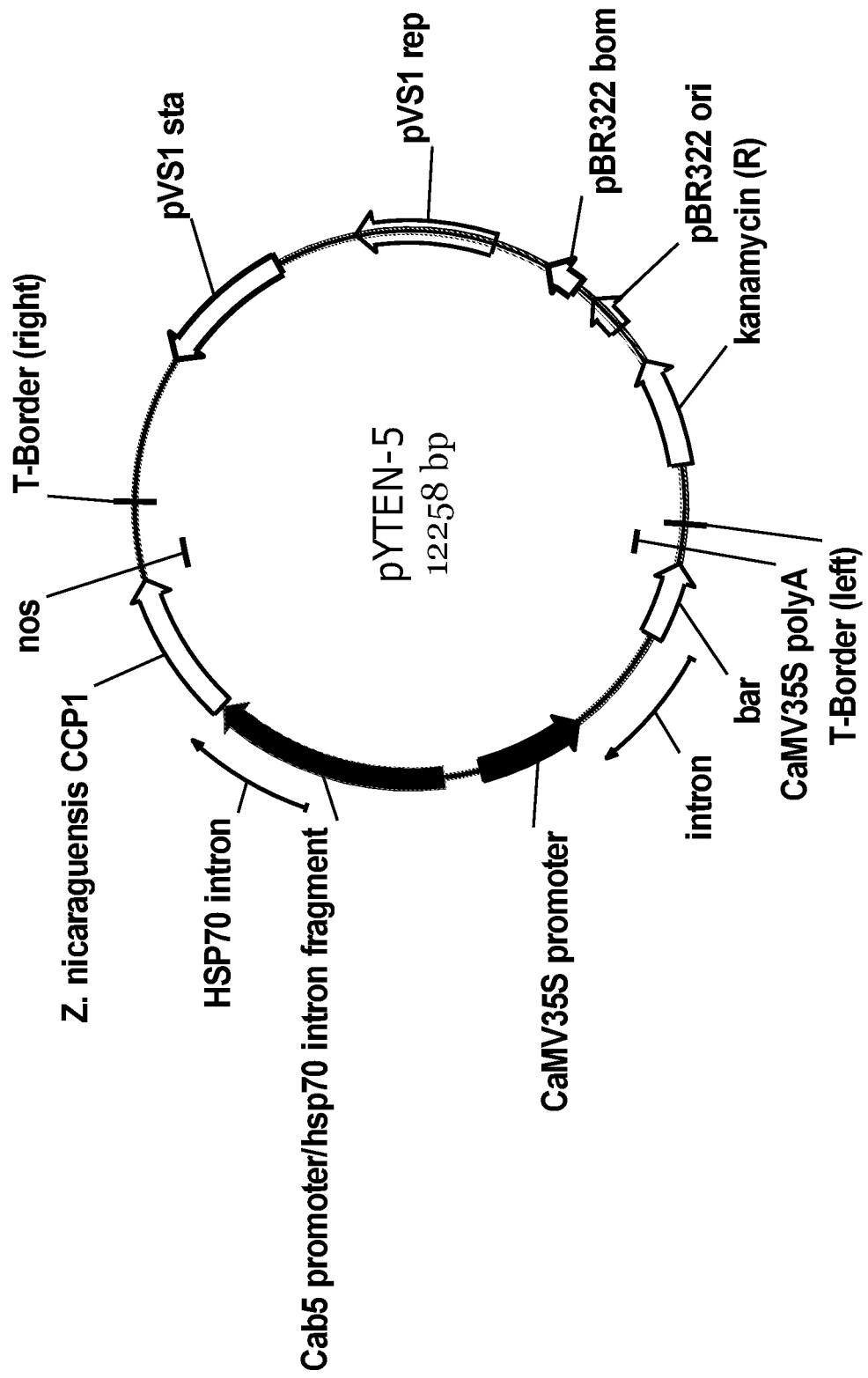
FIG. 6 shows a map for pYTEN-5 (SEQ ID NO: 49), a transformation vector designed for *Agrobacterium*-mediated transformation of monocots, including corn.

Example 3. *Agrobacterium*-Mediated Transformation of CCP1-Like Gene from *Z. nicaraguensis* into Maize For *Agrobacterium*-mediated transformation of maize, a binary vector containing a promoter, the CCP1 gene, and a terminator is constructed and an expression cassette for a selectable marker, such as the bar gene imparting resistance to the herbicide bialophos, are included.

pYTEN-5 (SEQ ID NO: 49; FIG. 6) is a transformation vector designed for *Agrobacterium*-mediated transformation of monocots, including corn. The CCP1 gene from *Z. nicaraguensis* is expressed from the hybrid cab5/hsp70 promoter, consisting of the maize chlorophyll a/b-binding protein promoter (Sullivan et al., 1989, Mol. Gen. Genet., 215, 431-440; this promoter is equivalent to the cab-m5 promoter described in later work by Becker et al., 1992, Plant Mol. Biol. 20, 49-60), fused to the hsp70 intron (U.S. Pat. No. 5,593,874). The plasmid also contains an expression cassette for the bar selectable marker for selection, imparting transgenic plant material resistance to the herbicide bialophos.

In preparation for transformation, pYTEN-5 is transformed into an *Agrobacterium tumefaciens* strain, such as *A. tumefaciens* strain EHA101. *Agrobacterium*-mediated transformation of maize can be performed following a previously described procedure (Frame et al., 2006, *Agrobacterium* Protocols Wang K., ed., Vol. 1, pp 185 199, Humana Press) as follows.

Plant Material: Plants grown in a greenhouse are used as an explant source. Ears are harvested 9-13 d after pollination and surface sterilized with 80% ethanol.

Explant Isolation, Infection and Co-Cultivation: Immature zygotic embryos (1.2-2.0 mm) are aseptically dissected from individual kernels and incubated in *A. tumefaciens* strain EHA101 culture (grown in 5 ml N6 medium supplemented with 100 µM acetosyringone for stimulation of the bacterial vir genes for 2-5 h prior to transformation) at room temperature for 5 min. The infected embryos are transferred scutellum side up on to a co-cultivation medium (N6 agar-solidified medium containing 300 mg/l cysteine, 5 µM silver nitrate and 100 µM acetosyringone) and incubated at 20° C., in the dark for 3 d. Embryos are transferred to N6 resting medium containing 100 mg/l cefotaxime, 100 mg/l vancomycin and 5 µM silver nitrate and incubated at 28° C., in the dark for 7 d.

Callus Selection: All embryos are transferred on to the first selection medium (the resting medium described above supplemented with 1.5 mg/l bialaphos) and incubated at 28° C., in the dark for 2 weeks followed by subculture on a selection medium containing 3 mg/l bialaphos. Proliferating pieces of callus are propagated and maintained by subculture on the same medium every 2 weeks.

Plant Regeneration and Selection: Bialaphos-resistant embryogenic callus lines are transferred on to regeneration medium I (MS basal medium supplemented with 60 g/l sucrose, 1.5 mg/l bialaphos and 100 mg/l cefotaxime and solidified with 3 g/l Gelrite) and incubated at 25° C., in the dark for 2 to 3 weeks. Mature embryos formed during this period are transferred on to regeneration medium II (the same as regeneration medium I with 3 mg/l bialaphos) for germination in the light (25° C., 80-100 µE/m²/s light intensity, 16/8-h photoperiod). Regenerated plants are ready for transfer to soil within 10-14 days.

Figure 7:
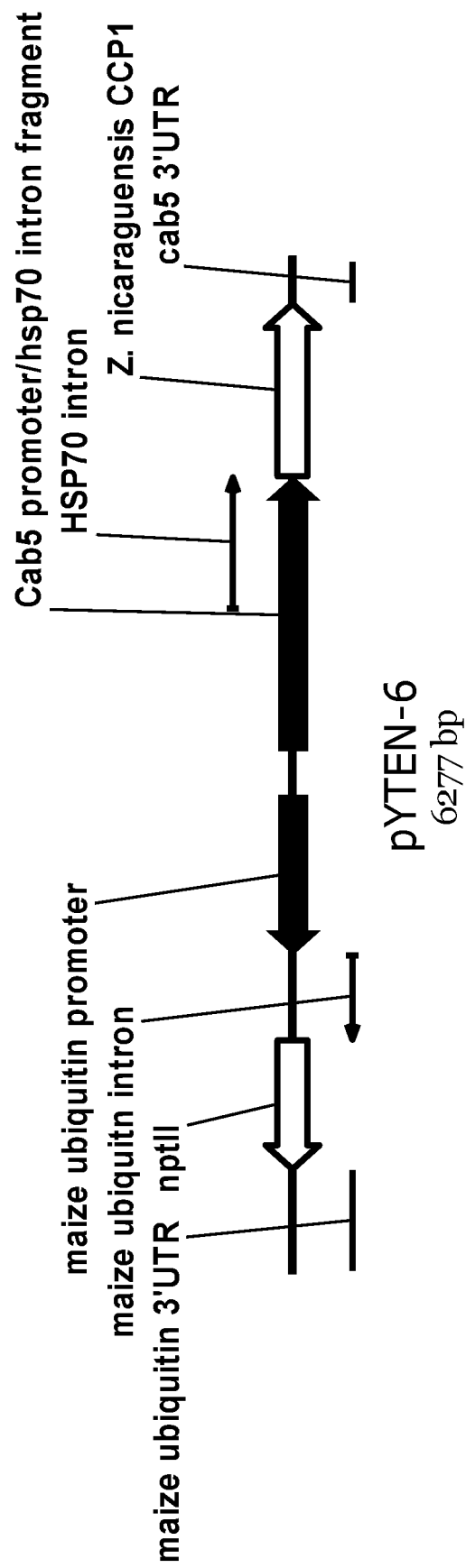
FIG. 7 shows a map for pYTEN-6 (SEQ ID NO: 50), a DNA cassette for biolistic transformation (also known as microparticle bombardment) of monocots such as corn.

Example 4. Transformation of CCP1-Like Gene from *Z. nicaraguensis* into Maize Using Biolistics pYTEN-6 (SEQ ID NO: 50; FIG. 7) is a DNA cassette for biolistic transformation (also known as microparticle bombardment) of monocots such as corn. It has been designed without the use of plant pest sequences to ease the regulatory path through USDA-*APHIS*, and extraneous vector backbone material has been removed. USDA-*APHIS* has previously provided an opinion that maize transformed through biolistic mediated procedures with DNA that does not contain plant pest sequences is not considered a regulated material (website: aphis.usda.gov/biotechnology/downloads/reg_loi/13-242-01_air_response.pdf).

In DNA fragment pYTEN-6, the CCP1 gene from *Z. nicaraguensis* is expressed from the hybrid maize cab5 promoter containing the maize HSP70 intron. There is an NPTII gene, encoding neomycin phosphotransferase from *Escherichia coli* K-12, conferring resistance to kanamycin for selection of transformants. The NPTII gene is expressed from the maize ubiquitin promoter with a 3' UTR from the maize ubiquitin gene. It will be apparent to those skilled in the art that many selectable markers can be used that are not derived from plant pest sequences for selection purposes. These include maize acetolactate synthase/acetohydroxy acid synthase (ALS/AHAS) mutant genes conferring resistance to a range of herbicides from the ALS family of herbicides, including chlorsulfuron and imazethapyr; a 5-enolpyruvoylshikimate-3-phosphate synthase (EPSPS) mutant gene from maize, providing resistance to glyphosate; as well as multiple other selectable markers that are all reviewed in Que et al., 2014 (Que, Q. et al., Front. Plant Sci. 5 Aug. 2014; doi.org/10.3389/fpls.2014.00379).

DNA fragment pYTEN-6 can be transformed into maize protoplasts, calli, or immature embryos using biolistics as reviewed in Que et al., 2014.

Example 5. Transformation of CCP1-Like Gene from *Z. nicaraguensis* Expressed from a Seed-Specific Promoter into Maize Using Biolistics In some cases, it will be advantageous to express CCP1 from a seed-specific promoter. There are many seed-specific promoters known and it will be apparent to those skilled in the art that seed-specific promoters from multiple different sources can be used to practice the invention, including the seed-specific promoters listed in TABLE 2.

Figure 8:
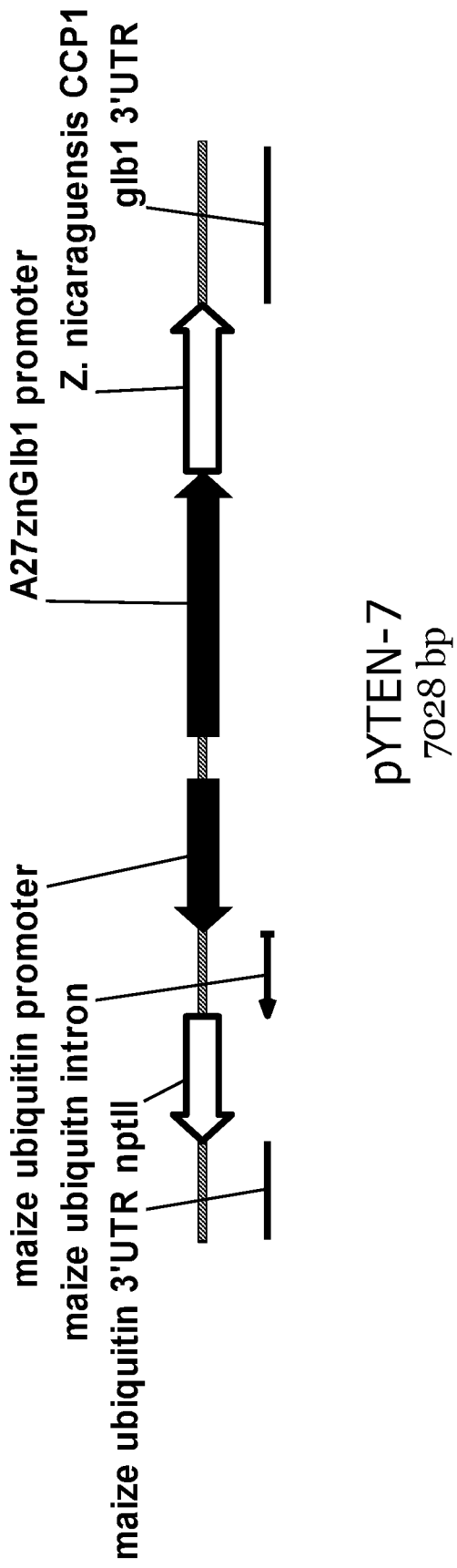
FIG. 8 shows a map for pYTEN-7 (SEQ ID NO: 51), another DNA cassette for biolistic transformation of monocots such as corn
Figure 9:
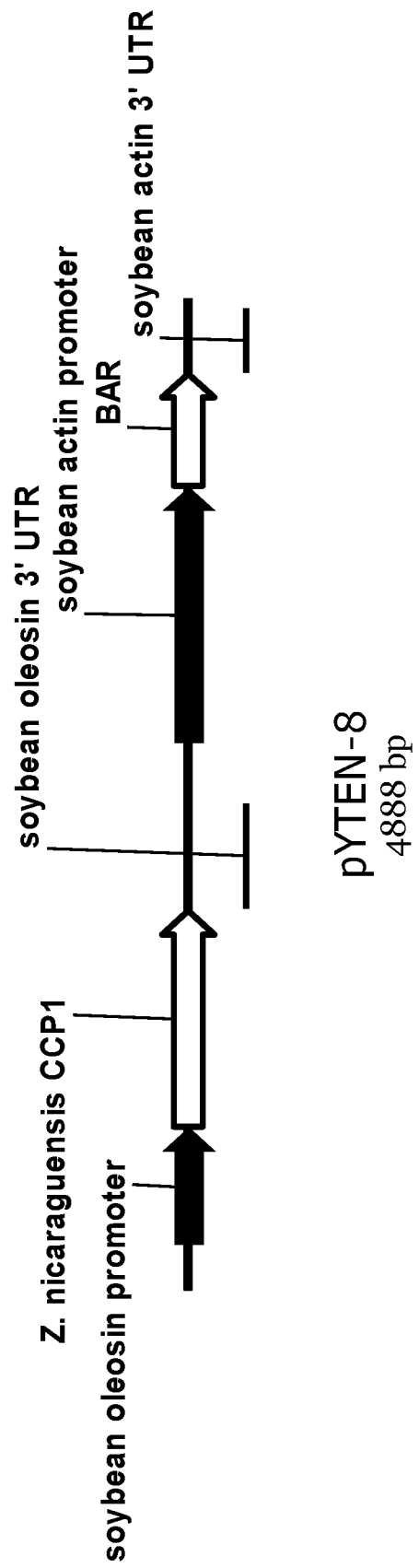
FIG. 9 shows a map for pYTEN-8 (SEQ ID NO: 52), a DNA cassette for biolistic transformation of a dicot, canola.

DNA fragment pYTEN-7 (SEQ ID NO: 51; FIG. 8) is designed for biolistic transformation of monocots such as corn. It contains the A27znG1b1 chimeric promoter (Accession number EF064989) consisting of a portion of the promoter from the *Zea mays* 27 kDa gamma zein gene and a portion of the promoter from the *Zea mays* globulin-1 gene (Shepard & Scott, 2009, Biotechnol. Appl. Biochem., 52, 233-243) controlling the expression of the CCP1 gene. This promoter has been shown by Shepard and Scott to be active in both the embryo and endosperm of corn kernels. The CCP1 gene is flanked at the 3' end by the 3' UTR, polyA, and terminator from the globulin-1 gene (Accession AH001354.2). It also contains the NPTII gene expressed from the maize ubiquitin promoter with a 3' UTR from the maize ubiquitin gene, for selection of transformants.

DNA fragment pYTEN-7 can be transformed into maize protoplasts, calli, or immature embryos using biolistics as reviewed in Que et al, 2014.

Example 6. Transformation of CCP1-Like Gene from Z. nicaraguensis Expressed from a Seed-Specific Promoter into Canola Protoplasts Transformation of protoplasts of *Brassica napus* can be performed as follows.

To express the CCP1-like gene from *Z. nicaraguensis* in canola, a linear DNA fragment, pYTEN-8 (SEQ ID NO: 52; FIG. 9) is prepared containing an expression cassette for CCP1, controlled by the soybean oleosin promoter (SEQ ID NO: 48) and the 3' UTR from the soybean oleosin gene (soybean oleosin Gene ID Glyma.16G071800), as well as an expression cassette for the selectable marker bar, controlled by the soybean actin promoter (SEQ ID NO: 42) and the 3' UTR from the soybean actin gene (soybean actin Gene ID Glyma.19G147900). The bar gene imparts the transgenic plant resistance to the herbicides bialophos or phosphinothricin. The pYTEN-8 linear fragment is transformed into protoplasts of canola as follows.

Protoplast isolation: Seeds of *Brassica napus* are surface sterilized with 70% ethanol for 2 min followed by gentle shaking in 0.4% hypochlorite solution for 20 min. The seeds are washed three times in double distilled water, and sown on sterilized ½ MS media in Petri plates that are placed without the lids in sterile MAGENTA jars. Protoplasts are isolated from 40 newly expanding leaves of *Brassica* plants. The mid vein is removed and the abaxial surface of the leaves are gently scored with a sterile scalpel. The leaves are then floated with abaxial side down in Petri plates containing 15 ml of Enzyme B2 solution (B5 salts, 1% Onozuka R 10, 0.2% Macerozyme R 10, 13% sucrose, 5 mM $CaCl_2 \cdot 2H_2O$, 0.5% Polyvinylpyrrolidone, 1 mg/L NAA, 1 mg/L 2, 4-D, 1 mg/L BA, MES 0.05%, pH 6.0). Petri plates are sealed with PARAFILM and leaves incubated overnight at 22° C. in the dark without shaking. Following the overnight incubation the plates are gently agitated by hand and incubation continued for 15-20 min on a rotary shaker set at 20 rpm. The digested material, consisting of a crude protoplast suspension, is then filtered through a funnel lined with 63 μm nylon screen and the filtrate collected in 50 ml falcon centrifuge tubes. An equal volume of 17% B5 wash solution (B5 salts, 5 mM $CaCl_2 \cdot 2H_2O$, 17% sucrose, 0.06% IVIES, pH 6.0) is added to the filtrate and centrifuged at 100 g for 10 minutes. The protoplast enriched fraction (~4 ml) floating in the form of a ring is carefully removed and transferred to fresh 15 ml FALCON tubes and 11 ml of WW5-2 media (0.1 M $CaCl_2 \cdot 2H_2O$, 0.2 M NaCl, 4 mM KCl, 0.08% Glucose, 0.1% MES, pH 6.0) is added per tube. The resulting suspension is gently mixed by inversion and then centrifuged at 100 g for 5 minutes. After centrifugation the supernatant is carefully decanted and discarded and the pellet consisting of an enriched protoplast fraction is retained. Protoplasts are washed twice with WW5-2 solution followed by centrifugation at 100 g and resuspended in 5 ml of WW5-2 media. The density of protoplasts is counted with a hemocytometer using a small drop of the protoplast suspension. The suspension is cooled in a refrigerator (2-8° C.) for 40-45 min.

*Brassica napus* protoplast transfection and culture: For protoplast transfection, the protoplasts after cold incubation are pelleted by centrifugation at 100 g for 3 minutes and then resuspended in WMMM media (15 mM $MgCl_2$-$6H_2O$, 0.4 M Mannitol, 0.1 M $(CaNO_3)2$, 0.1% MES, pH 6) to a density of $2\times10^6$ protoplasts per ml. 500 μl of protoplast suspension is dispensed into 15 ml FALCON tubes and 50 μl of a mixture consisting of 50 μg DNA of linear DNA fragment pYTEN-8 is added to protoplast suspension and mixed by shaking. 500 μl of PEGB2 (40% PEG 4000, 0.4 M Mannitol, 0.1 M Calcium Nitrate, 0.1% MES, pH 6.0) is added gently to protoplast DNA mixture while continuously shaking the tube. The mixture is incubated for 20 min with periodic gentle shaking. Subsequently WW5-2 media is gradually added in two stages, first a 5 ml aliquot of WW5-2 is added to the protoplast mixture which is then allowed to incubate for 10 minutes followed by addition of a second 5 ml aliquot of WW5-2 solution and incubation for 10 min. After the second incubation, the protoplasts are carefully resuspended and then pelleted by centrifugation. The protoplast pellet is resuspended in 12 ml of WW5-2 solution then pelleted by centrifugation at 100 g for 5 min. The pellet is washed once more in 10 ml of WW5-2 then pelleted by centrifugation at 100 g for 3 min. The protoplast pellet is resuspended in K3P4 medium (Kao's basal salts, 6.8% Glucose, 1% MES, 0.5% Ficoll 400, 2 mM $CaCl_2 \cdot 2H_2O$, 1 mg/L 2, 4-D, 1 mg/L NAA, 1 mg/L Zeatin, pH 5.8, 200 mg/L Carbenicillin, 200 mg/L Cefotaxime) at a density of $1\times10^5$ protoplasts per ml and 1.5 ml of the suspension is dispensed per 60×15 mm petri plate. The plates are sealed with PARAFILM and maintained in plastic boxes with opaque lids at 22° C., 16 h photoperiod, under dim fluorescent lights (25 $\mu Em^{-2} s^{-1}$).

*Brassica napus*, Proliferation of calli and regeneration of lines: After 4-5 days the protoplast cultures are fed with 1-1.25 ml of medium consisting of a 1:1 mixture of K3P4 medium and EmBed BI medium (MS Basal salts, 3.4% sucrose, 0.05% MES, 1 mg/L NAA, 1 mg/L 2,4-D and 1 mg/L BA, pH 6.0). The plates are resealed and placed under dim light for 1-2 days and then under medium light (60-80 $\mu Em^{-2} s^{-1}$). After 4-5 days, the protoplasts are fed with 4.5 ml of a 3:1 mixture of K3P4: Embed BI medium. The plate contents are then transferred to a 100×75 mm plate and 3 ml of lukewarm Embed BI medium containing 2.1% SeaPlaque agarose is added to the protoplast suspension. The contents of the plate are swirled to gently mix the protoplast suspension with the semi-solid media and the plates are allowed to solidify in the tissue culture flow hood. Plates are sealed and cultured under dim light conditions for a week. After 7-9 days, the embedded protoplast cultures in each plate are cut into 6-8 wedges and transferred onto two plates of Proliferation B1 media (MS Basal salts, 3.4% sucrose, 0.05% MES, 1 mg/L NAA, 1 mg/L 2,4-D and 1 mg/L BA, pH 6.0, 0.8% sea plaque agarose, 200 mg/L Carbenicillin, 200 mg/L Cefotaxime) with 60 mg/L L-phosphinothricin for selection. Proliferation plates are incubated under dim light for the first 1-2 days and then moved to bright light (150 $\mu Em^{-2} s^{-1}$). Green surviving colonies are obtained after 3 to 4 weeks at which point they are transferred to fresh Proliferation B 1 plates for an additional 2-3 weeks. Large green calli are transferred to Regeneration B2 Plates (MS Basal salts, 3% sucrose, 30 μM $AgNO_3$, 0.05% polyvinylpyrrolidone, 0.05% MES, 0.1 mg/L NAA, 5 mg/l N6-(2-isopentenyl)adenine (2-iP), 0.1 μg/L GA3, pH 5.8, 0.8% sea plaque agarose, 100 mg/L Carbenicillin, 100 mg/L Cefotaxime) with 10 mg/L L-phosphinothricin for selection. Calli are transferred to fresh Regeneration B2 plates every 3 to 4 weeks. Shoots with normal morphology are transferred to rooting medium (B5 salts+0.1 mg/L NAA) and incubated under dim light conditions. Plantlets are potted in a soilless mix (Sunshine Mix 4) in 6 inch (15 cm) pots and irrigated with NPK (20-20-20) fertilizer. Plantlets are acclimatized under plastic cups for 5-6 days and maintained in growth room at 22° C./18° C. and 16 hour photoperiod under 200-300 µEm$^{-2}$ s$^{-1}$ light.

Plants are allowed to set seed (T1 seed). T1 seeds are harvested and planted in soil and grown in a greenhouse. Plants are grown to maturity and T2 seed is harvested. Seed yield per plant and oil content of the seeds is measured.

Figure 10:
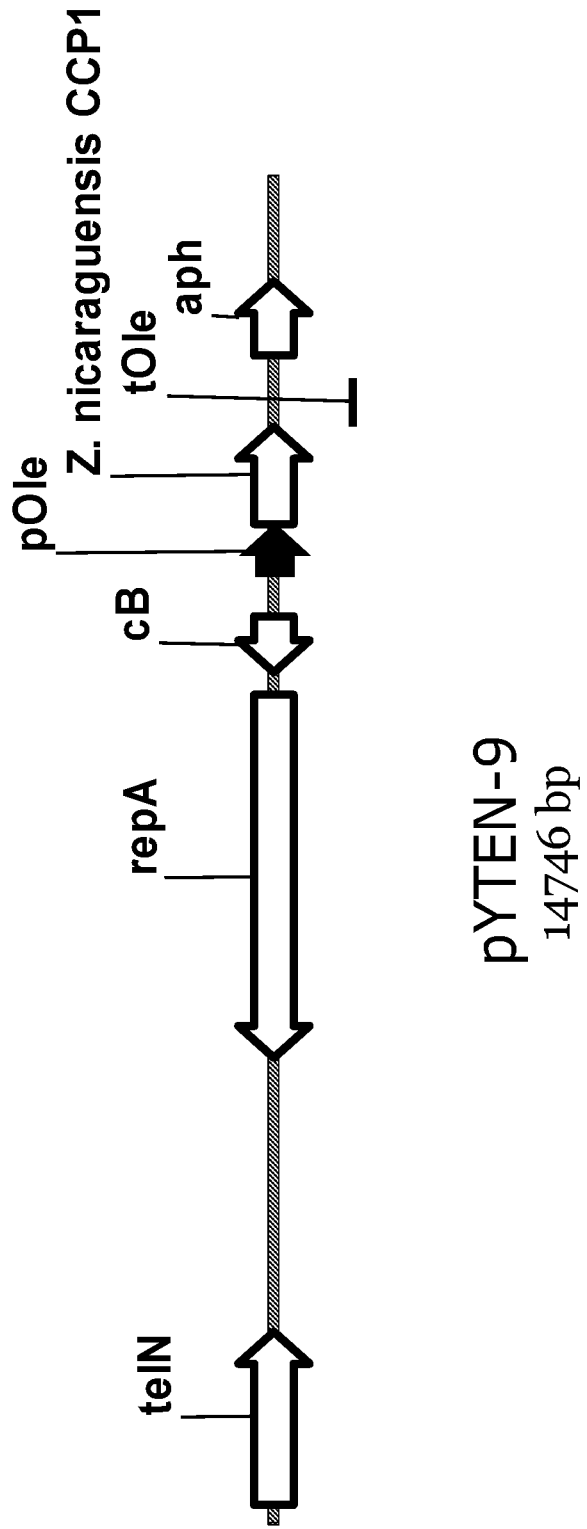
FIG. 10 shows a map for pYTEN-9 (SEQ ID NO: 53), a DNA cassette for biolistic transformation of a dicot, soybean.

Example 7. Transformation of CCP1-Like Gene from Z. nicaraguensis Expressed from a Seed-Specific Promoter into Soybean Using Biolistics A vector containing the Z. nicaraguensis CCP1 gene under the control of a seed-specific promoter from the soya bean oleosin isoform A gene is constructed. Plasmid pYTEN-9 (SEQ ID NO: 53; FIG. 10) is a derivative of the pJAZZ linear vector (Lucigen, Inc.) and was constructed using cloning techniques standard for those skilled in the art. The vector contains the Z. nicaraguensis CCP1 gene under the control of a seed-specific promoter from the soya bean oleosin isoform A gene. The CCP1 gene can have its native codon usage or can be codon optimized for expression in soybean. Here the native codon usage of the Z. nicaraguensis CCP1 gene is used. The cloning is designed to enable the excision of the CCP1 expression cassette, using restriction digestion. Digestion of pYTEN-9 with SmaI will release a 2.19 kb cassette containing the expression cassette consisting of oleosin promoter, CCP1, and oleosin terminator such that no vector backbone will be integrated into the plant.

The purified DNA fragment containing the CCP1 expression cassette is co-bombarded with DNA encoding an expression cassette for the hygromycin resistance gene via biolistics into embryogenic cultures of soybean Glycine max cultivars X5 and Westag97, to obtain transgenic plants. The hygromycin resistance gene is expressed from a plant promoter, such as the soybean actin promoter (SEQ ID NO: 42) and the 3' UTR from the soybean actin gene (soybean actin Gene ID Glyma.19G147900).

The transformation, selection, and plant regeneration protocol is adapted from Simmonds (2003) (Simmonds, 2003, Genetic Transformation of Soybean with Biolistics. In: Jackson J F, Linskens H F (eds) Genetic Transformation of Plants. Springer Verlag, Berlin, pp 159-174) and is performed as follows.

Induction and Maintenance of Proliferative Embryogenic Cultures: Immature pods, containing 3-5 mm long embryos, are harvested from host plants grown at 28/24° C. (day/night), 15-h photoperiod at a light intensity of 300-400 µmol m$^{-2}$ s$^{-1}$. Pods are sterilized for 30 s in 70% ethanol followed by 15 min in 1% sodium hypochlorite [with 1-2 drops of Tween 20 (Sigma, Oakville, ON, Canada)] and three rinses in sterile water. The embryonic axis is excised and explants are cultured with the abaxial surface in contact with the induction medium [MS salts, B5 vitamins (Gamborg O L, Miller R A, Ojima K. Exp Cell Res 50:151-158), 3% sucrose, 0.5 mg/L BA, pH 5.8), 1.25-3.5% glucose (concentration varies with genotype), 20 mg/l 2,4-D, pH 5.7]. The explants, maintained at 20° C. at a 20-h photoperiod under cool white fluorescent lights at 35-75 µmol m$^{-2}$ s$^{-1}$, are sub-cultured four times at 2-week intervals. Embryogenic clusters, observed after 3-8 weeks of culture depending on the genotype, are transferred to 125-ml Erlenmeyer flasks containing 30 ml of embryo proliferation medium containing 5 mM asparagine, 1-2.4% sucrose (concentration is genotype dependent), 10 mg/l 2,4-D, pH 5.0 and cultured as above at 35-60 µmol m$^{-2}$ s$^{-1}$ of light on a rotary shaker at 125 rpm. Embryogenic tissue (30-60 mg) is selected, using an inverted microscope, for subculture every 4-5 weeks.

Transformation: Cultures are bombarded 3 days after subculture. The embryogenic clusters are blotted on sterile Whatman filter paper to remove the liquid medium, placed inside a 10×30-mm Petri dish on a 2×2 cm$^2$ tissue holder (PeCap, 1 005 µm pore size, Band SH Thompson and Co. Ltd. Scarborough, ON, Canada) and covered with a second tissue holder that is then gently pressed down to hold the clusters in place. Immediately before the first bombardment, the tissue is air dried in the laminar air flow hood with the Petri dish cover off for no longer than 5 min. The tissue is turned over, dried as before, bombarded on the second side and returned to the culture flask. The bombardment conditions used for the Biolistic PDS-I000/He Particle Delivery System are as follows: 737 mm Hg chamber vacuum pressure, 13 mm distance between rupture disc (Bio-Rad Laboratories Ltd., Mississauga, ON, Canada) and macrocarrier. The first bombardment uses 900 psi rupture discs and a microcarrier flight distance of 8.2 cm, and the second bombardment uses 1100 psi rupture discs and 11.4 cm microcarrier flight distance. DNA precipitation onto 1.0 µm diameter gold particles is carried out as follows: 2.5 µl of 100 ng/µl of insert DNA of pYTEN-9 and 2.5 µl of 100 ng/µl selectable marker DNA (cassette for hygromycin selection) are added to 3 mg gold particles suspended in 50 µl sterile dH$_2$O and vortexed for 10 sec; 50 µl of 2.5 M CaCl$_2$ is added, vortexed for 5 sec, followed by the addition of 20 µl of 0.1 M spermidine which is also vortexed for 5 sec. The gold is then allowed to settle to the bottom of the microfuge tube (5-10 min) and the supernatant fluid is removed. The gold/DNA is resuspended in 200 µl of 100% ethanol, allowed to settle and the supernatant fluid is removed. The ethanol wash is repeated and the supernatant fluid is removed. The sediment is resuspended in 120 µl of 100% ethanol and aliquots of 8 µl are added to each macrocarrier. The gold is resuspended before each aliquot is removed. The macrocarriers are placed under vacuum to ensure complete evaporation of ethanol (about 5 min).

Selection: The bombarded tissue is cultured on embryo proliferation medium described above for 12 days prior to subculture to selection medium (embryo proliferation medium contains 55 mg/l hygromycin added to autoclaved media). The tissue is sub-cultured 5 days later and weekly for the following 9 weeks. Green colonies (putative transgenic events) are transferred to a well containing 1 ml of selection media in a 24-well multi-well plate that is maintained on a flask shaker as above. The media in multi-well dishes is replaced with fresh media every 2 weeks until the colonies are approximately 2-4 mm in diameter with proliferative embryos, at which time they are transferred to 125 ml Erlenmeyer flasks containing 30 ml of selection medium. A portion of the proembryos from transgenic events is harvested to examine gene expression by RT-PCR.

Plant regeneration: Maturation of embryos is carried out, without selection, at conditions described for embryo induction. Embryogenic clusters are cultured on Petri dishes containing maturation medium (MS salts, B5 vitamins, 6% maltose, 0.2% gelrite gellan gum (Sigma), 750 mg/l MgCl$_2$, pH 5.7) with 0.5% activated charcoal for 5-7 days and without activated charcoal for the following 3 weeks. Embryos (10-15 per event) with apical meristems are selected under a dissection microscope and cultured on a similar medium containing 0.6% phytagar (Gibco, Burlington, ON, Canada) as the solidifying agent, without the additional MgCl$_2$, for another 2-3 weeks or until the embryos become pale yellow in color. A portion of the embryos from transgenic events after varying times on gelrite are harvested to examine gene expression by RT-PCR.

Mature embryos are desiccated by transferring embryos from each event to empty Petri dish bottoms that are placed inside MAGENTA boxes (Sigma) containing several layers of sterile Whatman filter paper flooded with sterile water, for 100% relative humidity. The MAGENTA boxes are covered and maintained in darkness at 20° C. for 5-7 days. The embryos are germinated on solid B5 medium containing 2% sucrose, 0.2% gelrite and 0.075% $MgCl_2$ in Petri plates, in a chamber at 20° C., 20-h photoperiod under cool white fluorescent lights at 35-75 μmol $m^{-2}$ $s^{-1}$. Germinated embryos with unifoliate or trifoliate leaves are planted in artificial soil (Sunshine Mix No. 3, SunGro Horticulture Inc., Bellevue, WA, USA), and covered with a transparent plastic lid to maintain high humidity. The flats are placed in a controlled growth cabinet at 26/24° C. (day/night), 18 h photoperiod at a light intensity of 150 μmol $m^{-2}$ $s^{-1}$. At the 2-3 trifoliate stage (2-3 weeks), the plantlets with strong roots are transplanted to pots containing a 3:1:1:1 mix of ASB Original Grower Mix (a peat-based mix from Greenworld, ON, Canada):soil:sand:perlite and grown at 18-h photoperiod at a light intensity of 300-400 μmolm$^{-2}$ $s^{-1}$.

T1 seeds are harvested and planted in soil and grown in a controlled growth cabinet at 26/24° C. (day/night), 18 h photoperiod at a light intensity of 300-400 μmol $m^{-2}$ $s^{-1}$. Plants are grown to maturity and T2 seed is harvested. Seed yield per plant and oil content of the seeds is measured.

Exemplary Embodiments

The following are exemplary embodiments of the genetically engineered land plant that expresses a plant CCP1-like mitochondrial transporter protein as disclosed herein.

Embodiment A. A genetically engineered land plant that expresses a plant CCP1-like mitochondrial transporter protein, the genetically engineered land plant comprising a modified gene for the plant CCP1-like mitochondrial transporter protein, wherein:
the plant CCP1-like mitochondrial transporter protein is an ortholog of CCP1 of *Chlamydomonas reinhardtii* of SEQ ID NO: 1 derived from a source land plant;
the plant CCP1-like mitochondrial transporter protein is localized to mitochondria of the genetically engineered land plant based on a mitochondrial targeting signal intrinsic to the plant CCP1-like mitochondrial transporter protein;
the modified gene comprises (i) a promoter and (ii) a nucleic acid sequence encoding the plant CCP1-like mitochondrial transporter protein;
the promoter is non-cognate with respect to the nucleic acid sequence; and
the modified gene is configured such that transcription of the nucleic acid sequence is initiated from the promoter and results in expression of the plant CCP1-like mitochondrial transporter protein.

Embodiment B. The genetically engineered land plant of embodiment A, wherein the plant CCP1-like mitochondrial transporter protein is an ortholog of CCP1 of *Chlamydomonas reinhardtii* of SEQ ID NO: 1 based on comprising: (i) (a) a proline residue at position 268, (b) an aspartate residue or glutamine residue at position 270, (c) a lysine residue or arginine residue at position 273, and (d) a serine residue or threonine residue at position 274, with numbering of positions relative to CCP1 of *Chlamydomonas reinhardtii* of SEQ ID NO: 1, and (ii) an overall identity of at least 15%.

Embodiment C. The genetically engineered land plant of embodiments A or B, wherein the plant CCP1-like mitochondrial transporter protein is an ortholog of CCP1 of *Chlamydomonas reinhardtii* of SEQ ID NO: 1 based on comprising: (i) (a) a glycine residue at position 301, (b) a glycine residue at position 308, and (c) an arginine residue at position 315, with numbering of positions relative to CCP1 of *Chlamydomonas reinhardtii* of SEQ ID NO: 1, and (ii) an overall identity of at least 15%.

Embodiment D. The genetically engineered land plant of any one of embodiments A-C, wherein the plant CCP1-like mitochondrial transporter protein is an ortholog of CCP1 of *Chlamydomonas reinhardtii* of SEQ ID NO: 1 based on comprising: (i) one or more Tier 1 CCP1 signature sequences of (a) LLGIHFP (SEQ ID NO: 18) at position 104-110, (b) LRDMQGYAWFF (SEQ ID NO: 19) at position 212-222, (c) AGFGLWGSMF (SEQ ID NO: 20) at position 258-267, or (d) AIPVNA (SEQ ID NO: 21) at position 316-321, with numbering of positions relative to CCP1 of *Chlamydomonas reinhardtii* of SEQ ID NO: 1, and (ii) an overall identity of at least 60%.

Embodiment E. The genetically engineered land plant of any one of embodiments A-D, wherein the plant CCP1-like mitochondrial transporter protein comprises at least one of (a) a plant CCP1-like mitochondrial transporter protein of *Zea nicaraguensis*, (b) a plant CCP1-like mitochondrial transporter protein of *Erigeron breviscapus*, (c) a plant CCP1-like mitochondrial transporter protein of *Poa pratensis*, or (d) a plant CCP1-like mitochondrial transporter protein of *Cosmos bipinnatus*.

Embodiment F. The genetically engineered land plant of embodiment E, wherein the plant CCP1-like mitochondrial transporter protein comprises a plant CCP1-like mitochondrial transporter protein of *Zea nicaraguensis*.

Embodiment G. The genetically engineered land plant of any one of embodiments A-D, wherein the plant CCP1-like mitochondrial transporter protein comprises at least one of (a) a plant CCP1-like mitochondrial transporter protein of *Zea nicaraguensis* of SEQ ID NO: 7, (b) a plant CCP1-like mitochondrial transporter protein of *Erigeron breviscapus* of SEQ ID NO: 6, (c) a plant CCP1-like mitochondrial transporter protein of *Poa pratensis* of SEQ ID NO: 8, or (d) a plant CCP1-like mitochondrial transporter protein of *Cosmos bipinnatus* of SEQ ID NO: 9.

Embodiment H. The genetically engineered land plant of embodiment G, wherein the plant CCP1-like mitochondrial transporter protein comprises a plant CCP1-like mitochondrial transporter protein of *Zea nicaraguensis* of SEQ ID NO: 7.

Embodiment I. The genetically engineered land plant of any one of embodiments A-D, wherein the plant CCP1-like mitochondrial transporter protein comprises one or more of (a) a plant CCP1-like mitochondrial transporter protein of *Zea mays*, (b) a plant CCP1-like mitochondrial transporter protein of *Triticum aestivum*, (c) a plant CCP1-like mitochondrial transporter protein of *Solanum tuberosum*, (d) a plant CCP1-like mitochondrial transporter protein of *Glycine max*, (e) a plant CCP1-like mitochondrial transporter protein of *Oryza sativa*, or (f) a plant CCP1-like mitochondrial transporter protein of *Sorghum bicolor*.

Embodiment J. The genetically engineered land plant of embodiment I, wherein the plant CCP1-like mitochondrial transporter protein comprises a plant CCP1-like mitochondrial transporter protein of *Zea mays*.

Embodiment K. The genetically engineered land plant of any one of embodiments A-D, wherein the plant CCP1-like mitochondrial transporter protein comprises one or more of (a) a plant CCP1-like mitochondrial transporter protein of *Zea mays* of SEQ ID NO: 16, (b) a plant CCP1-like mitochondrial transporter protein of *Triticum aestivum* of SEQ ID NO: 12, (c) a plant CCP1-like mitochondrial transporter protein of *Solanum tuberosum* of SEQ ID NO: 13, (d) a plant CCP1-like mitochondrial transporter protein of *Glycine max* of SEQ ID NO: 14, (e) a plant CCP1-like mitochondrial transporter protein of *Oryza sativa* of SEQ ID NO: 15, or (f) a plant CCP1-like mitochondrial transporter protein of *Sorghum bicolor* of SEQ ID NO: 17.

Embodiment L. The genetically engineered land plant of embodiment K, wherein the plant CCP1-like mitochondrial transporter protein comprises a plant CCP1-like mitochondrial transporter protein of *Zea mays* of SEQ ID NO: 16.

Embodiment M. The genetically engineered land plant of any one of embodiments A-L, wherein the plant CCP1-like mitochondrial transporter protein is localized to mitochondria of the genetically engineered land plant to a greater extent than to chloroplasts of the genetically engineered land plant by a factor of at least 2, at least 5, or at least 10.

Embodiment N. The genetically engineered land plant of any one of embodiments A-M, wherein the plant CCP1-like mitochondrial transporter protein consists essentially of an amino acid sequence that is identical to that of a wild-type plant CCP1-like mitochondrial transporter protein.

Embodiment O. The genetically engineered land plant of any one of embodiments A-N, wherein the plant CCP1-like mitochondrial transporter protein is heterologous with respect to the genetically engineered land plant.

Embodiment P. The genetically engineered land plant of any one of embodiments A-N, wherein the plant CCP1-like mitochondrial transporter protein is homologous with respect to the genetically engineered land plant.

Embodiment Q. The genetically engineered land plant of any one of embodiments A-P, wherein the promoter is a constitutive promoter.

Embodiment R. The genetically engineered land plant of any one of embodiments A-P, wherein the promoter is a seed-specific promoter.

Embodiment S. The genetically engineered land plant of any one of embodiments A-R, wherein the modified gene is integrated into genomic DNA of the genetically engineered land plant.

Embodiment T. The genetically engineered land plant of any one of embodiments A-S, wherein the modified gene is stably expressed in the genetically engineered land plant.

Embodiment U. The genetically engineered land plant of any of embodiments A-T, wherein the genetically engineered land plant (i) expresses the plant CCP1-like mitochondrial transporter protein in a seed-specific manner, and (ii) expresses another plant CCP1-like mitochondrial transporter protein constitutively, the other plant CCP1-like mitochondrial transporter protein also corresponding to an ortholog of CCP1 of *Chlamydomonas reinhardtii* of SEQ ID NO: 1 derived from a source land plant.

Embodiment V. The genetically engineered land plant of any of embodiments A-U, wherein the genetically engineered land plant has a $CO_2$ assimilation rate that is at least 5% higher, at least 10% higher, at least 20% higher, or at least 40% higher, than for a corresponding reference land plant that does not comprise the modified gene.

Embodiment W. The genetically engineered land plant of any of embodiments A-V, wherein the genetically engineered land plant has a transpiration rate that is at least 5% lower, at least 10% lower, at least 20% lower, or at least 40% lower, than for a corresponding reference land plant that does not comprise the modified gene.

Embodiment X. The genetically engineered land plant of any of embodiments A-W, wherein the genetically engineered land plant has a seed yield that is at least 5% higher, at least 10% higher, at least 20% higher, at least 40% higher, at least 60% higher, or at least 80% higher, than for a corresponding reference land plant that does not comprise the modified gene.

Embodiment Y. The genetically engineered land plant of any of embodiments A-X, wherein the genetically engineered land plant is a C3 plant.

Embodiment Z. The genetically engineered land plant of any of embodiments A-X, wherein the genetically engineered land plant is a C4 plant.

Embodiment AA. The genetically engineered land plant of any of embodiments A-X, wherein the genetically engineered land plant is a food crop plant selected from the group consisting of maize, wheat, oat, barley, soybean, millet, sorghum, potato, pulse, bean, tomato, and rice.

Embodiment BB. The genetically engineered land plant of embodiment AA, wherein the genetically engineered land plant is maize.

Embodiment CC. The genetically engineered land plant of any of embodiments A-X, wherein the genetically engineered land plant is a forage crop plant selected from the group consisting of silage corn, hay, and alfalfa.

Embodiment DD. The genetically engineered land plant of embodiment CC, wherein the genetically engineered land plant is silage corn.

Embodiment EE. The genetically engineered land plant of any of embodiments A-X, wherein the genetically engineered land plant is an oilseed crop plant selected from the group consisting of *camelina*, *Brassica* species (e.g. *B. napus* (canola), *B. rapa*, *B. juncea*, and *B. carinata*), *crambe*, soybean, sunflower, safflower, oil palm, flax, and cotton.

The invention has been described with reference to the example embodiments described above. Modifications and alterations will occur to others upon a reading and understanding of this specification. Examples embodiments incorporating one or more aspects of the invention are intended to include all such modifications and alterations insofar as they come within the scope of the appended claims.

REFERENCE TO A "SEQUENCE LISTING," A TABLE, OR A COMPUTER PROGRAM LISTING APPENDIX SUBMITTED AS AN ASCII TEXT FILE

The material in the ASCII text file, named "YTEN-57557WO-Sequences_ST25.txt", created Jun. 12, 2018, file size of 159,744 bytes, is hereby incorporated by reference.

What is claimed is:

1. A genetically engineered land plant that expresses a plant protein of *Zea nicaraguensis* of SEQ ID NO: 7, the genetically engineered land plant comprising a modified gene for the plant protein, wherein:
   the modified gene comprises (i) a promoter and (ii) a nucleic acid sequence encoding the plant protein;
   the promoter is non-cognate with respect to the nucleic acid sequence;
   the modified gene is configured such that transcription of the nucleic acid sequence is initiated from the promoter and results in expression of the plant protein; and
   the genetically engineered land plant is an oilseed plant.

2. The genetically engineered land plant of claim 1, wherein the promoter is a constitutive promoter.

3. The genetically engineered land plant of claim 1, wherein the promoter is a seed-specific promoter.

4. The genetically engineered land plant of claim 1, wherein the modified gene is integrated into genomic DNA of the genetically engineered land plant.

5. The genetically engineered land plant of claim 1, wherein the modified gene is stably expressed in the genetically engineered land plant.

6. The genetically engineered land plant of claim 1, wherein the genetically engineered land plant is an oilseed crop plant selected from the group consisting of camelina, *Brassica* species, *Brassica napus, Brassica rapa, Brassica juncea, Brassica carinata, crambe*, soybean, sunflower, safflower, oil palm, flax, and cotton.

* * * * *

SEQUENCE LISTING

<160> NUMBER OF SEQ ID NOS: 53

<210> SEQ ID NO 1
<211> LENGTH: 358
<212> TYPE: PRT
<213> ORGANISM: Chlamydomonas reinhardtii

<400> SEQUENCE: 1

Met Ser Ser Asp Ala Met Thr Ile Asn Glu Ser Leu Met Glu Val Glu
1               5                   10                  15

His Thr Pro Ala Val His Lys Arg Ile Leu Asp Ile Leu Pro Gly Ile
            20                  25                  30

Ser Gly Gly Val Ala Arg Val Met Ile Gly Gln Pro Phe Asp Thr Ile
        35                  40                  45

Lys Val Arg Leu Gln Val Leu Gly Gln Gly Thr Ala Leu Ala Ala Lys
50                  55                  60

Leu Pro Pro Ser Glu Val Tyr Lys Asp Ser Met Asp Cys Ile Arg Lys
65                  70                  75                  80

Met Ile Lys Ser Glu Gly Pro Leu Ser Phe Tyr Lys Gly Thr Val Ala
                85                  90                  95

Pro Leu Val Gly Asn Met Val Leu Leu Gly Ile His Phe Pro Val Phe
            100                 105                 110

Ser Ala Val Arg Lys Gln Leu Glu Gly Asp Asp His Tyr Ser Asn Phe
        115                 120                 125

Ser His Ala Asn Val Leu Leu Ser Gly Ala Ala Gly Ala Ala Gly
130                 135                 140

Ser Leu Ile Ser Ala Pro Val Glu Leu Val Arg Thr Lys Met Gln Met
145                 150                 155                 160

Gln Arg Arg Ala Ala Leu Ala Gly Thr Val Ala Gly Ala Ala Ala
                165                 170                 175

Ser Ala Gly Ala Glu Glu Phe Tyr Lys Gly Ser Leu Asp Cys Phe Lys
            180                 185                 190

Gln Val Met Ser Lys His Gly Ile Lys Gly Leu Tyr Arg Gly Phe Thr
        195                 200                 205

Ser Thr Ile Leu Arg Asp Met Gln Gly Tyr Ala Trp Phe Phe Leu Gly
    210                 215                 220

Tyr Glu Ala Thr Val Asn His Phe Leu Gln Asn Ala Gly Pro Gly Val
225                 230                 235                 240

His Thr Lys Ala Asp Leu Asn Tyr Leu Gln Val Met Ala Ala Gly Val
                245                 250                 255

Val Ala Gly Phe Gly Leu Trp Gly Ser Met Phe Pro Ile Asp Thr Ile
            260                 265                 270

Lys Ser Lys Leu Gln Ala Asp Ser Phe Ala Lys Pro Gln Tyr Ser Ser
        275                 280                 285

Thr Met Asp Cys Leu Lys Lys Val Leu Ala Ser Glu Gly Gln Ala Gly
    290                 295                 300

Leu Trp Arg Gly Phe Ser Ala Ala Met Tyr Arg Ala Ile Pro Val Asn
305                 310                 315                 320

Ala Gly Ile Phe Leu Ala Val Glu Gly Thr Arg Gln Gly Ile Lys Trp
                325                 330                 335

Tyr Glu Glu Asn Val Glu His Ile Tyr Gly Gly Val Ile Gly Pro Ala
            340                 345                 350

Thr Pro Thr Ala Ala Gln
        355

<210> SEQ ID NO 2
<211> LENGTH: 356
<212> TYPE: PRT
<213> ORGANISM: Gonium pectorale

<400> SEQUENCE: 2

```
Met Val Ser Met Thr Met Asn Asp Thr Leu Asn Gln Val Glu His Thr
1               5                   10                  15

Pro Val Asn Pro Pro His Lys Lys Val Leu Glu Leu Pro Gly Ile
            20                  25                  30

Ser Gly Gly Val Ala Arg Val Met Ile Gly Gln Pro Phe Asp Thr Ile
        35                  40                  45

Lys Val Arg Leu Gln Val Leu Gly Ala Gly Thr Ala Leu Ala Ala Lys
50                  55                  60

Leu Pro Pro Ser Glu Val Tyr Lys Asp Ser Met Asp Cys Val Arg Lys
65                  70                  75                  80

Met Ile Arg Thr Glu Gly Pro Leu Ser Phe Tyr Lys Gly Thr Val Ala
                85                  90                  95

Pro Leu Ile Gly Asn Met Ile Leu Leu Gly Ile His Phe Pro Thr Phe
            100                 105                 110

Ser Ser Val Arg Lys Gln Leu Glu Gly Asp Asp His Tyr Ser Asn Phe
        115                 120                 125

Ser Tyr Thr Asn Thr Leu Ile Ala Gly Ala Ala Gly Ala Ala Gly
130                 135                 140

Ser Leu Val Ser Thr Pro Val Glu Leu Val Arg Thr Lys Met Gln Met
145                 150                 155                 160

Gln Arg Arg Ala Ala Leu Ala Gly Ser Val Ala Gly Ser Ala Ala Ser
                165                 170                 175

Ser Gly Ala Glu Glu Phe Tyr Lys Gly Ser Val Asp Cys Phe Lys Gln
            180                 185                 190

Val Leu Ser Lys His Gly Ile Lys Gly Leu Tyr Arg Gly Phe Thr Ser
        195                 200                 205

Thr Val Leu Arg Asp Met Gln Gly Tyr Ala Trp Phe Phe Leu Gly Tyr
210                 215                 220

Glu Ala Thr Val Asn Tyr Phe Leu Gln Asn Ala Gly Pro Gly Val His
225                 230                 235                 240

Ser Lys Ala Asp Leu Asn Tyr Leu Gln Val Met Ala Ala Gly Val Val
                245                 250                 255

Ala Gly Phe Gly Leu Trp Gly Ser Met Phe Pro Ile Asp Thr Ile Lys
            260                 265                 270

Ser Lys Met Gln Ala Asp Ser Leu Ala Lys Pro Gln Tyr Thr Thr Thr
        275                 280                 285

Met Asp Cys Leu Arg Lys Val Leu Lys Thr Glu Gly Gln Val Gly Leu
290                 295                 300

Trp Arg Gly Phe Ser Ala Ala Met Tyr Arg Ala Ile Pro Val Asn Ala
305                 310                 315                 320

Gly Ile Phe Leu Ala Val Glu Gly Ser Arg Gln Gly Ile Lys Trp Tyr
                325                 330                 335

Glu Glu Asn Val Glu His Ile Tyr Gly Gly Val Val Gly Ala Ala Pro
            340                 345                 350

Gly Ala Ala Ser
        355
```

<210> SEQ ID NO 3

<211> LENGTH: 354
<212> TYPE: PRT
<213> ORGANISM: Gonium pectorale

<400> SEQUENCE: 3

Met Ser Ser Met Thr Val Asn Asp Thr Leu Asn Glu Val Glu His Thr
1               5                   10                  15

Pro Lys Asp Pro His Lys Arg Val Leu Glu Leu Leu Pro Gly Ile
            20                  25                  30

Ser Gly Gly Val Ala Arg Val Met Ile Gly Gln Pro Phe Asp Thr Ile
                35                  40                  45

Lys Thr Arg Leu Gln Val Leu Gly Ala Gly Thr Ala Leu Ala Ala Lys
50                  55                  60

Leu Pro Pro Ser Glu Val Tyr Lys Asp Ser Met Asp Cys Val Arg Lys
65                  70                  75                  80

Met Val Arg Ser Glu Gly Pro Leu Ser Phe Tyr Lys Gly Thr Val Ala
                85                  90                  95

Pro Leu Phe Gly Asn Met Ile Leu Leu Gly Ile His Phe Pro Val Phe
            100                 105                 110

Ser His Val Arg Lys Gln Leu Glu Gly Asp Asp His Tyr Ser Asn Phe
        115                 120                 125

Ser Tyr Thr Asn Ala Leu Ile Ser Gly Ala Ala Gly Ala Ala Gly
    130                 135                 140

Ser Leu Val Ser Thr Pro Val Glu Leu Val Arg Thr Lys Met Gln Met
145                 150                 155                 160

Gln Arg Arg Ala Ala Leu Ala Gly Ser Ala Gly Ser Ala Ala Ser
                165                 170                 175

Ser Gly Ala Glu Val Phe Tyr Lys Gly Ser Val Asp Cys Phe Lys Gln
            180                 185                 190

Val Leu Ser Lys His Gly Val Lys Gly Leu Tyr Arg Gly Val Thr Ser
        195                 200                 205

Thr Val Leu Arg Asp Met Gln Gly Tyr Ala Trp Phe Phe Leu Gly Tyr
    210                 215                 220

Glu Ala Thr Val Asn Tyr Phe Leu Gln Asn Ala Gly Pro Gly Val His
225                 230                 235                 240

Ser Lys Ala Asp Leu Asn Tyr Leu Gln Val Met Ala Ala Gly Val Val
                245                 250                 255

Ala Gly Phe Gly Leu Trp Gly Ser Met Phe Pro Ile Asp Thr Ile Lys
            260                 265                 270

Ser Lys Met Gln Ala Asp Ser Leu Val Lys Pro Gln Tyr Ser Thr Thr
        275                 280                 285

Tyr Asp Cys Val Arg Lys Val Leu Lys Thr Glu Gly Asn Asn Gly Leu
    290                 295                 300

Trp Arg Gly Phe Ser Ala Ala Met Tyr Arg Ala Ile Pro Val Asn Ala
305                 310                 315                 320

Gly Ile Phe Leu Ala Val Glu Thr Arg Gln Gly Ile Lys Leu Tyr
                325                 330                 335

Glu Glu Asn Val Glu His Ile Tyr Gly Gly Val Val Gly Thr Thr Thr
            340                 345                 350

Ala Ala

<210> SEQ ID NO 4
<211> LENGTH: 339
<212> TYPE: PRT
<213> ORGANISM: Volvox carteri

<400> SEQUENCE: 4

```
Met Asn Asp Thr Leu Asn Gln Val Glu His Thr Pro Pro Val His Lys
1               5                   10                  15

Arg Ile Leu Asp Ile Leu Pro Gly Ile Ser Gly Gly Val Ala Arg Val
            20                  25                  30

Met Ile Gly Gln Pro Phe Asp Thr Ile Lys Val Arg Leu Gln Val Leu
        35                  40                  45

Gly Gln Gly Thr Ala Leu Ala Ala Gln Leu Pro Pro Ser Glu Val Tyr
    50                  55                  60

Lys Asp Ser Leu Asp Cys Val Arg Lys Met Val Arg Asn Glu Gly Pro
65                  70                  75                  80

Leu Ser Phe Tyr Lys Gly Thr Val Ala Pro Leu Val Gly Asn Met Val
                85                  90                  95

Leu Leu Gly Ile His Phe Pro Thr Phe Ser Tyr Val Arg Lys Gln Leu
            100                 105                 110

Glu Gly Asp Asp His Tyr Thr Asn Phe Ser Tyr Thr Asn Thr Leu Leu
        115                 120                 125

Ser Gly Ala Ala Ala Gly Ala Ala Gly Ser Leu Val Ser Thr Pro Val
130                 135                 140

Glu Leu Val Arg Thr Lys Met Gln Leu Gln Ser Ala Ala Ser Ser Ala
145                 150                 155                 160

Ser Asp Glu Phe Tyr Lys Gly Ser Val Asp Cys Phe Lys Gln Val Leu
                165                 170                 175

Ser Lys Tyr Gly Ile Lys Gly Leu Tyr Arg Gly Phe Thr Ala Thr Val
            180                 185                 190

Leu Arg Asp Met Gln Gly Tyr Ala Trp Phe Phe Leu Gly Tyr Glu Ser
        195                 200                 205

Thr Val Asn Tyr Phe Leu Gln Lys Ala Gly Pro Gly Leu His Ser Lys
    210                 215                 220

Ala Asp Leu Asn Tyr Met Gln Val Met Ser Ala Gly Val Val Ala Gly
225                 230                 235                 240

Phe Gly Leu Trp Gly Ser Met Phe Pro Ile Asp Thr Val Lys Ser Lys
                245                 250                 255

Leu Gln Ala Asp Thr Leu Ala Thr Pro Gln Tyr Arg Ser Thr Tyr Asp
            260                 265                 270

Cys Leu Ser Lys Val Leu Lys Ser Glu Gly Gln Ala Gly Leu Trp Arg
        275                 280                 285

Gly Phe Ser Ala Ala Met Tyr Arg Ala Ile Pro Val Asn Ala Gly Ile
    290                 295                 300

Phe Leu Ala Val Glu Gly Thr Arg Gln Gly Ile Lys Trp Tyr Glu Glu
305                 310                 315                 320

Asn Val Glu His Leu Tyr Gly Gly Val Val Gly Pro Ala Thr Pro Ala
                325                 330                 335

Ala Thr Ser
```

<210> SEQ ID NO 5
<211> LENGTH: 353
<212> TYPE: PRT
<213> ORGANISM: Ettlia oleoabundans

<400> SEQUENCE: 5

```
Met Pro Ala Thr Ala Gln Val Asn Asp Thr Leu Met Glu Val Glu
1               5                   10                  15
```

His Thr Pro Val His Lys Arg Ile Leu Asp Ile Leu Pro Gly Val
            20                  25                  30

Ser Gly Gly Val Ala Arg Ile Met Val Gly Gln Pro Phe Asp Thr Ile
        35                  40                  45

Lys Thr Arg Leu Gln Val Leu Gly Lys Gly Thr Ile Gly Ala Ala Gly
 50                  55                  60

Met Pro Pro Glu Met Val Tyr Asn Ser Gly Met Asp Cys Val Arg Lys
 65                  70                  75                  80

Met Met Lys Ser Glu Gly Pro Met Ser Leu Tyr Lys Gly Thr Val Ala
                85                  90                  95

Pro Leu Leu Gly Asn Met Val Leu Leu Gly Ile His Phe Pro Thr Phe
            100                 105                 110

Thr Lys Thr Arg Ala Tyr Leu Glu Ala Gly Asp Ala Pro Gly Ser Phe
        115                 120                 125

Ser Pro Trp Lys Ile Leu Ala Ala Gly Ala Ala Gly Ala Ala Gly
130                 135                 140

Ser Val Val Ser Ser Pro Thr Glu Leu Ile Arg Thr Lys Met Gln Met
145                 150                 155                 160

Val Arg Lys Asn Asn Ile Leu Ala Gln Ile Lys Gly Ser Ala Ala Gly
                165                 170                 175

Gly Leu Asn Pro Glu Glu Asn Tyr Lys Gly Asn Trp Asp Cys Ala Lys
            180                 185                 190

Lys Ile Phe Arg Asn His Gly Leu Arg Gly Met Tyr Ser Gly Tyr Leu
        195                 200                 205

Ser Thr Leu Leu Arg Asp Met Gln Gly Tyr Ala Trp Phe Phe Phe Gly
210                 215                 220

Tyr Glu Ala Thr Ile His Tyr Leu Ala Gly Pro Gly Lys Thr Lys Ala
225                 230                 235                 240

Asp Leu Asp Tyr Ser Gln Val Met Leu Ala Gly Val Met Ala Gly Phe
                245                 250                 255

Gly Leu Trp Gly Ser Met Phe Pro Ile Asp Thr Ile Lys Ser Lys Ile
            260                 265                 270

Gln Ala Asp Ser Leu Ser Lys Pro Glu Phe Lys Gly Thr Leu Asp Cys
        275                 280                 285

Val Arg Arg Ser Val Gln Ile Glu Gly Tyr Gly Gly Leu Trp Arg Gly
290                 295                 300

Val Thr Ala Ala Leu Trp Arg Ala Ile Pro Val Asn Ala Ala Ile Phe
305                 310                 315                 320

Leu Ala Val Glu Gly Thr Arg Gln Leu Ile Ala Asp Thr Glu Glu Ser
                325                 330                 335

Ile Asp Ala Phe Val Asp Gln Val Ser Gly Lys Thr Ser Glu Ala Ala
            340                 345                 350

Leu

<210> SEQ ID NO 6
<211> LENGTH: 352
<212> TYPE: PRT
<213> ORGANISM: Erigeron breviscapus

<400> SEQUENCE: 6

Met Pro Ala Thr Pro Gln Leu Met Asn Glu Thr Leu Met Glu Val Glu
 1               5                  10                  15

His Thr Pro Ala Val His Lys Arg Ile Leu Asp Ile Leu Pro Gly Val
            20                  25                  30

```
Ser Gly Gly Val Ala Arg Ile Met Val Gly Gln Pro Phe Asp Thr Ile
            35                  40                  45

Lys Thr Arg Leu Gln Val Leu Gly Lys Gly Thr Ile Gly Ala Ala Gly
 50                  55                  60

Met Pro Pro Glu Met Val Tyr Thr Ser Gly Met Asp Cys Val Arg Lys
 65                  70                  75                  80

Met Ile Lys Ser Glu Gly Pro Leu Ser Leu Tyr Lys Gly Thr Ile Ala
                 85                  90                  95

Pro Leu Leu Gly Asn Met Val Leu Leu Gly Ile His Phe Pro Thr Phe
                100                 105                 110

His Lys Thr Arg Ala Tyr Leu Glu Arg Glu Asp Ala Pro Gly Thr His
                115                 120                 125

Thr Pro Trp Lys Ile Leu Ala Ala Gly Ala Thr Ala Gly Ala Ala Gly
130                 135                 140

Ser Ile Val Ser Thr Pro Thr Glu Leu Ile Arg Thr Lys Met Gln Met
145                 150                 155                 160

Val Arg Lys Asn Asn Ile Leu Gln Ile Lys Gly Ala Gly Ala Gly Ala
                165                 170                 175

Gly Leu Asn Pro Glu Glu Asn Tyr Lys Gly Asn Trp Asp Cys Ala Lys
                180                 185                 190

Lys Ile Phe Arg Asn His Gly Val Arg Gly Leu Tyr Ser Gly Tyr Leu
                195                 200                 205

Ser Thr Leu Leu Arg Asp Met Gln Gly Tyr Ala Trp Phe Phe Phe Gly
                210                 215                 220

Tyr Glu Ala Thr Ile His Tyr Leu Ala Gly Pro Gly Lys Thr Lys Ala
225                 230                 235                 240

Asp Leu Asp Tyr Thr Gln Val Met Leu Ala Gly Val Ile Ala Gly Phe
                245                 250                 255

Gly Leu Trp Gly Ser Met Phe Pro Ile Asp Thr Ile Lys Ser Lys Ile
                260                 265                 270

Gln Ala Asp Ser Leu Ser Lys Pro Glu Phe Lys Gly Thr Leu Asp Cys
                275                 280                 285

Leu Lys Arg Ser Leu Ala Val Glu Gly Gln Arg Gly Leu Trp Arg Gly
290                 295                 300

Val Thr Ala Ala Leu Trp Arg Ala Ile Pro Val Asn Ala Ala Ile Phe
305                 310                 315                 320

Leu Ala Val Glu Gly Thr Arg Gln Leu Ile Ala Asp Thr Glu Glu Ser
                325                 330                 335

Val Asp Lys Phe Val Asn Asn Leu Thr Gly Lys Glu Thr Ala Ala Val
                340                 345                 350

<210> SEQ ID NO 7
<211> LENGTH: 354
<212> TYPE: PRT
<213> ORGANISM: Zea nicaraguensis

<400> SEQUENCE: 7

Met Pro Ile Ala Thr Gly Gln Val Met Asn Asp Thr Leu Met Glu Val
 1               5                  10                  15

Glu His Thr Pro Pro Val His Lys Arg Ile Leu Asp Ile Leu Pro Gly
                 20                  25                  30

Val Ser Gly Gly Val Ala Arg Ile Met Val Gly Gln Pro Phe Asp Thr
            35                  40                  45

Ile Lys Thr Arg Leu Gln Val Leu Gly Ala Gly Thr Ile Gly Ala Gln
 50                  55                  60
```

Gly Met Pro Ala Asp Met Val Tyr Asn Asn Gly Met Asp Cys Val Arg
65                  70                  75                  80

Lys Met Ile Lys Ser Glu Gly Pro Gly Ser Leu Tyr Lys Gly Thr Val
            85                  90                  95

Ala Pro Leu Leu Gly Asn Met Val Leu Leu Gly Ile His Phe Pro Thr
            100                 105                 110

Phe Thr Lys Thr Arg Ala Tyr Leu Glu Gln Gly Asp Ala Pro Gly Thr
            115                 120                 125

Phe Ser Pro Trp Lys Ile Leu Ala Ala Gly Ala Ala Gly Ala Ala
            130                 135                 140

Gly Ser Val Val Ser Thr Pro Thr Glu Leu Ile Arg Thr Lys Met Gln
145                 150                 155                 160

Met Val Arg Lys Asn Asn Leu Met Ala Gln Met Lys Gly Ala Ala Ala
                165                 170                 175

Thr Leu Asn Pro Glu Glu Asn Tyr Lys Gly Asn Trp Asp Cys Ala Lys
            180                 185                 190

Lys Ile Leu Arg Asn His Gly Leu Arg Gly Ile Tyr Ser Gly Tyr Val
            195                 200                 205

Ser Thr Leu Leu Arg Asp Met Gln Gly Tyr Ala Trp Phe Phe Phe Gly
210                 215                 220

Tyr Glu Ala Thr Ile His Met Met Cys Thr Glu Gly Lys Thr Lys Ala
225                 230                 235                 240

Asp Leu Asn Phe Leu Gln Val Met Gly Ala Gly Val Ile Ala Gly Phe
            245                 250                 255

Gly Leu Trp Gly Ser Met Phe Pro Ile Asp Thr Ile Lys Ser Lys Ile
            260                 265                 270

Gln Ala Asp Ser Leu Ser Lys Pro Glu Phe Lys Gly Thr Met Asp Cys
            275                 280                 285

Leu Lys Arg Ser Leu Ala Val Glu Gly His Ala Gly Leu Trp Arg Gly
            290                 295                 300

Val Thr Ala Ala Leu Trp Arg Ala Ile Pro Val Asn Ala Ala Ile Phe
305                 310                 315                 320

Val Ala Val Glu Gly Thr Arg Gln Leu Ile Ala Asp Thr Glu Glu Ser
            325                 330                 335

Val Asp Ala Phe Val Asn Asn Leu Thr Gly Ser Gly Ser Thr Ala Ala
            340                 345                 350

Ala Val

<210> SEQ ID NO 8
<211> LENGTH: 141
<212> TYPE: PRT
<213> ORGANISM: Poa pratensis

<400> SEQUENCE: 8

Tyr Lys Gly Asn Trp Asp Cys Ala Lys Lys Ile Leu Arg Asn His Gly
1               5                   10                  15

Leu Arg Gly Ile Tyr Ser Gly Tyr Val Ser Thr Leu Leu Arg Asp Met
            20                  25                  30

Gln Gly Tyr Ala Trp Phe Phe Phe Gly Tyr Glu Ala Thr Ile His Tyr
            35                  40                  45

Leu Ala Gly Gln His Gly Lys Thr Lys Ala Asp Leu Glu Tyr Trp Gln
            50                  55                  60

Val Met Gly Ala Gly Val Met Ala Gly Phe Gly Leu Trp Gly Ser Met
65                  70                  75                  80

Phe Pro Ile Asp Thr Ile Lys Ser Lys Ile Gln Ala Asp Ser Leu Ser
                85                  90                  95

Lys Pro Glu Phe Lys Gly Thr Ile Asp Cys Leu Lys Arg Ser Leu Ala
            100                 105                 110

Val Glu Gly Tyr Ala Gly Met Trp Arg Gly Val Thr Ala Ala Leu Trp
        115                 120                 125

Arg Ala Ile Pro Val Asn Ala Ala Ile Phe Leu Ala Val
    130                 135                 140

<210> SEQ ID NO 9
<211> LENGTH: 354
<212> TYPE: PRT
<213> ORGANISM: Cosmos bipinnatus

<400> SEQUENCE: 9

Met Pro Ser Ala Thr Pro Gln Val Ile Asn Asp Thr Leu Met Glu Val
1               5                   10                  15

Glu His Thr Pro Ala Val His Lys Arg Ile Leu Asp Ile Leu Pro Gly
            20                  25                  30

Val Ser Gly Gly Val Ala Arg Ile Met Val Gly Gln Pro Phe Asp Thr
        35                  40                  45

Ile Lys Thr Arg Leu Gln Val Leu Gly Lys Gly Thr Ile Gly Ala Lys
    50                  55                  60

Gly Met Pro Ala Asp Met Val Tyr Asn Asn Gly Met Asp Cys Val Arg
65                  70                  75                  80

Lys Met Ile Lys Ser Glu Gly Ala Gly Ser Leu Tyr Lys Gly Thr Val
                85                  90                  95

Ala Pro Leu Leu Gly Asn Met Val Leu Leu Gly Ile His Phe Pro Thr
            100                 105                 110

Phe Thr Lys Thr Arg Ala Tyr Leu Glu Gln Gly Asp Ala Pro Gly Thr
        115                 120                 125

Phe Ser Pro Ala Lys Ile Leu Ala Ala Gly Ala Ala Gly Ala Ala
    130                 135                 140

Gly Ser Val Val Ser Thr Pro Thr Glu Leu Ile Arg Thr Lys Met Gln
145                 150                 155                 160

Met Val Arg Lys Asn Asn Ile Leu Ala Gln Met Lys Gly Ala Ala Ala
                165                 170                 175

Thr Leu Asn Pro Glu Glu Asn Tyr Lys Gly Asn Trp Asp Cys Ala Lys
            180                 185                 190

Lys Ile Leu Arg Asn His Gly Leu Arg Gly Ile Tyr Ser Gly Tyr Val
        195                 200                 205

Ser Thr Leu Leu Arg Asp Met Gln Gly Tyr Ala Trp Phe Phe Phe Gly
    210                 215                 220

Tyr Glu Ala Thr Ile His Met Met Cys Thr Asp Gly Lys Thr Lys Ala
225                 230                 235                 240

Asp Leu Asn Phe Leu Gln Val Met Gly Ala Gly Val Ile Ala Gly Phe
                245                 250                 255

Gly Leu Trp Gly Ser Met Phe Pro Ile Asp Thr Ile Lys Ser Lys Ile
            260                 265                 270

Gln Ala Asp Ser Leu Ser Lys Pro Glu Phe Lys Gly Thr Met Asp Cys
        275                 280                 285

Leu Lys Arg Ser Leu Ala Val Glu Gly His Ala Gly Leu Trp Arg Gly
    290                 295                 300

Val Thr Ala Ala Leu Trp Arg Ala Ile Pro Val Asn Ala Ala Ile Phe

```
                305                 310                 315                 320
Val Ala Val Glu Gly Thr Arg Gln Leu Ile Ala Asp Thr Glu Ser
                    325                 330                 335

Val Asp Ala Phe Val Asn Asn Leu Thr Gly Ser Ser Thr Thr Ala
                340                 345                 350

Ala Val

<210> SEQ ID NO 10
<211> LENGTH: 307
<212> TYPE: PRT
<213> ORGANISM: Talaromyces stipitatus

<400> SEQUENCE: 10

Met Ala Leu Glu Glu Phe Asp Lys Val Glu Gln Glu Leu Ser Gln Gly
1               5                   10                  15

Trp Val Arg Thr Ala Lys Asp Leu Phe Ala Gly Ala Ser Gly Gly Ile
                20                  25                  30

Thr Gln Val Leu Leu Gly Gln Pro Phe Asp Ile Val Lys Val Arg Leu
            35                  40                  45

Gln Thr Thr Ser Gln Tyr Ser Ser Ala Leu Asp Cys Ala Lys Gln Ile
        50                  55                  60

Phe Lys Asn Glu Gly Pro Leu Ala Phe Tyr Lys Gly Thr Leu Thr Pro
65                  70                  75                  80

Leu Ile Gly Ile Gly Ala Cys Val Ser Val Gln Phe Gly Ala Phe His
                    85                  90                  95

Gln Ala Arg Arg Tyr Phe Glu Glu Glu Asn Leu Lys Lys Ser Pro Leu
                100                 105                 110

Ser Pro Gly Leu Ser Tyr Thr Gln Tyr Tyr Leu Ala Gly Ala Phe Ala
            115                 120                 125

Gly Val Thr Asn Ser Val Ile Ser Gly Pro Ile Glu His Val Arg Ile
        130                 135                 140

Arg Leu Gln Ala Gln Pro His Gly Ala Gly Arg Leu Tyr Asn Gly Pro
145                 150                 155                 160

Met Asp Cys Val Arg Lys Leu Ser Ala His Asn Gly Val Leu Arg Gly
                    165                 170                 175

Leu Tyr Arg Gly Glu Val Val Thr Ile Leu Arg Glu Ala Gln Ala Tyr
                180                 185                 190

Gly Met Trp Phe Leu Ala Phe Glu Tyr Leu Met Asn Gln Asp Ala Lys
            195                 200                 205

Arg Asn Asn Ile Lys Arg Glu Asp Ile Ser Ser Leu Lys Val Ala Thr
210                 215                 220

Tyr Gly Gly Leu Ala Gly Glu Ala Leu Trp Ile Phe Ser Tyr Pro Phe
225                 230                 235                 240

Asp Val Val Lys Ser Lys Met Gln Thr Asp Gly Phe Gly Thr Glu Gln
                    245                 250                 255

Lys Tyr Lys Ser Met Thr Asp Cys Phe Lys Lys Thr Leu Ala Ala Glu
                260                 265                 270

Gly Tyr Ala Gly Phe Trp Lys Gly Leu Gly Pro Thr Leu Leu Arg Ala
            275                 280                 285

Met Pro Val Ser Ala Gly Thr Phe Ala Thr Val Glu Leu Val Met Arg
        290                 295                 300

Ala Met Gly
305
```

<210> SEQ ID NO 11
<211> LENGTH: 303
<212> TYPE: PRT
<213> ORGANISM: Saitoella complicata

<400> SEQUENCE: 11

Met Ser Ala Glu Pro Ala Phe Glu Glu His Ser Asn Gly Gly Val Val
1               5                   10                  15

Arg Ala Leu Lys Asp Cys Leu Ala Gly Thr Cys Gly Gly Ile Ala Gln
            20                  25                  30

Val Leu Val Gly Gln Pro Phe Asp Thr Val Lys Val Arg Leu Gln Thr
        35                  40                  45

Gln Pro Arg Thr Gly Gly Leu Tyr Thr Gly Ala Ile Asp Cys Val Gln
    50                  55                  60

Lys Thr Phe Lys Ala Glu Gly Phe Gly Gly Phe Tyr Lys Gly Thr Ala
65                  70                  75                  80

Thr Pro Leu Val Gly Val Gly Leu Cys Val Ser Val Gln Phe Ala Val
                85                  90                  95

Phe Glu His Met Lys Arg Val Phe Arg Glu Arg Asn Gly Gly Glu Gly
            100                 105                 110

Leu Ser Gly Gly Gln Phe Tyr Ile Ala Gly Ala Ala Gly Ile Ala
        115                 120                 125

Asn Ser Ala Leu Ala Cys Pro Ile Glu His Val Arg Ile Arg Leu Gln
130                 135                 140

Thr Gln Thr Ala Thr Asn Ala Leu Tyr Asn Gly Pro Ile Asp Cys Ile
145                 150                 155                 160

Lys Lys Ile Tyr Ser Ser Tyr Gly Ile Arg Gly Ile Phe Lys Gly Tyr
                165                 170                 175

Gly Pro Thr Phe Ile Arg Glu Gly His Gly Met Gly Ala Tyr Phe Leu
            180                 185                 190

Ala Tyr Glu Ala Leu Val Asn Ser Asp Met Ser Lys Asn Ser Ile Thr
        195                 200                 205

Arg Asp Gln Ile Pro Ala Tyr Arg Leu Cys Leu Tyr Gly Ala Gly Ala
    210                 215                 220

Gly Tyr Ala Met Trp Phe Thr Ser Tyr Pro Ile Asp Val Ile Lys Ser
225                 230                 235                 240

Arg Leu Gln Thr Asp Gly Phe Ala Gly Glu Ala Lys Lys Tyr Leu Ser
                245                 250                 255

Gly Arg Asp Cys Leu Arg Lys Thr Trp Lys Gly Glu Gly Met Gly Gly
            260                 265                 270

Phe Trp Arg Gly Phe Gly Pro Thr Val Val Arg Ala Ala Pro Val Asn
        275                 280                 285

Ala Ala Thr Phe Leu Val Phe Glu Ala Ala Met Arg Ala Met Asn
    290                 295                 300

<210> SEQ ID NO 12
<211> LENGTH: 324
<212> TYPE: PRT
<213> ORGANISM: Triticum aestivum

<400> SEQUENCE: 12

Met Glu Phe Trp Pro Glu Phe Leu Ala Ser Ser Gly Gly His Glu Phe
1               5                   10                  15

Val Ala Gly Gly Val Gly Gly Met Ala Gly Val Leu Ala Gly His Pro
            20                  25                  30

Leu Asp Thr Leu Arg Ile Arg Leu Gln Gln Pro Pro Arg Pro Val Ser

```
                35                  40                  45
Pro Gly Ile Thr Ala Ala Arg Val Thr Arg Pro Pro Ser Ala Val Ala
 50                  55                  60

Leu Leu Arg Gly Ile Leu Arg Ala Glu Gly Pro Ser Ala Leu Tyr Arg
 65                  70                  75                  80

Gly Met Gly Ala Pro Leu Ala Ser Val Ala Phe Gln Asn Ala Met Val
                 85                  90                  95

Phe Gln Val Tyr Ala Ile Leu Ser Arg Ser Leu Asp Arg Arg Met Ser
            100                 105                 110

Thr Ser Glu Pro Pro Ser Tyr Thr Ser Val Ala Leu Ala Gly Val Gly
        115                 120                 125

Thr Gly Ala Leu Gln Thr Leu Ile Leu Ser Pro Val Glu Leu Val Lys
    130                 135                 140

Ile Arg Leu Gln Leu Glu Ala Ala Gly Arg Lys Arg Gln Gly Pro Val
145                 150                 155                 160

Asp Met Ala Arg Asp Ile Met Arg Arg Glu Gly Leu Arg Gly Ile Tyr
                165                 170                 175

Arg Gly Leu Thr Val Thr Ala Leu Arg Asp Ala Pro Ser His Gly Val
            180                 185                 190

Tyr Phe Trp Thr Tyr Glu Tyr Ala Arg Glu Arg Leu His Pro Gly Cys
        195                 200                 205

Arg Arg Thr Gly Gln Glu Ser Leu Ala Thr Met Leu Val Ser Gly Gly
    210                 215                 220

Leu Ala Gly Val Ala Ser Trp Val Cys Cys Tyr Pro Leu Asp Val Val
225                 230                 235                 240

Lys Ser Arg Leu Gln Ala Gln Thr Gln Thr His Pro Pro Ser Pro Arg
                245                 250                 255

Tyr Arg Gly Val Val Asp Cys Phe Arg Lys Ser Val Arg Glu Glu Gly
            260                 265                 270

Leu Pro Val Leu Trp Arg Gly Leu Gly Thr Ala Val Ala Arg Ala Phe
        275                 280                 285

Val Val Asn Gly Ala Ile Phe Ser Ala Tyr Glu Leu Ala Leu Arg Phe
    290                 295                 300

Leu Val Arg Asn Asn Gly Arg Gln Thr Leu Val Met Glu Glu Met Lys
305                 310                 315                 320

Cys His Asp His

<210> SEQ ID NO 13
<211> LENGTH: 323
<212> TYPE: PRT
<213> ORGANISM: Solanum tuberosum

<400> SEQUENCE: 13

Met Cys Asp Glu Leu Ser Arg Cys Leu Ile Trp Cys Cys Leu Arg Ser
 1                   5                  10                  15

Ala Ser Ile Ser Pro Ile Ser Val Phe Ser Gln Met Asp Ile Met Lys
                 20                  25                  30

Asp Leu Thr Ala Gly Thr Val Gly Gly Ala Ala Gln Leu Ile Val Gly
            35                  40                  45

His Pro Phe Asp Thr Ile Lys Val Lys Leu Gln Ser Gln Pro Thr Pro
        50                  55                  60

Leu Pro Gly Gln Pro Pro Lys Tyr Ala Gly Ala Ile Asp Ala Val Arg
 65                  70                  75                  80

Lys Thr Val Ala Ser Glu Gly Pro Arg Gly Leu Tyr Lys Gly Met Gly
```

```
            85                  90                  95
Ala Pro Leu Ala Thr Val Ala Ala Phe Asn Ala Leu Leu Phe Thr Val
            100                 105                 110

Arg Gly Gln Thr Glu Ala Leu Leu Arg Ser Glu Pro Gly Ala Pro Leu
            115                 120                 125

Thr Val Lys Gln Gln Ile Leu Cys Gly Ala Val Ala Gly Thr Ala Ala
        130                 135                 140

Ser Phe Leu Ala Cys Pro Thr Glu Leu Ile Lys Cys Arg Leu Gln Ala
145                 150                 155                 160

His Ser Ala Leu Ala Ser Val Gly Ser Ala Ser Val Ala Ile Lys Tyr
                165                 170                 175

Thr Gly Pro Met Asp Val Ala Arg His Val Leu Arg Ser Glu Gly Gly
            180                 185                 190

Val Arg Gly Leu Phe Lys Gly Met Cys Pro Thr Leu Ala Arg Glu Val
            195                 200                 205

Pro Gly Asn Ala Val Met Phe Gly Val Tyr Glu Ala Leu Lys Gln Tyr
        210                 215                 220

Phe Ala Gly Gly Met Asp Thr Ser Gly Leu Gly Arg Gly Ser Leu Ile
225                 230                 235                 240

Val Ala Gly Gly Leu Ala Gly Gly Ser Val Trp Phe Ala Val Tyr Pro
                245                 250                 255

Thr Asp Val Ile Lys Ser Val Ile Gln Val Asp Asp Tyr Arg Ser Pro
            260                 265                 270

Lys Tyr Ser Gly Ser Phe Asp Ala Leu Lys Lys Ile Leu Ala Ser Glu
            275                 280                 285

Gly Val Lys Gly Leu Tyr Lys Gly Phe Gly Pro Ala Ile Thr Arg Ser
        290                 295                 300

Ile Pro Ala Asn Ala Ala Cys Phe Leu Ala Tyr Glu Met Thr Arg Ser
305                 310                 315                 320

Ser Leu Gly

<210> SEQ ID NO 14
<211> LENGTH: 297
<212> TYPE: PRT
<213> ORGANISM: Glycine max

<400> SEQUENCE: 14

Met Gly Asp Val Ala Lys Asp Leu Thr Ala Gly Thr Val Gly Gly Ala
1               5                   10                  15

Ala Gln Leu Ile Val Gly His Pro Phe Asp Thr Ile Lys Val Lys Leu
            20                  25                  30

Gln Ser Gln Pro Thr Pro Leu Pro Gly Gln Leu Pro Lys Tyr Ser Gly
        35                  40                  45

Ala Ile Asp Ala Val Lys Gln Thr Val Ala Ala Glu Gly Pro Arg Gly
    50                  55                  60

Leu Tyr Lys Gly Met Gly Ala Pro Leu Ala Thr Val Ala Ala Phe Asn
65                  70                  75                  80

Ala Val Leu Phe Thr Val Arg Gly Gln Met Glu Ala Leu Leu Arg Ser
                85                  90                  95

His Pro Gly Ala Thr Leu Thr Ile Asn Gln Val Val Cys Gly Ala
            100                 105                 110

Gly Ala Gly Val Ala Val Ser Phe Leu Ala Cys Pro Thr Glu Leu Ile
        115                 120                 125

Lys Cys Arg Leu Gln Ala Gln Ser Val Leu Ala Gly Thr Gly Thr Ala
```

```
            130                 135                 140
Ala Val Ala Val Lys Tyr Gly Pro Met Asp Val Ala Arg Gln Val
145                 150                 155                 160

Leu Arg Ser Glu Gly Val Lys Gly Leu Phe Lys Gly Leu Val Pro
                165                 170                 175

Thr Met Ala Arg Glu Val Pro Gly Asn Ala Ala Met Phe Gly Val Tyr
                180                 185                 190

Glu Ala Leu Lys Arg Leu Leu Ala Gly Thr Asp Thr Ser Gly Leu
                195                 200                 205

Gly Arg Gly Ser Leu Met Leu Ala Gly Gly Val Ala Gly Ala Ala Phe
210                 215                 220

Trp Leu Met Val Tyr Pro Thr Asp Val Val Lys Ser Val Ile Gln Val
225                 230                 235                 240

Asp Asp Tyr Lys Asn Pro Lys Phe Ser Gly Ser Ile Asp Ala Phe Arg
                245                 250                 255

Arg Ile Ser Ala Ser Glu Gly Ile Lys Gly Leu Tyr Lys Gly Phe Gly
                260                 265                 270

Pro Ala Met Ala Arg Ser Val Pro Ala Asn Ala Ala Cys Phe Leu Ala
                275                 280                 285

Tyr Glu Met Thr Arg Ser Ala Leu Gly
                290                 295

<210> SEQ ID NO 15
<211> LENGTH: 296
<212> TYPE: PRT
<213> ORGANISM: Oryza sativa

<400> SEQUENCE: 15

Met Gly Asp Val Val Lys Asp Leu Val Ala Gly Thr Val Gly Gly Ala
1               5                   10                  15

Ala Asn Leu Ile Val Gly His Pro Phe Asp Thr Ile Lys Val Lys Leu
                20                  25                  30

Gln Ser Gln Pro Thr Pro Ala Pro Gly Gln Phe Pro Lys Tyr Ala Gly
                35                  40                  45

Ala Val Asp Ala Val Lys Gln Thr Ile Ala Thr Glu Gly Pro Arg Gly
            50                  55                  60

Leu Tyr Lys Gly Met Gly Ala Pro Leu Ala Thr Val Ala Ala Phe Asn
65                  70                  75                  80

Ala Leu Leu Phe Thr Val Arg Gly Gln Met Glu Ala Leu Leu Arg Ser
                85                  90                  95

Glu Pro Gly Gln Pro Leu Thr Val Asn Gln Val Val Ala Gly Ala
                100                 105                 110

Gly Ala Gly Val Ala Val Ser Phe Leu Ala Cys Pro Thr Glu Leu Ile
            115                 120                 125

Lys Cys Arg Leu Gln Ala Gln Ser Ala Leu Ala Glu Ala Ala Ala
            130                 135                 140

Ser Gly Val Ala Leu Pro Lys Gly Pro Ile Asp Val Ala Lys His Val
145                 150                 155                 160

Val Arg Glu Ala Gly Met Lys Gly Leu Phe Lys Gly Leu Val Pro Thr
                165                 170                 175

Met Gly Arg Glu Val Pro Gly Asn Ala Val Met Phe Gly Val Tyr Glu
                180                 185                 190

Gly Thr Lys Gln Tyr Leu Ala Gly Gly Gln Asp Thr Ser Asn Leu Gly
                195                 200                 205
```

Arg Gly Ser Leu Ile Leu Ser Gly Gly Leu Ala Gly Ala Val Phe Trp
    210                 215                 220

Leu Ser Val Tyr Pro Thr Asp Val Val Lys Ser Val Ile Gln Val Asp
225                 230                 235                 240

Asp Tyr Lys Lys Pro Arg Tyr Ser Gly Ser Val Asp Ala Phe Lys Lys
                245                 250                 255

Ile Leu Ala Ala Asp Gly Val Lys Gly Leu Tyr Lys Gly Phe Gly Pro
            260                 265                 270

Ala Met Ala Arg Ser Val Pro Ala Asn Ala Ala Thr Phe Leu Ala Tyr
        275                 280                 285

Glu Ile Thr Arg Ser Ala Leu Gly
    290                 295

<210> SEQ ID NO 16
<211> LENGTH: 296
<212> TYPE: PRT
<213> ORGANISM: Zea mays

<400> SEQUENCE: 16

Met Gly Asp Val Ala Lys Asp Leu Thr Ala Gly Thr Val Gly Gly Ala
1               5                   10                  15

Ala Asn Leu Ile Val Gly His Pro Phe Asp Thr Ile Lys Val Lys Leu
            20                  25                  30

Gln Ser Gln Pro Thr Pro Ala Pro Gly Gln Leu Pro Lys Tyr Ala Gly
        35                  40                  45

Ala Ile Asp Ala Val Lys Gln Thr Val Ala Ala Glu Gly Pro Arg Gly
    50                  55                  60

Leu Tyr Lys Gly Met Gly Ala Pro Leu Ala Thr Val Ala Ala Phe Asn
65                  70                  75                  80

Ala Val Leu Phe Ser Val Arg Gly Gln Met Glu Ala Phe Leu Arg Ser
                85                  90                  95

Glu Pro Gly Val Pro Leu Thr Val Lys Gln Gln Val Val Ala Gly Ala
            100                 105                 110

Gly Ala Gly Ile Ala Val Ser Phe Leu Ala Cys Pro Thr Glu Leu Ile
        115                 120                 125

Lys Cys Arg Leu Gln Ala Gln Ser Ser Leu Ala Glu Ala Ala Thr Ala
    130                 135                 140

Ser Gly Val Ala Leu Pro Lys Gly Pro Ile Asp Val Ala Lys His Val
145                 150                 155                 160

Val Arg Asp Ala Gly Ala Lys Gly Leu Phe Lys Gly Leu Val Pro Thr
                165                 170                 175

Met Gly Arg Glu Val Pro Gly Asn Ala Leu Met Phe Gly Val Tyr Glu
            180                 185                 190

Ala Thr Lys Gln Tyr Leu Ala Gly Gly Pro Asp Thr Ser Gly Leu Gly
        195                 200                 205

Arg Gly Ser Gln Val Leu Ala Gly Gly Leu Ala Gly Ala Ala Phe Trp
    210                 215                 220

Leu Ser Val Tyr Pro Thr Asp Val Val Lys Ser Val Ile Gln Val Asp
225                 230                 235                 240

Asp Tyr Lys Lys Pro Lys Tyr Ser Gly Ser Leu Asp Ala Leu Arg Lys
                245                 250                 255

Ile Val Ala Ala Asp Gly Val Lys Gly Leu Tyr Lys Gly Phe Gly Pro
            260                 265                 270

Ala Met Ala Arg Ser Val Pro Ala Asn Ala Ala Thr Phe Val Ala Tyr
        275                 280                 285

Glu Ile Thr Arg Ser Ala Leu Gly
    290                 295

<210> SEQ ID NO 17
<211> LENGTH: 296
<212> TYPE: PRT
<213> ORGANISM: Sorghum bicolor

<400> SEQUENCE: 17

Met Gly Asp Val Ala Arg Asp Leu Thr Ala Gly Thr Val Gly Gly Val
1               5                   10                  15

Ala Asn Leu Val Val Gly His Pro Phe Asp Thr Ile Lys Val Lys Leu
            20                  25                  30

Gln Ser Gln Pro Thr Pro Ala Pro Gly Gln Leu Pro Lys Tyr Ala Gly
        35                  40                  45

Ala Ile Asp Ala Val Lys Gln Thr Ile Ala Ala Glu Gly Pro Arg Gly
    50                  55                  60

Leu Tyr Lys Gly Met Gly Ala Pro Leu Ala Thr Val Ala Ala Phe Asn
65                  70                  75                  80

Ala Leu Leu Phe Ser Val Arg Gly Gln Met Glu Ala Leu Leu Arg Ser
                85                  90                  95

Glu Pro Gly Val Pro Leu Thr Val Lys Gln Gln Val Val Ala Gly Ala
            100                 105                 110

Gly Ala Gly Ile Ala Val Ser Phe Leu Ala Cys Pro Thr Glu Leu Ile
        115                 120                 125

Lys Cys Arg Leu Gln Ala Gln Ser Ser Leu Ala Glu Ala Ala Ala Ala
    130                 135                 140

Ser Gly Val Ala Leu Pro Lys Gly Pro Ile Asp Val Ala Lys His Val
145                 150                 155                 160

Val Arg Asp Ala Gly Ala Lys Gly Leu Phe Lys Gly Leu Val Pro Thr
                165                 170                 175

Met Gly Arg Glu Val Pro Gly Asn Ala Met Met Phe Gly Val Tyr Glu
            180                 185                 190

Ala Thr Lys Gln Tyr Leu Ala Gly Gly Pro Asp Thr Ser Asn Leu Gly
        195                 200                 205

Arg Gly Ser Gln Ile Leu Ala Gly Leu Ala Gly Ala Ala Phe Trp
    210                 215                 220

Leu Ser Val Tyr Pro Thr Asp Val Val Lys Ser Val Ile Gln Val Asp
225                 230                 235                 240

Asp Tyr Lys Lys Pro Arg Tyr Ser Gly Ser Leu Asp Ala Leu Arg Lys
                245                 250                 255

Ile Val Ala Ala Asp Gly Val Lys Gly Leu Tyr Lys Gly Phe Gly Pro
            260                 265                 270

Ala Met Ala Arg Ser Val Pro Ala Asn Ala Ala Thr Phe Val Ala Tyr
        275                 280                 285

Glu Ile Thr Arg Ser Ala Leu Gly
    290                 295

<210> SEQ ID NO 18
<211> LENGTH: 7
<212> TYPE: PRT
<213> ORGANISM: Chlamydomonas reinhardtii

<400> SEQUENCE: 18

Leu Leu Gly Ile His Phe Pro
1               5

<210> SEQ ID NO 19
<211> LENGTH: 11
<212> TYPE: PRT
<213> ORGANISM: Chlamydomonas reinhardtii

<400> SEQUENCE: 19

Leu Arg Asp Met Gln Gly Tyr Ala Trp Phe Phe
1               5                   10

<210> SEQ ID NO 20
<211> LENGTH: 10
<212> TYPE: PRT
<213> ORGANISM: Chlamydomonas reinhardtii

<400> SEQUENCE: 20

Ala Gly Phe Gly Leu Trp Gly Ser Met Phe
1               5                   10

<210> SEQ ID NO 21
<211> LENGTH: 6
<212> TYPE: PRT
<213> ORGANISM: Chlamydomonas reinhardtii

<400> SEQUENCE: 21

Ala Ile Pro Val Asn Ala
1               5

<210> SEQ ID NO 22
<211> LENGTH: 1500
<212> TYPE: DNA
<213> ORGANISM: Zea mays

<400> SEQUENCE: 22

```
agttttcgct tgtctattca ccctctatag gcaactttca attatgtaat cacttttttt    60
ttcttttttc tgtttaaaat ctcagtttca aacttccaat tgattttgaa tacgaggttt   120
gggtttaaat tcatattgga ggcaaaaatc gaaagttcca cgtgatgcta ggttttattt   180
cggttttcta tctcctattg tttttcacgt ttcaacttga ttcaaattct agttttttt    240
aacttaagca caattaaata caacataaaa acaacatgga ttcaagttct atttcaattt   300
ttattaacta ttatgttgtc tagtctgttc aagcacataa tacttataaa tataaaatta   360
aacgaaatca catatttcca caaatcttgg gtactacact cggagacgac gatggattcc   420
atctcaattt ggatgttgat tatagctcta tttcagttgt cactgttgtc ctaacacgcc   480
ctattgtgca tgatagtgca cgtgctcaac gtaaaagaaa agagatcagt aacaagtagc   540
agcactgtac aaggtaagcc gtgattcaat taaaactgtt tgagcaattc agttgctaga   600
tcgttccacc atcgataatt cgatatgtac gatgatataa aaagagccca taagtttgtc   660
ttgaaaggt tgatcaaata atttaaatta gatgataaaa acatggaag atgtgggagt    720
ggacgacggc tatgaagaat agtactatat caggtttata cgtaaaattt attttttgaaa   780
tgttttata atctgtttga attgtatttt ttgcttaatt atgtgattgg atgttttttc    840
atgaaatgtc gagttttatt ttaaataaaa ttctgtaaag agaagttgct gcgctgagaa    900
aactataaat cgatagtaaa ggctgtacgc aacgtttaag tccttgtttg aatgcgtatg    960
aatctgagaa agttcagaat gattaaatct ttttattta attttaattt gagagagatt   1020
aagttctctc caattctctt taatttagac gtaatcgaac aagctggttg ccaaactaga   1080
tgagtacatt ttgtccactg ccatagagcc atcgactaca aaagtctaga acacagtgga   1140
```

```
aagcaccaga caacgcgcga ccaaaagggc ccaggcccca gcgccccagt ccggggggttg    1200 tgttcgccga cctgtgcgtg cctgctcgtc acgtcacgtc cctatttgcc cgtcttcctc    1260
ccctccagac ccttctcgaa cgccccttcg ttctggatcc aacggtcggt ctctgccggg    1320
ctcgaacgtt ctcgaaacca cgtcaccccc gataaaaccc cacgcacagc ctcctccctt    1380
cctcaaccat cattgcaaaa gcgaagcaag caatccgaat tctctgcgat ttctctagat    1440
ctcgaccacc cctactagtt ttggttcctc ctttcgttcg agagagcgtt tctagtggca    1500
```

<210> SEQ ID NO 23
<211> LENGTH: 1500
<212> TYPE: DNA
<213> ORGANISM: Zea mays

<400> SEQUENCE: 23

```
caacttacaa gcgatgaggc caagacgatt agacgaatag ctacagaaca agacaatgag     60
agttcagcac tcactttttg ccagttcctt ctccttggca gcagccaggc gcttgagttt    120
agcagcttgt gcaaatgtgg acggcctaca gcagacatac aggcaaagaa gcgaggagta    180
atttgcagtt ggaaatcatt cttcgatcaa tagggaaact ctgagtcaca gcgaaaggaa    240
ggttaattgc ctacgttgac aactgatcag cctccttgag aagttgcttg atttcaagcc    300
gcactttgat ctgctcatca ctaagtcctc cgctctggat gacaaaagca cagaacgcat    360
gagtggcaag tggaaacact agagcgaaat aaatacaaaa ccgcagacta caggctaaca    420
gatagggaga ccgggaagac aaagactcga gcctgcattc aacagttaca gtcgcctcgg    480
ccaaaggttg agaaatttgc atcaaaatcc aaactgtcta gggccatggg aaatagttcc    540
tcggaatcag agttcaattc atggacgaaa tagatggaac tgatggtagg ctactcttcc    600
gcccaatcag aattcacgga agatccaggt ctcgagacta ggagacggat gggaggcgca    660
acgcgcgatg ggggaggggg cggcgctgac ctttctggcg aggtcgaggt agcggtagag    720
cagctgcagc gcggacacga tgaggaagac gaagatagcc gccagggaca tggtcgccgg    780
cggcggcgga gcgaggctga gccggtctct ccggcctccg atcggcgtta agttggggat    840
cgtaacgtga cgtgtctcct ctccacagat cgacacaacc ggcctactcg ggtgcacgac    900
gccgcgacaa gggtgagatg tccgtgcacg cagcccgttt ggagtcctcg ttgcccacga    960 accgaccccct tacagaacaa ggcctagccc aaaactattc tgagttgagc ttttgagcct   1020
agcccaccta gccgagcgt catgaactga tgaacccact accactagtc aaggcaaacc    1080
acaaccacaa atggatcaat tgatctagaa caatccgaag gaggggaggc cacgtcacac    1140
tcacaccaac cgaaatatct gccagtatca gatcaaccgg ccaataggac gccagcgagc    1200
ccaacaccta gcgacgccgc aaaattcacc gcgaggggca ccgggcacgg caaaaacaaa    1260
agcccggcgc ggtgagaata tctggcgact ggcggagacc tggtggccag cgcgcggcca    1320
catcagccac cccatccgcc cacctcacct ccggcgagcc aatggcaact cgtcttaaga    1380
ttccacgaga taaggacccg atcgccggcg acgctattta gccaggtgcg cccccacgg    1440 tacactccac cagcggcatc tatagcaacc ggtccaacac tttcacgctc agcttcagca    1500
```

<210> SEQ ID NO 24
<211> LENGTH: 1500
<212> TYPE: DNA
<213> ORGANISM: Zea mays

<400> SEQUENCE: 24

```
tctcataaaa gcaataaaac aatatctcac aaaatacaag tggcaaacat tatacaaaca    60
tacacatagt cagaaagtca caactcagga ccttaaaaaa tgaaactatc cgattgaaaa   120
tacattgata acaattgaac actagaaaat aatatcacaa atcaaactat ggagcatata   180
actagccata taactcttat aatacaataa taaaatcatc atatatttaa ataaaacact   240
agcaagtcta ataacatatg actatagaat caagatgtgt atgatgacat gacacttgca   300
attttatcat ctcctactac tcgacatagt caatataatt gatgtcctcc ttatctttaa   360
agtttccatg cgaattataa atatatgtat gaagagtaat gattgataag aaactataaa   420
taagagtcac aatagttcaa acaactctaa actatatatc attagataga tcttgatttt   480
agaaaaataa cgaaatcagt ttcataattt tctaagttaa gatgaattta caaagattag   540
tttagattta atatttttc tgaaaaaata ccgatttcgg aaacgggcaa aagagatcca   600
aactatttct gttttttttt accgatttca tttccgtatt ttcggtaacg gtttccggtt   660
tcgtatgacc ctaaattttg gtaaagtttc gaaaaaaaat attttaagaa ctgaaaatta   720
acgttcctgt tttcatccat actaatggct ctttaccgct aaaatgttgc ccacaatcat   780
tgagtaggtt tagacgtgag agcaaacagt acaacattac gattcgccct tgcccaaatt   840
tacatgcctt ttccctacgg aaacaacata gaatcaagtt gacggggtta cttacattga   900
agtggccaaa ctgatggtag ctgtagattt ggatgtatgt tttctataaa ttagtcaaaa   960
ttgagacaaa ataaactgca atttaaaact gaggaaatag taaaaaaaag gtgaagaagg  1020
gaggaagagg aaatcagaag caaaaaatgg gcaactttag gcccattatc tcgatggtct  1080
cgtcggagtc cagatatgtg attgacggat tggattgggc cgtacatctt gcatgagagt  1140
tcgccaagat ttcattgttt aacaagaagc gcgtgacaac aaaaccaagc ctatctcatc  1200 cactctttt ttcccttccc acaatggcaa gtggcagctc ctgattcgct ctggccattc  1260
ctacgtggca cacaccagga ttcttgtgtg ataggccact gggtcccacc caccaggtgc  1320
cacatcagac gccaagccat cccggcagaa ccaatcccag cccagcaaca gatggtctgc  1380
tatccagttc caactgtata aaagcagctg ctgtgttctg ttaatggcac agccatcaca  1440
cgcacgcata cacagcacag agtgaggtaa gcatccgaaa aaagctgtga tctgatcgac  1500
```

<210> SEQ ID NO 25
<211> LENGTH: 1500
<212> TYPE: DNA
<213> ORGANISM: Zea mays

<400> SEQUENCE: 25

```
cgagaatata tgttatcttc gtcgttagag aaatctagac agtatacaac aagatccacg    60
tactacaggt aaacttttag gggtattgtg aacaagagga tgagtaaact ctaaaagaac   120
aaagctccaa tgaaaattta ggttttatg tggttagtca tagggcaagt tgcaaacagg   180
tgttgatcta aaaaggaagt agtagggaaa tgtgaagtgt ctttgcgagg aattggaaaa   240
tgaagatcac attttctttg ggtgcatcat gggaagaacc atttgggact cttttaagga   300
ggcctaagaa tgccataaag tttgcaagat cttttttgaag agtgtctacc tataaacaat   360
agtaaatatc atgtcaaaat tttcatcttc gccattattc tttaggagaa tttagaatgt   420
tccgaataaa atatggatag aaaagaagtt cccaaagtca tccaattttc tacaaaatct   480
tcaactttaa gattgagagt gggtgttgta aagttcttgg aagatgagtt gaaccccatg   540
gaggcgttgg ctaaagtact gaaagcaatc taaagacatg gaggtggaag gcctgacgta   600
gatagagaag atgctcttag ctttcattgt ctttcttttg tagtcatctg atttacctct   660
```

```
ctcgttttata caactggttt tttaaacact ccttaacttt tcaaattgtc tctttctttta    720 ccctagacta gataattta atggtgattt tgctaatgtg gcgccatgtt agatagaggt       780
aaaatgaact agttaaaagc tcagagtgat aaatcaggct ctcaaaaatt cataaactgt     840
tttttaaata tccaaatatt tttacatgga aaataataaa atttagttta gtattaaaaa    900
attcagttga atatagtttt gtcttcaaaa attatgaaac tgatcttaat tattttttcct   960 taaaaccgtg ctctatcttt gatgtctagt ttgagacgat tatataattt ttttgtgct     1020 taactacgac gagctgaagt acgtagaaat actagtggag tcgtgccgcg tgtgcctgta    1080
gccactcgta cgctacagcc caagcgctag agcccaagag gccggaggtg gaaggcgtcg    1140
cggcactata gccactcgcc gcaagagccc aagaggccgg agctggaagg atgagggtct    1200
gggtgttcac gaattgcctg gaggcaggag gctcgtcgtc cggagccaca ggcgtggaga    1260
cgtccgggat aaggtgagca gccgctgcga taggggcgcg tgtgaacccc gtcgcgcccc    1320
acggatggta taagaataaa ggcattccgc gtgcaggatt cacccgttcg cctctcacct    1380
tttcgctgta ctcactcgcc acacacaccc cctctccagc tccgttggag ctccggacag    1440
cagcaggcgc ggggcggtca cgtagtaagc agctctcggc tccctctccc cttgctccat   1500
```

<210> SEQ ID NO 26
<211> LENGTH: 1500
<212> TYPE: DNA
<213> ORGANISM: Zea mays

<400> SEQUENCE: 26

```
cgataagaac aatgttggac acaacttaag tctgttttac aacaatgtct ctcaaaacta     60
tagttttaca atattatact ttgcaattat catgacaata atgtagtttc ggtagctcca    120
aaaatacagt agttttgaga acattgtttt agatacaata ttataaatca tgtattagac   180
aaaagatagc catgccatta aaactttgaa ttggactgta gttttttcaa tactccaaaa    240
atattatggt acctagaata cgatgtctag aaaacatatt ttttaaaatg caaccaaaca    300
tcatatgaca taaataatat agtattttt tgaaaaccat ggtattacct aaaaactaca    360
gaatacttca ttctgaaata ggtcctaaca agttgcagca gctaggtcgt acatcagcaa    420
atagctactt catcaatctc agaataaaca tattttatag atgagttaaa ctaaaaatat    480
agaagaacaa cgtacacgcg ttgaatcaca acgtagcgcg atatccattc aacttttttgg   540 aagtttttac tgagcacaaa ttcgaaaatg ggaagcgcca cgtaacacga gcgctgggcc    600
aatttctgcc agtgccagtt atcccggccc acatccaatc ctggggaaga cgcgaacccg    660
gctccgcggc acgagttgtc cgcacgtacg gcacgtcggg gctggctcgt ccgcccgcga    720
gtgggaggcc actgtttcct ctgcctcacc gggtcgtgtg gcggaggggc gtggggccat    780
ggttcgcagc gcggggcgac gagcgcgctc ctcctctcgc gcagcgccag cgccaccccg    840
caccgtggct ttatatacac ccctcctccc aaccctaccg aatcatcact accaccgctc    900
tctcttcctc tcctccatct ctcaacgcct gaagctcacc gcacctcccc tcctcgccgc    960
ggatccccca ctactccggt aaccgtctct ccattcaccc tgcctgctgt ctcgctagaa   1020
tcgcctgcct ctgccagcgc cgtgacgcgg gggcgcggta tggctctccc agatccgcct   1080
ggcattgctc gctcgggtcg tgccaggccg atctgatctc gcatttgctg cgcgctcctc   1140
ctgctgcgga tccaccggga tctcgctgga atcgagcgc gcgtctcttt gaaatgccgc    1200
agatctgcgt gcttgcgcgc gtgatctaag tccgggcctt tcgttaacga aatggtccga   1260
```

```
tctgtggttt ggtggaggca atgccatggt ttttccccgt gaattttttt tgctgatttt    1320
aggagctttt ttctactgtc ctatgttagt aggacaaaaa aaaagaaaca tagattagct    1380
tcaataggcg ccttttagaa cagattctgt acagcaactc gtggaaacaa atctgcttcc    1440
ttaatgatgt tgcttgtttt aacaaatgcg gcatcgggcg agcttttctg taggtagaaa    1500

<210> SEQ ID NO 27
<211> LENGTH: 1694
<212> TYPE: DNA
<213> ORGANISM: Zea mays

<400> SEQUENCE: 27
cacggaagat ccaggtctcg agactaggag acggatggga ggcgcaacgc gcgatgggga     60 gggggcggc gctgaccttt ctggcgaggt cgaggtagcg atcgagcagc tgcagcgcgg    120
acacgatgag gaagacgaag atagccgcca tggacatgtt cgccagcggc ggcggagcga    180
ggctgagccg gtctctccgg cctccggtcg gcgttaagtt ggggatcgta acgtgacgtg    240
tctcgtctcc acggatcgac acaaccggcc tactcgggtg cacgacgccg cgataagggc    300
gagatgtccg tgcacgcagc ccgtttggag tcctcgttgc ccacgaaccg accccttaca    360
gaacaaggcc tagcccaaaa ctattctgag ttgagctttt gagcctagcc cacctaagcc    420
gagcgtcatg aactgatgaa cccactacca ctagtcaagg caaaccacaa ccacaaatgg    480
atcaattgat ctagaacaat ccgaaggagg ggaggccacg tcacactcac accaaccgaa    540
atatctgcca gaatcagatc aaccggccaa taggacgcca gcgagcccaa cacctggcga    600
cgccgcaaaa ttcaccgcga ggggcaccgg gcacggcaaa aacaaaagcc cggcgcggtg    660
agaatatctg gcgactggcg gagacctggt ggccagcgcg cggccacatc agccaccccca    720 tccgcccacc tcacctccgg cgagccaatg gcaactcgtc ttaagattcc acgagataag    780
gacccgatcg ccggcgacgc tatttagcca ggtgcgcccc ccacggtaca ctccaccagc    840
ggcatctata gcaaccggtc cagcactttc acgctcagct tcagcaagat ctaccgtctt    900
cggtacgcgc tcactccgcc ctctgccttt gttactgcca cgtttctctg aatgctctct    960
tgtatggtga ttgctgagag tggtttagct ggatctagaa ttacactctg aaatcgtgtt    1020
ctgcctgtgc tgattacttg ccgtcctttg tagcagcaaa atatagggac atggtagtac    1080
gaaacgaaga tagaacctac acagcaatac gagaaatgtg taatttggtg catacgtat    1140 ttatttaagc acctgttgct gctataggc acttgtattc agaagtttgc tgttaattta    1200
ggcacaggct tcatactaca tgggtcaata gtatagggat tcatattata ggcgatacta    1260
taataatttg ttcgtctgca gagcttatta tttgccaaaa ttagatattc ctattctgtt    1320
tttgtttgtg tgctgttaaa ttgttaacgc ctgaaggaat aaatataaat gacgaaattt    1380
tgatgtttat ctctgctcct ttattgtgac gataagtcaa gatcagatgc acttgtttta    1440
aatattgttg tctgaagaaa taagtactga cagttttttg atgcattgat ctgcttgttt    1500
gttgtaacaa aattttaaaa taaagagttc ccttttttgtt gctctcctta cctcctgatg    1560
gtatctagta tctaccaact gatactatat tgcttctctt tacatacgta tcttgctcga    1620
tgccttctcc tagtgttgac cagtgttact cacatagtct ttgctcattt cattgtaatg    1680
cagataccaa gcgg                                                     1694

<210> SEQ ID NO 28
<211> LENGTH: 1500
<212> TYPE: DNA
<213> ORGANISM: Zea mays
```

<400> SEQUENCE: 28

```
tttaaatttg gaacgtcgat ccaacatcta acagaagcac caattttaca aagaacccct      60
ttcaccttcc tcacttggtg ggacggttct taatcaaatt aactgcagcc gctggtatac     120
atgtacatgt gggcccgcct agcccggcac ggcacaggcc cacaaaaaca cggtccacaa     180
aagcacgacc cacaaaagca catatctaat tatgggccgt gccgtgccag cacgtgtgcc     240
cagtcatcgg cccacaatta gttatgtgtg ccaggccgac ccaaatagcc caaaatacct     300
taatatgcca gaccggctca tatacataca acagtaatac atcaacaaaa cgtataaaat     360
atatatatga ccaaaataaa actaagatgt tttgtggatg cacattataa acctttggtc     420
agaaagaaaa aaatattaca actagctcac aaaaaatatc cagttctctg tttagtgttt     480
aattgagtac tatacatcca tacagaataa atatacaatg atcatcatca ctattcacta     540
tccatatcta ggtattggtt ctcgatggct tattaaagct ctagattctc caagttatgc     600
tagtcatgtg ggcttttgaca gaccttagtt aaatactgag tctatatttt gtgggcctta     660
gttaaatggg tcgtggcagg ccggcccgtg ggcttgactt gaggcccagg cacggcccac     720
aatgtgggcc gtgccggccc atgcccacaa ttaggttggg cagtgccaga tatgggccgt     780
gccagaaatt gtgtgctttg ggccggccta ttaggcacaa cataaatgta cacctatagc     840
cgcatagccg ctggatgtga gatgaatgtc tcagatttaa aatgtgcact tgagcaccgt     900
acctctttga caacagata tgttccttta agattgatgg tggaaaaaaa ttagtcagta      960
cctcactgta tggcggcatt gtttgattat ttcagttcgc acccgttgga ccttgctcat    1020
taaaaaagtt tataccatgg agtctttgca tgtagttgtg tagtagggga agagtggcat    1080
aggaggaatc acaacttcag ctagcttctc tagccttagg gtattttgt cttttgcag     1140
ttcggtcttt tcgcagccct gcgctgcccc ccctgtccgc ctgtccctag acctgttttg    1200
cgtcggcggg gaagacagtt gacaggaagg cacgatctt cgtgtccgat gccgatcttc    1260
atgcgagcag cgagccacta cgttgcgctg ccagtgtcgg ctatggtatc caggcattcg    1320
ttgtgcacgt tgacgatgag ctcgaagccg gtccgggtga acgcgagcag cacggtgagg    1380
tcaacgtcgt acatccgcac gtcgatgctg aggccagcca gcagcggcat gacagattgc    1440
ggcgtcagga gattgtgcca gtaggtggcg gggctggggg cagaccggca ggcgaggcct    1500
```

<210> SEQ ID NO 29
<211> LENGTH: 1500
<212> TYPE: DNA
<213> ORGANISM: Zea mays

<400> SEQUENCE: 29

```
caaaattttc tatttttaa aaaatatgaa ttctagattt gggattgaac acatctaggc      60
tacaacgttg aattgatgaa caatagtgct tgttaataaa ttgctcacat tcacattgtc    120
gctcttactt caaccatcat acatccatct acagtggtca cccatattta atcctatgga    180
ctaaagatga cagatgaact tctctcgtta tatatatcac tgtcctacat atatgagaaa    240
tgatatgtcc taaactcacc taaaaacaac aacatagttt aaatttaatc atagatgagc    300
ctacagaggt cgaacgtgat ttggaaacat agctctattg ttctctatct catgcataaa    360
tatggtgcaa tgaagaatat tagggttatg atgtcgaaat ctcactcgaa ctcgtgcctc    420
atcataaata gcacactatc aattgttcta tggctgttca aatagggaca atcttgaaac    480
aacatttctc acatgtaaaa cgttgtgaag tatgccaact gaaacggatg acacatacac    540
```

```
ttcgtgaacc aatcgatatt ttacttgctt ctatgttaaa aatgttata atacaatatt      600 ttattcaaat gctaaaactt attactagat aaaaataaaa tttaattatc ttcaaaaact      660
aaccaataga tattccatca taactacatt taccaaacta atatactaaa aaatatagga      720
taattactaa attaatcgtg caataatcag tatttatgag attgataatt ttaaattttg      780
tgggctacaa acaaaaatta aaacttactt ttcaagttgg agataagaac aatggtagac      840
gtagctcggg atggtatggc gtcggtgcag acggttaccc tttgtgcgaa gtggcgcggg      900
cacgagggtg gggacttggt acatgcatga gagagaggaa gaacgaaaca acttctcaaa      960
ttaaagcata tgaaaatcac ctaattttg tctgtcggtg aaactaata actagttttt     1020 attatctttt ttaataagga tccacgaaaa ttatttttga ccgatgaaaa tcctggatct     1080
tcgtattatg tttcgccttt tcccgactct ttgcatgcta gatttccatg cttggactaa     1140
aacgaagata ataaaaccaa tctatcattt tcacacgatg tattcatact tgcaatagat     1200
aaaccactac tccgacggga tttgctttct gacctctgaa atcttggaag gattatgtgt     1260
ctacacttct cgatcgaggg gaaaaagtcg tagtaccaag ttgtagttaa atttgtttct     1320
tcgatgacaa acaaaggag aggggcccgc gcggcgcagc gcagcgcagt tggctggttc     1380
cggaacacga aaaccaagca cactccacca gctgccatcc accgggttgg atggagatta     1440
caatactcga atagtcagcc agccagccgg cttgaacgtg cagttttccc ctataaaacg     1500
```

<210> SEQ ID NO 30  
<211> LENGTH: 1500  
<212> TYPE: DNA  
<213> ORGANISM: Zea mays

<400> SEQUENCE: 30

```
acacttgctc tcttcgcgtg gtcatttagc ccccgaacat tccaagaaaa aatagcacat       60
ttttgattca taaggtaaag actgccactc cacttaacac agcacgctgc caccacacat      120
ggattagcag gagagcctgc tgtaaaatcc taacaggagg gagaacctcc aaacaagggt      180
tcgccgagca aaaacacagc ccgaccacaa ccgacaacct gaaagaacaa cagagataca      240
caggcatgct gggggaccta gaccagcgcc cagaagtaat aacgccagcg gagatacaac      300
cgctccgaga gagcctgacc atctgagaac acattggtca ccaaaagcac caccaaccgg      360
cctagacaaa gcagctcagt tgaccccgc ctcgacatct tcgatggccg gcatcacctt      420
tctccccttc ttttttattct tcgctgtctt caccttgtct tgatttaaca gctccatgat      480
tgcatccatt tgcttcttgg agagaggctt tgtgagaagg cttgtcatct gctcaaatga      540
ctcatcaaag ttagtacatt ttgaagaact aattattatt atatagaatg cactgcacat      600
atattactat taccagtttt cttgggcaca gcagaaaaca tgcacacgca gatgaaaaaa      660
ggagaggcca taaaccaaaa ggctttaaga atatatgtaa agatatgtct aaatatatgg      720
ctatatctgg ttaagcaaga taacagggct ctggtcatca gtagtagtgg ccttttgccc      780 ttgccccct ctctcaccct ctttttctca gccttgcttc cgatggatcc catcccactg      840
ccatcctttc tttcccttgc gcgcattgcc tagccggccg gccggcctgc tattaaacca      900
ctttacccgc cccctctcgc tcacgctcga cgcagctccc ttttccttgt ttgcttattg      960
caagtctctg caagaacctg ctagagagga acaaggtaga gtagtatcgc ttttttccat     1020
ctaggttatc tcttttttaca tgaaaaattt cagccgtatt tcgttctcca tcagtcctgc     1080
gataatatat acgcgcgtct tgtgtgatcc ggcatatgta tagttcctgc taactgatcg     1140
agatcgctct cgtttgtact ttctcccttt gaggaaagag tttcccctttt tctgtgcttc     1200
```

| | |
|---|---|
| aagttcttgt aaggaaaacc atgcctgcca gcttcttctg ctacttgtat gatgattctt | 1260 |
| atttgcttat tacttgattt ccgttttttt tcttgctttc tatatgtatg tatctgggct | 1320 |
| gtcttcccct gcgtctcgtt actgctaagc tttggaaggt ttcaactctt tgtatacgat | 1380 |
| gaggtttctg ctcctagtag cagatccgcg catatgacta gatgtttgag gaaaagaaaa | 1440 |
| gggcaagacg ctatatatat atgcagcacg cagtcgcaca tatattcagt tttccaatct | 1500 |

<210> SEQ ID NO 31
<211> LENGTH: 1500
<212> TYPE: DNA
<213> ORGANISM: Oryza sativa

<400> SEQUENCE: 31

| | |
|---|---|
| gcagctgttt tcgcggtaca gggtgcaaca aaagcccatg acggcccaca cctgcctctc | 60 |
| tccgctccaa acaccgaaac aaggggggtgg gtgcaatggg ccggcgctcg aagaccgcga | 120 |
| actctttcca acagcccagc gcattagccc ctcctcctac tctctctacc ttcttttttaa | 180 |
| catgcgactt tctttctgtg gacgacggca tcaacgacgg gagcaggagc ggggggctgaa | 240 |
| gcacggtgcg tgggctcctg gagtggcgac ggcctctccg gcgagcttcc tctggcgaac | 300 |
| tccctccgct cctcctatgg cgaaatccaa acaagggtca gtttcgactc caaccttctc | 360 |
| ccaccaccac ctcctgaccg tgccaccacc cggccttgtc ggcactgaaa ggcgtcaact | 420 |
| tgtcagcgcg ggcctgctcg gtcggtctcc tcctccccta tttcgtttag ctttgccccc | 480 |
| gccaccaaca ccggcccacg gcccatggcc gaccccgcgg cttggcgcc gccatcgcta | 540 |
| tctcgccgct gtccttttttt catgaccttc ggtgccatcc ctctaaattc gatgcacctc | 600 |
| cctggctcta tctcccttta cctccgaaat cctaacccta cccataatct ctagtgagtc | 660 |
| ttgtctttat ttatggcctc tttgaatcgc aggattgata aaacgtagga ttttgatagg | 720 |
| aatgtaagtg taaaacacat gattgtaaaa tagaggaaaa acataggaat ggccgtttga | 780 |
| ttgaaccgca gaaaaaacac aggaattaga tgagagagat agactcaaag ttactaagag | 840 |
| attgaagctt ttgctaaatt tcctccaaaa tctctatagg attggccatt ccatagaaat | 900 |
| ttcaaaagat ttaataggat tcaatccttt gtttcaaaaa acttcataga aaattttttct | 960 |
| atagaattaa aatcctctaa aattcctatg tttttttctcc aattcaaagg ggcccttagg | 1020 |
| ttggaatttg gaaagtgttc gcgagaaatc aagcggtcgc acgttagcga attaggattt | 1080 |
| ccggaaacaa aggaccgact ccgcctatcc atcgtcacga gcacagtgta gaacctccca | 1140 |
| gacctcaaga gaccgttcaa aaagcgcgcg cccaagcggg gccccaccaac gcgtccccac | 1200 |
| cgtgtcgcct cctgattggt tgtcccctct tcctttcacg cgaaccggca ccctcccgac | 1260 |
| ccttccagaa cccccaatcc gacggccagg atcgcccgcg cgcgaacgtt ctagacccc | 1320 |
| gccacctccg ccacaaaacc tctgcccctc ccctctcccc ccgcttcgtc tcgttcgaga | 1380 |
| aatcagaaag agagagaaat tcccacgcag cagcaagcaa tccaatccga gagcgcgcgt | 1440 |
| ttgcgattat tcgctttcga ttccgcgagg tttttggaga gggaggagaa ggaggaggag | 1500 |

<210> SEQ ID NO 32
<211> LENGTH: 1500
<212> TYPE: DNA
<213> ORGANISM: Oryza sativa

<400> SEQUENCE: 32

| | |
|---|---|
| acagcattta ttgtagtctg gtcaagcgtg tcacgctgca tgcaacgcag tacagcgcgt | 60 |

```
tcctttaccc ggtctgtgac cagtcacaga ccggtcagat cacgggttag gtggcgactg      120
gcggtctgac gcacgccttg ccccatcccg tcaagacgaa agcctctagg cactcgtctc      180
aagccggagc tagcgtgtta tctcttagag atggcacgtt agccctggtt agatttatac      240
caggcttcat cctaaccatt acaggcaagg tgttacacga agaagggcaa acatgcacg       300 ttgttaaact gacgcgtggg ggacaagaat gaccggtctg acactggtcg catcagcaac      360
gggcagccac gatcccgcgt catctccgtc tccgccggga gtggaggtag gtgtgggctg      420
tcccatcaga agggctcccg gatggaaacc gtaccgatct ccgcccatta agagaaaaa       480 gaacagtcca gtttggaaag agaagggtgc atgtggtatc cccttgaagt ataaaaggag      540
gaccttgccc atagagaagg gggttgattc tttccagatt cagagcctag aacgagggag     600
aggtgggctc acactttgta acttgtccat acacaaatcc acaaaaacac aggagtaggg      660
tattacgctt ccgagcggcc cgaacctgta tagatcgtcc gtgtctcgcg tttcttgctg      720
gctgacgatc cttccacata cagagagaga gagcttgg gatctcaccc taagcccccg        780
gccgaaccgg caaggggggg cctgcgcggt ctcccggtga ggagcctcga gctccgtcag      840
acatgttcag tttcattata ttatgaaatg tcacgtactg tttgttctag ttagtgaatt      900
gtcatatggt aagaatatat aaaaattagg ttttctggac tctatcttcc aatgtatttt      960
tggatcctat aacaaaatat tttcataaat atatttttta agaatctaaa cttttttgaa     1020 ataaagagc aacaaagaaa ataaaaacgc tctctcgtaa gtaactcgtg aagatccatc      1080
gagagccact cgtttgaatc gtcgacacaa agaacactt cattgattgc ttttcgtcaa      1140
ttagccgcac agcacagtac tctccaatct gctaaaccaa accaatctc atccatccat      1200 acccttcttg acaccaagtg gcaactcctg attggacgcg ccctatccta catggcaccc     1260
ccaagattct ctcgataggc tacaggggcc acaccgaccc tccacgtcat cgtccacgtc     1320
accctcatcc cggcccatcc agccaatccc agcccagcaa aaatcttcc caagtggcca      1380 ccagataagc ctctccacgt attaatacgc caagtgttcg tcgccatgac acagcacgca     1440
cacacacccc accagcagca gcagcagtag ctgagcttga agcagcagag cgaggtagac     1500
```

<210> SEQ ID NO 33
<211> LENGTH: 1500
<212> TYPE: DNA
<213> ORGANISM: Oryza sativa

<400> SEQUENCE: 33

```
tccacctctg ttggttgcat cgacgtcgct tccctagctc ccgtctctag tccggatcct       60
attcctcctt ggagaccgaa gctaccgcaa ccattgctcg gtggttagcg agcgtggagc      120
tgtcctcccc actttcgcgt cctcgttcgc caccacagcc atacttcgca tggtgatgtc      180
ttctccttca ctcaccgcta aactcagtgc aaccgtttct accctagccc cggccgccgc      240
tctcatagag gtgaaagttc atttacatgt aggtcccaca tgttttatgt ttttattttt      300
tcttttactg attagcatgc cacgtaaatc aaaacaacaa tccatagtgt tttaagtatt      360
tttatttaat acgtgagatg gagtacaaaa acgagagatg caaagtgaac ttgctaaaac      420
acattttctg gttgattaca gtcgcttgtt gagccattgg atcggtcata ggattcgtgc      480
tagcatactt aattacgcgt aactagttgt gctttatagg ttacaggtcg ctaattagcg      540
gtctactgga gaactttgct actatttttt tcttcactgc atgcactcga tcaagtatga      600
gtatttgtac cgaccagcga aacacatatg taattaaagt ataaatatgt aattagtata      660
tattagtagt atatttagac agtagttaca ccctacatac acaccactta catatataat      720
```

```
tagtatgtaa ttttgtaact tacatatgta attttagtac ttacatatgt aattttgaga      780
cttacattgt aaatacacta aaattacata tgtaatttag taacctacaa tgtaaataca      840
tgccgactaa cttttgatga aaaatatggt gttataaata tagctactcc cgaactttat      900
tccttctctg tgagatatca gtggaaacgc tcggtgaat cggggagta tttgggagca        960 cgcgccgacg cgcgcgtcgt gcgtgccgtc gtctttgtcg cggtggagcg gagcgcgccc     1020
acttgcgcgc ctgggccgga ggcgggcgcg ccggggttc gggaatcccc tggagccaca     1080
cgtaaaggcg cgggcgggag ggagggaggg gccagctagg ataaggcacg cgcggccgct     1140
gcgattgggg cgcttgtgaa caccggggcg ccacgtggag aggacgttac actccagccg     1200
ccaaatttcc actcccacac ccgcgctccc ctccctctc ttttccgtga tcgcacctcg       1260
cccacgcgcc ccccgccaca cacaatctct gcagctctcc agcttcgttg gaactcgcga     1320
atctctctcc gatcccaggt aaagcagcga acgacgtcac gcacgacgct gctcggtgga     1380
tttcgttcct tgctggggaa aaccatgcag agacgaaggt gaatgatctg cttttgtgta     1440
cttgcgttta ccaggtgaag cgcgagcttg gagttggagg ggagatcgat cagggccagg     1500

<210> SEQ ID NO 34
<211> LENGTH: 1500
<212> TYPE: DNA
<213> ORGANISM: Oryza sativa

<400> SEQUENCE: 34
ataattaatt aattaatcaa tcacttttcg tgctgtaaaa aatctcaccc gatttgctga       60
aacgaactga gccgggcgac tgtgatattc tttcacgatt tctgtttgtg gcagtgggac      120
attgctgttt attcgaaaca attttcaagt aaaaaaaaat actcaatggt aaggttgcta      180
gtaatagttt aacagtttgt ttgcagctca gcaaatttcg tttcctcaca gatgacacat      240
aactgaaagc actcaatgta atgttgtgct tagctgctaa agcatgtcac gtcttagaaa      300
acaactactc caccatggag aattttttcct cctacttact cctcacatac ttaccatctc     360
catataagtt cccttgtcgt atcatatgtc ttattcttct tgagcacagt tattacagca     420
gattttgtag aatagttatc gcatcaaaat tttcctatgt cacctttgat catgtgttat     480
gtgtgcctct tgagtcttag ggttaatgtg gttgtaatgt gtttaaaaaa ctatatgaaa    540
gctcgtgtgt tgctacggga gagagatacc tcgaatgaat gtgagagatc tccatttgag     600
ttgtgtacct tgagagagtg aaagatcaca ctatttatag acggtaata atggttactg     660 aggtcgattc accacatcgt cttaaacatt taatgagcat cctccacgtg aaaagtagag     720
atgatagcgt gtaagagtgg ttcggccgat atccctcagc cgcctttcac tatcttttt     780 gcccgagtca ttgtcatgtg aaccttggca tgtataatcg gtgaattgcg tcgatttcc     840 tcttataggt gggccaatga atccgtgtga tcgcgtctga ttggctagag atatgtttct    900
tccttgttgg atgtattttc atacataatc atatgcatac aaatatttca ttacacttta     960
tagaaatggt cagtaataaa ccctatcact atgtctggtg tttcatttta tttgctttta    1020
aacgaaaatt gacttcctga ttcaatattt aaggatcgtc aacggtgtgc agttactaaa   1080
ttctggtttg taggaactat agtaaactat tcaagtcttc acttattgtg cactcacctc     1140
tcgccacatc accacagatg ttattcacgt cttaaatttg aactacacat catattgaca    1200
caatattttt tttaaataag cgattaaaac ctagcctcta tgtcaacaat ggtgtacata    1260
accagcgaag tttagggagt aaaaaacatc gccttacaca aagttcgctt taaaaaataa     1320
```

```
agagtaaatt ttactttgga ccaccctcca accaatgttt cactttagaa cgagtaattt    1380
tattattgtc actttggacc accctcaaat ctttttttcca tctacatcca atttatcatg    1440
tcaaagaaat ggtctacata cagctaagga gatttatcga cgaatagtag ctagcataag    1500
```

<210> SEQ ID NO 35
<211> LENGTH: 1945
<212> TYPE: DNA
<213> ORGANISM: Oryza sativa

<400> SEQUENCE: 35

```
aaggtttcat gcgtatcgtg acagatgtta cataatgaca aattcccag ctggagcacc      60 tttatccctg ctgtttgcat gaaattagct tgtcttgtag ttccctccag caaaaagaag    120
tctgaaacaa aacaacattt cgaaaaaaag gcatccatga gttagcattt ctacagttgt    180
ctatagaggg gaaggctgca cgacaaagtt tccaggcttg gaaacaacct cttatgtaaa    240 attttttcgta tgtatcagat gatttgtttt cgttacggca tctccaccta acatcacctt    300
catcatgcgc ctatggtctt tctcttgcct gttttatacg taaaattgga aacgacagaa    360
acttttgcca tctttattaa aggaaggcaa atatgcaaat ataggcatca agatcacagt    420
tagtggatta tcatctttgt aggttaacat gtcctacccc aggggagctt atactcaagt    480
actccatgca ttttcatgaa atgagaaaaa acgatttttta agagaaatgt actttcttgt    540
atttatgcca aatggcaagg actgaaaggg aaaaactaag aaagggaacg ttacagtaag    600
gctctgtggg gactggggac ttcagagaaa cgtgaaccct gcttccttcc tctgcatgaa    660
cataacacca gaggtttcca gcctttcaca cagttgttga tggcttcaca caattcatct    720
ctacctcctg actctttata aggaccccca gcatcaccac aattgcacaa gtacaggcat    780
tagatccaca agaacacttg gcaggcaag cacctctttg atctttaagc cgttgttatg    840
ttctatttct gagcatatgg tttctagtta tattcttttt cttcattcgt ttcatatctt    900
tgaagtgttg atgcaaatgc ggtgaacaac tatcaactgt gtactctcca agtgaatgcg    960
aataatcatt tcctgtgaga attgtgggct agataaacga atgaaatgct gttttatcta   1020
tgtcatgtgt ggaaatttag ttaatttttcc ggtctttta tgcattgaga tgggtatgct   1080 gttttttttag ttgggtccca tcatcttgag aattctttca aatttccttt tctttatcct   1140
atataaagga tagagaaggc gtatgcctag gtgcaccaac cctgaaagtt ttattctaat   1200
tgcgggaatg gtttgtaatt tttgcttgtt caggttcttt ttcgtggcct ttctttttttt   1260 tccccttatt ttgcttagtc tttcacagtc caattttttgg gaagtagtat atcttagttt   1320
ggtcctaagg caccatgttg tactgcagga aaaaaagag taattgtatt ctgttttttc   1380
cttgattact atatccctgt tttaattaat tttgtgcctt tgttgtttga tgttggaact   1440
tcaatgccca taattagtca tttgacttgt tttgggtttt gacgctatct tgagtgccat   1500
aggaaactgg tagaatttag taataatttt atatagactg aatgttgagc ccaccacaaa   1560
tggtttcctt ctgtacaagt atttaataac tcaagcacag gaaacatcag atctctaatc   1620
taaaggttaa caatgggctc aagcaggagc agtagttcag ctctatctgt atatttagaa   1680
gggctggatc tacctgtcca ccagctttta atttttacccct ggcagctgga taacttcttg   1740
tctgttaatt tcatttagtg ctgtgttatt tcttcttgt tgttcaggat ggatgctttt   1800
gaatttctgg aatttcgtat tttgttctat ctctttatga aatgacgtta tggcacactt   1860
tttctgcata ttcttgatga aaataattac ctagtcattt ttttagttgc aggtttgtct   1920
gggactttga gtacccatgc aattc                                           1945
```

<210> SEQ ID NO 36
<211> LENGTH: 2315
<212> TYPE: DNA
<213> ORGANISM: Oryza sativa

<400> SEQUENCE: 36

| | | | | | |
|---|---|---|---|---|---|
| gttcaagatt | tattttttggt | atttaattta | cttgcttaag | tcagatatat | tcccatcgtt | 60 |
| gcaggtttgt | cacttagtat | tattattaag | cgctctagca | ctaggactct | ggataaataa | 120 |
| gaaagtttat | tcacgaggct | agagtagtaa | tcaataacat | aagcgtggtg | tctaggtcag | 180 |
| cggttatctt | catatgtagt | gtgctccatg | aaagtgagg | taggaggaag | gtggtgacag | 240 |
| tcccgtccgt | cctttgtatc | cctccatgtt | cgggtatatc | atagagctac | aggctagact | 300 |
| tagcttggca | gactagggga | gagccggtgc | tcgaagcaat | ccatgaggct | ttacatttaa | 360 |
| cataagttag | taaattaacc | cataggaatc | atctctagac | tgaacctacc | agtagttgtg | 420 |
| cttggatata | attatattcc | tacatataca | tacacgttcc | ctgcgattag | ataccttgg | 480 |
| aatactctaa | ggtgaagtgc | tacagcggta | tccgtgcgct | tgcggattta | tctgtgaccg | 540 |
| tatcaaatac | caacaggtag | atacaaggaa | tcatctctcc | tatccattgg | tttatcatct | 600 |
| tttaaaatta | tctcttgctc | tcctattgcc | tctgcaactg | cggataggtg | tttctcaaca | 660 |
| atgaaggttg | tgaagaatgc | tttgtgcaac | aagatggatg | acaagtatct | cagccatagc | 720 |
| ctcatttgct | ttgtagaaaa | ggatatgtcg | gacacaatca | ctaagtatca | ccgtggaaag | 780 |
| gatgcactgt | atgccctatc | tatatttacc | atttagtaat | atttatatgg | cttgtgctaa | 840 |
| ctttatgttg | tctttacagg | caataacatt | atttggaagg | catatctata | tattactatt | 900 |
| taagataatg | taatatctca | aagttttat | aagctgcaat | gaggtgagtt | tcacttagct | 960 |
| ttctaacttg | ttatgagtta | tagatgcatg | ccaccagtca | ttttttatct | tgcatcagcc | 1020 |
| cctgcctgtt | agaatatgtt | tctttgtctg | ggagtccatg | tcaactagcc | aatttccaaa | 1080 |
| tatatgaaca | aaactatgtg | gcctttgtaa | cccaaatgag | ataaagacta | ctctccatag | 1140 |
| aaatttagca | acatggcac | tcaaagaaaa | tgtgttggat | agtttcatca | tgcatacaaa | 1200 |
| agcaacactt | ttgaactacc | attccaaatc | cttttttgtaa | attatctttg | cttaacacta | 1260 |
| cccctttgag | caaatgtggc | tttgtgcgga | aaaaactcaa | acttggtagg | gtagacatcc | 1320 |
| atttatataa | ttggatccat | gtacataagt | tgttgagtac | ttcaagtact | tacccttgtg | 1380 |
| atatacatct | caaatatatt | gaagaagaga | agttcttttt | ttgagagagg | ttgaagaaga | 1440 |
| gaagtttgtc | catagctgaa | gaggagtttt | atagtgtcta | gcttaccttg | ctgctgattg | 1500 |
| catgtctaaa | atgtcgttta | atttgggcta | taatgaaata | ttcaccaata | tttctgctgg | 1560 |
| tctattaaag | tttaatagtt | actcgtaact | catttatttt | gggctataat | ttaatattca | 1620 |
| cctatgtttt | tgttagtcta | ttttatttcc | ctagtgtgca | ctagcttaac | cccaaattag | 1680 |
| ttttgaacac | ttaacctaaa | tgtgtctatt | atggtcagac | actctctcac | ggcactctaa | 1740 |
| caaaaagtga | attttgttgt | tatgtttttg | tcatgatctc | acaagcaatg | tacatgtacg | 1800 |
| tttctagagt | gcaatcttat | gctagcctga | ttgtgaattt | agtgtagttt | gtttttctctt | 1860 |
| tttgtagcta | cactaccaat | aacctattgt | cctctagtca | taccacgtaa | tcacaaggca | 1920 |
| aatccctaac | tctcaccttt | aaaagcatgt | ctttattttc | ttgggtggca | ctaatacaaa | 1980 |
| atctttttca | gcattcctat | gtgcgatagc | aagaaaacat | ggcataactc | ttgcttcact | 2040 |
| ctaacaaaaa | aaacactttt | ccaactttaa | aacaatggta | tctatgtgtt | taatgatcaa | 2100 |

| | |
|---|---|
| tcaagcatat aatgacttac aagttttttac ctatgcccctt tttgcatcat cttgtttgca | 2160 |
| acagacaaac tagatattcc tttaggctat aaacacatca gcatgataaa gagattaggt | 2220 |
| aagtttgtta tcccttttg catatattct cgtctactcc gtgtatataa gcccctctcc | 2280 |
| tccaactcgt ccatccatca ccaagagcag tggga | 2315 |

<210> SEQ ID NO 37
<211> LENGTH: 1194
<212> TYPE: DNA
<213> ORGANISM: Oryza sativa

<400> SEQUENCE: 37

| | |
|---|---|
| ttgcatgccg tcgtcttaag cgtccgcgtg tgaaaatcgg attttcgcat acggttgaac | 60 |
| cggtcgcatg caaagatcgc gatcttcgca gacgatttgg cacatgcggt tgcaccaacc | 120 |
| gtatgcgaaa acccttctcg cccgtatgca aaaccatct ttgttgtagt gtacggttca | 180 |
| caatggtttg gatgggaaat cattgtgaac caaaagtgat agactgattt cgacgagtgt | 240 |
| ttttttttaa gtagtgccac aattttggtc atcatacgtc gtgtctaaaa ttgtaacttt | 300 |
| tgaaaaccaa tttacattaa attaaattta taagactaaa taaagacgat ggtcattgaa | 360 |
| caattgttga gaaaaatcta cacacatgtg tgtccaacac aaatgtttac acatatacta | 420 |
| ctatgttcat agtcgaagtt agattttttt tttccttaaa gggaaagtct gttttcaaat | 480 |
| tttagacctc actccttccg tttcaaatat atcgtgtatt ttttttttcta gggcaagctt | 540 |
| ttgaccaatg attactctat tatgacacaa tgttaaaggg atagattcat attcaaaatt | 600 |
| actattataa ttataatttt gtcatataaa taatatttta agcaattgtt agccaaaatc | 660 |
| tcgtcctaac gaaacaaaat acgccttatt tttaaaaaca cggagtatat ccttaaatat | 720 |
| ttctctatcc aatataaaag gtcaatcttt taaaattccg atcatcaata atttctcaaa | 780 |
| taattacttt gaaataaaaa aacatatgca aatttgtgtc gtcataatat ccaatgaact | 840 |
| tattcaaatt tataaactta ttttaattca aatttgatc attaattttt tttttaaaaa | 900 |
| aaaaccaaat cttatcataa acgtcaaata tattttgat agtgggggcg ataataccat | 960 |
| aaaactaaca acagaagaga catgatacta ctactgtaat cctaatacgt acgtacgtat | 1020 |
| acttctacgc cggatgcata acttcagcct tgtgagacac aacagttgct gcctagctcg | 1080 |
| tggtcgttgg ttttttcgct cgagaaacca ctacgcgtaa accgtgaagt atattatata | 1140 |
| tagccaactg gtcttctcgc aaatccgcac atcccttct gcccctcgtc ttct | 1194 |

<210> SEQ ID NO 38
<211> LENGTH: 1500
<212> TYPE: DNA
<213> ORGANISM: Oryza sativa

<400> SEQUENCE: 38

| | |
|---|---|
| gcaaagaagg ccagtggcct ttgcagctaa gctagctagc tagcccttct tcctctcttt | 60 |
| cctgctttcc ctttgccttc tcctattaat cctctgcacc tcacacagca gcagaaaacc | 120 |
| caccaactgg agctctcctt tcctactcca agaaacgaag gtagagaaag aaagatcaga | 180 |
| tcagcttcag gaccaatttt agctaggtta tatatctctt tgcgtgctaa tgtgttttag | 240 |
| ttatctgggt gtgtgtagag ttctttgtta aggcactgat tcagctgcag tttagattca | 300 |
| agtttgtatg ttctctcttt gaggaaaaga aacccttttc ctgtgcttcg agttcttgca | 360 |
| aagagaaact gtgatgcttg gcttccagtt tgatgcttct tgttcagat tggaaattct | 420 |
| tcctagcttc tttctctatt tatgtagcaa ggattctttc cggcccagtg atcctggttt | 480 |

```
cttttggaag gtttcagttt tttcgttctt tcttgaaatt tctcttcttg ccttaggcag      540
atctttgatc ttgtgaggag acaggagaaa aggaagaagc tagtttcctg cggccgacct      600
cttgcttctc actttgtgat gagttttctt tggtcaattc ttagctagat atgttaagat      660
agttagttaa gcaaatcgaa attgctagct tttccatgct ttcttaaaca tgattcttca      720
gatttggttg gttctttttt ttcctttttg tggagacgtg ctgttcttgc atcttatcct      780
tcttgattca tctacccatc tggttctttg agctttcttt ttcgcttctt cccttcatta      840
tttcgagcaa tctctgcaca tctgaaagtt ttgtttcttg agactacttt tgctagatct      900
tgtttactcg atcactctat acttgcatct aggctccttt ctaaataggc gatgattgag      960
ctttgcttat gtcaaatgat gggatagata ttgtcccagt ctccaaattt gatccatatc     1020
cgccaagtct ttcatcatct ttttctttct tttttatgag caaaaatcat cttttttctt     1080
caaagttcag ctttttttctc ttgttttacc cctctttagc tatagctggt ttcttattcc     1140
ttttggattt acatgtataa acatgcttg aatttgttag atcgatcact ttatacacat      1200
actatgtgaa tcacgatctc agatctctca gtatagttga attcattaat ttcttagatc     1260
gatcagcgtg tgatgtagta ctgtaaatca ctactagatc tttcatcagt ctcttttctg     1320
catctatcaa tttctcatgc aagttttagt tgtttcttta atccggtctc tctctctttt     1380
ttaatcagct gagagtttgt gctgttcttt aatcattacc agatctttca tcagtactct     1440
ctcttctgca tctatcaaac ttctcatgca atgtttttgc tgttctttga tctgatctct     1500

<210> SEQ ID NO 39
<211> LENGTH: 1148
<212> TYPE: DNA
<213> ORGANISM: Glycine max

<400> SEQUENCE: 39
gcaacagaag acccaaaact caaaaaagtt agtttcgggc caacatttcc tcttgaggga      60
tgacacgtga cctgctactc tggcccttat ctggcatgtc catccttctt ggcgcgacat     120
ttaattcgtc gtcagaaata actgaaggac accttgcttg tttctctttt ggccgccacc     180
ggtcttgtca tcgtcgaagg cgcccttgcg cttgtcggca gaaccttttt cggcgaccct     240
cttgcctttt cctttggcct tgttcgtcat ttctacagag aatgcaatga gaccaacgcc     300
aattgcatgg ttagagttag agaaatggag agaggaagaa gtgcgtgact agagtgtgtg     360
taactgtgaa gaacgacgag tccaaaatga attttactgt aaataatttg aggaaaaaag     420
tgatcaatac atatcatgcg gtgcatacaa gaatcggcca ttggtcaact tgtgagagga     480
aaaaatcatt taactaatac caaataatct taaaattaat aaaataattt aactaattaa     540
cccacggaag aaccttcttc cgttgactct ggcggaagaa gttcttccgc atagttccat     600
ggaagatggt tcttccgcag ttcttctttc gttgacactc gcggaagaaa tgttccacgg     660
gcgtccgcgg aagaactttc ttccgcaaag ctaaagagca ttttttgccat gtcgaaatca     720 tcgccaatga ccagggtaac agaaccacgc cctcttatgt tggtttcacc gattcagagc     780
gtttgatcgg tgatgccgcc aagaatcagg tcgccatgaa ccccgtcaac accgtcttcg     840
gtaagatccc tagccgacac ttcgcctttt caggatttgc attgttccta gattttggaa     900
tctgttgttt gaaactccac ttttctattt tggtaatttt tagtttttatt ttgtaatcct     960 gctgtttata tgtcttattg ttattattaa tcgttgcatg gtctgaactg gtttagaact     1020
ctacttgtat tgtttgttaa aatcttattt gaaatcgaat agtaatataa ttttaatcga    1080
```

```
atggtgatat gcataaacat cgtatttgtt cgtcgaattc tggttttgaa ttgaataata    1140
ttgttatg                                                             1148
```

<210> SEQ ID NO 40
<211> LENGTH: 1378
<212> TYPE: DNA
<213> ORGANISM: Glycine max

<400> SEQUENCE: 40

```
ctagaaatta aatgttttta acaggtaatt tgagaaaaat gtacttcaaa ataattagtt      60
ttaccagttt atgtcttctt tttctctttt ttatctttat tctatgtttc aaattctaat     120
aatacatcat ttaaatattt ttaatttaaa agtgcttact aaattttaaa aaaatcatat     180
ttatcaaata acttctactt taaatttaaa cttcattatt tttaacttaa aaataacttt     240
taaattaaaa aaatgaaaac aaacactacc taaaccctaa acactatcta tctaagtcac     300
attacttaat gattcttaat ttatgttctt tgtaaacttt catttcttcc tccttttggc     360
tatacatgtt catttctgtg tactttacta tattattagt aaaagccttt tataggta      420 tatcaaatca ataattaat ataatatata attctcttaa tttcatttct tcatataaat     480
gtatttcaaa agtatttctt ctagaataaa ctaaagctat tacagatgaa aaattcttaa     540
aaaattattt gaccttcata tatgggtcct tttctaatta ataattaact ataggtgc      600 attctaaatg ctcctatatt atctgctttc tcctcttctt tcctttttc ctagtcgctc     660 acgaaaatct cctataatcc tctgcagttt tcgaaatcaa taaccgactc ctagaacctg     720
tccatgtcta acttaataaa tcgtgagggt gtgattgtga ttactttgaa tctttaattt     780
ttgacattaa aacaagacca aacaaaaacc ttcaggttac gtgagactcc aacctaccca     840
agttatgtat tagttttcc tggtccagaa gaaaagagcc atgcattagt ttattacaac     900
taactatatt tcaatttcat gtaagtgtgc cccctcatta aaatcgacct gtgtaaccat     960
caacctgtag ttcgctcttt tcaccatttg tctctctgtc tttatcttcc ctcccccatt   1020
gccaatattt gttgcaatac aacatctctc cgttgcaatc actcatttca aattttgtgg    1080
ttctcatttg ccctagtaca acattagatg tggacccaaa aatatctcac attgaaagca    1140
tatcagtcac acaattcaat caatttttc cacatcacct cctaaattga ataacatgag    1200
aaaaaaatag ctaagtgcac atacatatct actggaatcc catagtccta cgtggaagac    1260
ccacattggc cacaaaacca tacgaagaat ctaacccatt tagtggatta tgggggtgcc    1320
aagtgtacca aacaaaatct caaaccccca atgagattgt agcaatagat agcccaag     1378
```

<210> SEQ ID NO 41
<211> LENGTH: 1500
<212> TYPE: DNA
<213> ORGANISM: Glycine max

<400> SEQUENCE: 41

```
gatcctcaca aacctcactt ggagacatag gtgtgagggt aaccttttc cctttatgta      60 caaatgaaaa tttgtttgtg acaccattat ggacaacatc cttacactac taaaaaagct    120
tttttttacg acatcatatt tacgacagtc atacaaaaac gtcttagtat gtataaggat    180
ggcaatttcg taaatatttc aaacatttca aaggcagttt cagaaaaccg tctttgaatg    240
cggccatttt aatttttaac gcgcccctcg catccgttcc tcttcttcc gcaaatgtgg     300 tgctcgttcc ttttctttcc cagctggcat ctgttcctct ccccactcgc tagctatctt    360
ctgcttctcc tcttctctcc tcttcccatt acatttctcc accttctccc tggtaccacc    420
```

```
accgcccccc actccacatt cgtcctccgc ccccattccc ctatcctcca gtaaaattac    480 aaaaaacccct aacaccaaaa aaacccaaac ccctgtcgca atgaaatctc caccccccaaa    540 tagctctttg aatagaatc aaggaactta ccaaatccat tatatgctat tggggttttg    600
gcatgtttcc ggtgtgaaag aaggaaaaag aaatgcgtat gcgatggtga tgtacgtagg    660
tacgccgaag gactacgaat tctacatagc catactcgtg cttctcaaat cgctggctac    720
gctcgacgtt gaaattgatc ttgctgtgat tgcttccctt gatgttcctc ctcgatggat    780
tcgagctctg taagtctcac tccttcacca tcatttgcca ctttatttt atgtactttt    840 actttattat tatttgtaac ctgtattttt atttggtttc ggatatctgt tgctttatta    900
ttcaccctgg aatttggttg attttattat ttttgaaaaa taaggaaaga gatttatttg    960
ttagcttaat tgttttaatt ggcgaatatg ttttctttt ccctttttg cacagagtga   1020 agctttgttc ttagggtaat ggattccctt ttttgtgatg ctagtggatg atttgactga   1080
ttagtgttta gtggaatgaa gaaccagaac tagtagtagg tagagggaat cacttttggt   1140
tttggatgta aacttagaaa tgtgcagcac tgcacagaat tgatatttga tcgtgggtca   1200
aattgtcaaa atgtgcaaag aatacaaagg cacaggtgat atcattccat tttacgtttt   1260
ttaacgaagc tgttagtttc aattcaatta tttacatata taataaatat attgatactt   1320
gctttagttt catgaattaa aagaatttga ttttgtaaat ttcatttgaa tttgtttttg   1380
tacaagctct caacttttat tatatgaacg agaagtttct tttttccttt ttgagtttat   1440
ttgaacttgt ggtgttctaa ttgtatatat ttttgtgcag gtgtcaatcg gtactactac   1500
```

<210> SEQ ID NO 42
<211> LENGTH: 1261
<212> TYPE: DNA
<213> ORGANISM: Glycine max

<400> SEQUENCE: 42

```
atctctcgac agttgcgaac tgaacgctga gttggtaatg ctatgcccta tcgcttttttg    60 caccgtccca tgatcatttc ccccacacca ccccatcaac ctctaaaaag ttaagagtga   120
aaattacaca caccccgagga gaagaaaagc tgcttcttct aagcatcaca acctagttac   180
tttacttgta gggccttttc catttcccct aaattacccc tcttttcatc atatgataat   240
aatatccagc tcagactata gtatgatatt atgatgtcag cataataggt tggcactaaa   300
gtcttaaagg gcattgtaca tgttgcacct ggcattcaaa ttcataaata ctaacactgt   360
gaaatagatt ataaatcctc aaataaatgt cacacggttg gggttcgaat ccactcaaaa   420
aggctaatgg gatgggattt aagtgccaag gaatatacca tggactttaa cagcaacaca   480
atttacaatc taaaatgtat tactttttt tttcaaaaaa gatatacaaa ataaggtacc   540
aagaataaaa ggagtattta gaaacagtgg caccaattta ataaattatt tatataaaat   600
gacacttatt taatttatca atgataaaag taatattgat ttattctctg attaactgtt   660
caattaatag tgttattatc ataatctgtc gcaaaagtta tttttatcaa caacaataat   720
tgatacaagt agtataaaat taagcctctt agttaatata gactacttga tactaaaacc   780
atgttacacc aaaagtaat ttttatgtca cttgtctata taataattac gactaaatta   840
ataattttta aaaatattac tgaatccatt aaccgaactt ttataatgaa agtattttta   900
tgctttaaaa tcacaaacat tgaataaact aaaaatgata ccacggaatt ggaacaagag   960
acgttccaca caaaagaaaa aaatatgttg aataattgaa acggtgacaa gaaaagtgga  1020
```

| | |
|---|---:|
| ataataatac aaagatggca gatggggtta ttgttattgg aggagatgag tgaaataatg | 1080 |
| agtgagggggg gtgtaactgg aaagcaagaa aaagcgcaag agtgccagct atttccaaca | 1140 |
| acaaacgtgg cccgtgggat gcgatattcg taacgaacgg cgaggatgga aggacgtgca | 1200 |
| atttgcgctt catttgaggc gaatttcatt tggccagacc ttcctttttt aaaccacagg | 1260 |
| g | 1261 |

<210> SEQ ID NO 43
<211> LENGTH: 1094
<212> TYPE: DNA
<213> ORGANISM: Glycine max

<400> SEQUENCE: 43

| | |
|---|---:|
| tgtgtcaatg ttgtttctgg tgaattgaca taatgaattc tacctgtacg gagtagagaa | 60 |
| taactattta cccaacaaga atgattatct cattaatttt tgaagtagac gcaataacga | 120 |
| atatattata cattcagaaa aatttcacca tattattctc aaatcacaac aataatttgt | 180 |
| tttttttttg cttgatataa aaccaatact ctatactttt taaggttaat ttaaacttaa | 240 |
| agagtatttt taagatgcat gtactttaag gaataataga acatgacaa catcataaaa | 300 |
| gaatgaagaa actgaatcat aacgtagttt gttacgcctt ccatttggtg gttgatttgg | 360 |
| atacaatcta gattggtttg ctaaatggtt tataagttat gtagacgttt ttattactac | 420 |
| tattttagac aaatcaaata cacaccttca ctttattcta ttcaaataac atgattttc | 480 |
| ctaacatttt ttaaaaaat tacttttttaa atataaacta attattttag aaatagtttt | 540 |
| ataaaaatcc acgccaaaaa aattaagttg ttttttataaa tataaacatc gggcttcaat | 600 |
| cttaaattta taaatgtacg aaataatttg acagttaaat ggaaattgct agcatggaag | 660 |
| tgttttttatc atttatcaaa ctcaaccaaa ctgaacatca gaataattat tagtgacaaa | 720 |
| ttttgcagca tatgaagtgg cttgcatagc tccaaggctg gcgatcatat gtcagattag | 780 |
| agcaggctct ctttggtact atgatacatt tcaagcaaat aacaaccgta aaaattcacg | 840 |
| ccaaaatttt tggaacgaat ctatatatta ttatttatt tcttttgatt tcatgtacgt | 900 |
| acagtgcccg taattgacat gtctttgttc cttaatgcct ttcccacgtg aacaggcac | 960 |
| ctagaaactt ggactaagta gggaattgag ggccatggac tatagtgcca aaccaacatc | 1020 |
| attttatata tatatatata tatatatata tatatgctat tgttttctat agttttggga | 1080 |
| aattaatact tatc | 1094 |

<210> SEQ ID NO 44
<211> LENGTH: 1449
<212> TYPE: DNA
<213> ORGANISM: Glycine max

<400> SEQUENCE: 44

| | |
|---|---:|
| atttgtacta aaaaaaaata tgtagattaa attaaactcc aatttttaatt ggagaacaat | 60 |
| acaaacaaca cttaaaaacct gtaattaatt tttcttcttt ttaaaagtgg ttcaacaaca | 120 |
| caagcttcaa gttttaaaag gaaaaatgtc agccaaaaac tttaaataaa atggtaacaa | 180 |
| ggaaattatt caaaaattac aaacctcgtc aaaataggaa agaaaaaaag tttagggatt | 240 |
| tagaaaaaac atcaatctag ttccaccctta ttttatagag agaagaaact aatatataag | 300 |
| aactaaaaaa cagaagaata gaaaaaaaaa gtattgacag gaaagaaaaa gtagctgtat | 360 |
| gcttataagt actttgagga tttgaattct ctcttataaa acacaaacac aattttttaga | 420 |
| ttttattaa ataatcatca atccgattat aattatttat atattttct atttttcaaag | 480 |

| | | |
|---|---|---|
| aagtaaatca tgagcttttc caactcaaca tctattttt ttctctcaac cttttcaca | 540 | |
| tcttaagtag tctcaccctt tatatatata acttatttct tacctttac attatgtaac | 600 | |
| ttttatcacc aaaaccaaca actttaaaat tttattaaat agactccaca agtaacttga | 660 | |
| cactcttaca ttcatcgaca ttaactttta tctgtttat aaatattatt gtgatataat | 720 | |
| ttaatcaaaa taaccacaaa ctttcataaa aggttcttat taagcatggc atttaataag | 780 | |
| caaaaacaac tcaatcactt tcatataggr ggtagcctaa gtacgtactc aaaatgccaa | 840 | |
| caaataaaaa aaagttgct ttaataatgc caaacaaat taataaaaca cttacaacac | 900 | |
| cggatttttt ttaattaaaa tgtgccattt aggataaata gttaatatttt ttaataatta | 960 | |
| tttaaaaagc cgtatctact aaaatgattt ttatttggtt gaaaatatta atatgtttaa | 1020 | |
| atcaacacaa tctatcaaaa ttaaactaaa aaaaaaataa gtgtacgtgg ttaacattag | 1080 | |
| tacagtaata taagaggaaa atgagaaatt aagaaattga aagcgagtct aattttaaa | 1140 | |
| ttatgaacct gcatatataa aaggaaagaa agaatccagg aagaaaagaa atgaaaccat | 1200 | |
| gcatggtccc ctcgtcatca cgagtttctg ccatttgcaa tagaaacact gaaacacctt | 1260 | |
| tctctttgtc acttaattga gatgccgaag ccacctcaca ccatgaactt catgaggtgt | 1320 | |
| agcacccaag gcttccatag ccatgcatac tgaagaatgt ctcaagctca gcaccctact | 1380 | |
| tctgtgacgt gtccctcatt caccttcctc tcttccctat aaataaccac gcctcaggtt | 1440 | |
| ctccgcttc | 1449 | |

<210> SEQ ID NO 45
<211> LENGTH: 1321
<212> TYPE: DNA
<213> ORGANISM: Glycine max

<400> SEQUENCE: 45

| | | |
|---|---|---|
| aaaaacacaa aaaaaaatta tacaaaaatg tttctcacaa catgagaagt aaaatccctc | 60 | |
| aaagaatttc acatcatcat atcagaatca aaggaatcaa aatcataggt caaaaataca | 120 | |
| aaaacaccaa gaacactcaa tttattaact aatttgcatc atgacatcaa ttggtccatc | 180 | |
| aaacacaaca atcttgtaat tataatcgta acgaaagaat tacaatgcaa taaacatccc | 240 | |
| aaaataaacc tcaatttaat cctctaagga tccctataca tgttcattct aaccccaatt | 300 | |
| gtgataaatt catcccttac ctctaagcag gctcacgtgt gtagtctggc agtgatagag | 360 | |
| gcatctctag tggttttcta atagtcctca agcttgtttt tcctctagtt gttctgttag | 420 | |
| gattttcaag cgttagagag aagaagaaga gattggagcc tctatttcac tgttaccgta | 480 | |
| caagggatat ttttctcacc ataaacatta ttttgcaaat cccaacgaag gagatgtccg | 540 | |
| tacataagtt cgaaacctgg tgctcgaatt tcacgacgat tcaatggtta acaagtccaa | 600 | |
| gattgtattt ttactgtgac agatttgagt gtatacaaga aaagagagc tccatgcgag | 660 | |
| gaatatttct ctcacagtag acattatttc ataaatccca atggtaaaaa tatgcaaaaa | 720 | |
| tgagtttcaa acctgctttt aaaatttcat gacgactcaa cggttaacgt gtccgggatt | 780 | |
| atattttcac tggaacaagt ttgagtgcat gcgggaaaag agagggtttt gggagaggaa | 840 | |
| aaaaggaaaa caaatttaag aggaagagag agcgtaaaaa tttatcgtaa atgtaaaaaa | 900 | |
| tgacctaata tatctctatt tataactagg gtactctcaa tctattattt actcatttt | 960 | |
| ttatttattt atttttataaa aaagaattttt attttacttc ctatcaaatt aataaataaa | 1020 | |
| acattcttct tattttctaa gatcacatat ttattttatt taccttaaaa tcatcatttt | 1080 | |

```
aattaataaa attattctt cttatttatt taattacaaa aatcttatta tttttttaaa    1140 atttattta ttttaaata aaatattttt taatttattt tataaaaaat gagatgttac    1200
attgaattat aaaataaata gccaacaata aatagccgac ttgcttttgc attgactaag    1260
gaagtcaagt catcaataaa tataatttcc agttggcaat attctcaaag ttggtctata    1320
t                                                                   1321

<210> SEQ ID NO 46
<211> LENGTH: 514
<212> TYPE: DNA
<213> ORGANISM: Glycine max

<400> SEQUENCE: 46
agatttgatc gatacttcat taaattgaca ttttatttta acacataata cattattaaa      60
aatataaata aacatttaca gcgaagttat ataattaaaa gcctggtcta tgtaatggta     120
ggaaatttga aaatctaaaa gcaaacaaaa attgttgttt atggtgctaa gttgcacctg     180
gaaagatgca ttgtttagct aaaacattca cgtcgagtac ttggtttggg aaaaaaagcc     240
attcaagctt agctggtcct ctctcctgtc tctctctctc tgtctgtctc tctctgtctg     300
tctctctctc aagcacatac acaaacaaag taagggctat aaataggagg gatggaagtg     360
gaagaaagtc tatagcgaag tttcatttct ttggattaga aattttttccc aaagctgatc    420 gagaagccag ccaggccagg tctgtagttt tcttttttttc tttttaatat taattcatta    480
ttgtgttctt catcatataa tataattaag cctt                                 514

<210> SEQ ID NO 47
<211> LENGTH: 702
<212> TYPE: DNA
<213> ORGANISM: Glycine max

<400> SEQUENCE: 47
cgcgccgtac gtaagtacgt actcaaaatg ccaacaaata aaaaaaaagt tgctttaata      60
atgccaaaac aaattaataa aacacttaca acaccggatt ttttttaatt aaaatgtgcc    120
atttaggata aatagttaat atttttaata attatttaaa aagccgtatc tactaaaatg    180
atttttattt ggttgaaaat attaatatgt ttaaatcaac acaatctatc aaaattaaac    240
taaaaaaaaa ataagtgtac gtggttaaca ttagtacagt aatataagag gaaaatgaga    300
aattaagaaa ttgaaagcga gtctaatttt taaattatga acctgcatat ataaaaggaa    360
agaaagaatc caggaagaaa agaaatgaaa ccatgcatgg tcccctcgtc atcacgagtt    420
tctgccattt gcaatagaaa cactgaaaca cctttctctt tgtcacttaa ttgagatgcc    480
gaagccacct cacaccatga acttcatgag gtgtagcacc caaggcttcc atagccatgc    540
atactgaaga atgtctcaag ctcagcaccc tacttctgtg acgtgtccct cattcacctt    600
cctctcttcc ctataaataa ccacgcctca ggttctccgc ttcacaactc aaacattctc    660
tccattggtc cttaaacact catcagtcat caccgcggcc gc                       702

<210> SEQ ID NO 48
<211> LENGTH: 579
<212> TYPE: DNA
<213> ORGANISM: Glycine max

<400> SEQUENCE: 48
acgcgccgta cgtagtgttt atctttgttg cttttctgaa caatttattt actatgtaaa      60
tatattatca atgtttaatc tatttttaatt tgcacatgaa ttttcatttt attttttactt   120
```

| | |
|---|---|
| tacaaaacaa ataaatatat atgcaaaaaa atttacaaac gatgcacggg ttacaaacta | 180 |
| atttcattaa atgctaatgc agattttgtg aagtaaaact ccaattatga tgaaaaatac | 240 |
| caccaacacc acctgcgaaa ctgtatccca actgtcctta ataaaaatgt taaaaagtat | 300 |
| attattctca tttgtctgtc ataatttatg taccccactt taattttcct gatgtactaa | 360 |
| accgagggca aactgaaacc tgttcctcat gcaaagcccc tactcaccat gtatcatgta | 420 |
| cgtgtcatca cccaacaact ccacttttgc tatataacaa caccccgtc acactctccc | 480 |
| tctctaacac acacccccact aacaattcct tcacttgcag cactgttgca tcatcatctt | 540 |
| cattgcaaaa ccctaaactt caccttcaac cgcggccgc | 579 |

<210> SEQ ID NO 49
<211> LENGTH: 12258
<212> TYPE: DNA
<213> ORGANISM: Artificial Sequence
<220> FEATURE:
<223> OTHER INFORMATION: Synthetic construct pYTEN-5

<400> SEQUENCE: 49

| | |
|---|---|
| gtaaacctaa gagaaaagag cgtttattag aataacggat atttaaaagg gcgtgaaaag | 60 |
| gtttatccgt tcgtccattt gtatgtgcat gccaaccaca gggttcccct cgggatcaaa | 120 |
| gtactttgat ccaacccctc cgctgctata gtgcagtcgg cttctgacgt tcagtgcagc | 180 |
| cgtcttctga aaacgacatg tcgcacaagt cctaagttac gcgacaggct gccgccctgc | 240 |
| ccttttcctg gcgttttctt gtcgcgtgtt ttagtcgcat aaagtagaat acttgcgact | 300 |
| agaaccggag acattacgcc atgaacaaga gcgccgccgc tggcctgctg ggctatgccc | 360 |
| gcgtcagcac cgacgaccag gacttgacca accaacgggc cgaactgcac gcggccggct | 420 |
| gcaccaagct gttttccgag aagatcaccg gcaccaggcg cgaccgcccg gagctggcca | 480 |
| ggatgcttga ccacctacgc cctggcgacg ttgtgacagt gaccaggcta gaccgcctgg | 540 |
| cccgcagcac ccgcgaccta ctggacattg ccgagcgcat ccaggaggcc ggcgcgggcc | 600 |
| tgcgtagcct ggcagagccg tgggccgaca ccaccacgcc ggccggccgc atggtgttga | 660 |
| ccgtgttcgc cggcattgcc gagttcgagc gttccctaat catcgaccgc acccggagcg | 720 |
| ggcgcgaggc cgccaaggcc cgaggcgtga agtttggccc ccgccctacc ctcacccccg | 780 |
| cacagatcgc gcacgcccgc gagctgatcg accaggaagg ccgcaccgtg aaagaggcgg | 840 |
| ctgcactgct tggcgtgcat cgctcgaccc tgtaccgcgc acttgagcgc agcgaggaag | 900 |
| tgacgcccac cgaggccagg cggcgcggtg ccttccgtga ggacgcattg accgaggccg | 960 |
| acgccctggc ggccgccgag aatgaacgcc aagaggaaca agcatgaaac cgcaccagga | 1020 |
| cggccaggac gaaccgtttt tcattaccga agagatcgag gcggagatga tcgcggccgg | 1080 |
| gtacgtgttc gagccgcccg cgcacgtctc aaccgtgcgg ctgcatgaaa tcctggccgg | 1140 |
| tttgtctgat gccaagctgg cggcctggcc ggccagcttg gccgctgaag aaaccgagcg | 1200 |
| ccgccgtcta aaaaggtgat gtgtatttga gtaaaacagc ttgcgtcatg cggtcgctgc | 1260 |
| gtatatgatg cgatgagtaa ataaacaaat acgcaagggg aacgcatgaa ggttatcgct | 1320 |
| gtacttaacc agaaaggcgg gtcaggcaag acgaccatcg caacccatct agcccgcgcc | 1380 |
| ctgcaactcg ccggggccga tgttctgtta gtcgattccg atcccagggg cagtgcccgc | 1440 |
| gattgggcgg ccgtgcggga agatcaaccg ctaaccgttg tcggcatcga ccgcccgacg | 1500 |
| attgaccgcg acgtgaaggc catcggccgg cgcgacttcg tagtgatcga cggagcgccc | 1560 |

-continued

```
caggcggcgg acttggctgt gtccgcgatc aaggcagccg acttcgtgct gattccggtg   1620
cagccaagcc cttacgacat atgggccacc gccgacctgg tggagctggt taagcagcgc   1680
attgaggtca cggatggaag gctacaagcg gcctttgtcg tgtcgcgggc gatcaaaggc   1740
acgcgcatcg gcggtgaggt tgccgaggcg ctggccgggt acgagctgcc cattcttgag   1800
tcccgtatca cgcagcgcgt gagctaccca ggcactgccg ccgccggcac aaccgttctt   1860
gaatcagaac ccgagggcga cgctgccgc gaggtccagg cgctggccgc tgaaattaaa    1920
tcaaaactca tttgagttaa tgaggtaaag agaaaatgag caaaagcaca aacacgctaa   1980
gtgccggccg tccgagcgca cgcagcagca aggctgcaac gttggccagc ctggcagaca   2040
cgccagccat gaagcgggtc aactttcagt tgccggcgga ggatcacacc aagctgaaga   2100
tgtacgcggt acgccaaggc aagaccatta ccgagctgct atctgaatac atcgcgcagc   2160
taccagagta aatgagcaaa tgaataaatg agtagatgaa ttttagcggc taaggaggc    2220 ggcatggaaa atcaagaaca accaggcacc gacgccgtgg aatgcccat gtgtggagga    2280 acgggcggtt ggccaggcgt aagcggctgg gttgtctgcc ggccctgcaa tggcactgga   2340
acccccaagc ccgaggaatc ggcgtgacgg tcgcaaacca tccggcccgg tacaaatcgg   2400
cgcggcgctg ggtgatgacc tggtggagaa gttgaaggcc gcgcaggccg cccagcggca   2460
acgcatcgag gcagaagcac gccccggtga atcgtggcaa gcggccgctg atcgaatccg   2520
caaagaatcc cggcaaccgc cggcagccgg tgcgccgtcg attaggaagc cgcccaaggg   2580
cgacgagcaa ccagattttt tcgttccgat gctctatgac gtgggcaccc gcgatagtcg   2640
cagcatcatg gacgtggccg ttttccgtct gtcgaagcgt gaccgacgag ctggcgaggt   2700
gatccgctac gagcttccag acgggcacgt agaggtttcc gcagggccgg ccggcatggc   2760
cagtgtgtgg gattacgacc tggtactgat ggcggtttcc catctaaccg aatccatgaa   2820
ccgataccgg gaagggaagg gagacaagcc cggccgcgtg ttccgtccac acgttgcgga   2880
cgtactcaag ttctgccggc gagccgatgg cggaaagcag aaagacgacc tggtagaaac   2940
ctgcattcgg ttaaacacca cgcacgttgc catgcagcgt acgaagaagg ccaagaacgg   3000
ccgcctggtg acggtatccg agggtgaagc cttgattagc cgctacaaga tcgtaaagag   3060
cgaaaccggg cggccggagt acatcgagat cgagctagct gattggatgt accgcgagat   3120
cacagaaggc aagaacccgg acgtgctgac ggttcacccc gattacttt tgatcgatcc    3180 cggcatcggc cgttttctct accgcctggc acgccgcgcc gcaggcaagg cagaagccag   3240
atggttgttc aagacgatct acgaacgcag tggcagcgcc ggagagttca agaagttctg   3300
tttcaccgtg cgcaagctga tcgggtcaaa tgacctgccg gagtacgatt tgaaggagga   3360
ggcggggcag gctggcccga tcctagtcat gcgctaccgc aacctgatcg agggcgaagc   3420
atccgccggt tcctaatgta cggagcagat gctagggcaa attgccctag caggggaaaa   3480
aggtcgaaaa ggtctctttc ctgtggatag cacgtacatt gggaacccaa agccgtacat   3540
tgggaaccgg aacccgtaca ttgggaaccc aaagccgtac attgggaacc ggtcacacat   3600
gtaagtgact gatataaaag agaaaaaagg cgatttttcc gcctaaaact ctttaaaact   3660
tattaaaact cttaaaaccc gcctggcctg tgcataactg tctggccagc gcacagccga   3720
agagctgcaa aaagcgccta cccttcggtc gctgcgctcc ctacgccccg ccgcttcgcg   3780
tcggcctatc gcggccgctg gccgctcaaa aatggctggc ctacggccag gcaatctacc   3840
agggcgcgga caagccgcgc cgtcgccact cgaccgccgg cgcccacatc aaggcaccct   3900
gcctcgcgcg tttcggtgat gacggtgaaa acctctgaca catgcagctc ccggagacgg   3960
```

```
tcacagcttg tctgtaagcg gatgccggga gcagacaagc ccgtcagggc gcgtcagcgg   4020
gtgttggcgg gtgtcggggc gcagccatga cccagtcacg tagcgatagc ggagtgtata   4080
ctggcttaac tatgcggcat cagagcagat tgtactgaga gtgcaccata tgcggtgtga   4140
aataccgcac agatgcgtaa ggagaaaata ccgcatcagg cgctcttccg cttcctcgct   4200
cactgactcg ctgcgctcgg tcgttcggct gcggcgagcg gtatcagctc actcaaaggc   4260
ggtaatacgg ttatccacag aatcagggga taacgcagga agaacatgt gagcaaaagg   4320 ccagcaaaag gccaggaacc gtaaaaaggc cgcgttgctg gcgtttttcc ataggctccg   4380
cccccctgac gagcatcaca aaaatcgacg ctcaagtcag aggtggcgaa acccgacagg   4440
actataaaga taccaggcgt ttccccctgg aagctccctc gtgcgctctc ctgttccgac   4500
cctgccgctt accggatacc tgtccgcctt tctcccttcg ggaagcgtgg cgctttctca   4560
tagctcacgc tgtaggtatc tcagttcggt gtaggtcgtt cgctccaagc tgggctgtgt   4620
gcacgaaccc cccgttcagc ccgaccgctg cgccttatcc ggtaactatc gtcttgagtc   4680
caacccggta agacacgact tatcgccact ggcagcagcc actggtaaca ggattagcag   4740
agcgaggtat gtaggcggtg ctacagagtt cttgaagtgg tggcctaact acggctacac   4800
tagaaggaca gtatttggta tctgcgctct gctgaagcca gttaccttcg gaaaaagagt   4860
tggtagctct tgatccggca aacaaaccac cgctggtagc ggtggttttt ttgtttgcaa   4920
gcagcagatt acgcgcagaa aaaaggatc tcaagaagat cctttgatct tttctacggg   4980
gtctgacgct cagtggaacg aaaactcacg ttaagggatt ttggtcatgc attctaggta   5040
ctaaaacaat tcatccagta aaatataata ttttattttc tcccaatcag gcttgatccc   5100
cagtaagtca aaaatagct cgacatactg ttcttccccg atatcctccc tgatcgaccg   5160
gacgcagaag gcaatgtcat accacttgtc cgccctgccg cttctcccaa gatcaataaa   5220 gcccacttact ttgccatctt tcacaaagat gttgctgtct cccaggtcgc cgtgggaaaa   5280
gacaagttcc tcttcgggct tttccgtctt taaaaaatca tacagctcgc gcggatcttt   5340
aaatggagtg tcttcttccc agttttcgca atccacatcg gccagatcgt tattcagtaa   5400
gtaatccaat tcggctaagc ggctgtctaa gctattcgta tagggacaat ccgatatgtc   5460
gatggagtga aagagcctga tgcactccgc atacagctcg ataatctttt cagggctttg   5520
ttcatcttca tactcttccg agcaaaggac gccatcggcc tcactcatga gcagattgct   5580
ccagccatca tgccgttcaa agtgcaggac ctttggaaca ggcagctttc cttccagcca   5640
tagcatcatg tcctttttccc gttccacatc ataggtggtc cctttatacc ggctgtccgt   5700
cattttaaaa tataggtttt cattttctcc caccagctta tataccttag caggagacat   5760
tccttccgta tcttttacgc agcggtattt ttcgatcagt ttttcaatt ccggtgatat   5820 tctcatttta gccatttatt atttccttcc tcttttctac agtatttaaa gataccccaa   5880
gaagctaatt ataacaagac gaactccaat tcactgttcc ttgcattcta aaaccttaaa   5940
taccagaaaa cagcttttc aaagttgttt tcaaagttgg cgtataacat agtatcgacg   6000
gagccgattt tgaaaccgcg gtgatcacag gcagcaacgc tctgtcatcg ttacaatcaa   6060
catgctaccc tccgcgagat catccgtgtt tcaaacccgg cagcttagtt gccgttcttc   6120
cgaatagcat cggtaacatg agcaaagtct gccgccttac aacggctctc ccgctgacgc   6180
cgtcccggac tgatgggctg cctgtatcga gtggtgattt tgtgccgagc tgccggtcgg   6240
ggagctgttg gctggctggt ggcaggatat attgtggtgt aaacaaattg acgcttagac   6300
```

-continued

```
aacttaataa cacattgcgg acgttttaa tgtactgaat taacgccgaa ttaattcggg      6360
ggatctggat tttagtactg gattttggtt ttaggaatta gaaattttat tgatagaagt      6420
attttacaaa tacaaataca tactaagggt ttcttatatg ctcaacacat gagcgaaacc      6480
ctataggaac cctaattccc ttatctggga actactcaca cattattatg gagaaactcg      6540
agtcaaatct cggtgacggg caggaccgga cggggcggta ccggcaggct gaagtccagc      6600
tgccagaaac ccacgtcatg ccagttcccg tgcttgaagc cggccgcccg cagcatgccg      6660
cgggggggcat atccgagcgc ctcgtgcatg cgcacgctcg ggtcgttggg cagcccgatg      6720
acagcgacca cgctcttgaa gccctgtgcc tccaggggact tcagcaggtg ggtgtagagc      6780
gtggagccca gtcccgtccg ctggtggcgg ggggagacgt acacggtcga ctcggccgtc      6840
cagtcgtagg cgttgcgtgc cttccagggg cccgcgtagg cgatgccggc gacctcgccg      6900
tccacctcgg cgacgagcca gggatagcgc tcccgcagac ggacgaggtc gtccgtccac      6960
tcctgcggtt cctgcggctc ggtacggaag ttgaccgtgc ttgtctcgat gtagtggttg      7020
acgatggtgc agaccgccgg catgtccgcc tcggtggcac ggcggatgtc ggccgggcgt      7080
cgttctgggc tcatggtaga ccgcttggta tctgcattac aatgaaatga gcaaagacta      7140
tgtgagtaac actggtcaac actagggaga aggcatcgag caagatacgt atgtaaagag      7200
aagcaatata gtgtcagttg gtagatacta gataccatca ggaggtaagg agagcaacaa      7260
aaaggaaact ctttattttt aaattttgtt acaacaaaca agcagatcaa tgcatcaaaa      7320
tactgtcagt acttatttct tcagacaaca atatttaaaa caagtgcatc tgatcttgac      7380
ttatggtcac aataaaggag cagagataaa catcaaaatt tcgtcattta tatttattcc      7440
ttcaggcgtt aacaatttaa cagcacacaa acaaaaacag aataggaata tctaattttg      7500
gcaaataata agctctgcag acgaacaaat tattatagta tcgcctataa tatgaatccc      7560
tatactattg acccatgtag tatgaagcct gtgcctaaat taacagcaaa cttctgaatc      7620
caagtgccct ataacaccaa catgtgctta aataaatacc gctaagcacc aaattacaca      7680
tttctcgtat tgctgtgtag gttctatctt cgtttcgtac taccatgtcc ctatattttg      7740
ctgctacaaa ggacggcaag taatcagcac aggcagaaca cgatttcaga gtgtaattct      7800
agatccagct aaaccactct cagcaatcac cacacaagag agcattcaga gaaacgtggc      7860
agtaacaaag gcagagggcg gagtgagcgc gtaccgaaga cggtctcgag agagatagat      7920
ttgtagagag agactggtga tttcagcgtg tcctctccaa atgaaatgaa cttccttata      7980
tagaggaagg tcttgcgaag gatagtggga ttgtgcgtca tcccttacgt cagtggagat      8040
atcacatcaa tccacttgct ttgaagacgt ggttggaacg tcttcttttt ccacgatgct      8100
cctcgtgggt gggggtccat ctttgggacc actgtcggca gaggcatctt gaacgatagc      8160
cttttccttta tcgcaatgat ggcatttgta ggtgccacct tcctttttcta ctgtcctttt      8220
gatgaagtga cagatagctg ggcaatgaaa tccgaggagg tttcccgata ttaccctttg      8280
ttgaaaagtc tcaatagccc tttggtcttc tgagactgta tctttgatat tcttggagta      8340
gacgagagtg tcgtgctcca ccatgttatc acatcaatcc acttgctttg aagacgtggt      8400
tggaacgtct tcttttttcca cgatgctcct cgtgggtggg ggtccatctt tgggaccact      8460
gtcggcagag gcatcttgaa cgatagcctt tcctttatcg caatgatggc atttgtaggt      8520
gccaccttcc ttttctactg tccttttgat gaagtgacag atagctgggc aatggaatcc      8580
gaggaggttt cccgatatta cccttttgttg aaaagtctca atagcccttt ggtcttctga      8640
gactgtatct ttgatattct tggagtagac gagagtgtcg tgctccacca tgttggcaag      8700
```

```
ctgctctagc caatacgcaa accgcctctc cccgcgcgtt ggccgattca ttaatgcagc    8760
tggcacgaca ggtttcccga ctggaaagcg ggcagtgagc gcaacgcaat taatgtgagt    8820
tagctcactc attaggcacc ccaggcttta cactttatgc ttccggctcg tatgttgtgt    8880
ggaattgtga gcggataaca atttcacaca ggaaacagct atgaccatga ttacgaattg    8940
gggtttaaac cacggaagat ccaggtctcg agactaggag acggatggga ggcgcaacgc    9000
gcgatgggga gggggcggc gctgaccttt ctggcgaggt cgaggtagcg atcgagcagc    9060
tgcagcgcgg acacgatgag gaagacgaag atagccgcca tggacatgtt cgccagcggc    9120
ggcggagcga ggctgagccg gtctctccgg cctccggtcg gcgttaagtt ggggatcgta    9180
acgtgacgtg tctcgtctcc acggatcgac acaaccggcc tactcgggtg cacgacgccg    9240
cgataagggc gagatgtccg tgcacgcagc ccgtttggag tcctcgttgc ccacgaaccg    9300
acccccttaca gaacaaggcc tagcccaaaa ctattctgag ttgagctttt gagcctagcc    9360
cacctaagcc gagcgtcatg aactgatgaa cccactacca ctagtcaagg caaaccacaa    9420
ccacaaatgg atcaattgat ctagaacaat ccgaaggagg ggaggccacg tcacactcac    9480
accaaccgaa atatctgcca gaatcagatc aaccggccaa taggacgcca gcgagcccaa    9540
cacctggcga cgccgcaaaa ttaccgcga ggggcaccgg gcacggcaaa aacaaaagcc    9600
cggcgcggtg agaatatctg gcgactggcg gagacctggt ggccagcgcg cggccacatc    9660
agccacccca tccgcccacc tcacctccgg cgagccaatg gcaactcgtc ttaagattcc    9720
acgagataag gacccgatcg ccggcgacgc tatttagcca ggtgcgcccc ccacggtaca    9780
ctccaccagc ggcatctata gcaaccggtc cagcactttc acgctcagct tcagcaagat    9840
ctaccgtctt cggtacgcgc tcactccgcc ctctgccttt gttactgcca cgtttctctg    9900
aatgctctct tgtgtggtga ttgctgagag tggtttagct ggatctagaa ttacactctg    9960
aaatcgtgtt ctgcctgtgc tgattacttg ccgtcctttg tagcagcaaa atatagggac   10020
atggtagtac gaaacgaaga tagaacctac acagcaatac gagaaatgtg taatttggtg   10080
cttagcggta tttatttaag cacatgttgg tgttataggg cacttggatt cagaagtttg   10140
ctgttaattt aggcacaggc ttcatactac atgggtcaat agtataggga ttcatattat   10200
aggcgatact ataataattt gttcgtctgc agagcttatt atttgccaaa attagatatt   10260
cctattctgt ttttgtttgt gtgctgttaa attgttaacg cctgaaggaa taaatataaa   10320
tgacgaaatt ttgatgttta tctctgctcc tttattgtga ccataagtca agatcagatg   10380
cacttgtttt aaatattgtt gtctgaagaa ataagtactg acagtatttt gatgcattga   10440
tctgcttgtt tgttgtaaca aaatttaaaa ataaagagtt ccttttttgt tgctctcctt   10500
acctcctgat ggtatctagt atctaccaac tgatactata ttgcttctct ttacatacgt   10560
atcttgctcg atgccttctc ctagtgttga ccagtgttac tcacatagtc tttgctcatt   10620
tcattgtaat gcagatacca agcggttaat taaatgccta ttgcaaccgg tcaggtcatg   10680
aacgacactc tgatggaggt cgagcacact cctcctgtgc acaagcgcat cctggacatc   10740
ctgccaggag tgtctggagg cgttgctcgt atcatggtcg gtcagcccct tgacactatc   10800
aagactcgcc tgcaagtgct tggcgcgggc accattggcg ctcagggcat gcctgctgac   10860
atggtgtaca caacggcat ggactgcgtg cgcaagatga tcaagtcaga gggccctggc   10920
tccctgtaca agggtacagt tgccccactg ctgggtaaca tggtactgct gggcatccac   10980
ttccccacct tcaccaagac ccgtgcctac ctggagcagg gagatgcccc cggcaccttc   11040
```

```
tcccccctgga agatccttgc tgctggtgct gctgctggtg cagctggcag tgtggtcagc    11100 acccccaactg agctgatcag aaccaagatg cagatggtgc gcaagaacaa ccttatggct    11160
cagatgaagg gcgcagcggc aaccctcaac ccagaggaga actacaaggg caactgggac    11220
tgtgccaaga agatcctgcg caaccatggc ctgcgtggca tctacagcgg ctatgtgtcc    11280
accctgctgc gtgacatgca aggttacgcc tggttcttct ttggctatga agctaccatc    11340
cacatgatgt gcactgaagg caagaccaag gcagacctca acttcctgca ggtcatgggt    11400
gctggtgtga ttgctggctt tggtctgtgg ggtagcatgt tccccattga caccatcaag    11460
tccaagattc aggctgacag cctgagcaag cccgagttca agggcaccat ggactgcctg    11520
aagcgcagtc tggcagtgga aggacacgca ggactgtgga ggggtgtgac tgctgccctc    11580
tggcgtgcaa ttcccgtcaa tgcagccatc tttgtagcag ttgagggtac aaggcagctt    11640
attgcagaca cagaggagag tgtagatgca tttgtgaaca acctcacagg cagcggcagc    11700
acagcagcag ctgtatgagg cgcgccatcg ttcaaacatt tggcaataaa gtttcttaag    11760
attgaatcct gttgccggtc ttgcgatgat tatcatataa tttctgttga attacgttaa    11820
gcatgtaata attaacatgt aatgcatgac gttatttatg agatgggttt ttatgattag    11880
agtcccgcaa ttatacattt aatacgcgat agaaaacaaa atatagcgcg caaactagga    11940
taaattatcg cgcgcggtgt catctatgtt actagatccg atgataagct gtcaaacatg    12000
acctcaggat gaagcttggc actggccgtc gttttacaac gtcgtgactg ggaaaaccct    12060
ggcgttaccc aacttaatcg ccttgcagca catcccccctt tcgccagctg gcgtaatagc    12120
gaagaggccc gcaccgatcg cccttcccaa cagttgcgca gcctgaatgg cgaatgctag    12180
agcagcttga gcttggatca gattgtcgtt tcccgccttc agtttaaact atcagtgttt    12240
gacaggatat attggcgg                                                   12258
```

<210> SEQ ID NO 50
<211> LENGTH: 6277
<212> TYPE: DNA
<213> ORGANISM: Artificial Sequence
<220> FEATURE:
<223> OTHER INFORMATION: Synthetic construct pYTEN-6

<400> SEQUENCE: 50

```
tttaatgtaa tcactcaaat aaataatatg aatctgagct atactacgag aacttctgga      60
ttcagcaaga actagcagca atcagaaccc aatagcatag caacaaaccg aacaatcaac     120
catatattag gagacggtag atagaaccac gttaacatta aggggggtgtt tgaatgcact     180 gaaactaatt gttagttggc taaaaattgt tagttgaatt agctagctaa caaataacta     240
cctcactatt aactaatttt ccaaaaatag ctaatagttc aactattagc tatggtgttt     300
ggatgtttta actaattta gccactaact attagtttta gtgcattcaa acacctccta     360
agtaagaaac ggtagatagc cagtacctgc aggcaaatat taggagacaa ctgaaagaca     420
gaacataatg agcacaggct ttaatttcaa acatcaaact tattcatgat ttgtcatagt     480
tctgggtagt acgcacacac aacacaaccg gtccattatt aaaccaacac tgacacgact     540
catgacacga acagcagata ctttgacaac ctccatatgg agagagggca ccagacgacg     600
caggcacatc ggcagcttaa acgacccatg actcgagtca gaagaactcg tcaagaaggc     660
gatagaaggc gatgcgctgc gaatcggag cggcgatacc gtaaagcacg aggaagcggt     720
cagcccattc gccgccaagc tcttcagcaa tatcacgggt agccaacgct atgtcctgat     780
agcggtccgc cacacccagc cggccacagt cgatgaatcc agaaaagcgg ccatttttcca     840
```

```
ccatgatatt cggcaagcag gcatcgccgt gggtcacgac gagatcctcg ccgtcgggca    900
tccgcgcctt gagcctggcg aacagttcgg ctggcgcgag cccctgatgc tcttcgtcca    960
gatcatcctg atcgacaaga ccggcttcca tccgagtacg tgctcgctcg atgcgatgtt   1020
tcgcttggtg gtcgaatggg caggtagccg gatcaagcgt atgcagccgc cgcattgcat   1080
cagccatgat ggatactttc tcggcaggag caaggtgaga tgacaggaga tcctgccccg   1140
gcacttcgcc aatagcagc cagtcccttc ccgcttcagt gacaacgtcg agcacagctg    1200
cgcaaggaac gcccgtcgtg gccagccacg atagccgcgc tgcctcgtcc tgcagttcat   1260
tcagggcacc ggacaggtcg gtcttgacaa aaagaaccgg gcgcccctgc gctgacagcc   1320
ggaacacggc ggcatcagag cagccgattg tctgttgtgc ccagtcatag ccgaatagcc   1380
tctccaccca gcggccgga gaacctgcgt gcaatccatc ttgttcaatc atggtagact    1440
gcagaagtaa caccaaacaa cagggtgagc atcgacaaaa gaaacagtac caagcaaata   1500
aatagcgtat gaaggcaggg ctaaaaaaat ccacatatag ctgctgcata tgccatcatc   1560
caagtatatc aagatcaaaa taattataaa acatacttgt ttattataat agataggtac   1620
tcaaggttag agcatatgaa tagatgctgc atatgccatc atgtatatgc atcagtaaaa   1680
cccacatcaa catgtatacc tatcctagat cgatcccgtc tgcggaacgg ctagagccat   1740
cccaggattc cccaaagaga aacactggca agttagcaat cagaacgtgt ctgacgtaca   1800
ggtcgcatcc gtgtacgaac gctagcagca cggatctaac acaaacacgg atctaacaca   1860
aacatgaaca gaagtagaac taccgggccc taaccatgga ccggaacgcc gatctagaga   1920
aggtagagag ggggggggg ggaggacgag cggcgtacct tgaagcggag gtgccgacgg    1980
gtggatttgg gggagatctg gttgtgtgtg tgtgcgctcc gaacaacacg aggttgggga   2040
aagagggtgt ggaggggtg tctatttatt acggcgggcg aggaagggaa agcgaaggag    2100
cggtgggaaa ggaatccccc gtagctgccg gtgccgtgag aggaggagga ggccgcctgc   2160
cgtgccggct cacgtctgcc gctccgccac gcaatttctg gatgccgaca gcggagcaag   2220
tccaacggtg gagcggaact ctcgagaggg gtccagaggc agcgacagag atgccgtgcc   2280
gtctgcttcg cttggcccga cgcgacgctg ctggttcgct ggttggtgtc cgttagactc   2340
gtcgatcgac ggcgtttaac aggctggcat tatctactcg aaacaagaaa aatgtttcct   2400
tagtttttt aatttcttaa agggtatttg tttaattttt agtcacttta ttttattcta    2460
ttttatatct aaattattaa ataaaaaaac taaatagag ttttagtttt cttaatttag    2520
aggctaaaat agaataaaat agatgtacta aaaaaattag tctataaaaa ccattaaccc   2580
taaaccctaa atggatgtac taataaaatg gatgaagtat tatataggtg aagctatttg   2640
caaaaaaaa ggagaacaca tgcacactaa aaagataaaa ctgtagagtc ctgttgtcaa    2700
aatactcaat tgtcctttag accatgtcta actgttcatt tatatgattc tctaaaacac   2760
tgatattatt gtagtactat agattatatt attcgtagag taaagtttaa atatatgtat   2820
aaagatagat aaactgcact tcaaacaagt gtgacaaaaa aatatgtgg taatttttta    2880
taacttagac atgcaatgct cattatctct agagagggc acgaccgggt cacgctgcac    2940
tgcagtgctc caccatgttg gcaagctgct ctagccaata cgcaaaccgc ctctccccgc   3000
gcgttggccg attcattaat gcagctggca cgacaggttt cccgactgga aagcgggcag   3060
tgagcgcaac gcaattaatg tgagttagct cactcattag gcaccccagg ctttacactt   3120
tatgcttccg gctcgtatgt tgtgtggaat tgtgagcgga taacaatttc acacaggaaa   3180
```

-continued

```
cagctatgac catgattacg aattggggtt taaaccacgg aagatccagg tctcgagact    3240
aggagacgga tgggaggcgc aacgcgcgat ggggaggggg gcggcgctga cctttctggc    3300
gaggtcgagg tagcgatcga gcagctgcag cgcggacacg atgaggaaga cgaagatagc    3360
cgccatggac atgttcgcca gcggcggcgg agcgaggctg agccggtctc tccggcctcc    3420
ggtcggcgtt aagttgggga tcgtaacgtg acgtgtctcg tctccacgga tcgacacaac    3480
cggcctactc gggtgcacga cgccgcgata agggcgagat gtccgtgcac gcagcccgtt    3540
tggagtcctc gttgcccacg aaccgacccc ttacagaaca aggcctagcc caaaactatt    3600
ctgagttgag cttttgagcc tagcccacct aagccgagcg tcatgaactg atgaacccac    3660
taccactagt caaggcaaac cacaaccaca aatggatcaa ttgatctaga acaatccgaa    3720
ggaggggagg ccacgtcaca ctcacaccaa ccgaaatatc tgccagaatc agatcaaccg    3780
gccaatagga cgccagcgag cccaacacct ggcgacgccg caaaattcac cgcgaggggc    3840
accgggcacg gcaaaaacaa aagcccggcg cggtgagaat atctggcgac tggcggagac    3900
ctggtggcca gcgcgcggcc acatcagcca ccccatccgc ccacctcacc tccggcgagc    3960
caatggcaac tcgtcttaag attccacgag ataaggaccc gatcgccggc gacgctattt    4020
agccaggtgc gcccccacg gtacactcca ccagcggcat ctatagcaac cggtccagca    4080
ctttcacgct cagcttcagc aagatctacc gtcttcggta cgcgctcact ccgccctctg    4140
cctttgttac tgccacgttt ctctgaatgc tctcttgtgt ggtgattgct gagagtggtt    4200
tagctggatc tagaattaca ctctgaaatc gtgttctgcc tgtgctgatt acttgccgtc    4260
ctttgtagca gcaaaatata gggacatggt agtacgaaac gaagatagaa cctacacagc    4320
aatacgagaa atgtgtaatt tggtgcttag cggtatttat ttaagcacat gttggtgtta    4380
tagggcactt ggattcagaa gtttgctgtt aatttaggca caggcttcat actacatggg    4440
tcaatagtat agggattcat attataggcg atactataat aatttgttcg tctgcagagc    4500
ttattatttg ccaaaattag atattcctat tctgtttttg tttgtgtgct gttaaattgt    4560
taacgcctga aggaataaat ataaatgacg aaattttgat gtttatctct gctcctttat    4620
tgtgaccata agtcaagatc agatgcactt gttttaaata ttgttgtctg aagaaataag    4680
tactgacagt attttgatgc attgatctgc ttgtttgttg taacaaaatt taaaaataaa    4740
gagtttcctt tttgttgctc tccttacctc ctgatggtat ctagtatcta ccaactgata    4800
ctatattgct tctctttaca tacgtatctt gctcgatgcc ttctcctagt gttgaccagt    4860
gttactcaca tagtctttgc tcatttcatt gtaatgcaga taccaagcgg ttaattaaat    4920
gcctattgca accggtcagg tcatgaacga cactctgatg gaggtcgagc acactcctcc    4980
tgtgcacaag cgcatcctgg acatcctgcc aggagtgtct ggaggcgttg ctcgtatcat    5040
ggtcggtcag ccctttgaca ctatcaagac tcgcctgcaa gtgcttggcg cgggcaccat    5100
tggcgctcag ggcatgcctg ctgacatggt gtacaacaac ggcatggact gcgtgcgcaa    5160
gatgatcaag tcagagggcc ctggctccct gtacaagggt acagttgccc cactgctggg    5220
taacatggta ctgctgggca tccacttccc caccttcacc aagacccgtg cctacctgga    5280
gcagggagat gccccggca ccttctcccc tggaagatc cttgctgctg gtgctgctgc    5340
tggtgcagct ggcagtgtgg tcagcacccc aactgagctg atcagaacca agatgcagat    5400
ggtgcgcaag aacaacctta tggctcagat gaagggcgca gcggcaaccc tcaacccaga    5460
ggagaactac aagggcaact gggactgtgc caagaagatc ctgcgcaacc atggcctgcg    5520
tggcatctac agcggctatg tgtccaccct gctgcgtgac atgcaaggtt acgcctggtt    5580
```

| | |
|---|---|
| cttctttggc tatgaagcta ccatccacat gatgtgcact gaaggcaaga ccaaggcaga | 5640 |
| cctcaacttc ctgcaggtca tgggtgctgg tgtgattgct ggctttggtc tgtggggtag | 5700 |
| catgttcccc attgacacca tcaagtccaa gattcaggct gacagcctga gcaagcccga | 5760 |
| gttcaagggc accatggact gcctgaagcg cagtctggca gtggaaggac acgcaggact | 5820 |
| gtggagggt gtgactgctg ccctctggcg tgcaattccc gtcaatgcag ccatctttgt | 5880 |
| agcagttgag ggtacaaggc agcttattgc agacacagag gagagtgtag atgcatttgt | 5940 |
| gaacaacctc acaggcagcg gcagcacagc agcagctgta tgaggcgcgc cgctcaacgg | 6000 |
| ctatgctatg caacttcatt gtctttcgga tcggagaggg tgtacgtacg tggattgatt | 6060 |
| gatgctgcga gatgcatgtg tgtcttttgt ttcacgttgc attgcatagg caagtcgaga | 6120 |
| tgatgagtgg gcgttgtaca ctaagatgaa ccatgtttgt gcaatagtgg tggttttgt | 6180 |
| ttcctgctgg ttaattgttg atatccatta atttgttttt cttcaaaaaa aaaaaaaaa | 6240 |
| atgataagct gtcaaacatg acctcaggat gaagctt | 6277 |

<210> SEQ ID NO 51
<211> LENGTH: 7028
<212> TYPE: DNA
<213> ORGANISM: Artificial Sequence
<220> FEATURE:
<223> OTHER INFORMATION: Synthetic construct pYTEN-7

<400> SEQUENCE: 51

| | |
|---|---|
| tttaatgtaa tcactcaaat aaataatatg aatctgagct atactacgag aacttctgga | 60 |
| ttcagcaaga actagcagca atcagaaccc aatagcatag caacaaaccg aacaatcaac | 120 |
| catatattag gagacggtag atagaaccac gttaacatta aggggtgtt tgaatgcact | 180 |
| gaaactaatt gttagttggc taaaaattgt tagttgaatt agctagctaa caaataacta | 240 |
| cctcactatt aactaatttt ccaaaaatag ctaatagttc aactattagc tatggtgttt | 300 |
| ggatgtttta actaattta gccactaact attagtttta gtgcattcaa acacctccta | 360 |
| agtaagaaac ggtagatagc cagtacctgc aggcaaatat taggagacaa ctgaaagaca | 420 |
| gaacataatg agcacaggct ttaatttcaa acatcaaact tattcatgat ttgtcatagt | 480 |
| tctgggtagt acgcacacac aacacaaccg gtccattatt aaaccaacac tgacacgact | 540 |
| catgacacga acagcagata cttttgacaac ctccatatgg agagagggca ccagacgacg | 600 |
| caggcacatc ggcagcttaa acgacccatg actcgagtca gaagaactcg tcaagaaggc | 660 |
| gatagaaggc gatgcgctgc gaatcgggag cggcgatacc gtaaagcacg aggaagcggt | 720 |
| cagcccattc gccgccaagc tcttcagcaa tatcacgggt agccaacgct atgtcctgat | 780 |
| agcggtccgc cacacccagc cggccacagt cgatgaatcc agaaaagcgg ccattttcca | 840 |
| ccatgatatt cggcaagcag gcatcgccgt gggtcacgac gagatcctcg ccgtcgggca | 900 |
| tccgcgcctt gagcctggcg aacagttcgg ctggcgcgag cccctgatgc tcttcgtcca | 960 |
| gatcatcctg atcgacaaga ccggcttcca tccgagtacg tgctcgctcg atgcgatgtt | 1020 |
| tcgcttggtg gtcgaatggg caggtagccg gatcaagcgt atgcagccgc cgcattgcat | 1080 |
| cagccatgat ggatactttc tcggcaggag caaggtgaga tgacaggaga tcctgccccg | 1140 |
| gcacttcgcc caatagcagc cagtcccttc ccgcttcagt gacaacgtcg agcacagctg | 1200 |
| cgcaaggaac gcccgtcgtg gccagccacg atagccgcgc tgcctcgtcc tgcagttcat | 1260 |
| tcagggcacc ggacaggtcg gtcttgacaa aaagaaccgg gcgcccctgc gctgacagcc | 1320 |

```
ggaacacggc ggcatcagag cagccgattg tctgttgtgc ccagtcatag ccgaatagcc    1380
tctccaccca agcggccgga gaacctgcgt gcaatccatc ttgttcaatc atggtagact    1440
gcagaagtaa caccaaacaa cagggtgagc atcgacaaaa gaaacagtac caagcaaata    1500
aatagcgtat gaaggcaggg ctaaaaaaat ccacatatag ctgctgcata tgccatcatc    1560
caagtatatc aagatcaaaa taattataaa acatacttgt ttattataat agataggtac    1620
tcaaggttag agcatatgaa tagatgctgc atatgccatc atgtatatgc atcagtaaaa    1680
cccacatcaa catgtatacc tatcctagat cgatcccgtc tgcggaacgg ctagagccat    1740
cccaggattc cccaaagaga aacactggca agttagcaat cagaacgtgt ctgacgtaca    1800
ggtcgcatcc gtgtacgaac gctagcagca cggatctaac acaaacacgg atctaacaca    1860
aacatgaaca gaagtagaac taccgggccc taaccatgga ccggaacgcc gatctagaga    1920
aggtagagag ggggggggg gaggacgag cggcgtacct tgaagcggag gtgccgacgg    1980
gtggatttgg gggagatctg ttgtgtgtg tgtgcgctcc gaacaacacg aggttgggga    2040
aagagggtgt ggagggggtg tctatttatt acggcgggcg aggaagggaa agcgaaggag    2100
cggtgggaaa ggaatccccc gtagctgccg gtgccgtgag aggaggagga ggccgcctgc    2160
cgtgccggct cacgtctgcc gctccgccac gcaatttctg gatgccgaca gcggagcaag    2220
tccaacggtg gagcggaact ctcgagaggg gtccagaggc agcgacagag atgccgtgcc    2280
gtctgcttcg cttggcccga cgcgacgctg ctggttcgct ggttggtgtc cgttagactc    2340
gtcgatcgac ggcgtttaac aggctggcat tatctactcg aaacaagaaa aatgtttcct    2400
tagttttttt aatttcttaa agggtatttg tttaattttt agtcacttta ttttattcta    2460
ttttatatct aaattattaa ataaaaaaac taaaatagag ttttagtttt cttaatttag    2520
aggctaaaat agaataaaat agatgtacta aaaaaattag tctataaaaa ccattaaccc    2580
taaaccctaa atggatgtac taataaaatg gatgaagtat tatataggtg aagctatttg    2640
caaaaaaaaa ggagaacaca tgcacactaa aaagataaaa ctgtagagtc ctgttgtcaa    2700
aatactcaat tgtcctttag accatgtcta actgttcatt tatatgattc tctaaaacac    2760
tgatattatt gtagtactat agattatatt attcgtagag taaagtttaa atatatgtat    2820
aaagatagat aaactgcact tcaaacaagt gtgacaaaaa aaatatgtgg taattttta    2880 taacttagac atgcaatgct cattatctct agagaggggc acgaccgggt cacgctgcac    2940
tgcagtgctc caccatgttg gcaagctgct ctagccaata cgcaaaccgc ctctccccgc    3000
gcgttggccg attcattaat gcagctggca cgacaggttt cccgactgga aagcgggcag    3060
tgagcgcaac gcaattaatg tgagttagct cactcattag gcaccccagg ctttacactt    3120
tatgcttccg gctcgtatgt tgtgtggaat tgtgagcgga taacaatttc acacaggaaa    3180
cagctatgac catgattacg aattggggtt taaaccacgg aagatccagg tctcgagact    3240
aggagacgga tggaggcgc aacgcgcgat ggggagggggg gcggcgctga cctttctggc    3300
gaggtcgagg tagcgatcga gcagctgcag cgcggacacg atgaggaaga cgaagatagc    3360
cgccatggac atgttcgcca gcggcggcgg agcgaggctg agccggtctc tccggcctcc    3420
ggtcggcgtt aagttgggga tcgtaacgtg acgtgtctcg tctccacgga tcgacacaac    3480
cggcctactc gggtgcacga cgccgcgata agggcgagat gtccgtgcac gcagcccgtt    3540
tggagtcctc gttgcccacg aaccgacccc ttacagaaca aggcctagcc caaaactatt    3600
ctgagttgag cttttgagcc tagcccacct aagccgagcg tcatgaactg atgaacccac    3660
taccactagt caaggcaaac cacaaccaca aatggatcaa ttgatctaga acaatccgaa    3720
```

-continued

| | | | | | |
|---|---|---|---|---|---|
| ggaggggagg | ccacgtcaca | ctcacaccaa | ccgaaatatc | tgccagaatc | agatcaaccg | 3780 |
| gccaatagga | cgccagcgag | cccaacacct | ggcgacgccg | caaaattcac | cgcgaggggc | 3840 |
| accgggcacg | gcaaaaacaa | aagcccggcg | cggtgagaat | atctggcgac | tggcggagac | 3900 |
| ctggtggcca | gcgcgcggcc | acatcagcca | ccccatccgc | ccacctcacc | tccggcgagc | 3960 |
| caatggcaac | tcgtcttaag | attccacgag | ataaggaccc | gatcgccggc | gacgctattt | 4020 |
| agccaggtgc | gccccccacg | gtacactcca | ccagcggcat | ctatagcaac | cggtccagca | 4080 |
| ctttcacgct | cagcttcagc | aagatctacc | gtcttcggta | cgcgctcact | ccgccctctg | 4140 |
| cctttgttac | tgccacgttt | ctctgaatgc | tctcttgtgt | ggtgattgct | gagagtggtt | 4200 |
| tagctggatc | tagaattaca | ctctgaaatc | gtgttctgcc | tgtgctgatt | acttgccgtc | 4260 |
| ctttgtagca | gcaaaatata | gggacatggt | agtacgaaac | gaagatagaa | cctacacagc | 4320 |
| aatacgagaa | atgtgtaatt | tggtgcttag | cggtatttat | ttaagcacat | gttggtgtta | 4380 |
| tagggcactt | ggattcagaa | gtttgctgtt | aatttaggca | caggcttcat | actacatggg | 4440 |
| tcaatagtat | agggattcat | attataggcg | atactataat | aatttgttcg | tctgcagagc | 4500 |
| ttattatttg | ccaaaattag | atattcctat | tctgttttg | tttgtgtgct | gttaaattgt | 4560 |
| taacgcctga | aggaataaat | ataaatgacg | aaattttgat | gtttatctct | gctcctttat | 4620 |
| tgtgaccata | agtcaagatc | agatgcactt | gttttaaata | ttgttgtctg | aagaaataag | 4680 |
| tactgacagt | attttgatgc | attgatctgc | ttgtttgttg | taacaaaatt | taaaaataaa | 4740 |
| gagtttcctt | tttgttgctc | tccttacctc | ctgatggtat | ctagtatcta | ccaactgata | 4800 |
| ctatattgct | tctctttaca | tacgtatctt | gctcgatgcc | ttctcctagt | gttgaccagt | 4860 |
| gttactcaca | tagtctttgc | tcatttcatt | gtaatgcaga | taccaagcgg | ttaattaaat | 4920 |
| gcctattgca | accggtcagg | tcatgaacga | cactctgatg | gaggtcgagc | acactcctcc | 4980 |
| tgtgcacaag | cgcatcctgg | acatcctgcc | aggagtgtct | ggaggcgttg | ctcgtatcat | 5040 |
| ggtcggtcag | ccctttgaca | ctatcaagac | tcgcctgcaa | gtgcttggcg | cgggcaccat | 5100 |
| tggcgctcag | ggcatgcctg | ctgacatggt | gtacaacaac | ggcatggact | gcgtgcgcaa | 5160 |
| gatgatcaag | tcagagggcc | ctggctccct | gtacaagggt | acagttgccc | cactgctggg | 5220 |
| taacatggta | ctgctgggca | tccacttccc | caccttcacc | aagacccgtg | cctacctgga | 5280 |
| gcagggagat | gccccggca | ccttctcccc | ctggaagatc | cttgctgctg | gtgctgctgc | 5340 |
| tggtgcagct | ggcagtgtgg | tcagcacccc | aactgagctg | atcagaacca | agatgcagat | 5400 |
| ggtgcgcaag | aacaaccttta | tggctcagat | gaagggcgca | gcggcaaccc | tcaacccaga | 5460 |
| ggagaactac | aagggcaact | gggactgtgc | caagaagatc | ctgcgcaacc | atggcctgcg | 5520 |
| tggcatctac | agcggctatg | tgtccaccct | gctgcgtgac | atgcaaggtt | acgcctggtt | 5580 |
| cttctttggc | tatgaagcta | ccatccacat | gatgtgcact | gaaggcaaga | ccaaggcaga | 5640 |
| cctcaacttc | ctgcaggtca | tgggtgctgg | tgtgattgct | ggctttggtc | tgtgggtag | 5700 |
| catgttcccc | attgacacca | tcaagtccaa | gattcaggct | gacagcctga | gcaagcccga | 5760 |
| gttcaagggc | accatggact | gcctgaagcg | cagtctggca | gtggaaggac | acgcaggact | 5820 |
| gtggaggggt | gtgactgctg | ccctctggcg | tgcaattccc | gtcaatgcag | ccatctttgt | 5880 |
| agcagttgag | ggtacaaggc | agcttattgc | agacacagag | gagagtgtag | atgcatttgt | 5940 |
| gaacaacctc | acaggcagcg | gcagcacagc | agcagctgta | tgaggcgcgc | cgccaaaacg | 6000 |
| agcaggaagc | aacgagaggg | tggcgcgcga | ccgacgtgcg | tacgtagcat | gagcctgagt | 6060 |

-continued

```
ggagacgttg gacgtgtatg tatataccto totgcgtgtt aactatgtac gtaagcggca    6120
ggcagtgcaa taagtgtggc tctgtagtat gtacgtgcgg gtacgatgct gtaagctact    6180
gaggcaagtc cataaataaa taatgacacg tgcgtgttct ataatctctt cgcttcttca    6240
tttgtcccct tgcggagttt ggcatccatt gatgccgtta cgctgagaac agacacagca    6300
gacgaaccaa aagtgagttc ttgtatgaaa ctatgaccct tcatcgctag gctcaaacag    6360
caccccgtac gaacacagca aattagtcat ctaactatta gccctacat gtttcagacg     6420
atacataaat atagcccatc cttagcaatt agctattggc cctgcccatc ccaagcaatg    6480
atctcgaagt attttaata tatagtattt ttaatatgta gcttttaaaa ttagaagata     6540
attttgagac aaaaatctcc aagtatttt ttgggtattt tttactgcct ccgttttct      6600
ttatttctcg tcacctagtt taattttgtg ctaatcggct ataaacgaaa cagagagaaa    6660
agttactcta aaagcaactc caacagatta gatataaatc ttatatcctg cctagagctg    6720
ttaaaaagat agacaacttt agtggattag tgtatgcaac aaactctcca aatttaagta    6780
tcccaactac ccaacgcata tcgttccctt ttcattggcg cacgaacttt cacctgctat    6840
agccgacgta catgttcgtt tttttgggc ggcgcttact ttcttcccg ttcgttctca      6900
gcatcgcaac tcaatttgtt atggcggaga agcccttgta tcccaggtag taatgcacag    6960
atatgcatta ttattattca taaaacgaat tctgataagc tgtcaaacat gacctcagga    7020
tgaagctt                                                             7028
```

<210> SEQ ID NO 52
<211> LENGTH: 4888
<212> TYPE: DNA
<213> ORGANISM: Artificial Sequence
<220> FEATURE:
<223> OTHER INFORMATION: Synthetic construct pYTEN-8

<400> SEQUENCE: 52

```
gtttaaactg aaggcgggaa acgacaatct gatccaagct caagctgctc tagcattcgc      60
cattcaggct gcgcaactgt tgggaagggc gatcggtgcg ggcctcttcg ctattacgcc    120
agctggcgaa aggggatgt gctgcaaggc gattaagttg ggtaacgcca gggttttccc     180
agtcacgacg ttgtaaaacg acggccagtg ccaagcttgt acgtagtgtt tatctttgtt    240
gcttttctga acaatttatt tactatgtaa atatattatc aatgtttaat ctattttaat    300
ttgcacatga attttcattt tatttttact ttacaaaaca aataaatata tatgcaaaaa    360
aatttacaaa cgatgcacgg gttacaaact aatttcatta aatgctaatg cagattttgt    420
gaagtaaaac tccaattatg atgaaaaata ccaccaacac cacctgcgaa actgtatccc    480
aactgtcctt aataaaatg ttaaaagta tattattctc atttgtctgt cataatttat      540
gtaccccact ttaattttc tgatgtacta aaccgagggc aaactgaaac ctgttcctca    600
tgcaaagccc ctactcacca tgtatcatgt acgtgtcatc acccaacaac tccacttttg    660
ctatataaca acacccccgt cacactctcc ctctctaaca cacacccccac taacaattcc   720
ttcacttgca gcactgttgc atcatcatct tcattgcaaa accctaaact tcaccttcaa    780
ccgcggccgc ttcgaaaaaa tgcctattgc aaccggtcag gtcatgaacg acactctgat    840
ggaggtcgag cacactcctc ctgtgcacaa gcgcatcctg gacatcctgc aggagtgtc     900
tggaggcgtt gctcgtatca tggtcggtca gcccttgac actatcaaga ctcgcctgca    960
agtgcttggc gcgggcacca ttggcgctca gggcatgcct gctgacatgg tgtacaacaa   1020
cggcatggac tgcgtgcgca agatgatcaa gtcagagggc cctggctccc tgtacaaggg   1080
```

```
tacagttgcc ccactgctgg gtaacatggt actgctgggc atccacttcc ccaccttcac   1140
caagacccgt gcctacctgg agcagggaga tgcccccggc accttctccc cctggaagat   1200
ccttgctgct ggtgctgctg ctggtgcagc tggcagtgtg gtcagcaccc caactgagct   1260
gatcagaacc aagatgcaga tggtgcgcaa gaacaacctt atggctcaga tgaagggcgc   1320
agcggcaacc ctcaacccag aggagaacta caagggcaac tgggactgtg ccaagaagat   1380
cctgcgcaac catggcctgc gtggcatcta cagcggctat gtgtccaccc tgctgcgtga   1440
catgcaaggt tacgcctggt tcttctttgg ctatgaagct accatccaca tgatgtgcac   1500
tgaaggcaag accaaggcag acctcaactt cctgcaggtc atgggtgctg gtgtgattgc   1560
tggctttggt ctgtggggta gcatgttccc cattgacacc atcaagtcca agattcaggc   1620
tgacagcctg agcaagcccg agttcaaggg caccatggac tgcctgaagc gcagtctggc   1680
agtggaagga cacgcaggac tgtggagggg tgtgactgct gccctctggc gtgcaattcc   1740
cgtcaatgca gccatctttg tagcagttga gggtacaagg cagcttattg cagacacaga   1800
ggagagtgta gatgcatttg tgaacaacct cacaggcagc ggcagcacag cagcagctgt   1860
atgacgaaat ttaaatgcgg ccgctgagta attctgatat tagagggagc attaatgtgt   1920
tgttgtgatg tggtttatat ggggaaatta aataaatgat gtatgtacct cttgcctatg   1980
taggtttgtg tgttttgttt tgttgtctag ctttggttat taagtagtag ggacgttcgt   2040
tcgtgtctca aaaaagggg tactaccact ctgtagtgta tatggatgct ggaaatcaat   2100
gtgttttgta tttgttcacc tccattgttg aattcaatgt caaatgtgtt ttgcgttggt   2160
tatgtgtaaa attactatct ttctcgtccg atgatcaaag ttttaagcaa caaaaccaag   2220
ggtgaaattt aaactgtgct tgttgaaga ttcttttatc atattgaaaa tcaaattact   2280
agcagcagat tttacctagc atgaaatttt atcaacagta cagcactcac taaccaagtt   2340
ccaaactaag atgcgccatt aacatcagcc aataggcatt ttcagcaacc tcagcactag   2400
tcgtcaaagg gcgacacccc ctaattagcc caattcgtaa tcatggtcat agctgtttcc   2460
tgtgtgaaat tgttatccgc tcacaattcc acacaacata cgagccggaa gcataaagtg   2520
taaagcctgg ggtgcctaat gagtgagcta actcacatta attgcgttgc gctcactgcc   2580
cgctttccag tcgggaaacc tgtcgtgcca gctgcattaa tgaatcggcc aacgcgcggg   2640
gagaggcggt ttgcgtattg gctagagcag cttgccaaca tggtggagca atctctcgac   2700
agttgcgaac tgaacgctga gttggtaatg ctatgcccta tcgcttttg caccgtccca   2760 tgatcatttc ccccacacca ccccatcaac ctctaaaaag ttaagagtga aaattacaca   2820
cacccgagga gaagaaaagc tgcttcttct aagcatcaca acctagttac tttacttgta   2880
gggccttttc catttcccct aaattacccc tcttttcatc atatgataat aatatccagc   2940
tcagactata gtatgatatt atgatgtcag cataataggt tggcactaaa gtcttaaagg   3000
gcattgtaca tgttgcacct ggcattcaaa ttcataaata ctaacactgt gaatagatt   3060 ataaatcctc aaataaatgt cacacggttg gggttcgaat ccactcaaaa aggctaatgg   3120
gatgggattt aagtgccaag gaatatacca tggactttaa cagcaacaca atttacaatc   3180
taaaatgtat tacttttttt tttcaaaaaa gatatacaaa ataaggtacc aagaataaaa   3240
ggagtattta gaaacagtgg caccaattta ataaattatt tatataaaat gacacttatt   3300
taatttatca atgataaaag taatattgat ttattctctg attaactgtt caattaatag   3360
tgttattatc ataatctgtc gcaaaagtta ttttatcaa caacaataat tgatacaagt   3420
```

| | |
|---|---|
| agtataaaat taagcctctt agttaatata gactacttga tactaaaacc atgttacacc | 3480 |
| aaaaagtaat ttttatgtca cttgtctata taataattac gactaaatta ataatttta | 3540 |
| aaaatattac tgaatccatt aaccgaactt ttataatgaa agtattttta tgctttaaaa | 3600 |
| tcacaaacat tgaataaact aaaaatgata ccacggaatt ggaacaagag acgttccaca | 3660 |
| caaaagaaaa aaatatgttg aataattgaa acggtgacaa gaaaagtgga ataataatac | 3720 |
| aaagatggca gatggggtta ttgttattgg aggagatgag tgaaataatg agtgagggg | 3780 |
| gtgtaactgg aaagcaagaa aaagcgcaag agtgccagct atttccaaca acaaacgtgg | 3840 |
| cccgtgggat gcgatattcg taacgaacgg cgaggatgga aggacgtgca atttgcgctt | 3900 |
| catttgaggc gaatttcatt tggccagacc ttccttttt aaaccacagg gctcgagtct | 3960 |
| accatgagcc cagaacgacg cccggccgac atccgccgtg ccaccgaggc ggacatgccg | 4020 |
| gcggtctgca ccatcgtcaa ccactacatc gagacaagca cggtcaactt ccgtaccgag | 4080 |
| ccgcaggaac cgcaggagtg gacggacgac ctcgtccgtc tgcgggagcg ctatccctgg | 4140 |
| ctcgtcgccg aggtggacgg cgaggtcgcc ggcatcgcct acgcgggccc ctggaaggca | 4200 |
| cgcaacgcct acgactggac ggccgagtcg accgtgtacg tctcccccg ccaccagcgg | 4260 |
| acgggactgg gctccacgct ctacacccac ctgctgaagt ccctggaggc cagggcttc | 4320 |
| aagagcgtgg tcgctgtcat cgggctgccc aacgacccga gcgtgcgcat gcacgaggcg | 4380 |
| ctcggatatg ccccccgcgg catgctgcgg gcggccggct tcaagcacgg gaactggcat | 4440 |
| gacgtgggtt tctggcagct ggacttcagc ctgccggtac cgccccgtcc ggtcctgccc | 4500 |
| gtcaccgaga tttgactcga gttataatca tggagtgtga agctggacc agggaaatta | 4560 |
| ctatttatac aaatactaca aaaataccat ctagtggttg aggaactttc atttcctact | 4620 |
| cttaccatc ctttatcta tcttgttttt gtgttttcct ttctttggta tgttgagata | 4680 |
| agagcatgaa ggctagcaag atatgtaaga ttcttttttt tttctcccgt tctgttgtag | 4740 |
| aagagatgtg aattgttacc tatttggttt ggttgaatta caaattctt ttcatgaagt | 4800 |
| attctgatta acatagtggt acggtacgtg cttgatttat acattaaaaa cgtccgcaat | 4860 |
| gtgttattaa gttgtctaag cgtcaatt | 4888 |

<210> SEQ ID NO 53
<211> LENGTH: 14746
<212> TYPE: DNA
<213> ORGANISM: Artificial Sequence
<220> FEATURE:
<223> OTHER INFORMATION: Synthetic construct pYTEN-9

<400> SEQUENCE: 53

| | |
|---|---|
| gcgtataatg gactattgtg tgctgataag gagaacataa gcgcagaaca atatgtatct | 60 |
| attccggtgt tgtgttcctt tgttattctg ctattatgtt ctcttatagt gtgacgaaag | 120 |
| cagcataatt aatcgtcact tgttctttga ttgtgttacg atatccagag acttagaaac | 180 |
| gggggaaccg ggatgagcaa ggtaaaaatc ggtgagttga tcaacacgct tgtgaatgag | 240 |
| gtagaggcaa ttgatgcctc agaccgccca caaggcgaca aaacgaagag aattaaagcc | 300 |
| gcagccgcac ggtataagaa cgcgttattt aatgataaaa gaaagttccg tgggaaagga | 360 |
| ttgcagaaaa gaataaccgc gaatactttt aacgcctata tgagcagggc aagaaagcgg | 420 |
| tttgatgata aattacatca tagctttgat aaaaatatta taaattatc ggaaaagtat | 480 |
| cctctttaca gcgaagaatt atcttcatgg ctttctatgc ctacggctaa tattcgccag | 540 |
| cacatgtcat cgttacaatc taaattgaaa gaaataatgc cgcttgccga agagttatca | 600 |

```
aatgtaagaa taggctctaa aggcagtgat gcaaaaatag caagactaat aaaaaaatat    660
ccagattgga gttttgctct tagtgattta aacagtgatg attggaagga gcgccgtgac    720
tatctttata agttattcca acaaggctct gcgttgttag aagaactaca ccagctcaag    780
gtcaaccatg aggttctgta ccatctgcag ctaagccctg cggagcgtac atctatacag    840
caacgatggg ccgatgttct gcgcgagaag aagcgtaatg ttgtggttat tgactaccca    900
acatacatgc agtctatcta tgatattttg aataatcctg cgactttatt tagtttaaac    960
actcgttctg gaatggcacc tttggccttt gctctggctg cggtatcagg gcgaagaatg   1020
attgagataa tgtttcaggg tgaatttgcc gtttcaggaa agtatacggt taatttctca   1080
gggcaagcta aaaacgctc tgaagataaa agcgtaacca gaacgattta tctttatgc    1140
gaagcaaaat tattcgttga attattaaca gaattgcgtt cttgctctgc tgcatctgat   1200
ttcgatgagg ttgttaaagg atatggaaag gatgatacaa ggtctgagaa cggcaggata   1260
aatgctattt tagcaaaagc atttaaccct tgggttaaat cattttcgg cgatgaccgt   1320
cgtgtttata agatagccg cgctatttac gctcgcatcg cttatgagat gttcttccgc   1380
gtcgatccac ggtggaaaaa cgtcgacgag gatgtgttct tcatggagat tctcggacac   1440
gacgatgaga acacccagct gcactataag cagttcaagc tggccaactt ctccagaacc   1500
tggcgacctg aagttgggga tgaaaacacc aggctggtgg ctctgcagaa actggacgat   1560
gaaatgccag gctttgccag aggtgacgct ggcgtccgtc tccatgaaac cgttaagcag   1620
ctggtggagc aggacccatc agcaaaaata accaacagca ctctccgggc ctttaaattt   1680
agcccgacga tgattagccg gtacctggag tttgccgctg atgcattggg gcagttcgtt   1740
ggcgagaacg ggcagtggca gctgaagata gagacacctg caatcgtcct gcctgatgaa   1800
gaatccgttg agaccatcga cgaaccggat gatgagtccc aagacgacga gctggatgaa   1860
gatgaaattg agctcgacga gggtggcggc gatgaaccaa ccgaagagga agggccagaa   1920
gaacatcagc caactgctct aaaacccgtc ttcaagcctg caaaaaataa cggggacgga   1980
acgtacaaga tagagtttga atacgatgga aagcattatg cctggtccgg ccccgccgat   2040
agccctatgg ccgcaatgcg atccgcatgg gaaacgtact acagctaaaa gaaaagccac   2100
cggtgttaat cggtggcttt tttattgagg cctgtcccta cccatcccct gcaagggacg   2160
gaaggattag gcgaaactg cagctgcaac tacggacatc gccgtcccga ctgcagggac   2220
ttccccgcgt aaagcggggc ttaaattcgg gctggccaac cctattttc tgcaatcgct   2280
ggcgatgtta gtttcgtgga tagcgtttcc agcttttcaa tggccagctc aaaatgtgct   2340
ggcagcacct tctccagttc cgtatcaata tcggtgatcg gcagctctcc acaagacata   2400
ctccggcgac cgccacgaac tacatcgcgc agcagctccc gttcgtagac acgcatgttg   2460
cccagagccg tttctgcagc cgttaatatc cggcgcagct cggcgatgat tgccgggaga   2520
tcatccacgg ttattgggtt cggtgatggg ttcctgcagg cgcggcggag agccatccag   2580
acgccgctaa cccatgcgtt acggtactga aaactttgtg ctatgtcgtt tatcaggccc   2640
cgaagttctt cttttctgccg ccagtccagt ggttcaccgg cgttcttagg ctcaggctcg   2700
acaaaagcat actcgccgtt tttccggata gctggcagaa cctcgttcgt cacccacttg   2760
cggaaccgcc aggctgtcgt cccctgtttc accgcgtcgc ggcagcggag gattatggtg   2820
tagagaccag attccgatac cacatttact tccctggcca tccgatcaag ttttgtgcc    2880
tcggttaaac cgagggtcaa ttttcatca tgatccagct tacgcaatgc atcagaaggg   2940
```

```
ttggctatat tcaatgcagc acagatatcc agcgccacaa accacgggtc accaccgaca    3000
agaaccaccc gtatagggtg gctttcctga aatgaaaaga cggagagagc cttcattgcg    3060
cctccccgga tttcagctgc tcagaaaggg acagggagca gccgcgagct tcctgcgtga    3120
gttcgcgcgc gacctgcaga agttccgcag cttcctgcaa atacagcgtg gcctcataac    3180
tggagatagt gcggtgagca gagcccacaa gcgcttcaac ctgcagcagg cgttcctcaa    3240
tcgtctccag caggccctgg gcgtttaact gaatctggtt catgcgatca cctcgctgac    3300
cgggatacgg gctgacagaa cgaggacaaa acggctggcg aactggcgac gagcttctcg    3360
ctcggatgat gcaatggtgg aaaggcggtg gatatgggat tttttgtccg tgcggacgac    3420
agctgcaaat ttgaatttga acatggtatg cattcctatc ttgtataggg tgctaccacc    3480
agagttgaga atctctatag gggtggtagc ccagacaggg ttctcaacac cggtacaaga    3540
agaaaccggc ccaaccgaag ttggccccat ctgagccacc ataattcagg tatgcgcaga    3600
tttaacacac aaaaaaacac gctggcgcgt gttgtgcgct tcttgtcatt cggggttgag    3660
aggcccggct gcagattttg ctgcagcggg gtaactctac cgccaaagca gaacgcacgt    3720
caataattta ggtggatatt ttaccccgtg accagtcacg tgcacaggtg ttttttatagt    3780 ttgctttact gactgatcag aacctgatca gttattggag tccggtaatc ttattgatga    3840
ccgcagccac cttagatgtt gtctcaaacc ccatacggcc acgaatgagc cactggaacg    3900
gaatagtcag caggtacagc ggaacgaacc acaaacggtt cagacgctgc cagaacgtcg    3960
catcacgacg ttccatccat tcggtattgt cgacgacctg gtaagcgtat tgtcctggcg    4020 ttttttgctgc ttccgagtag caatcctctt caccacaaag aaagttactt atctgcttcc    4080
agttttcgaa cccttcttct ttgagccgct tttccagctc attcctccac aaaacaggca    4140
cccatcctct gcgataaatc atgattattt gtcctttaaa taaggctgta gaactgcaaa    4200
atcgctctcg ttcacatgct gtacgtagat gcgtagcaaa ttgccgttcc atccctgtaa    4260
tccaccttct ttggaaagat cgtccttgac ctcacgaaga accttatcca atagccctgc    4320
ggcacaagaa attgcctgct ctggatcagc aaattcatat tgattaatag gtgattgcca    4380
cacaccaaaa acaggaatca tcttttcggc taaacgcctc tcctgttctt tcttaatctc    4440
aagttgtaag cggaccagct caccatccat catttttttgt agatcatgcg ccactattca    4500
cccccactgg ccatcagcaa ataaagcttc tactcggac accggcaggc ggcttccacg    4560
gattgaaagg tcaagccaac cacgtccaga tgggtcagcc ttatccgatt cttcccaccg    4620
ttctgcagct gtagcaacca ggcattctac cgccttcatg tagtcttctg tacggaacca    4680
gccgtagtta atgccaccat cagtaactgc ccaggccatc ttttttctctt cggcctcaat    4740 agcccggatg cggttatcgc acagctcgcg acagtacttc agctgttcgt aatccagttg    4800
cttcaggaac tctggtgtcg acgtcatagt ggcttcacct tataggcttt tagaagcgcc    4860
ctggcttcgt ctgtgtggtc ttccatgctc ttatcgctgg caatgcagca ataaactccc    4920
tcactatctg agaacccgtt catccgaatg atcgtgaatg gaagttcccg gccagtttta    4980
taatcgctat agcttgtcgc gtcgtggctg accttgacca cataagggtc gtagccctcc    5040
acgatgacaa ggcattcccg ttgttttccc attacccctc cggttatatc gccacggctt    5100
gccgctggct tagaaacgct ttcagcagcc ttatttcgcg tactgatagc aggtccataa    5160
attcggtcat gtacagcgag gcgaacgttc tcgcgatgct ggccactggc cacaggcgta    5220
ccgcctccat ttcggttgct ggcaacgcgt tctccgccca cgcctccggt accgccaccg    5280
ggatagcctc cagtgcctgg ataattactg attgtggggc gtccggaacg tgctctgttt    5340
```

```
tggatcgagg gttaccatgt atatctatat ttagatccaa atcgcgatcc acttcgatgg   5400
tggttttttc caccttacgt gcgtgaattg ataaaccggc ctcgcggcgc ttctccacga   5460
tattcatgag gaactcgacc gagtccgggt caatggaacg catcgtgggg cgtgcatcgc   5520
cgtctctggc gcgtctggtc ttactggata gccccataga ctccaggatg cctatgcaga   5580
ggtctgcagg cgcttctctt ttgcctttct ctgtgttgaa gccgccgatg cgtaaaacgt   5640
tgtttagcag atcgcgccgt tccggcgtga gcaggttatc tctggcgcgt ttgagggcgt   5700
ccatgtctgc ttcaccttcc agggttttg gatcgatacc gcagtcgcgg aagtactgct    5760
gcagcgtcgc cgatttgagg gtgtagaaac cacgcatgcc tatctcaaca gcaggggtcg   5820
atttcactcg gtaatcggtt atggccggga atttagcctg gaactctgcg tcggcctgtt   5880
cccgcgtcat ggccgtagtg acgaactgct gccatcttcc ggcaacgcga taagcgtagg   5940
taaagtgaat caacgcttct tcacggtcaa ggcgacgggc ggttatctca tccagctgca   6000
tggtttcaaa caggcgcact tttttcaggc cgccgtcgaa atagaatttt aacgccacct   6060
cgtcgacatc cagctgcagc tccttttcga tgtcccagcg gaccagctgg gcctgctcat   6120
ccagggacag ggtgcgtttt tttatcaact catcgtgttc ggcctggtca ggagtatcga   6180
cactcaggtg gcgctccata agctgctcaa agaccagttc acgggcttct ttacgtaaat   6240
ccttaccgat gctgtttgca agcgcgtcgg tggccatagg cgcgacctga tagccatcat   6300
catgcatgat gcaaatcatg ttgctggcat aatcatttct ggccgatgcc tcgagcgcgg   6360
cggcttttaat tttgagctgc atgaatgaag agttagccac gccgagtgaa attcggtcac   6420
cgtcaaagac aacgtctgtc agcagcccgg agtggccagc cgtttcgagc aaggcctgcg   6480
cgtaggcgcg tttgattttt tccggatcgg tttcacgttt accgcgaagc ttgtcgaaac   6540
cgataatgta ttcctgagct gtacggtcgc ggcgcagcat ctggatggcg tcgctgggga   6600
ccacttcgcc gcagaacatg ccgaaatggc ggtggaagtg tttctcctca atcgatacac   6660
ctgaagatat cgacgggctg tagatgaggc cgtcatattt tttcaccatc actttaggct   6720
ggttggtgaa atcgtcgact tccttctcct gtttgttttt ctggttaacg cagagaaact   6780
ttttgtcagg gaactgtagt ctcagctgca tggtaacgtc ttcggcgaac gtcgaactgt   6840
cggtggccag catgattcgt tcgccgcgtt gcactgcagc gataacctcg gtcatgatcc   6900
gatttttctc ggtataaaat acgcggatag gcttgttggt ttcgcggttg cgaacgtcga   6960
ccgggagttc aatcacgtga atttgcagcc aggcaggtag gcccagctcc tcgcgtcgct   7020
tcatcgccag ttcagccagg tcaacaagca gatcgttggc atcggcatcc accataatgg   7080
catgctcttc agtacgcgcc agcgcgtcga taagcgtgtt gaatacgcct accgggtttt   7140
ccatcgcacg cccggccaga atggcacgca ggccctgtgt tgcttcatcg aagccgaaga   7200
agtcatgctg gcgcatcagc ggttgccagc agcctttaag tatggagttg atgcaaatag   7260
tcagcttgtt ggcatatggc gccatttcct gatagccggg atcctgataa tgcagaatgt   7320
cggctttcgc gccttttccct tcggtcatca tttcatgcag gccgcctatc agggatacgc   7380
ggtgcgcgac ggaaacgcca cgcgtggact gcagcatcag tggacgcagg aggcctgtcg   7440
atttacccga ccccatcccg gcgcggacaa taacgatgcc ctgcagctgt gcggcgtatg   7500
tcatcacctc atcggtcatc ctggaggttt caaaccgttt gtaagtgatg tgtgacgggc   7560
gaaggttcgg gttggtgatg cgttcactga acgaacgtga tgtttgcgcg gcacggcatt   7620
tgcgattcaa ccggcgcgta atgtgatctt taacggtacc gttataaatt tctgcgatac   7680
```

-continued

```
ccatatcccg cagcgtgctg ctgaaaaggc gcataagttc tttcgggctg tttggtaccg    7740
ggcatgtcag catgccaata tcaacggcgc gaagcagttc tttggcaaaa gtgcgtctgt    7800
tcagacgcgg gagagtacgc agcttattca gcgtgatcga caacagatcg gttgcacggc    7860
tcagatgatt tctcgttaac tggcgagcga cttccttcag ccctctcagg ctgtgcaggt    7920
cgttaaaatc gctgcattcc agctcagggt catcctcaaa agttgggtaa acacatttga    7980
cgccggaaaa cttctccatg atgtcgaatc cggtgcggag gcctgtgttg ccttttcctt    8040
cagctgagga tttgcggtcg ttatcgagag cgcaagtgat ttgcgcagcc gggtacatgt    8100
tcaccagctg ctcgacaacg tgaatcatgt tgttagcgga aaccgcaatg actaccgcgt    8160
caaagcgttt tttcgggtcg tttctggtcg ccagccagat ggatgccccg gtggcgaaac    8220
cctctgcagt cgcaattttt tgcgccccct gcaggtcgcc aataacaaag catgcaccga    8280
cgaaatcacc gttagtgatg cgctggtct ggaacttgcc accattcaga tcgatacgtt    8340
gccagccaac aatccgcccg tcttttcttc cgtccaggtg ggacagaggt atcgccatgt    8400
aagttgttgg tccacggctc catttcgcac tgtcgtgact ggtcacgcga cgtatatcac    8460
aagcgccaaa tacgtcacga attccctttt ttaccgcata aggccaggag ccatcttcag    8520
ctggcgaatg ttcccaggcg cgatggaaag ccaaccatcc aagcaggcgt tcctgctcca    8580
tctgattgtt ttttaaatca ttaacgcgtt gttgttcagc tcggaggcgg cgtgcttcag    8640
cctggcgctc catgcgtgca cgttcttctt ccggctgagc gaccacggtc gcaccattcc    8700
gttgctgttc acggcgatac tccgaaaaca ggaatgaaaa gccactccag gagccagcgt    8760
catgcgcttt tcaacgaag ttaacgaaag gataactgat gccatccttg ctctgctcaa    8820
ggcgtgaata gatttccaca cggccttaa ggctcttctg cagagcttcc ggggaggaat    8880
tattgtaggt ggtatagcgc tctacaccac cgcgcggatt gagctgaatc ttatcagcac    8940
acgcaggcca gttgataccg gccatcttcg ccagctcagt cagctcatca cgtgccgcgt    9000
caagcagtga aaacggatcg ctgccaaagc gctccgcgta gaattcttgt aaggtcattt    9060
tttagccttt ccatgcgaat tagcattttt tcgggttgaa aaaatccgca ggagcagcca    9120
caataaacgc actatctttc tgaaggacgt atctgcgtta tcgtggctac ttcctgaaaa    9180
aggcccgagt ttgccgactc gggttttttt tcgtcttttt tcggctgcta cggtctggtt    9240
caaccccgac aaagtataga tcggattaaa ccagaattat agtcagcaat aaaccctgtt    9300
attgtatcat ctaccctcaa ccatgaacga tttgatcgta ccgactactt ggtgcacaaa    9360
ttgaagatca cttttatcat ggataacccg ttgagagtta gcactatcaa ggtagtaatg    9420
ctgctcgtca taacgggcta atcgttgaat tgtgatctcg ccgttattat cacaaaccag    9480
tacatcctca cccggtacaa gcgtaagtga agaatcgacc aggataacgt ctcccggctg    9540
gtagtttcgc tgaatctggt tcccgaccgt cagtgcgtaa acggtgttcc gttgactcac    9600
gaacggcagg aatcgctctg tgttggcagg ttctccaggc tgccagtctc tatccggtcc    9660
ggtctctgtc gtaccaataa caggaacgcg gtctggatca gattcagtgc catacagtat    9720
ccattgcacg ggcttacgca ggcattttgc cagcgatagc ccgatctcca gcgacggcat    9780
cacgtcgcca cgttctaagt tttgacgcc cggaagagag attcctacag cttctgccac    9840
ttgcttcagc gtcagtttca gctctaaacg gcgtgctttc agtcgttcgc ctcgtgtttt    9900 catacccctta atcataaatg atctctttat agctggctat aatttttata aattatacct    9960
agctttaatt ttcacttatt gattataata atccccatga aacccgaaga acttgtgcgc   10020
catttcggcg atgtggaaaa agcagcggtt ggcgtgggcg tgacacccgg cgcagtctat   10080
```

```
caatggctgc aagctgggga gattccacct ctacgacaaa gcgatataga ggtccgtacc   10140
gcgtacaaat taaagagtga tttcacctct cagcgcatgg gtaaggaagg cataacagg    10200
ggatcctcta gacgcagaaa ggcccacccg aaggtgagcc agtgtgatta catttgcggc   10260
ctaactgtgg ccagtccagt tacgctggag tcactagtgc ggccgcgaca acttgtctag   10320
ggcccaatgg cccgggactg gcgcgccgta cgtagtgttt atctttgttg cttttctgaa   10380
caatttattt actatgtaaa tatattatca atgtttaatc tattttaatt tgcacatgaa   10440
ttttcatttt attttttactt tacaaaacaa ataaatatat atgcaaaaaa atttacaaac   10500
gatgcacggg ttacaaacta atttcattaa atgctaatgc agattttgtg aagtaaaact   10560
ccaattatga tgaaaaatac caccaacacc acctgcgaaa ctgtatccca actgtcctta   10620
ataaaaatgt taaaaagtat attattctca tttgtctgtc ataatttatg taccccactt   10680
taattttttct gatgtactaa accgagggca aactgaaacc tgttcctcat gcaaagcccc   10740
tactcaccat gtatcatgta cgtgtcatca cccaacaact ccacttttgc tatataacaa   10800
caccccgtc acactctccc tctctaacac acacccact aacaattcct tcacttgcag     10860
cactgttgca tcatcatctt cattgcaaaa ccctaaactt caccttcaac cgcggccgcg   10920
gtaccaaaat gcctattgca accggtcagg tcatgaacga cactctgatg gaggtcgagc   10980
acactcctcc tgtgcacaag cgcatcctgg acatcctgcc aggagtgtct ggaggcgttg   11040
ctcgtatcat ggtcggtcag cccttttgaca ctatcaagac tcgcctgcaa gtgcttggcg   11100
cgggcaccat tggcgctcag ggcatgcctg ctgacatggt gtacaacaac ggcatggact   11160
gcgtgcgcaa gatgatcaag tcagagggcc ctggctccct gtacaagggt acagttgccc   11220
cactgctggg taacatggta ctgctgggca tccacttccc caccttcacc aagacccgtg   11280
cctacctgga gcagggagat gcccccggca ccttctcccc ctggaagatc cttgctgctg   11340
gtgctgctgc tggtgcagct ggcagtgtgg tcagcacccc aactgagctg atcagaacca   11400
agatgcagat ggtgcgcaag aacaaccttta tggctcagat gaagggcgca gcggcaaccc   11460
tcaacccaga ggagaactac aagggcaact gggactgtgc caagaagatc ctgcgcaacc   11520
atggcctgcg tggcatctac agcggctatg tgtccaccct gctgcgtgac atgcaaggtt   11580
acgcctggtt cttctttggc tatgaagcta ccatccacat gatgtgcact gaaggcaaga   11640
ccaaggcaga cctcaacttc ctgcaggtca tgggtgctgg tgtgattgct ggctttggtc   11700
tgtggggtag catgttcccc attgacacca tcaagtccaa gattcaggct gacagcctga   11760
gcaagcccga gttcaagggc accatggact gcctgaagcg cagtctggca gtggaaggac   11820
acgcaggact gtggaggggt gtgactgctg ccctctggcg tgcaattccc gtcaatgcag   11880
ccatctttgt agcagttgag ggtacaaggc agcttattgc agacacagag gagagtgtag   11940
atgcatttgt gaacaaccctc acaggcagcg gcagcacagc agcagctgta tgatctagag   12000
cggccgctga gtaattctga tattagaggg agcattaatg tgttgttgtg atgtggttta   12060
tatgggaaa ttaaataaat gatgtatgta cctcttgcct atgtaggttt gtgtgttttg    12120
ttttgttgtc tagctttggt tattaagtag tagggacgtt cgttcgtgtc tcaaaaaaag   12180
gggtactacc actctgtagt gtatatggat gctggaaatc aatgtgtttt gtatttgttc   12240
acctccattg ttgaattcaa tgtcaaatgt gttttgcgtt ggttatgtgt aaaattacta   12300
tctttctcgt ccgatgatca aagttttaag caacaaaacc aagggtgaaa tttaaactgt   12360
gctttgttga agattctttt atcatattga aaatcaaatt actagcagca gattttacct   12420
```

```
agcatgaaat tttatcaaca gtacagcact cactaaccaa gttccaaact aagatgcgcc    12480
attaacatca gccaataggc attttcagca aggcgcgcca gtcccgggcc attagacttg    12540
aagtcaagcg gccgcttaca actggacctt gctggtacat agaactgatt aactgaccat    12600
ttaaatcata ccaacatggt caaataaaac gaaaggctca gtcgaaagac tgggcctttc    12660
gttttaatct gatcggcacg taagaggttc aactttcac  cataatgaaa taagatcact    12720
accgggcgta ttttgagtt  atcgagattt tcaggagcta aggaagctaa aatgagccat    12780
attcaacggg aaacgtcttg ctcgaggccg cgattaaatt ccaacatgga tgctgattta    12840
tatgggtata aatgggctcg cgataatgtc gggcaatcag gtgcgacaat ctatcgattg    12900
tatgggaagc ccgatgcgcc agagttgttt ctgaaacatg gcaaaggtag cgttgccaat    12960
gatgttacag atgagatggt caggctaaac tggctgacgg aatttatgcc tcttccgacc    13020
atcaagcatt ttatccgtac tcctgatgat gcatggttac tcaccactgc gatcccaggg    13080
aaaacagcat tccaggtatt agaagaatat cctgattcag gtgaaaatat tgttgatgcg    13140
ctggcagtgt tcctgcgccg gttgcattcg attcctgttt gtaattgtcc ttttaacggc    13200
gatcgcgtat ttcgtctcgc tcaggcgcaa tcacgaatga ataacggttt ggttggtgcg    13260
agtgattttg atgacgagcg taatggctgg cctgttgaac aagtctggaa agaaatgcat    13320
aaacttttgc cattctcacc ggattcagtc gtcactcatg gtgatttctc acttgataac    13380
cttatttttg acgaggggaa attaataggt tgtattgatg ttggacgagt cggaatcgca    13440
gaccgatacc aggatcttgc catcctatgg aactgcctcg gtgagttttc tccttcatta    13500
cagaaacggc ttttttcaaaa atatggtatt gataatcctg atatgaataa attgcagttt    13560
cacttgatgc tcgatgagtt tttctaacct aggtgacaga agtcaaaagc ctccggtcgg    13620
aggcttttga ctttctgcta gatctgtttc aatgcggtga agggccaggc agctggggat    13680
tatgtcgaga cccggccagc atgttggttt tatcgcatat tcagcgttgt cgcgtttacc    13740
caggtaaaat ggaagcagtg tatcgtctgc gtgaatgtgc aaatcaggaa cgtaaccgtg    13800
gtacatagat gcagtcccct tgcgggtcgt tcccttcaacg agtatgacgc ggtgcccttg    13860
caaggctaac cattgcgcct ggtgtactgc agatgaggtt ttataaaccc ctcccttgtg    13920
tgacataacg gaaagtacaa ccgggttttt atcgtcaggt ctttggtttg ggttaccaaa    13980
cacactccgc atatggctaa tttggtcaat tgtgtagcca gcgcgacgtt ctactcggcc    14040
cctcatctca aaatcaggag ccggtagacg accagctttt tccgcgtctc tgatagcctg    14100
cggtgttacg ccgatcaggt ctgcaacttc tgttataccc cagcggcgag taatacgacg    14160
cgcttccggg ctgtcatcgc cgaactgtgc gatggcaata gcgcgcgtca tttcctgacc    14220
gcgattgata cagtctttca gcaaattaat taacgacatc ctgtttcctc tcaaacatgc    14280
ccttatcttt gtgttttca  tcatactta  cgttttaaa  gcaaagcaac ataaaaaaag    14340
caaagtgact tagaaaacgc aaagttaagg ttcaaatcaa ttttttgatg cgctacagaa    14400
gctatttagc ttcatctaag cgcaacggta ttacttacgt tggtatattt aaaacctaac    14460
ttaatgattt taaatgataa taaatcatac caattgctat caaaagttaa gcgaacatgc    14520
tgattttcac gctgtttata cactttgagg catctctatc tcttccgtct ctatattgaa    14580
acacaatcaa agaacatcaa tccatgtgac atcccccact atctaagaac accataacag    14640
aacacaacat aggaatgcaa cattaatgta tcaataattc ggaacatatg cactatatca    14700
tatctcaatt acggaacata tcagcacaca attgcccatt atacgc                  14746
```